United States Patent
Loew et al.

(10) Patent No.: US 12,247,060 B2
(45) Date of Patent: Mar. 11, 2025

(54) CALRETICULIN BINDING CONSTRUCTS AND ENGINEERED T CELLS FOR THE TREATMENT OF DISEASES

(71) Applicant: MARENGO THERAPEUTICS, INC., Cambridge, MA (US)

(72) Inventors: Andreas Loew, Cambridge, MA (US); Brian Edward Vash, Cambridge, MA (US)

(73) Assignee: Marengo Therapeutics, Inc., Cambridge, MA (US)

( * ) Notice: Subject to any disclaimer, the term of this patent is extended or adjusted under 35 U.S.C. 154(b) by 1273 days.

(21) Appl. No.: 16/960,704

(22) PCT Filed: Jan. 9, 2019

(86) PCT No.: PCT/US2019/012900
§ 371 (c)(1),
(2) Date: Jul. 8, 2020

(87) PCT Pub. No.: WO2019/139987
PCT Pub. Date: Jul. 18, 2019

(65) Prior Publication Data
US 2021/0137982 A1    May 13, 2021

Related U.S. Application Data

(60) Provisional application No. 62/615,270, filed on Jan. 9, 2018.

(51) Int. Cl.
| | | |
|---|---|---|
| *A61K 39/00* | (2006.01) | |
| *A61K 35/17* | (2015.01) | |
| *C07K 14/705* | (2006.01) | |
| *C07K 14/725* | (2006.01) | |
| *C07K 16/18* | (2006.01) | |
| *C07K 16/28* | (2006.01) | |

(52) U.S. Cl.
CPC .......... *C07K 14/7051* (2013.01); *A61K 35/17* (2013.01); *A61K 39/4611* (2023.05); *A61K 39/4631* (2023.05); *A61K 39/4644* (2023.05); *C07K 14/70521* (2013.01); *C07K 14/70578* (2013.01); *C07K 16/18* (2013.01); *C07K 16/28* (2013.01); *C07K 2317/565* (2013.01); *C07K 2317/92* (2013.01); *C07K 2319/03* (2013.01)

(58) Field of Classification Search
CPC ...... C07K 16/18; C07K 16/30; C07K 14/705; A61K 39/395; A61K 39/0011
See application file for complete search history.

(56) References Cited

U.S. PATENT DOCUMENTS

| | | |
|---|---|---|
| 861,745 A | 7/1907 | Maxwell |
| 4,433,059 A | 2/1984 | Chang et al. |
| 4,439,196 A | 3/1984 | Higuchi |
| 4,444,878 A | 4/1984 | Paulus |
| 4,447,224 A | 5/1984 | DeCant, Jr. et al. |
| 4,447,233 A | 5/1984 | Mayfield |
| 4,475,196 A | 10/1984 | La Zor |
| 4,486,194 A | 12/1984 | Ferrara |
| 4,487,603 A | 12/1984 | Harris |
| 4,522,811 A | 6/1985 | Eppstein et al. |
| 4,596,556 A | 6/1986 | Morrow et al. |
| 4,676,980 A | 6/1987 | Segal et al. |
| 4,737,456 A | 4/1988 | Weng et al. |
| 4,790,824 A | 12/1988 | Morrow et al. |
| 4,816,567 A | 3/1989 | Cabilly et al. |
| 4,941,880 A | 7/1990 | Burns |
| 5,057,423 A | 10/1991 | Hiserodt et al. |
| 5,064,413 A | 11/1991 | McKinnon et al. |
| 5,116,615 A | 5/1992 | Gokcen et al. |
| 5,208,020 A | 5/1993 | Chari et al. |
| 5,223,409 A | 6/1993 | Ladner et al. |
| 5,225,539 A | 7/1993 | Winter |
| 5,273,743 A | 12/1993 | Ahlem et al. |
| 5,312,335 A | 5/1994 | McKinnon et al. |
| 5,374,548 A | 12/1994 | Caras |
| 5,383,851 A | 1/1995 | McKinnon, Jr. et al. |
| 5,391,377 A | 2/1995 | Barnwell |
| 5,399,163 A | 3/1995 | Peterson et al. |
| 5,399,331 A | 3/1995 | Loughrey et al. |
| 5,416,016 A | 5/1995 | Low et al. |
| 5,416,064 A | 5/1995 | Chari et al. |
| 5,500,362 A | 3/1996 | Robinson et al. |
| 5,534,254 A | 7/1996 | Huston et al. |
| 5,571,894 A | 11/1996 | Wels et al. |
| 5,582,996 A | 12/1996 | Curtis |
| 5,585,089 A | 12/1996 | Queen et al. |

(Continued)

FOREIGN PATENT DOCUMENTS

| | | |
|---|---|---|
| AU | 2001278662 B2 | 9/2006 |
| CA | 3016563 A1 | 9/2017 |

(Continued)

OTHER PUBLICATIONS

Holmstrom et al., Leukemia, 2016, vol. 30:2413-2416.*

(Continued)

*Primary Examiner* — Xiaozhen Xie
(74) *Attorney, Agent, or Firm* — Wilson Sonsini Goodrich & Rosati

(57) ABSTRACT

Provided herein are nucleic acid constructs, polypeptides and T cells related to antigen binding domains that bind to mutant calreticulin; and methods of use thereof for the treatment of diseases, including cancer.

24 Claims, No Drawings
Specification includes a Sequence Listing.

(56) References Cited

U.S. PATENT DOCUMENTS

| | | |
|---|---|---|
| 5,587,458 A | 12/1996 | King et al. |
| 5,591,828 A | 1/1997 | Bosslet et al. |
| 5,624,821 A | 4/1997 | Winter et al. |
| 5,626,561 A | 5/1997 | Butler et al. |
| 5,635,483 A | 6/1997 | Pettit et al. |
| 5,635,602 A | 6/1997 | Cantor et al. |
| 5,637,481 A | 6/1997 | Ledbetter et al. |
| 5,641,870 A | 6/1997 | Rinderknecht et al. |
| 5,648,237 A | 7/1997 | Carter |
| 5,648,260 A | 7/1997 | Winter et al. |
| 5,693,761 A | 12/1997 | Queen et al. |
| 5,693,762 A | 12/1997 | Queen et al. |
| 5,712,374 A | 1/1998 | Kuntsmann et al. |
| 5,714,586 A | 2/1998 | Kunstmann et al. |
| 5,731,116 A | 3/1998 | Matsuo et al. |
| 5,731,168 A | 3/1998 | Carter et al. |
| 5,739,116 A | 4/1998 | Hamann et al. |
| 5,747,036 A | 5/1998 | Brenner et al. |
| 5,750,373 A | 5/1998 | Garrard et al. |
| 5,766,947 A | 6/1998 | Rittershaus et al. |
| 5,767,285 A | 6/1998 | Hamann et al. |
| 5,770,429 A | 6/1998 | Lonberg et al. |
| 5,770,701 A | 6/1998 | McGahren et al. |
| 5,770,710 A | 6/1998 | McGahren et al. |
| 5,773,001 A | 6/1998 | Hamann et al. |
| 5,780,588 A | 7/1998 | Pettit et al. |
| 5,787,900 A | 8/1998 | Butler et al. |
| 5,789,199 A | 8/1998 | Joly et al. |
| 5,811,097 A | 9/1998 | Allison et al. |
| 5,821,337 A | 10/1998 | Carter et al. |
| 5,831,012 A | 11/1998 | Nilsson et al. |
| 5,837,242 A | 11/1998 | Holliger et al. |
| 5,837,821 A | 11/1998 | Wu |
| 5,840,523 A | 11/1998 | Simmons et al. |
| 5,843,069 A | 12/1998 | Butler et al. |
| 5,844,094 A | 12/1998 | Hudson et al. |
| 5,849,500 A | 12/1998 | Breitling et al. |
| 5,849,589 A | 12/1998 | Tedder et al. |
| 5,861,155 A | 1/1999 | Lin |
| 5,864,019 A | 1/1999 | King et al. |
| 5,869,046 A | 2/1999 | Presta et al. |
| 5,869,620 A | 2/1999 | Whitlow et al. |
| 5,877,296 A | 3/1999 | Hamann et al. |
| 5,902,745 A | 5/1999 | Butler et al. |
| 5,910,573 A | 6/1999 | Plueckthun et al. |
| 5,913,998 A | 6/1999 | Butler et al. |
| 5,932,448 A | 8/1999 | Tso et al. |
| 5,959,083 A | 9/1999 | Bosslet et al. |
| 5,959,177 A | 9/1999 | Hein et al. |
| 5,968,753 A | 10/1999 | Tseng-Law et al. |
| 5,980,889 A | 11/1999 | Butler et al. |
| 5,989,830 A | 11/1999 | Davis et al. |
| 6,005,079 A | 12/1999 | Casterman et al. |
| 6,040,498 A | 3/2000 | Stomp et al. |
| 6,075,181 A | 6/2000 | Kucherlapati et al. |
| 6,120,766 A | 9/2000 | Hale et al. |
| 6,150,584 A | 11/2000 | Kucherlapati et al. |
| 6,171,586 B1 | 1/2001 | Lam et al. |
| 6,172,197 B1 | 1/2001 | McCafferty et al. |
| 6,194,551 B1 | 2/2001 | Idusogie et al. |
| 6,239,259 B1 | 5/2001 | Davis et al. |
| 6,248,516 B1 | 6/2001 | Winter et al. |
| 6,267,958 B1 | 7/2001 | Andya et al. |
| 6,291,158 B1 | 9/2001 | Winter et al. |
| 6,294,353 B1 | 9/2001 | Pack et al. |
| 6,333,396 B1 | 12/2001 | Filpula et al. |
| 6,352,694 B1 | 3/2002 | June et al. |
| 6,417,429 B1 | 7/2002 | Hein et al. |
| 6,420,548 B1 | 7/2002 | Vezina et al. |
| 6,476,198 B1 | 11/2002 | Kang |
| 6,511,663 B1 | 1/2003 | King et al. |
| 6,534,055 B1 | 3/2003 | June et al. |
| 6,582,915 B1 | 6/2003 | Griffiths et al. |
| 6,593,081 B1 | 7/2003 | Griffiths et al. |
| 6,602,684 B1 | 8/2003 | Umana et al. |
| 6,630,579 B2 | 10/2003 | Chari et al. |
| 6,632,427 B1 | 10/2003 | Finiels et al. |
| 6,670,453 B2 | 12/2003 | Frenken et al. |
| 6,696,245 B2 | 2/2004 | Winter et al. |
| 6,703,199 B1 | 3/2004 | Koide |
| 6,737,056 B1 | 5/2004 | Presta |
| 6,743,896 B2 | 6/2004 | Filpula et al. |
| 6,756,523 B1 | 6/2004 | Kahn et al. |
| 6,765,087 B1 | 7/2004 | Casterman et al. |
| 6,809,185 B1 | 10/2004 | Schoonjans et al. |
| 6,818,418 B1 | 11/2004 | Lipovsek et al. |
| 6,833,441 B2 | 12/2004 | Wang et al. |
| 6,838,254 B1 | 1/2005 | Hamers et al. |
| 6,905,680 B2 | 6/2005 | June et al. |
| 6,979,546 B2 | 12/2005 | Moretta et al. |
| 6,982,321 B2 | 1/2006 | Winter |
| 7,041,870 B2 | 5/2006 | Tomizuka et al. |
| 7,083,785 B2 | 8/2006 | Browning et al. |
| 7,087,409 B2 | 8/2006 | Barbas, III et al. |
| 7,105,149 B1 | 9/2006 | Dalla-Favera |
| 7,125,978 B1 | 10/2006 | Vezina et al. |
| 7,129,330 B1 | 10/2006 | Little et al. |
| 7,183,076 B2 | 2/2007 | Arathoon et al. |
| 7,186,804 B2 | 3/2007 | Gillies et al. |
| 7,189,826 B2 | 3/2007 | Rodman |
| 7,250,297 B1 | 7/2007 | Beste et al. |
| 7,276,241 B2 | 10/2007 | Schneider et al. |
| 7,332,581 B2 | 2/2008 | Presta |
| 7,361,360 B2 | 4/2008 | Kitabwalla et al. |
| 7,371,826 B2 | 5/2008 | Presta |
| 7,402,314 B2 | 7/2008 | Sherman |
| 7,431,380 B1 | 10/2008 | Buresh |
| 7,476,724 B2 | 1/2009 | Dennis et al. |
| 7,498,298 B2 | 3/2009 | Doronina et al. |
| 7,501,121 B2 | 3/2009 | Tchistiakova et al. |
| 7,517,966 B2 | 4/2009 | Moretta et al. |
| 7,521,056 B2 | 4/2009 | Chang et al. |
| 7,521,541 B2 | 4/2009 | Eigenbrot et al. |
| 7,527,787 B2 | 5/2009 | Chang et al. |
| 7,527,791 B2 | 5/2009 | Adams et al. |
| 7,534,866 B2 | 5/2009 | Chang et al. |
| 7,563,441 B2 | 7/2009 | Graus et al. |
| 7,601,803 B1 | 10/2009 | Fiedler et al. |
| 7,612,181 B2 | 11/2009 | Wu et al. |
| 7,642,228 B2 | 1/2010 | Carter et al. |
| 7,700,739 B2 | 4/2010 | Lacy et al. |
| 7,741,446 B2 | 6/2010 | Pardridge et al. |
| 7,750,128 B2 | 7/2010 | Gegg et al. |
| 7,767,429 B2 | 8/2010 | Bookbinder et al. |
| 7,799,902 B2 | 9/2010 | Browning et al. |
| 7,803,376 B2 | 9/2010 | Velardi et al. |
| 7,807,160 B2 | 10/2010 | Presta et al. |
| 7,829,289 B2 | 11/2010 | Lantz et al. |
| 7,855,275 B2 | 12/2010 | Eigenbrot et al. |
| 7,858,759 B2 | 12/2010 | Brandt et al. |
| 7,906,118 B2 | 3/2011 | Chang et al. |
| 7,919,257 B2 | 4/2011 | Hoogenboom et al. |
| 7,943,743 B2 | 5/2011 | Korman et al. |
| 7,999,077 B2 | 8/2011 | Pastan et al. |
| 8,003,774 B2 | 8/2011 | Stavenhagen et al. |
| 8,008,449 B2 | 8/2011 | Korman et al. |
| 8,012,465 B2 | 9/2011 | Elias et al. |
| 8,034,326 B2 | 10/2011 | Hjorth et al. |
| 8,202,517 B2 | 6/2012 | Bookbinder et al. |
| 8,216,805 B2 | 7/2012 | Carter et al. |
| 8,299,220 B2 | 10/2012 | Dalla-Favera |
| 8,354,509 B2 | 1/2013 | Carven et al. |
| 8,362,213 B2 | 1/2013 | Elkins et al. |
| 8,450,470 B2 | 5/2013 | Bookbinder et al. |
| 8,466,260 B2 | 6/2013 | Elkins et al. |
| 8,552,156 B2 | 10/2013 | Takayanagi et al. |
| 8,580,252 B2 | 11/2013 | Bookbinder et al. |
| 8,586,713 B2 | 11/2013 | Davis et al. |
| 8,592,562 B2 | 11/2013 | Kannan et al. |
| 8,609,089 B2 | 12/2013 | Langermann et al. |
| 8,617,545 B2 | 12/2013 | Hsu et al. |
| 8,617,559 B2 | 12/2013 | Elkins et al. |
| 8,658,135 B2 | 2/2014 | O'Connor-McCourt et al. |
| 8,703,132 B2 | 4/2014 | Imhof-Jung et al. |

(56) References Cited

U.S. PATENT DOCUMENTS

| | | |
|---|---|---|
| 8,772,246 B2 | 7/2014 | Bookbinder et al. |
| 8,790,895 B2 | 7/2014 | Fiedler et al. |
| 8,821,883 B2 | 9/2014 | Ambrose et al. |
| 8,846,042 B2 | 9/2014 | Zhou |
| 8,871,912 B2 | 10/2014 | Davis et al. |
| 8,920,776 B2 | 12/2014 | Gaiger et al. |
| 8,945,571 B2 | 2/2015 | Mössner et al. |
| 8,993,524 B2 | 3/2015 | Bedi et al. |
| 9,000,130 B2 | 4/2015 | Bhakta et al. |
| 9,034,324 B2 | 5/2015 | Kalled et al. |
| 9,056,905 B2 | 6/2015 | Olson et al. |
| 9,145,588 B2 | 9/2015 | Throsby et al. |
| 9,200,060 B2 | 12/2015 | Kannan et al. |
| 9,243,058 B2 | 1/2016 | Armitage et al. |
| 9,309,311 B2 | 4/2016 | Gurney et al. |
| 9,340,621 B2 | 5/2016 | Kufer et al. |
| 9,358,286 B2 | 6/2016 | De Kruif et al. |
| 9,359,437 B2 | 6/2016 | Davis et al. |
| 9,382,323 B2 | 7/2016 | Brinkmann et al. |
| 9,387,237 B2 | 7/2016 | Kalled et al. |
| 9,416,187 B2 | 8/2016 | Tedder et al. |
| 9,447,159 B2 | 9/2016 | Ast et al. |
| 9,447,185 B2 | 9/2016 | Romagne et al. |
| 9,545,086 B2 | 1/2017 | Mackay et al. |
| 9,593,376 B2 | 3/2017 | Zitvogel et al. |
| 9,663,577 B2 | 5/2017 | Pierres et al. |
| 9,676,863 B2 | 6/2017 | Lo |
| 9,833,476 B2 | 12/2017 | Zhang et al. |
| 10,150,816 B2 * | 12/2018 | Abbot ................ C07K 16/3061 |
| 10,294,300 B2 | 5/2019 | Raum et al. |
| 10,308,721 B2 | 6/2019 | Williams et al. |
| 10,478,509 B2 | 11/2019 | Torgov et al. |
| 10,610,571 B2 | 4/2020 | Ptacin et al. |
| 10,676,516 B2 | 6/2020 | Viney et al. |
| 10,730,942 B2 | 8/2020 | Pule et al. |
| 10,815,311 B2 | 10/2020 | Wesche et al. |
| 11,033,634 B2 | 6/2021 | Stull et al. |
| 11,291,721 B2 | 4/2022 | Loew et al. |
| 11,292,838 B2 | 4/2022 | Schendel et al. |
| 11,673,953 B2 | 6/2023 | Zhang et al. |
| 11,692,031 B2 | 7/2023 | Dahlhoff et al. |
| 11,845,797 B2 | 12/2023 | Tan et al. |
| 11,965,025 B2 | 4/2024 | Tan et al. |
| 2002/0004587 A1 | 1/2002 | Miller et al. |
| 2002/0041865 A1 | 4/2002 | Austin et al. |
| 2002/0062010 A1 | 5/2002 | Arathoon et al. |
| 2002/0076406 A1 | 6/2002 | Leung |
| 2002/0103345 A1 | 8/2002 | Zhu |
| 2002/0164328 A1 | 11/2002 | Shinkawa et al. |
| 2003/0115614 A1 | 6/2003 | Kanda et al. |
| 2003/0130496 A1 | 7/2003 | Winter et al. |
| 2003/0157108 A1 | 8/2003 | Presta |
| 2003/0175884 A1 | 9/2003 | Umana et al. |
| 2003/0207346 A1 | 11/2003 | Arathoon et al. |
| 2003/0211078 A1 | 11/2003 | Heavner |
| 2004/0009530 A1 | 1/2004 | Wilson et al. |
| 2004/0093621 A1 | 5/2004 | Shitara et al. |
| 2004/0109865 A1 | 6/2004 | Niwa et al. |
| 2004/0110282 A1 | 6/2004 | Kanda et al. |
| 2004/0110704 A1 | 6/2004 | Yamane et al. |
| 2004/0132140 A1 | 7/2004 | Satoh et al. |
| 2004/0175756 A1 | 9/2004 | Kolkman et al. |
| 2004/0219643 A1 | 11/2004 | Winter et al. |
| 2004/0220388 A1 | 11/2004 | Mertens et al. |
| 2004/0241817 A1 | 12/2004 | Umana et al. |
| 2004/0242847 A1 | 12/2004 | Fukushima et al. |
| 2005/0003403 A1 | 1/2005 | Rossi et al. |
| 2005/0004352 A1 | 1/2005 | Kontermann et al. |
| 2005/0014934 A1 | 1/2005 | Hinton et al. |
| 2005/0048512 A1 | 3/2005 | Kolkman et al. |
| 2005/0053973 A1 | 3/2005 | Kolkman et al. |
| 2005/0069552 A1 | 3/2005 | Bleck et al. |
| 2005/0079170 A1 | 4/2005 | Le Gall et al. |
| 2005/0079574 A1 | 4/2005 | Bond |
| 2005/0090648 A1 | 4/2005 | Tsurushita et al. |
| 2005/0100543 A1 | 5/2005 | Hansen et al. |
| 2005/0119455 A1 | 6/2005 | Fuh et al. |
| 2005/0123546 A1 | 6/2005 | Umana et al. |
| 2005/0136049 A1 | 6/2005 | Ledbetter et al. |
| 2005/0136051 A1 | 6/2005 | Scallon |
| 2005/0163782 A1 | 7/2005 | Glaser et al. |
| 2005/0260186 A1 | 11/2005 | Bookbinder et al. |
| 2005/0266000 A1 | 12/2005 | Bond et al. |
| 2005/0266425 A1 | 12/2005 | Zauderer et al. |
| 2006/0008844 A1 | 1/2006 | Stemmer et al. |
| 2006/0025576 A1 | 2/2006 | Miller et al. |
| 2006/0083747 A1 | 4/2006 | Winter et al. |
| 2006/0104968 A1 | 5/2006 | Bookbinder et al. |
| 2006/0120960 A1 | 6/2006 | Deyev et al. |
| 2006/0141581 A1 | 6/2006 | Gillies et al. |
| 2006/0204493 A1 | 9/2006 | Huang et al. |
| 2006/0263367 A1 | 11/2006 | Fey et al. |
| 2007/0004909 A1 | 1/2007 | Johnson et al. |
| 2007/0036783 A1 | 2/2007 | Humeau et al. |
| 2007/0061900 A1 | 3/2007 | Murphy et al. |
| 2007/0087381 A1 | 4/2007 | Kojima |
| 2007/0105105 A1 | 5/2007 | Clelland et al. |
| 2007/0117126 A1 | 5/2007 | Sidhu et al. |
| 2007/0128150 A1 | 6/2007 | Norman |
| 2007/0141049 A1 | 6/2007 | Bredehorst et al. |
| 2007/0154901 A1 | 7/2007 | Thogersen et al. |
| 2007/0160598 A1 | 7/2007 | Dennis et al. |
| 2007/0178106 A1 | 8/2007 | Romagne |
| 2007/0184052 A1 | 8/2007 | Lin et al. |
| 2007/0231322 A1 | 10/2007 | Romagne et al. |
| 2007/0237764 A1 | 10/2007 | Birtalan et al. |
| 2007/0274985 A1 | 11/2007 | Dubel et al. |
| 2007/0292936 A1 | 12/2007 | Barthelemy et al. |
| 2008/0050370 A1 | 2/2008 | Glaser et al. |
| 2008/0063717 A1 | 3/2008 | Romagne et al. |
| 2008/0069820 A1 | 3/2008 | Fuh et al. |
| 2008/0152645 A1 | 6/2008 | Pardridge et al. |
| 2008/0171855 A1 | 7/2008 | Rossi et al. |
| 2008/0241884 A1 | 10/2008 | Shitara et al. |
| 2008/0247944 A1 | 10/2008 | Graziano et al. |
| 2008/0254512 A1 | 10/2008 | Capon |
| 2008/0260738 A1 | 10/2008 | Moore et al. |
| 2008/0299137 A1 | 12/2008 | Svendsen et al. |
| 2009/0002360 A1 | 1/2009 | Chen et al. |
| 2009/0010843 A1 | 1/2009 | Spee et al. |
| 2009/0130106 A1 | 5/2009 | Christopherson et al. |
| 2009/0148905 A1 | 6/2009 | Ashman et al. |
| 2009/0155275 A1 | 6/2009 | Wu et al. |
| 2009/0162359 A1 | 6/2009 | Klein et al. |
| 2009/0162360 A1 | 6/2009 | Klein et al. |
| 2009/0175851 A1 | 7/2009 | Klein et al. |
| 2009/0175867 A1 | 7/2009 | Thompson et al. |
| 2009/0214533 A1 | 8/2009 | Clynes |
| 2009/0232811 A1 | 9/2009 | Klein et al. |
| 2009/0234105 A1 | 9/2009 | Gervay-Hague et al. |
| 2009/0263392 A1 | 10/2009 | Igawa et al. |
| 2009/0274649 A1 | 11/2009 | Qu et al. |
| 2009/0280116 A1 | 11/2009 | Smith et al. |
| 2009/0324538 A1 | 12/2009 | Wong et al. |
| 2010/0015133 A1 | 1/2010 | Igawa et al. |
| 2010/0028330 A1 | 2/2010 | Collins et al. |
| 2010/0047169 A1 | 2/2010 | Mandelboim et al. |
| 2010/0168393 A1 | 7/2010 | Clube et al. |
| 2010/0260704 A1 | 10/2010 | Berenguer et al. |
| 2010/0316645 A1 | 12/2010 | Imhof-Jung et al. |
| 2011/0014659 A1 | 1/2011 | Balazs et al. |
| 2011/0054151 A1 | 3/2011 | Lazar et al. |
| 2011/0091372 A1 | 4/2011 | Ghayur et al. |
| 2011/0150892 A1 | 6/2011 | Thudium et al. |
| 2011/0177073 A1 | 7/2011 | Van Berkel et al. |
| 2011/0177093 A1 | 7/2011 | Kalled et al. |
| 2011/0250170 A1 | 10/2011 | Pedretti et al. |
| 2011/0287056 A1 | 11/2011 | Gu et al. |
| 2011/0293613 A1 | 12/2011 | Brinkmann et al. |
| 2012/0034221 A1 | 2/2012 | Bonvini et al. |
| 2012/0039906 A1 | 2/2012 | Olive |
| 2012/0114649 A1 | 5/2012 | Langermann et al. |
| 2012/0149876 A1 | 6/2012 | Von Kreudenstein et al. |
| 2012/0184716 A1 | 7/2012 | Fischer et al. |

(56) References Cited

U.S. PATENT DOCUMENTS

| | | |
|---|---|---|
| 2012/0201746 A1 | 8/2012 | Liu et al. |
| 2012/0213768 A1 | 8/2012 | Oh et al. |
| 2012/0294857 A1 | 11/2012 | Sentman et al. |
| 2013/0017200 A1 | 1/2013 | Scheer et al. |
| 2013/0022601 A1 | 1/2013 | Brinkmann et al. |
| 2013/0078249 A1 | 3/2013 | Ast et al. |
| 2013/0129723 A1 | 5/2013 | Blankenship et al. |
| 2013/0165638 A1 | 6/2013 | Hsu et al. |
| 2013/0178605 A1 | 7/2013 | Blein et al. |
| 2013/0195849 A1 | 8/2013 | Spreter Von Kreudenstein et al. |
| 2013/0243775 A1 | 9/2013 | Papadopoulos et al. |
| 2013/0266568 A1 | 10/2013 | Brinkmann et al. |
| 2013/0267686 A1 | 10/2013 | Brinkmann et al. |
| 2013/0273055 A1 | 10/2013 | Borges et al. |
| 2013/0273089 A1 | 10/2013 | Getts et al. |
| 2013/0280208 A1 | 10/2013 | Stepkowski et al. |
| 2013/0303396 A1 | 11/2013 | Igawa et al. |
| 2013/0317200 A1 | 11/2013 | Elson et al. |
| 2014/0037621 A1 | 2/2014 | Tsurushita et al. |
| 2014/0044728 A1 | 2/2014 | Takayanagi et al. |
| 2014/0051833 A1 | 2/2014 | Fischer et al. |
| 2014/0051835 A1 | 2/2014 | Dixit et al. |
| 2014/0072528 A1 | 3/2014 | Gerdes et al. |
| 2014/0072581 A1 | 3/2014 | Dixit et al. |
| 2014/0079689 A1 | 3/2014 | Elliott et al. |
| 2014/0079691 A1 | 3/2014 | McConnell et al. |
| 2014/0099254 A1 | 4/2014 | Chang et al. |
| 2014/0154254 A1 | 6/2014 | Kannan et al. |
| 2014/0199294 A1 | 7/2014 | Mimoto et al. |
| 2014/0200331 A1 | 7/2014 | Corper et al. |
| 2014/0227265 A1 | 8/2014 | Wu et al. |
| 2014/0242075 A1 | 8/2014 | Parren et al. |
| 2014/0242077 A1 | 8/2014 | Choi et al. |
| 2014/0256916 A1 | 9/2014 | Kruip et al. |
| 2014/0308285 A1 | 10/2014 | Yan et al. |
| 2014/0322212 A1 | 10/2014 | Brogdon et al. |
| 2014/0322221 A1 | 10/2014 | Miller et al. |
| 2014/0348839 A1 | 11/2014 | Chowdhury et al. |
| 2014/0363426 A1 | 12/2014 | Moore et al. |
| 2014/0377269 A1 | 12/2014 | Mabry et al. |
| 2015/0017187 A1 | 1/2015 | Thanos et al. |
| 2015/0018529 A1 | 1/2015 | Humphreys et al. |
| 2015/0056199 A1 | 2/2015 | Kumar et al. |
| 2015/0098900 A1 | 4/2015 | Ebens et al. |
| 2015/0133638 A1 | 5/2015 | Wranik et al. |
| 2015/0166661 A1 | 6/2015 | Chen et al. |
| 2015/0166670 A1 | 6/2015 | Castoldi et al. |
| 2015/0175707 A1 | 6/2015 | De Jong et al. |
| 2015/0203591 A1 | 7/2015 | Yancopoulos et al. |
| 2015/0211001 A1 | 7/2015 | Ohrn et al. |
| 2015/0218260 A1 | 8/2015 | Klein et al. |
| 2015/0232560 A1 | 8/2015 | Heindl et al. |
| 2015/0315296 A1 | 11/2015 | Schaefer et al. |
| 2015/0337049 A1 | 11/2015 | Labrijn et al. |
| 2015/0344570 A1 | 12/2015 | Igawa et al. |
| 2015/0353636 A1 | 12/2015 | Parren et al. |
| 2015/0368351 A1 | 12/2015 | Vu et al. |
| 2015/0368352 A1 | 12/2015 | Liu |
| 2015/0376287 A1 | 12/2015 | Vu et al. |
| 2016/0015749 A1 | 1/2016 | Gottschalk et al. |
| 2016/0039947 A1 | 2/2016 | Demarest et al. |
| 2016/0075785 A1 | 3/2016 | Ast et al. |
| 2016/0102135 A1 | 4/2016 | Escobar-Cabrera |
| 2016/0114057 A1 | 4/2016 | Dixit et al. |
| 2016/0130347 A1 | 5/2016 | Bruenker et al. |
| 2016/0131654 A1 | 5/2016 | Berenson et al. |
| 2016/0145340 A1 | 5/2016 | Borges et al. |
| 2016/0145354 A1 | 5/2016 | Bacac et al. |
| 2016/0176973 A1 | 6/2016 | Kufer et al. |
| 2016/0194389 A1 | 7/2016 | Regula et al. |
| 2016/0229915 A1 | 8/2016 | Igawa et al. |
| 2016/0244523 A1 | 8/2016 | Blank et al. |
| 2016/0257763 A1 | 9/2016 | Von Kreudenstein et al. |
| 2016/0264685 A1 | 9/2016 | Fouque et al. |
| 2016/0297885 A1 | 10/2016 | Kuo et al. |
| 2016/0311915 A1 | 10/2016 | Pulé et al. |
| 2016/0368985 A1 | 12/2016 | Hotzel et al. |
| 2016/0368988 A1 | 12/2016 | Bakker et al. |
| 2017/0022284 A1 | 1/2017 | Timmer et al. |
| 2017/0035905 A1 | 2/2017 | Abrams et al. |
| 2017/0037128 A1 | 2/2017 | Little et al. |
| 2017/0051068 A1 | 2/2017 | Pillarisetti et al. |
| 2017/0066827 A1 | 3/2017 | Pulé et al. |
| 2017/0151281 A1 | 6/2017 | Wagner et al. |
| 2017/0204176 A1 | 7/2017 | Bonvini et al. |
| 2017/0269092 A1* | 9/2017 | Kralovics ............ A61K 39/395 |
| 2017/0275362 A1* | 9/2017 | Brentjens ......... C07K 14/70578 |
| 2017/0298445 A1 | 10/2017 | Ogg |
| 2017/0334998 A1 | 11/2017 | Pulé et al. |
| 2017/0368169 A1 | 12/2017 | Loew et al. |
| 2018/0153938 A1 | 6/2018 | Keating et al. |
| 2018/0235887 A1 | 8/2018 | Garidel et al. |
| 2018/0256716 A1 | 9/2018 | Schendel et al. |
| 2019/0062448 A1 | 2/2019 | Soros et al. |
| 2019/0209612 A1 | 7/2019 | Puléet al. |
| 2019/0315883 A1 | 10/2019 | Ast et al. |
| 2019/0322763 A1 | 10/2019 | Ast et al. |
| 2020/0071417 A1 | 3/2020 | Loew et al. |
| 2020/0109195 A1 | 4/2020 | Watkins et al. |
| 2020/0129638 A1 | 4/2020 | Van Berkel et al. |
| 2020/0140549 A1 | 5/2020 | Cordoba et al. |
| 2020/0172591 A1 | 6/2020 | Hosse et al. |
| 2020/0172868 A1 | 6/2020 | Wickham et al. |
| 2020/0200756 A1 | 6/2020 | Pulé et al. |
| 2020/0230208 A1 | 7/2020 | Wang et al. |
| 2020/0277384 A1 | 9/2020 | Chang et al. |
| 2020/0291089 A1 | 9/2020 | Loew et al. |
| 2020/0299349 A1 | 9/2020 | Garcia et al. |
| 2020/0306301 A1 | 10/2020 | Andresen et al. |
| 2020/0308242 A1 | 10/2020 | Lowe et al. |
| 2020/0317787 A1 | 10/2020 | Li et al. |
| 2020/0332003 A1 | 10/2020 | Britanova et al. |
| 2020/0377571 A1 | 12/2020 | Loew et al. |
| 2020/0385472 A1 | 12/2020 | Loew et al. |
| 2021/0009711 A1 | 1/2021 | Loew et al. |
| 2021/0024631 A1 | 1/2021 | Kley et al. |
| 2021/0079114 A1 | 3/2021 | Hudson |
| 2021/0198369 A1 | 7/2021 | Chang et al. |
| 2021/0221863 A1 | 7/2021 | Kang et al. |
| 2021/0230311 A1 | 7/2021 | Nezu et al. |
| 2021/0238280 A1 | 8/2021 | Loew et al. |
| 2021/0246227 A1 | 8/2021 | Loew et al. |
| 2021/0277119 A1 | 9/2021 | Tan et al. |
| 2021/0363250 A1 | 11/2021 | Kamikawaji et al. |
| 2021/0371523 A1 | 12/2021 | Loew et al. |
| 2021/0380670 A1 | 12/2021 | Loew et al. |
| 2021/0380682 A1 | 12/2021 | Loew et al. |
| 2021/0380691 A1 | 12/2021 | Loew et al. |
| 2021/0380692 A1 | 12/2021 | Loew et al. |
| 2021/0380715 A1 | 12/2021 | Yoshida et al. |
| 2022/0064255 A1 | 3/2022 | Loew et al. |
| 2022/0064297 A1 | 3/2022 | Tan et al. |
| 2022/0112286 A1 | 4/2022 | Britanova et al. |
| 2022/0288200 A1 | 9/2022 | Loew et al. |
| 2023/0025484 A1 | 1/2023 | Tan et al. |
| 2023/0031734 A1 | 2/2023 | Tan et al. |
| 2023/0034161 A1 | 2/2023 | Tan et al. |
| 2023/0048244 A1 | 2/2023 | Loew |
| 2023/0127740 A1 | 4/2023 | Tan et al. |
| 2023/0142522 A1 | 5/2023 | Tan et al. |
| 2023/0174650 A1 | 6/2023 | Tan et al. |
| 2023/0192848 A1 | 6/2023 | Loew |
| 2023/0227552 A1 | 7/2023 | Tan et al. |
| 2023/0333112 A1 | 10/2023 | Loew et al. |
| 2023/0348593 A1 | 11/2023 | Loew et al. |
| 2023/0357395 A1 | 11/2023 | Loew et al. |
| 2023/0374133 A1 | 11/2023 | Tan et al. |
| 2024/0002543 A1 | 1/2024 | Loew et al. |

(56) References Cited

U.S. PATENT DOCUMENTS

| | | |
|---|---|---|
| 2024/0076377 A1 | 3/2024 | Tan et al. |
| 2024/0301060 A1 | 9/2024 | Tan et al. |

FOREIGN PATENT DOCUMENTS

| | | |
|---|---|---|
| CN | 101802010 A | 8/2010 |
| CN | 101985476 A | 3/2011 |
| CN | 104203981 A | 12/2014 |
| CN | 104769103 A | 7/2015 |
| CN | 105916876 A | 8/2016 |
| CN | 106103475 A | 11/2016 |
| CN | 106163547 A | 11/2016 |
| CN | 107206024 A | 9/2017 |
| CN | 107903325 A | 4/2018 |
| CN | 108026171 A | 5/2018 |
| CN | 109153728 A | 1/2019 |
| DE | 10261223 A1 | 7/2004 |
| EP | 0125023 A1 | 11/1984 |
| EP | 0171496 A2 | 2/1986 |
| EP | 0173494 A2 | 3/1986 |
| EP | 0184187 A2 | 6/1986 |
| EP | 0346087 A2 | 12/1989 |
| EP | 0368684 A1 | 5/1990 |
| EP | 0388151 A1 | 9/1990 |
| EP | 0404097 A2 | 12/1990 |
| EP | 0519596 A1 | 12/1992 |
| EP | 0171496 B1 | 5/1993 |
| EP | 0616640 A1 | 9/1994 |
| EP | 0425235 B1 | 9/1996 |
| EP | 0403156 B1 | 9/1997 |
| EP | 1176195 A1 | 1/2002 |
| EP | 0125023 B2 | 3/2002 |
| EP | 0368684 B2 | 9/2004 |
| EP | 0616640 B1 | 9/2004 |
| EP | 1301605 B1 | 11/2005 |
| EP | 1870459 A1 | 12/2007 |
| EP | 2581113 A1 | 4/2013 |
| EP | 1846020 B1 | 8/2013 |
| EP | 2699259 A1 | 2/2014 |
| EP | 2467165 B1 | 1/2015 |
| EP | 2847231 A1 | 3/2015 |
| EP | 2982694 A1 | 2/2016 |
| EP | 3023437 A1 | 5/2016 |
| EP | 1870459 B1 | 6/2016 |
| EP | 2982694 B1 | 6/2016 |
| EP | 3029068 A1 | 6/2016 |
| EP | 2699259 B1 | 7/2016 |
| EP | 3055329 A1 | 8/2016 |
| EP | 3137500 A1 | 3/2017 |
| EP | 3059246 B1 | 7/2018 |
| EP | 2723380 B1 | 8/2019 |
| EP | 3294768 B1 | 8/2019 |
| EP | 3149031 B1 | 12/2019 |
| EP | 3590967 A1 | 1/2020 |
| EP | 3626739 A1 | 3/2020 |
| EP | 3642228 A1 | 4/2020 |
| EP | 3189132 B1 | 6/2020 |
| EP | 3303392 B1 | 8/2020 |
| EP | 4087871 A1 | 11/2022 |
| GB | 2188638 A | 10/1987 |
| GB | 2599228 A | 3/2022 |
| GB | 2616354 A | 9/2023 |
| JP | H0787994 A | 4/1995 |
| JP | H08502246 A | 3/1996 |
| JP | H09509307 A | 9/1997 |
| JP | 2011524743 A | 9/2011 |
| JP | 2013515509 A | 5/2013 |
| JP | 2016512557 A | 4/2016 |
| JP | 6153947 B2 | 6/2017 |
| JP | 2017143838 A | 8/2017 |
| JP | 2018517712 A | 7/2018 |
| JP | 2018531939 A | 11/2018 |
| WO | WO-8500817 A1 | 2/1985 |
| WO | WO-8601533 A1 | 3/1986 |
| WO | WO-8702671 A1 | 5/1987 |
| WO | WO-9002809 A1 | 3/1990 |
| WO | WO-9100906 A1 | 1/1991 |
| WO | WO-9103493 A1 | 3/1991 |
| WO | WO-9110741 A1 | 7/1991 |
| WO | WO-9117271 A1 | 11/1991 |
| WO | WO-9201047 A1 | 1/1992 |
| WO | WO-9203917 A1 | 3/1992 |
| WO | WO-9203918 A1 | 3/1992 |
| WO | WO-9209690 A2 | 6/1992 |
| WO | WO-9215679 A1 | 9/1992 |
| WO | WO-9218619 A1 | 10/1992 |
| WO | WO-9220791 A1 | 11/1992 |
| WO | WO-9209690 A3 | 12/1992 |
| WO | WO-9301161 A1 | 1/1993 |
| WO | WO-9301288 A1 | 1/1993 |
| WO | WO-9308829 A1 | 5/1993 |
| WO | WO-9311161 A1 | 6/1993 |
| WO | WO-9311236 A1 | 6/1993 |
| WO | WO-9323537 A1 | 11/1993 |
| WO | WO-9404678 A1 | 3/1994 |
| WO | WO-9405801 A1 | 3/1994 |
| WO | WO-9409131 A1 | 4/1994 |
| WO | WO-9411026 A2 | 5/1994 |
| WO | WO-9412625 A2 | 6/1994 |
| WO | WO-9425591 A1 | 11/1994 |
| WO | WO-9429351 A2 | 12/1994 |
| WO | WO-9509917 A1 | 4/1995 |
| WO | WO-9516038 A2 | 6/1995 |
| WO | WO-9637621 A2 | 11/1996 |
| WO | WO-9730087 A1 | 8/1997 |
| WO | WO-9814206 A1 | 4/1998 |
| WO | WO-9856915 A2 | 12/1998 |
| WO | WO-9858964 A1 | 12/1998 |
| WO | WO-9904820 A2 | 2/1999 |
| WO | WO-9916873 A1 | 4/1999 |
| WO | WO-9922764 A1 | 5/1999 |
| WO | WO-9945110 A1 | 9/1999 |
| WO | WO-9951642 A1 | 10/1999 |
| WO | WO-9964460 A1 | 12/1999 |
| WO | WO-0006605 A2 | 2/2000 |
| WO | WO-0034784 A1 | 6/2000 |
| WO | WO-0060070 A1 | 10/2000 |
| WO | WO-0061739 A1 | 10/2000 |
| WO | WO-0104144 A2 | 1/2001 |
| WO | WO-0129246 A1 | 4/2001 |
| WO | WO-0136630 A2 | 5/2001 |
| WO | WO-0164942 A1 | 9/2001 |
| WO | WO-0198357 A2 | 12/2001 |
| WO | WO-0231140 A1 | 4/2002 |
| WO | WO-02070647 A2 | 9/2002 |
| WO | WO-02072635 A2 | 9/2002 |
| WO | WO-03002609 A2 | 1/2003 |
| WO | WO-03011878 A2 | 2/2003 |
| WO | WO-03014161 A2 | 2/2003 |
| WO | WO-03056914 A1 | 7/2003 |
| WO | WO-03084570 A1 | 10/2003 |
| WO | WO-03085107 A1 | 10/2003 |
| WO | WO-03085119 A1 | 10/2003 |
| WO | WO-03093318 A1 | 11/2003 |
| WO | WO-2004003019 A2 | 1/2004 |
| WO | WO-2004024927 A1 | 3/2004 |
| WO | WO-2004033685 A1 | 4/2004 |
| WO | WO-2004056312 A2 | 7/2004 |
| WO | WO-2004056392 A1 | 7/2004 |
| WO | WO-2004056873 A1 | 7/2004 |
| WO | WO-2004057002 A2 | 7/2004 |
| WO | WO-2004058821 A2 | 7/2004 |
| WO | WO-2004065540 A2 | 8/2004 |
| WO | WO-2004081026 A2 | 9/2004 |
| WO | WO-2004081051 A1 | 9/2004 |
| WO | WO-2004101790 A1 | 11/2004 |
| WO | WO-2004106368 A2 | 12/2004 |
| WO | WO-2005035572 A2 | 4/2005 |
| WO | WO-2005035586 A1 | 4/2005 |
| WO | WO-2005035778 A1 | 4/2005 |
| WO | WO-2005053742 A1 | 6/2005 |
| WO | WO-2005100402 A1 | 10/2005 |
| WO | WO-2006000830 A2 | 1/2006 |
| WO | WO-2006020258 A2 | 2/2006 |

(56) References Cited

FOREIGN PATENT DOCUMENTS

| | | |
|---|---|---|
| WO | WO-2006029879 A2 | 3/2006 |
| WO | WO-2006044908 A2 | 4/2006 |
| WO | WO-2006079372 A1 | 8/2006 |
| WO | WO-2006106905 A1 | 10/2006 |
| WO | WO-2006121168 A1 | 11/2006 |
| WO | WO-2006135886 A2 | 12/2006 |
| WO | WO-2007005874 A2 | 1/2007 |
| WO | WO-2007044887 A2 | 4/2007 |
| WO | WO-2007059782 A1 | 5/2007 |
| WO | WO-2007005874 A3 | 7/2007 |
| WO | WO-2007095338 A2 | 8/2007 |
| WO | WO-2007110205 A2 | 10/2007 |
| WO | WO-2007137760 A2 | 12/2007 |
| WO | WO-2008017859 A2 | 2/2008 |
| WO | WO-2008077546 A1 | 7/2008 |
| WO | WO-2008087219 A1 | 7/2008 |
| WO | WO-2008119353 A1 | 10/2008 |
| WO | WO-2009021754 A2 | 2/2009 |
| WO | WO-2009068630 A1 | 6/2009 |
| WO | WO-2009077993 A2 | 6/2009 |
| WO | WO-2009089004 A1 | 7/2009 |
| WO | WO-2009101611 A1 | 8/2009 |
| WO | WO-2009103538 A1 | 8/2009 |
| WO | WO-2009114335 A2 | 9/2009 |
| WO | WO-2009147137 A1 | 12/2009 |
| WO | WO-2010019570 A2 | 2/2010 |
| WO | WO-2010027797 A1 | 3/2010 |
| WO | WO-2010027827 A2 | 3/2010 |
| WO | WO-2010029513 A2 | 3/2010 |
| WO | WO-2010077634 A1 | 7/2010 |
| WO | WO-2010129304 A2 | 11/2010 |
| WO | WO-2011066342 A2 | 6/2011 |
| WO | WO-2011090762 A1 | 7/2011 |
| WO | WO-2011131746 A2 | 10/2011 |
| WO | WO-2011155607 A1 | 12/2011 |
| WO | WO-2012079000 A1 | 6/2012 |
| WO | WO-2012088309 A1 | 6/2012 |
| WO | WO-2012107417 A1 | 8/2012 |
| WO | WO-2012131555 A2 | 10/2012 |
| WO | WO-2012138475 A1 | 10/2012 |
| WO | WO-2012143498 A1 | 10/2012 |
| WO | WO-2013019615 A2 | 2/2013 |
| WO | WO-2013033626 A2 | 3/2013 |
| WO | WO-2013037484 A2 | 3/2013 |
| WO | WO-2013060867 A2 | 5/2013 |
| WO | WO-2013079174 A1 | 6/2013 |
| WO | WO-2013103912 A1 | 7/2013 |
| WO | WO-2013170168 A1 | 11/2013 |
| WO | WO-2014008218 A1 | 1/2014 |
| WO | WO-2014100823 A1 | 6/2014 |
| WO | WO-2014159940 A1 | 10/2014 |
| WO | WO-2015052230 A1 | 4/2015 |
| WO | WO-2015066379 A2 | 5/2015 |
| WO | WO-2015095811 A2 | 6/2015 |
| WO | WO-2015107015 A1 | 7/2015 |
| WO | WO-2015107025 A1 | 7/2015 |
| WO | WO-2015107026 A1 | 7/2015 |
| WO | WO-2015121383 A1 | 8/2015 |
| WO | WO-2015127158 A1 | 8/2015 |
| WO | WO-2015132598 A1 | 9/2015 |
| WO | WO-2015164815 A1 | 10/2015 |
| WO | WO-2015166073 A1 | 11/2015 |
| WO | WO-2015181805 A1 | 12/2015 |
| WO | WO-2015197582 A1 | 12/2015 |
| WO | WO-2015197593 A1 | 12/2015 |
| WO | WO-2015197598 A2 | 12/2015 |
| WO | WO-2016016299 A1 | 2/2016 |
| WO | WO-2016019969 A1 | 2/2016 |
| WO | WO-2016026943 A1 | 2/2016 |
| WO | WO-2016033555 A1 | 3/2016 |
| WO | WO-2016071376 A2 | 5/2016 |
| WO | WO-2016071377 A1 | 5/2016 |
| WO | WO-2016079081 A1 | 5/2016 |
| WO | WO-2016087416 A1 | 6/2016 |
| WO | WO-2016087514 A1 | 6/2016 |
| WO | WO-2016087650 A1 | 6/2016 |
| WO | WO-2016090327 A2 | 6/2016 |
| WO | WO-2016110468 A1 | 7/2016 |
| WO | WO-2016110584 A1 | 7/2016 |
| WO | WO-2016115274 A1 | 7/2016 |
| WO | WO-2016118641 A1 | 7/2016 |
| WO | WO-2016168149 A1 | 10/2016 |
| WO | WO-2016180969 A1 | 11/2016 |
| WO | WO-2016193301 A1 | 12/2016 |
| WO | WO-2017021349 A1 | 2/2017 |
| WO | WO-2017021450 A1 | 2/2017 |
| WO | WO-2017037634 A1 | 3/2017 |
| WO | WO-2017040930 A2 | 3/2017 |
| WO | WO-2017055391 A1 | 4/2017 |
| WO | WO-2017059551 A1 | 4/2017 |
| WO | WO-2017062604 A1 | 4/2017 |
| WO | WO-2017077382 A1 | 5/2017 |
| WO | WO-2017134140 A1 | 8/2017 |
| WO | WO-2017165464 A1 | 9/2017 |
| WO | WO-2017167919 A1 | 10/2017 |
| WO | WO-2017180913 A2 | 10/2017 |
| WO | WO-2018057955 A1 | 3/2018 |
| WO | WO-2018098365 A2 | 5/2018 |
| WO | WO-2018144777 A2 | 8/2018 |
| WO | WO-2018201047 A1 | 11/2018 |
| WO | WO-2018224844 A1 | 12/2018 |
| WO | WO-2018237192 A1 | 12/2018 |
| WO | WO-2019005641 A1 | 1/2019 |
| WO | WO-2019035938 A1 | 2/2019 |
| WO | WO-2019040700 A1 | 2/2019 |
| WO | WO-2019040780 A1 | 2/2019 |
| WO | WO-2019055677 A1 | 3/2019 |
| WO | WO-2019067805 A1 | 4/2019 |
| WO | WO-2019086865 A1 | 5/2019 |
| WO | WO-2019101695 A1 | 5/2019 |
| WO | WO-2019132738 A1 | 7/2019 |
| WO | WO-2019139987 A1 | 7/2019 |
| WO | WO-2019158764 A1 | 8/2019 |
| WO | WO-2019178362 A1 | 9/2019 |
| WO | WO-2019178364 A2 | 9/2019 |
| WO | WO-2019178364 A3 | 10/2019 |
| WO | WO-2019191519 A1 | 10/2019 |
| WO | WO-2019226617 A1 | 11/2019 |
| WO | WO-2019231920 A1 | 12/2019 |
| WO | WO-2020005819 A1 | 1/2020 |
| WO | WO-2020010250 A2 | 1/2020 |
| WO | WO-2020018708 A1 | 1/2020 |
| WO | WO-2020010250 A3 | 2/2020 |
| WO | WO-2020025928 A1 | 2/2020 |
| WO | WO-2020057646 A1 | 3/2020 |
| WO | WO-2020082048 A1 | 4/2020 |
| WO | WO-2020084290 A1 | 4/2020 |
| WO | WO-2020086758 A1 | 4/2020 |
| WO | WO-2020088459 A1 | 5/2020 |
| WO | WO-2020089644 A1 | 5/2020 |
| WO | WO-2020091635 A2 | 5/2020 |
| WO | WO-2020106708 A1 | 5/2020 |
| WO | WO-2020139171 A1 | 7/2020 |
| WO | WO-2020139175 A2 | 7/2020 |
| WO | WO-2020142672 A2 | 7/2020 |
| WO | WO-2020142672 A3 | 8/2020 |
| WO | WO-2020172571 A1 | 8/2020 |
| WO | WO-2020172596 A1 | 8/2020 |
| WO | WO-2020172598 A1 | 8/2020 |
| WO | WO-2020172601 A1 | 8/2020 |
| WO | WO-2020172605 A1 | 8/2020 |
| WO | WO-2020183245 A2 | 9/2020 |
| WO | WO-2021089704 A1 | 5/2021 |
| WO | WO-2021097325 | 5/2021 |
| WO | WO-2021138407 A2 | 7/2021 |
| WO | WO-2021138474 A2 | 7/2021 |
| WO | WO-2021138474 A3 | 9/2021 |
| WO | WO-2021188454 A1 | 9/2021 |
| WO | WO-2021217085 A1 | 10/2021 |
| WO | WO-2022046920 A2 | 3/2022 |
| WO | WO-2022046922 A2 | 3/2022 |
| WO | WO-2022047046 A1 | 3/2022 |
| WO | WO-2022046920 A3 | 4/2022 |
| WO | WO-2022046922 A3 | 4/2022 |

(56) References Cited

FOREIGN PATENT DOCUMENTS

| | | |
|---|---|---|
| WO | WO-2022216993 A2 | 10/2022 |
| WO | WO-2022216993 A3 | 11/2022 |
| WO | WO-2022240688 A1 | 11/2022 |
| WO | WO-2023081412 A2 | 5/2023 |
| WO | WO-2023122206 A2 | 6/2023 |
| WO | WO-2023141297 A2 | 7/2023 |
| WO | WO-2023081412 A3 | 8/2023 |
| WO | WO-2023122206 A3 | 8/2023 |
| WO | WO-2023141297 A3 | 8/2023 |
| WO | WO-2024081329 A1 | 4/2024 |
| WO | WO-2024081381 A1 | 4/2024 |

OTHER PUBLICATIONS

Knappik et al., J. Mol. Biol., 2000, vol. 296(1):57-86.*
Nair et al., 2002, J. Immunol., vol. 168(5):2371-2382.*
Hongyan, et al., "Fc Engineering for Developing Therapeutic Bispecific Antibodies and Novel Scaffolds" Frontiers In Immunology, (2017) vol. 8.
International Search Report and Written Opinion for PCT Application No. PCT/US2019/022282 issued Jul. 1, 2019.
International Search Report and Written Opinion for corresponding PCT Application No. PCT/US2019/012900 dated Jul. 5, 2019.
PCT/US2020/019324 International Preliminary Report on Patentability dated Aug. 10, 2021.
PCT/US2020/019324 International Search Report and Written Opinion dated Jun. 10, 2020.
Stein, et al., "A new monoclonal antibody (CAL2) detects CALRETICULIN mutations in formalin-fixed and paraffin-embedded bone marrow biopsies," Leukemia, Jul. 23, 2015, vol. 30, No. 1, pp. 131-135.
Ten Hacken, et al., "Calreticulin as a novel B-cell receptor antigen in chronic lymphocytic leukemia," Haematologica, Oct. 31, 2017, vol. 102, No. 10, pp. e394-e396.
Vannucchi, et al., "Calreticulin mutation-specific immunostaining in myeloproliferative neoplasms: pathogenetic insight and diagnostic value" Leukemia (2014) 28, p. 1811-1818.
Vyas et al.: Natural ligands and antibody-based fusion proteins: harnessing the immune system against cancer. Trends Mol Med. 20(2):72-82 (2014).
Adachi, O. et al., "Targeted Disruption of the MyD88 Gene Results in Loss of IL-1-and IL-8-Mediated Function", Immunity, 1998, vol. 9, pp. 143-150.
Agata et al. Expression of the PD-1 antigen on the surface of stimulated mouse T and B lymphocytes. Int. Immunol 8:765-75 (1996).
Agostinis, P. et al, "Photodynamic Therapy of Cancer: An Update", CA Cancer J. Clin, 2011, vol. 61, No. 4, pp. 250-281.
Aigner et al.: An effective tumor vaccine optimized for costimulation via bispecific and trispecific fusion proteins. Int J Oncol. 32(4):777-789 (2008).
Akers, Michael J, et al., Formulation development of protein dosage forms. Pharm Biotechnol 14:47-127 (2002).
Akiyama et al.: TNFalpha induces rapid activation and nuclear translocation of telomerase in human lymphocytes. Biochem Biophys Res Commun. 316(2):528-532 (2004).
"Ala-Aho, R. et al., "Collagenases in cancer", Biochimie, 2005, vol. 87, pp. 273-286".
Al-Aghbar, M.A. et al., "High-affinity ligands can trigger T cell receptor signaling without CD45 segregation," Frontiers in Immunology, 2018;9(713):1-18.
Ali et al.: Modulation of human natural killer cytotoxicity by influenza virus and its subunit protein. Immunology 52(4):687-695 (1984).
Al-Lazikani, B. et al., "Standard Conformations for Canonical Structures of Immunoglobulins", J. Mol. Biol., 1997, vol. 273, pp. 927-948.
Almagro et al. Humanization of antibodies. Front Biosci 13:1619-1633 (2008).

Altschul, et al. Basic Local Alignment Search Tool. Journal of Molecular Biology. vol. 215, Issue No. 3 (1990): 403-410.
Altschul, et al. Gapped BLAST and PSI-BLAST: A New Generation Of Protein Database Search Programs. Nucleic Acids Research. vol. 25, Issue No. 17 (1997): 3389-3402.
Amarante-Mendes GP, Griffith TS. Therapeutic applications of TRAIL receptor agonists in cancer and beyond. Pharmacol Ther. Nov. 2015;155:117-31. Epub Sep. 5, 2015.
Arai, R. et al., "Design of the linkers which effectively separate domains of a bifunctional fusion protein", Protein Engineering, 2001, vol. 14, No. 8, pp. 529-532.
Arenas-Ramirez et al.: Interleukin-2: Biology, Design and Application. Trends in Immunology 36(12):763-777 (2015).
Arnon, T.I. et al., "Recognition of viral hemagglutinins by NKp44 but not by NKp30", Eur J. Immunol., 2001, vol. 31, No. 9, pp. 2680-2689.
Aslan, J.E. et al., "S6K1 and mTOR regulate Rac1-driven platelet activation and aggregation", Blood, 2011, vol. 118, No. 11, pp. 3129-3136.
Sastry, K., et al., "Targeting hepatitis B virus-infected cells with a T-cell receptor-like antibody," J. Virol., 2011, vol. 85, No. 5, pp. 1935-1942.
Aversa, et al., "Molecular T-Cell Repertoire Analysis as Source of Prognostic and Predictive biomarkers for Checkpoint blockade Immunotherapy" International Journal of Molecular Sciences (2020), 21, 2378, p. 1-19.
Baca et al.: Antibody humanization using monovalent phage display. J Biol Chem 272(16):10678-10684 (1997).
Banerjee, et al., 33rd annual Meeting & Pre-Conference Programs of the Society for Immunotherapy of Cancer (SITC) 2018 p. 1-192.
Barbas, C.F. et al., "Assembly of combinatorial antibody libraries on phage surfaces: The gene III site", PNAS, 1991, vol. 88, pp. 7978-7982.
Batzer et al., Enhanced Evolutionary PCR Using Oligonucleotides With Inosine At The 3'-terminus. Nucleic Acids Research 19(18):5081 (1991).
Beidler, C.B. et al., "Cloning and high level expression of a chimeric antibody with specificity for human carcinoembryonic antigen", J. Immuno, 1988, vol. 141, pp. 4053-4060.
Berge, et al., "Selective expansion of a peripheral blood CD8+ memory T cell subset expressing both granzyme B and I-selectin during primary viral infection in renal allograft recipients", Transplantation Proceedings, 1998, vol. 30, pp. 3975-3977.
Better, M. et al., "*Escherichia coli* Secretion of an Active Chimeric Antibody Fragment", Science, 1988, vol. 240, No. 4855, pp. 1041-1043.
Beun, G. et al., "T cell Retargeting Using Bispecific Monoclonal Antibodies in a Rat Colon Carcinoma Model", The Journal of Immunology, 1993, vol. 150, No. 6, pp. 2305-2315.
Bierer, B. et al., "Cyclosporin A and FK506: molecular mechanisms of immunosuppression and probes for transplantation biology", Curr. Opin. Immun., 1993, vol. 5, No. 5, pp. 763-773.
Bird et al., Single-Chain Antigen-binding Proteins. Science 242(4877):423-426 (1988).
Blank et al., Interaction of PD-L1 on Tumor Cells with PD-1 on Tumor-Specific T cells as a Mechanism of Immune Evasion: Implications for Tumor Immunotherapy. Cancer Immunol Immunother 54:307-314 (2005) (Published Online on Dec. 15, 2004).
Bloeman et al. Adhesion molecules: a new target for immunoliposome-mediated drug delivery. FEBS Lett. 357:140 (1995).
Bluemel, C. et al., "Epitope distance to the target cell membrane and antigen size determine the potency of T cell-mediated lysis by BiTE antibodies specific for a large melanoma surface antigen", Cancer Immunology, Immunotherapy, 2010, vol. 59, No. 8, pp. 1197-1209.
Boerner et al. Production of antigen-specific human monoclonal antibodies from in vitro-primed human splenocytes. J Immunol. 147(1):86-95 (Jul. 1, 1991).
Bolt, S. et al., "The generation of a humanized, non-mitogenic CD3 monoclonal antibody which retains in vitro immunosuppressive properties," Eur. J. Immunol., 1993;23:403-411.
Borrebaeck, C. Antibody engineering. Oxford University Press, 1995.

(56) References Cited

OTHER PUBLICATIONS

Breman, E. et al., "Overcoming target driven fratricide for T Cell Therapy," Frontiers in Immunology, 2018;9(2940):1-11.
Brennan et al. Preparation of bispecific antibodies by chemical recombination of monoclonal immunoglobulin G1 fragments. Science 229:81-83, 1985.
Briscoe et al. Delivery of superoxide dismutase to pulmonary epithelium via pH-sensitive liposomes. Am. J. Physiol. 1233:134 (1995).
Brodeur et al.: In: Monoclonal Antibody Production Techniques and Applications. New York: Marcel Dekker:51-63 (1987).
Bruggemann, M. et al., Designer Mice: The Production of Human Antibody Repertoires in Transgenic Animals, Terhorst C. Malavasi F, Albertini A (eds): Generation of Antibodies by Cell and Gene Immortalization, Year Immunol, 1993, vol. 7, pp. 33-40.
Bruggemann, M. et al., "Human antibody production in transgenic mice: expression from 100kb of the human IgH locus", Eur J. Immunol, 1991, vol. 21, pp. 1323-1326.
Buchwald, H. et al., "Long-term, continuous intravenous heparin administration by an implantable infusion pump in ambulatory patients with recurrent venous thrombosis", Surgery, 1980, vol. 88, No. 4, 507-516.
Cadwell, R. C. et al., "Randomization of Genes by PCR Mutagenesis", PCR Methods Appl., 1992, vol. 2, No. 1, pp. 28-33.
Cain, C. et al., "Crossing over to bispecificity", SciBX, 2011, vol. 4, pp. 1-3.
Carter et al.: Humanization of an anti-p185HER2 antibody for human cancer therapy. PNAS USA 89(10):4285-4289 (1992).
Carter et al. PD-1: PD-L inhibitory pathway affects both CD4(+) and CD8(+) T cells and is overcome by IL-2. Eur J Immunol 32:634-643 (2002).
Cazzola, Mario, et al., From Janus kinase 2 to calreticulin: the clinically relevant genomic landscape of myeloproliferative neoplasms. Blood 123(24):3714-3719 (2014).
Chang et al.: A therapeutic T cell receptor mimic antibody targets tumor-associated PRAME peptide/HLA-I antigens. J Clin Invest. 127(7):2705-2718 (2017).
Chao, G. et al., "Isolating and engineering human antibodies using yeast surface display", Nature Protocols, 2006, vol. 1, No. 2, pp. 755-768.
Chari et al.: Immunoconjugates containing novel maytansinoids: promising anticancer drugs. Cancer Res. 52(1):127-131 (1992).
CHARLTON. Chapter 14: Expression and Isolation of Recombinant Antibody Fragments in E. coli. Methods in Molecular Biology 248:245-254 (2003).
Chaudry, et al. EpCAM an immunotherapeutic target for gastrointestinal malignancy: current experience and future challenges. Br J Cancer. Apr. 10, 2007;96(7):1013-9. Epub Feb. 27, 2007.
Chen et al.: Chromosome X-encoded cancer/testis antigens show distinctive expression patterns in developing gonads and in testicular seminoma. Hum Reprod. 26(12):3232-3243 doi:10.1093/humrep/der330 (2011).
Chen et al.: Selection And Analysis Of An Optimized Anti-VEGF Antibody: Crystal Structure Of An Affinity-matured Fab In Complex With Antigen. Journal of Molecular Biology 293(4):865-881 (1999).
Chen et al.: The nuclear localization sequences of the BRCA1 protein interact with the importin-alpha subunit of the nuclear transport signal receptor. J Biol Chem. 271(51):32863-32868 (1996).
Chiang, E. et al., "Abstract 3527: Potent anti-tumor activity of AbGn-100, an anti-CD326 x anti-TCR bispecific antibody to CD326-expressing solid tumors," Cancer Res., 2012;72(8_supplement):3527.
Chichili, V.P.R. et al., "Linkers in the structural biology of protein-protein interactions," Protein Science, 2013;22:153-167.
Chinese Patent Application No. 201780028089.4 2nd Office Action dated Apr. 18, 2022.

"Schmittnaegel, M. et al., "Activation of cytomegalovirus-specific CD8+ T-cell response by antibody-mediated peptide-major histocompatibility class I complexes", OncoImmunology, 2015, vol. 5, No. 1, pp. 1-3".
Chothia, C. et al., "Canonical Structures for the Hypervariable Regions of Immunoglobulins", J. Mol. Biol, 1987, vol. 196, pp. 901-917.
Chothia et al., Structural repertoire of the human VH segments. J Mol Biol 227:799-817 (1992).
Chowdhury. Engineering hot spots for affinity enhancement of antibodies. Methods Mol. Biol. 207:179-196 (2008).
Ciccone, E. et al., "A monoclonal antibody specific for a common determinant of the human T cell receptor gamma/delta directly activates CD3+WT31-lymphocytes to express their functional program(s)," J Exp Med., 1988;168(1):1-11.
Clackson, T. et al., Making antibody fragments using phage display libraries, Nature, 1991, vol. 352, pp. 624-628.
Clynes et al. Fc receptors are required in passive and active immunity to melanoma. PNAS USA 95(2):652-656 (1998).
Colcher, D. et al., "Single-Chain Antibodies in Pancreatic Cancer", Ann Ny Acad Sci, 1999, vol. 880, pp. 263-280.
Coloma, J. et al., "Design and production of novel tetravalent bispecific antibodies", Nature Biotech, 1997, vol. 15, pp. 159-163.
Costa-Mattioli, M. et al., "RAPping production of type I interferon in pDCs through mTOR", 2008, Nature Immunol, vol. 9, No. 10, pp. 1097-1099.
Cragg et al. Antibody specificity controls in vivo effector mechanisms of anti-CD20 reagents. Blood 103(7):2738-2743 (2004).
Cragg et al.: Complement-mediated lysis by anti-CD20 mAb correlates with segregation into lipid rafts. Blood 101(3):1045-1052 (2003).
Cui, et al., "T cell receptor B-chain repertoire analysis of tumor-infiltrating lymphocytes in pancreatic cancer" Cancer Science (2018) 60-71.
Cunningham and Wells, High-resolution epitope mapping of hGH-receptor interactions by alanine-scanning mutagenesis. Science, 244(4908):1081-1085, 1989.
Dall'Acqua, et al.: Antibody humanization by framework shuffling. Methods. 36(1):43-60 (2005).
Dao, T. et al., "Targeting the intracellular WT1 oncogene product with a therapeutic human antibody," Sci Transl Med, 2013, vol. 5, No. 176, pp. 1-22.
Davis, J. et al., "SEEDbodies: fusion proteins based on strand-exchange engineered domain (SEED) CH3 heterodimers in an Fc analogue platform for asymmetric binders or immunofusions and bispecific antibodies", Protein Engineering, Design & Selection, 2010, vol. 23, No. 4, pp. 195-202.
Dela Cruz et al.: Anti-HER2/neu IgG3-(IL-2) and anti-HER2/neu IgG3-(GM-CSF) promote HER2/neu processing and presentation by dendritic cells: Implications in immunotherapy and vaccination strategies. Molecular Immunology 43(6):667-676 (2006).
Dickopf, S. et a., "Formal and geometries matter: Structure-based design defines the functionality of bispecific antibodies", Computational and Structural Biotechnology Journal, 2020, vol. 18, pp. 1221-1227.
Dimasi et al. Development of a trispecific antibody designed to simultaneously and efficiently target three different antigens on tumor cells. Mol Pharm 12(9):3490-3501 (2015).
Dimasi, Nazzareno, et al., The design and characterization of oligospecific antibodies for simultaneous targeting of multiple disease mediators. Journal of molecular biology 393(3):672-692 (2009).
Dong et al., B7-H1 Pathway and its Role in the Evasion of Tumor Immunity. J Mol Med 81:281-287 (Apr. 30, 2003).
Doyle, S. et al., "IRF3 Mediates a TLR3/TLR4-Specific Antiviral Gene Program", Immunity, 2002, vol. 17, pp. 251-263.
Dubowchik, Gene M, et al., Doxorubicin immunoconjugates containing bivalent, lysosomally-cleavable dipeptide linkages. Bioorganic & medicinal chemistry letters 12(11):1529-32 (2002).
Duhen et al., Co-expression of $CD_{39}$ and $CD_{103}$ identifies tumor-reactive CD8 T cells in human solid tumors. Nat Commun. 9(1):2724, pp. 1-13 (2018).
Duncan et al. The binding site for C1q on IgG. Nature 332(6166):738-40 (1988).

(56) References Cited

OTHER PUBLICATIONS

During, M. J. et al., "Controlled release of dopamine from a polymeric brain implant: in vivo characterization", American Neurological Association, 1989, vol. 25, pp. 351-356.
Edwards et al., The Remarkable Flexibility of the Human Antibody Repertoire; Isolation of over One Thousand Different Antibodies to a Single Protein. BLyS. J Mol Biol. 334(1):103-18 (2003).
"Sefton, Michael V., "Implantable Pumps", CRC Crit. Ref. Biomed. Eng., 1987, vol. 14, No. 3, pp. 201-240".
El Achi, H. et al., "CD123 as a Biomarker in Hematolymphoid Malignancies: Principles of Detection and Targeted Therapies," Cancers, 2020;12(11):3087.
Sergeeva, A. et al., "An anti-PR1/HLA-A2 T-cell receptor-like antibody mediates complement-dependent cytotoxicity against acute myeloid leukemia progenitor cells," Blood, 2011, vol. 117, No. 16, pp. 4262-4272.
European Patent Application No. 17 718 441.3 Office Action dated Jan. 24, 2022.
European Search Report issued in EP20736073, dated Aug. 2, 2022.
Falini et al.: Cytoplasmic nucleophosmin in acute myelogenous leukemia with a normal karyotype. N Engl J Med. 352(3):254-266 doi: 10.1056/NEJMoa041974 (2005).
Farrar et al.: The Molecular Cell Biology Of Interferon-gamma And Its Receptor. Annu Rev Immunol 11:571-611 (1993).
Fellouse, et al. Synthetic antibodies from a four-amino-acid code: a dominant role for tyrosine in antigen recognition. Proc Natl Acad Sci U S A. Aug. 24, 2004;101(34):12467-72. Epub Aug. 11, 2004.
"Fernandez-Malave, et al., "An natural anti-T-cell receptor monoclonal antibody protects against experimental autoimmune encephalomyelitis" Journal of Neuroimmunology 234 (2011) 63-70".
Flatman et al., Process analytics for purification of monoclonal antibodies. J. Chromatogr. B 848:79-87 (2007).
Fontana, et al., Probing the partly folded states of proteins by limited proteolysis. Folding & design 2(2):R17-26 (1997).
Freeman et al. Engagement of the PD-1 immunoinhibitory receptor by a novel B7 family member leads to negative regulation of lymphocyte activation. J Exp Med 192:1027-1034 (2000).
Frost, G. et al., "A Microtiter-Based Assay for Hyaluronidase Activity Not Requiring Specialized Reagents", Analytical Biochemistry, 1997, vol. 251, pp. 263-269.
Fuchs, P. et al., "Targeting Recombinant Antibodies to the surface of *Escherichia coli*: Fusion to the Peptidoglycan associated Lipoprotein", Biotechnology (N Y) 1991, vol. 9, No. 12, pp. 1369-1372.
Funayama et al.: Embryonic axis induction by the armadillo repeat domain of beta-catenin: evidence for intracellular signaling. J Cell Biol. 128(5):959-968 (1995).
Gao et al.: Alg14 recruits Alg13 to the cytoplasmic face of the endoplasmic reticulum to form a novel bipartite UDP-N-acetylglucosamine transferase required for the second step of N-linked glycosylation. J Biol Chem. 280(43):36254-36262 doi:10.1074/jbc. M507569200 (2005).
Garland, R.J., et al., "The use of Teflon cell culture bags to expand functionally active CD8+ cytotoxic T lymphocytes", Journal of Immunological Methods, 1999, vol. 227, pp. 53-63.
Garrard, L. et al., "FAB Assembly and Enrichment in a Monovalent Phage Display System", Nat Biotechnol 1991, vol. 9, pp. 1373-1377.
Garrity, D. et al., "The activating NKG2D receptor assembles in the membrane with two signaling dimers into a hexameric structure", Proc Natl Acad Sci USA, 2005, vol. 102, No. 21, pp. 7641-7646.
Gazzano-Santoro, H. et al., A non-radioactive complement-dependent cytotoxicity assay for anti-CD20 monoclonal antibody, Journal of Immunol. Methods, vol. 202, (1996):163-171.
GB Exam Report for GB2109794.4 dated Jun. 21, 2020.
Gerngross. Advances in the production of human therapeutic proteins in yeasts and filamentous fungi. Nat Biotech 22:1409-1414 (2004).
Gillies, S.D. et al., "Bi-functional cytokine fusion proteins for gene therapy and antibody-targeted treatment of cancer," Cancer Immunol Immunotherapy, 2002;51:449-460.

Gjerstorff et al.: GAGE cancer-germline antigens are recruited to the nuclear envelope by germ cell-less (GCL). PLoS One 7(9):e45819:1-12 doi:10.1371/journal.pone.0045819 (2012).
Goel, M. et a., "Plasticity within the Antigen-Combining site may manifest as molecular mimicry in the humoral immune response," J Immunology, 2004; 173(12):7358-7367.
Gohal, G. et al., "T-cell receptor phenotype pattern in atopic children using commercial fluorescently labeled antibodies against 21 human class-specific v segments for the tcrβ chain (vβ) of peripheral blood: a cross sectional study," Allergy Asthma Clin Immunol., 2016;12:10.
Gokden et al.: Diagnostic utility of renal cell carcinoma marker in cytopathology. Appl Immunohistochem Mol Morphol. Abstract Only. 11(2):116-119 doi:10.1097/00129039-200306000-00004 (2003).
Gordon, E.D. et al., "Alternative splicing of interleukin-33 and type 2 inflammation in asthma," PNAS, 2016;113(31):8765-8770.
Graham et al. Characteristics of a human cell line transformed by DNA from human adenovirus type 5. J. Gen Virol. 36:59-74 (1977).
Gram, H. et al., In vitro selection and affinity maturation of antibodies from a naïve combinatorial immunoglobulin library, PNAS, 1992, vol. 89, pp. 3576-3580.
Green, et al., "TCR validation toward gene therapy for cancer" (2019) Methods in Enzymology, vol. 629 chapter 21, p. 419-439.
Green, L.L. et al., "Antigen-specific human monoclonal antibodies from mice engineered with human Ig heavy and light chain YACS", Nature Genet, 1994, vol. 7, pp. 13-21.
Griffiths, A.D. et al., "Human anti-self antibodies with high specificity from phage display libraries", The EMBO Journal, 1993, vol. 12, No. 2, pp. 725-734.
Gruber et al., Efficient tumor cell lysis mediated by a bispecific single chain antibody expressed in *Escherichia coli*. J. Immunol. 152: 5368 (1994).
Gulley, J.L. et al., "New drugs on the horizon," Eur J Cancer, 2022;174(S1):S5.
Gupta, S. et al., "T cell activation via the T cell receptor: a comparison between WT31 (defining alpha/beta TcR)-induced and anti-CD3-induced activation of human T lymphocytes," Cell Immunol., 1991;132(1):26-44.
Gussow et al., Chapter 5: Humanization of Monoclonal Antibodies. Methods in Enzymology. 203:99-121 (1991).
Haanen, J. et al., "Selective Expansion of Cross-reactive CD8+ Memory T Cells by Viral Variants", J. Exp. Med., 1999, vol. 190, No. 9, pp. 1319-1328.
Halin, C. et al., "Synergistic Therapeutic Effects of a Tumor Targeting Antibody Fragment, Fused to Interleukin 12 and to Tumor Necrosis Factor a1," Cancer Research, 2003;63:3202-3210.
Hall, M. et al., "Expansion of tumor-infiltrating lymphocytes (TIL)from human pancreatic tumors", Journal for Immuno Therapy of Cancer, 2016, vol. 4, pp. 1-12.
Hamers-Casterman et al. Naturally occurring antibodies devoid of light chains. Nature 363(6428):446-8 (1993).
Hamid, O. et al., "Safety and Tumor Responses with Lambrolizumab (Anti-PD-1) in Melanoma", The New England Journal of Medicine, 2013, vol. 369, No. 2, pp. 134-144.
Hamming et al. Crystal Structure of Interleukin-21 Receptor (IL-21R) Bound to IL-21 Reveals That Sugar Chain Interacting with WSXWS Motif Is Integral Part of IL-21R. The Journal of Biological Chemistry 287(12):9454-9460 (2012).
Hawkins, R. et al., "Selection of phage antibodies by binding affinity. Mimicking affinity maturation", J. Mol. Biol., 1992, vol. 226, No. 3, pp. 889-896.
Hay, B. et al., "Bacteriophage cloning and *Escherichia coli* expression of a human IgM Fab" Hum Antibodies Hybridomas, 1992, vol. 3, No. 2, pp. 81-85.
"Henderson, D.J. et al., "Comparison of the effects of FK-506, cyclosporin A and rapamycin on IL-2 production", Immunology, 1991, vol. 73, No. 2, pp. 316-321".
Herskovitz, O. et al., "NKp44 receptor mediates interaction of the envelope glycoproteins from the West-Nile and dengue viruses with Natural Killer cells," The Journal of Immunology, 2009;183(4):2610-2621.

(56) References Cited

OTHER PUBLICATIONS

"Shimabukuro-Vornhagen, A. et al., "Cytokine release syndrome", Journal for Immuno Therapy of Cancer, 2018, vol. 6, No. 56, pp. 1-14".
Hinman, et al. Preparation and characterization of monoclonal antibody conjugates of the calicheamicins: a novel and potent family of antitumor antibiotics. Cancer Res. Jul. 15, 1993;53(14):3336-3342.
Hirai et al.: Nucleolar scaffold protein, WDR46, determines the granular compartmental localization of nucleolin and DDX21. Genes Cells 18(9):780-797 (2013).
Shitaoka, et al., "Identification of Tumoricidal TCRs from Tumor-Infiltrating Lymphocytes by Single-Cell Analysis" (2018) Cancer Immunology Research 6(4), p. 378-389.
Hiyama, K. et al., "Crystallization and Some Properties of Chondroitinase from Arthrobacter aurescens", The Journal of Biological Chemistry, 1975, vol. 250, No. 5, pp. 1824-1828.
Hiyama, K. et al., "The mode of Action of Two Chondroitinase-AC Preparations of Different Origin", J. Biochem, 1976, vol. 80, pp. 1201-1207.
Hollinger, P. et al., "Engineered antibody fragments and the rise of single domains," Nature Biotechnology, 2005, vol. 23, No. 9, pp. 1126-1136.
Hollinger, Philipp, et al., "Diabodies": small bivalent and bispecific antibody fragments. Proceedings of the National Academy of Sciences of the United States of America 90:6444-6448 (1993).
Hombach, A.A. et al., "Antibody-IL2 Fusion Proteins for Tumor Targeting," Antibody Engineering, 2012:611-626.
Hoogenboom, et al. By-passing immunisation. Human antibodies from synthetic repertoires of germline VH gene segments rearranged in vitro. J Mol Biol. Sep. 20, 1992;227(2):381-8.
Hoogenboom et al.: Overview of antibody phage-display technology and its applications. In: Methods in Molecular Biology. 178:1-37 (2001).
Hoogenboom, H.R. et al., "Multi-subunit proteins on the surface of filamentous phage: methodologies for displaying antibody (Fab) heavy and light chains", Nuc Acid Res, 1991, vol. 19, No. 15, pp. 4133-4137.
"Howard, M.A. et al., "Intracerebral drug delivery in rats with lesion-induced memory deficits", J. Neurosurg, 1989, vol. 71, pp. 105-112".
"Shpilberg, O. et al., "Subcutaneous administration of rituximab (MabThera) and trastuzumab (Herceptin) using hyaluronidase," British Journal of Cancer, 2013, vol. 109, pp. 1556-1561".
Hudson et al.: Engineered Antibodies. Nature Medicine 9(1):129-134 (2003).
Hudspeth et al.: Natural cytotoxicity receptors: broader expression patterns and functions in innate and adaptive immune cells. Frontiers in Immunology 4(69):1-15 (2013).
Hunig, T. et al., "A monoclonal antibody to a constant determinant of the rat t cell antigen receptor that induces t cell activation", J. Exp. Med., 1989, vol. 169, pp. 73-86.
Huse, W. et al., "Generation of a large combinatorial library of the immunoglobulin repertoire in phage lambda" Science, 1989, vol. 246, No. 4935, pp. 1275-1281.
Huston et al., Protein Engineering Of Antibody Binding Sites: Recovery Of Specific Activity In An Anti-digoxin Single-chain Fv Analogue Produced In *Escherichia Coli.* PNAS USA 85(16):5879-5883 (1988).
Idusogie et al.: Mapping of the C1q binding site on rituxan, a chimeric antibody with a human IgG1 Fc. J Immunol. 164(8):4178-84 (2000).
Imai-Nishiya H. et al., Double knockdown of α1,6-fucosyltransferase (FUT8) and GDP-mannose 4,6-dehydratase (GMD) in antibody-producing cells: a new strategy for generating fully non-fucosylated therapeutic antibodies with enhanced ADCC. BMC Biotechnology 7(84):1-13 (2007).
International Preliminary Report on Patentability issued in PCT/US2017/023483, dated Sep. 25, 2018.

"International Preliminary Report on Patentability issued in PCT/US2018/029951, dated Oct. 29, 2019."
International Preliminary Report on Patentability issued in PCT/US2019/040592, dated Jan. 5, 2021.
International Preliminary Report on Patentability issued in PCT/US2020/012162, dated Jun. 16, 2021.
International Preliminary Report on Patentability issued in PCT/US2020/019291, dated Aug. 10, 2021.
International Preliminary Report on Patentability issued in PCT/US2020/019319, dated Aug. 10, 2021.
International Preliminary Report on Patentability issued in PCT/US2020/019321, dated Aug. 10, 2021.
International Preliminary Report on Patentability issued in PCT/US2020/060557 dated May 17, 2022.
International Preliminary Report on Patentability issued in PCT/US/2020/067543, dated Jul. 5, 2022.
International Preliminary Report on Patentability issued in PCT/US2021/022408, dated Sep. 20, 2022.
International Preliminary Report on Patentability issued in PCT/US2021/028970, dated Oct. 25, 2022.
International Search Report and Written Opinion issued in PCT/US2017/023483, mailed Aug. 29, 2017.
"International Search Report and Written Opinion issued in PCT/US2018/029951, mailed Mar. 7, 2018."
International Search Report and Written Opinion issued in PCT/US2019/040592, mailed Jan. 9, 2020.
International Search Report and Written Opinion issued in PCT/US2020/012162 mailed Jun. 26, 2020.
International Search Report and Written Opinion issued in PCT/US2020/019291, mailed Jun. 15, 2020.
International Search Report and Written Opinion issued in PCT/US2020/019319, mailed Jun. 26, 2020.
International Search Report and Written Opinion issued in PCT/US2020/019321, mailed Aug. 10, 2020.
International Search Report and Written Opinion issued in PCT/US2020/060557, mailed Mar. 30, 2021.
International Search Report and Written Opinion issued in PCT/US2020/067543, mailed Jul. 7, 2021.
International Search Report and Written Opinion issued in PCT/US2021/022408, mailed Aug. 31, 2021.
International Search Report and Written Opinion issued in PCT/US2021/028970 mailed Oct. 4, 2021.
International Search Report and Written Opinion issued in PCT/US2021/047571, dated Feb. 14, 2022.
International Search Report and Written Opinion issued in PCT/US2022/023922, mailed Oct. 17, 2022.
"Islam, et al., "changes in the Peripheral blood T-Cell Receptor VB Repertoire In vivo and In Vitro during Shigellosis" Infection and Immunity (1996),vol. 64, No. 4, p. 1391-1399".
Jameson, Stephen C., "T cell receptor antagonism in vivo, at last", Proc. Natl. Acad. Sci., 1998, vol. 95, pp. 14001-14002.
Jeffrey, Scott C, et al., Dipeptide-based highly potent doxorubicin antibody conjugates. Bioorganic & medicinal chemistry letters 16(2):358-62 (2006).
Jiang, B. et al., "A novel peptide isolated from a phage display peptide library with trastuzumab can mimic antigen epitope of HER-2*," The Journal of Biological Chemistry, 2005;280(6):4656-4662.
Jiang et al.: Nuclear expression of CDK4 correlates with disease progression and poor prognosis in human nasopharyngeal carcinoma. Histopathology 64(5):722-730 doi:10.1111/his.12319 (2013).
Johnsson et al. Comparison of methods for immobilization to carboxymethyl dextran sensor surfaces by analysis of the specific activity of monoclonal antibodies. J. Mol. Recognit. 8:125-131 (1995).
Johnsson et al. Immobilization of proteins to a carboxymethyldextran-modified gold surface for biospecific interaction analysis in surface plasmon resonance sensors. Anal Biochem. 198(2):268-277 (1991).
Jones et al., Replacing The Complementarity-determining Regions In A Human Antibody With Those From A Mouse. Nature 321(6069):522-525 (1986).
Jonsson et al. Introducing a biosensor based technology for real-time biospecific interaction analysis. Ann Biol Clin 51:19-26 (1993).

(56) References Cited

OTHER PUBLICATIONS

Jonsson et al. Real-time biospecific interaction analysis using surface plasmon resonance and a sensor chip technology. Biotechniques 11:620-627 (1991).

Ju et al.: Structure-function analysis of human interleukin-2. Identification of amino acid residues required for biological activity. The Journal of Biological Chemistry 262(12):5723-5731 (1987).

Kabat et al., Sequences of Proteins of Immunological Interest, 5th Ed. Public Health Service, National Institutes of Health, Bethesda, Md. (1991), pp. 647-669.

Kam, Nadine Wong Shi et al. "Carbon nanotubes as multifunctional biological transporters and near-infrared agents for selective cancer cell destruction." Proceedings of the National Academy of Sciences of the United States of America vol. 102,33 (2005): 11600-5. doi:10.1073/pnas.0502680102.

Kanagawa, et al., "In Vivo T Cell Tumor Therapy With Monoclonal Antibody Directed to the VB chain of T Cell Antigen Receptor" J. Exp. Med., vol. 170, (1989) p. 1513-1519.

Kanagawa, et al., "The T Cell Receptor VB6 Domain Imparts Reactivity to the Mls-1a Antigen" Cellular Immunology 119, 412-426 (1989).

Kanda et al. Comparison of cell lines for stable production of fucose-negative antibodies with enhanced ADCC. Biotechnol. Bioeng. 94(4):680-688 (2006).

Karlin et al.: Applications And Statistics For Multiple High-Scoring Segments In Molecular Sequences. PNAS USA 90(12):5873-5877 (1993).

Kashmiri et al.: SDR grafting—a new approach to antibody humanization, Methods vol. 36, No. 1, pp. 25-34 (2005).

Kato et al.: The structure and binding mode of interleukin-18. Nature Structural Biology 10(11):366-971 (2003).

Kato, Y. et al., "Molecular analysis of the pathophysiological binding of the platelet aggregation-inducing factor podoplanin to the C-type lectin-like receptor CLEC-2", Cancer Sci, Jan. 2008, vol. 99, No. 1, pp. 54-61.

"Kawaguchi, M. et al., "Differential activation through the TCR-CD3 complex affects the requirement for costimulation of human T cells", Hum Immunol., 1995, vol. 43, No. 2, pp. 136-148".

Keinanen, K. et al., "Biosynthetic lipid-tagging of antibodies", FEBS Lett., vol. 346, pp. 123, pp. 123-126.

Kellner et al.: Enhancing natural killer cell-mediated lysis of lymphoma cells by combining therapeutic antibodies with CD20-specific immunoligands engaging NKG2D or NKp30. Oncoimmunology 5(1 )e1058459 [1-12] (2016).

Kerkela, E. et al., "Expression of Human Macrophage Metalloelastase (MMP-12) by Tumor Cells in Skin Cancer", Journal of Investigative Dermatology, 2000, vol. 114, No. 6, pp. 1113-1119.

Kiefer, J.D. et al., "Immunocytokines and bispecific antibodies: two complementary strategies for the selective activation of immune cells at the tumor site," Immunol Rev., 2016;270(1):178-192.

Killion, J.J. et al., Systemic targeting of liposome-encapsulated immunomodulators to macrophages for treatment of cancer metastasis, Immunomethods, vol. 4, (1994):273-279.

Kim, E.J. et al., "Interleukin-2 fusion protein with anti-CD3 single-chain Fv (sFv) selectively protects T cells from dexamethasone-induced apoptosis," Vaccine, 2002;20:608-615.

King, H.D. et al., Monoclonal antibody conjugates of doxorubicin prepared with branched peptide linkers: inhibition of aggregation by methaxytriethyleneglycol chains, J Med Chem, vol. 45, (2002): 4336-4343.

Kirkin, et al. Melanoma-associated antigens recognized by cytotoxic T lymphocytes. APMIS. Jul. 1998;106(7):665-79.

Kitaura, K. et al., "A new high-throughput sequencing method for determining diversity and similarity of T cell receptor (TCR) α and β repertoires and identifying potential new invariant TCR α chains," BMC Immunology, 2016, vol. 17, No. 38, pp. 1-16.

Klampfl, T. et al., "Somatic Mutations of Calreticulin in Myeloproliferative Neoplasms", N Engl J Med., 2013, vol. 369, No. 25, pp. 2379-2390.

Klein, C. et al., "Progress in overcoming the chain association issue in bispecific heterodimeric IgG antibodies", mAbs, 2012, vol. 4, No. 6, pp. 653-663.

Klimka et al.: Human anti-CD30 recombinant antibodies by guided phage antibody selection using cell panning. British Journal of Cancer. 83(2):252-260 (2000).

Koch et al.: Activating natural cytotoxicity receptors of natural killer cells in cancer and infection. Trends Immunol. 34(4):182-191 doi:10.1016/j.it.2013.01.003 (2013).

Konishi et al., B7-H1 Expression On Non-Small Cell Lung Cancer Cells And Its Relationship With Tumor-Infiltrating Lymphocytes And Their PD-1 Expression. Clinical Cancer Research 10:5094-5100 (Aug. 1, 2004).

Kostelny et al. Formation of a bispecific antibody by the use of leucine zippers. J. Immunol. 148(5):1547-1553 (1992).

Kozbor et al.: A human hybrid myeloma for production of human monoclonal antibodies. J Immunol. 133(6):3001-3005 (1984).

Kratz, F, et al., Prodrugs of anthracyclines in cancer chemotherapy. Current Medicinal Chemistry 13(5):477-523 (2006).

Kunkel, Thomas A., "Rapid and efficient site-specific mutagenesis without phenotypic selection", Proc Natl Acad Sci, 1985, vol. 82, No. 2, pp. 488-492.

Kushner et al.: Aberrant expression of cyclin A and cyclin B1 proteins in oral carcinoma. J Oral Pathol Med. 28(2):77-81 (1999).

Labrijn, A. et al., "Controlled Fab-arm exchange for the generation of stable bispecific IgG1", Nature Protocols, 2014, vol. 9, No. 10, pp. 2450-2463.

Labrijn, A. et al., "Efficient generation of stable bispecific IgG1 by controlled Fab-arm exchange", PNAS, 2013, vol. 113, No. 13, pp. 5145-5150.

Lain et al.: Accumulating active p53 in the nucleus by inhibition of nuclear export: a novel strategy to promote the p53 tumor suppressor function. Exp Cell Res. 253(2):315-324 (1999).

Langer, Robert, "New Methods of Drug Delivery", Science, 1990, vol. 249, No. 4976, pp. 1527-1533.

Langer, R.S. et al., "Chemical and Physical Structure of Polymers as Carriers for Controlled Release of Bioactive Agents: A Review", J. Macromol. Sci. Rev. Macromol. Chem., 1983, vol. 23, No. 1, pp. 61-126.

"Langer, R.S. et al., "Medical Applications of Controlled Release", 1984, vol. 2, pp. 115-138".

Lanier, L.L. et al., "Distinct epitopes on the t cell antigen receptor of HPB-ALL tumor cells identified by monoclonal antibodies," J Immunol. 1986;137(7):2286-2292.

Latchman et al. PD-L2 is a second ligand for PD-1 and inhibits T cell activation. Nat Immunol 2:261-268 (2001).

Leclercq, G. et al., "Dissecting the mechanism of cytokine release induced by T-cell engagers highlights the contribution of neutrophils," Oncoimmunology, 2022;11(1):e2039432.

Lee, C. M. et al., "Selection of human antibody fragments by phage display", Nat Protoc., 2007, vol. 2, No. 11, pp. 3001-3008.

Lee, et al. Bivalent antibody phage display mimics natural immunoglobulin. J Immunol Methods. Jan. 2004;284(1-2):119-132.

Lee, et al. High-affinity human antibodies from phage-displayed synthetic Fab libraries with a single framework scaffold. J Mol Biol. Jul. 23, 2004;340(5):1073-1093.

Lee, K.D et al., "Construction and characterization of a novel fusion protein consisting of anti-CD3 antibody fused to recombinant interleukin-2," Oncology Reports, 2006;15:1211-1216.

Leonard, E.K. et al., "Engineered cytokine/antibody fusion proteins improve delivery of IL-2 to pro-inflammatory cells and promote antitumor activity," bioRxiv, 2023:1-36.

Leong et al.: Optimized expression and specific activity of IL-12 by directed molecular evolution. Proc. Natl. Acad. Sci. USA; 100(3): 1163-1168 (2003).

Leutkens et al.: Functional autoantibodies against SSX-2 and NY-ESO-1 in multiple myeloma patients after allogeneic stem cell transplantation. Cancer Immunol Immunother. 63(11):1151-1162 (2014).

Levy, R.J. et al., "Inhibition of Calcification of Bioprosthetic Heart Valves by Local Controlled-Release Diphosphonate", Science, 1985, vol. 228, No. 4696, pp. 190-192.

(56) References Cited

OTHER PUBLICATIONS

Li, B. et al., "Landscape of tumor-infiltrating T cell repertoire of human cancers," Nature Genetics, 2016, vol. 48, No. 7, pp. 725-735.
Li, et al. Human antibodies for immunotherapy development generated via a human B cell hybridoma technology. Proc Natl Acad Sci U S A. Mar. 7, 2006;103(10):3557-62. Epub Feb. 27, 2006.
Li et al.: Optimization of humanized IgGs in glycoengineered Pichia pastoris. Nat Biotechnol. 24(2):210-215 (2006).
Li, F. et al., "T cell receptor B-chain-targeting chimeric antigen receptor T cells against T cell malignancies," Nature Communications, 2022;13:4334.
Li, H. et al., "Tumor Microenvironment: The Role of the Tumor Stroma in Cancer", Journal of Cellular Biochemistry, 2007, vol. 101, pp. 805-815.
LI P. et al., "Design and synthesis of paclitaxel conjugated with an ErbB2-recognizing peptide," EC-1, 2007, Biopolymers, vol. 87, No. 4, pp. 225-230.
Liddy et al.: Monoclonal TCR-redirected tumor cell killing. Nat Med. 18(6):980-987 doi:10.1038/nm.2764 (2012).
Lifely, M.R, et al., Glycosylation and biological activity of CAMPATH-1H expressed in different cell lines and grown under different culture conditions.Glycobiology 5(8):813-22 (1995).
Liu, A. et al., "Production of a mouse-human chimeric monoclonal antibody to CD20 with potent Fc-dependent biologic activity", J Immunol, 1987, vol. 139, No. 10, pp. 3521-3526.
Liu, A.Y. et al., "Chimeric mouse-human IgG1 antibody that can mediate lysis of cancer cells", PNAS, 1987, vol. 84, pp. 3439-3443.
Liu, D.V. et al., "Engineered Interleukin-2 Antagonists for the Inhibition of Regulatory T Cells," J. Immunother., 2009;32(9):887-894.
Liu, D.Z. et al., "Synthesis of 2'-paclitaxel 2-glucopyranosyl succinate for specific targeted delivery to cancer cells", Bioorganic & Medicinal Chemistry Letters, 2007, vol. 17, pp. 617-620.
Liu, J. et al., "Calcineurin is a common target of cyclophilin-cyclosporin A and FKBP-FK506 complexes", Cell, 1991, vol. 66, pp. 807-815.
Liu, K. et al., "CD123 and its potential clinical application in leukemias," Life Sciences, 2015;122:59-64.
Lloyd et al., Modelling the Human Immune Response: Performance of a 10" Human Antibody Repertoire Against a Broad Panel of Therapeutically Relevant Antigens. Protein Engineering Design & Selection. 22(3):159-168 (2009).
Lobuglio, A. et al., "Phase I Clinical Trial of CO17-1A Monoclonal Antibody", Hybridomia, 1986, vol. 5, No. 1, pp. S117-S123.
Lode, et al. Targeted therapy with a novel enediyene antibiotic calicheamicin theta(I)1 effectively suppresses growth and dissemination of liver metastases in a syngeneic model of murine neuroblastoma. Cancer Res. Jul. 15, 1998;58(14):2925-2928.
Lonberg et al., Antigen-specific human antibodies from mice comprising four distinct genetic modifications. Nature 368:856-859 (1994).
Lonberg et al., Human antibodies from transgenic animals. Nature Biotechnology 23(9):1117-1125 (2005).
Lonberg, Nils, Fully human antibodies from transgenic mouse and phage display platforms. Current opinion in immunology 20(4):450-459 (2008).
Luo, S. et al., "Worldwide genetic variation of the IGHV and TRBV immune receptor gene families in humans" (2019) Life Sciences Alliance, vol. 2, No. 2, p. 1-9.
Lustgarten, J. et al., "Redirecting Effector T Cells through their IL-2 receptors," J Immunology, 1999;162:359-365.
Maciocia, P. M. et al., "Targeting the T cell receptor β-chain constant region for immunotherapy of T cell malignancies", Nature Medicine, 2017, vol. 23, No. 12, pp. 1416-1423.
Mackay, C.R. et al., "Gamma/delta T cells express a unique surface molecule appearing late during thymic development," Eur J Immunol., 1989;19(8):1477-1483.

Macor, P. et al., "Bispecific antibodies targeting tumor-associated antigens and neutralizing complement regulators increase the efficacy of antibody-based immunotherapy in mice", Leukemia, 2015, vol. 29, pp. 406-414.
Mandelboim, O. et al., "Recognition of hemagglutinins on virus-infected cells by NKp46 activates lysis by human NK cells", Nature, 2001, vol. 409, No. 6823, pp. 1055-1060.
Mao et al.: Inhibition of human natural killer cell activity by influenza virions and hemagglutinin. Journal of Virology 84(9 ):4148-4157 (2010).
Marks, et al. Selection of human antibodies from phage display libraries. In: Methods in Molecular Biology. Lo B., ed. Totowa, N.J.:Human Press. 2003; 248:161-176.
Marks, J.D. et al., Selection of Human antibodies from phage display libraries, J. Mol. Biol., vol. 222, (1992): 581-597.
"Martens, T. et al., "A Novel One-Armed Anti-c-Met Antibody Inhibits Glioblastoma Growth In vivo", Clin Cancer Res, 2006, vol. 12, No. 20, pp. 6144-6152".
Martin, A. et al., "Chapter 3: Protein Sequence and Structure Analysis of Antibody Variable Domains", In: Antibody Engineering Lab Manual (Ed: Duebel, S. and Kontermann, R., Springer-Verlag, Heidelberg), 2010, vol. 2, pp. 33-51.
Martin, F. et al., "The affinity-selection of a minibody polypeptide inhibitor of human interleukin-6", EMBO J., 1994, vol. 13, No. 22, pp. 5303-5309.
McCafferty, et al. Phage antibodies: filamentous phage displaying antibody variable domains. Nature. Dec. 6, 1990;348(6301):552-4.
McConnell, S.J. et al., "Tendamistat as a scaffold for conformationally constrained phage peptide libraries", J Mol Biol, 1995, vol. 250, No. 4, pp. 460-470.
McElroy et al.: Structural and Biophysical Studies of the Human IL-7/IL-7R alpha Complex. Structure 17(1):54-65 (2009).
Merchant, A.M. et al., "An efficient route to human bispecific IgG," Nature Biotechnology, 1998;16(7):677-681.
Meschendoerfer, W. et al., "SPR-based assays enable the full functional analysis of bispecific molecules," Journal of Pharmaceutical and Biomedical Analysis, 2017, vol. 5, No. 132, pp. 141-147.
Meyers, E. et al., "Optimal alignments in linear space", CABIOS, 1988, vol. 4, No. 1, pp. 11-17.
"Michelacci, Y. et al., "A Comparative Study Between a Chondroitinase B and a Chondroitinase AC from *Flavobacterium heparinum*", Biochem J., 1975, vol. 151, pp. 121-129".
Michelacci, Y. et al., "Isolation and Partial Characterization of an Induced Chondroitinase B from *Flavobacterium Heparinum*", Biochemical and Biophysical Research Communications, 1974, vol. 56, No. 4, pp. 973-980.
Miller et al.: Trispecific Killer Engagers (TrikEs) that contain IL-15 to make NK cells antigen specific and to sustain their persistence and expansion. Blood 126(23):232-232 (2015).
Milone, M. C. et al., "Chimeric receptors containing CD137 signal transduction domains mediate enhanced survival of T cells and increased antileukemic efficacy in vivo", Mol. Ther., 2009, vol. 17, No. 8, pp. 1453-1464.
Milstein et al.: Hybrid hybridomas and their use in immunohistochemistry. Nature 305(5934):537-540 (1983).
Mitra, S. et al., "Interleukin-2 Activity can be Fine-Tuned with Engineering Receptor Signaling Clamps," Immunity, 2015;42(5):826-838.
Modak et al.: Disialoganglioside GD2 and a novel tumor antigen: potential targets for immunotherapy of desmoplastic small round cell tumor. Med Pediatr Oncol. 39(6):547-551 (2002).
Moore, G. et al., "A novel bispecific antibody format enables simultaneous bivalent and monovalent co-engagement of distinct target antigens", mAbs, 2011, vol. 3, No. 6, pp. 546-557.
Morel et al.: Processing of some antigens by the standard proteasome but not by the immunoproteasome results in poor presentation by dendritic cells. Immunity. 12(1):107-117 doi:10.1016/s1074-7613(00)80163-6 (2000).
Morris, Glenn E, et al., Epitope Mapping Protocols. Methods in Molecular Biology 66: (1996).
Morrison, Sherie L., "Transfectomas provide novel chimeric antibodies", Science, 1985, vol. 229, No. 4719, pp. 1202-1207.

(56) References Cited

OTHER PUBLICATIONS

Morrison, S.L. et al., "Chimeric human antibody molecules: Mouse antigen-binding domains with human constant region domains", Proc Natl Acad Sci, 1984, vol. 81, pp. 6851-6855.
Murer, P. et al., "Antibody-cytokine fusion proteins: A novel class of biopharmaceuticals for the therapy of cancer and of chronic inflammation", New Biotechnology, 2019, vol. 52, pp. 42-53.
"Murzin, A. G. et al., "SCOP: a structural classification of proteins database for the investigation of sequences and structures," J. Mol. Biol., 1995, vol. 247, pp. 536-540".
Nagarajan et al.: Ligand binding and phagocytosis by CD16 (Fc gamma receptor III) isoforms. Phagocytic signaling by associated zeta and gamma subunits in Chinese hamster ovary cells. Journal of Biological Chemistry J Biol Chem. 270(43):25762-25770 (1995).
Nagy, Attila, et al., Stability of cytotoxic luteinizing hormone-releasing hormone conjugate (AN-152) containing doxorubicin 14-O-hemiglutarate in mouse and human serum in vitro: Implications for the design of preclinical studies. Biological Sciences 97(2): 829-834 (2000).
Naing, et al., "Strategies for improving the management of immune-related adverse events" Journal for ImmunoTherapy of Cancer, (2020) p. 1-9.
Nandi et al.: CD28-mediated costimulation is necessary for optimal proliferation of murine NK cells. J Immunol. 152(7):3361-3369 (1994).
Nangalia, J. et al., "Somatic CALR Mutations in Myeloproliferative Neoplasms with Nonmutated JAK2", N Engl J Med., 2013, vol. 369, No. 25, pp. 2391-2405.
Natsume et al. Engineered Antibodies of IgG1/IgG3 Mixed Isotype With Enhanced Cytotoxic Activities. Cancer Res 68(10):3863-72 (2008).
Needleman et al., A General Method Applicable to the Search for Similarities in the Amino Acid Sequence of Two Proteins. Journal of Molecular Biology 48:444-453 (1970).
Newman et al.: Combining Early Heat Shock Protein Vaccination with Directed IL-2 Leads to Effective Anti-Tumor Immunity in Autologous Hematopoietic Cell Transplantation Recipients. Blood 118(21):998-998 (2011).
Niederberger, N. et al., "Thymocyte stimulation by anti-TCR-b, but not by anti-TCR-a, leads to induction of developmental transcription program," Journal of Leukoeyte Biology, 2005;77(5):830-841.
Nishimura, Y. et al., "Recombinant Human-Mouse Chimeric Monoclonal Antibody Specific for Common Acute Lymphocytic Leukemia Antigen", Canc. Res, 1987, vol. 47, pp. 999-1005.
No Author "PE anti-human TCR VB23 Antibody" (2012).
No Author "PE anti-mouse TCR VB6 Antibody" (2012).
Nolo, R. et al., "Targeting P-selection blocks neuroblastoma growth", Oncotarget, 2017, vol. 8, No. 49, pp. 86657-86670.
Novellino et al.: A listing of human tumor antigens recognized by T cells: Mar. 2004 update. Cancer Immunol Immunother. 54(3):187-207 doi: 10.1007/s00262-004-0560-6 (2005).
"Oh, J. et al., "Single variable domains from the T cell receptor β chain function as mono- and bifunctional CARs and TCRs", Scientific Reports, 2019, vol. 9, No. 1, pp. 1-12".
Ohtsuka et al., An Alternative Approach To Deoxyoligonucleotides As Hybridization Probes By Insertion Of Deoxyinosine At Ambiguous Codon Positions. Journal of Biological Chemistry 260(5):2605-2608 (1985).
Oi, V. et al., "Chimeric Antibodies", BioTechniques, 1986, vol. 4, No. 3, pp. 214-221.
Okazaki et al.: Fucose depletion from human IgG1 oligosaccharide enhances binding enthalpy and association rate between IgG1 and FcgammaRIIIa. J Mol Biol. 336(5):1239-49 (Mar. 5, 2004).
"Ortiz-Sanchez, E. et al., "Antibody-cytokine fusion proteins: applications in cancer therapy," Expert Opin Biol Ther, 2008, vol. 8, No. 5, pp. 609-632".
Osbourn et al.: From rodent reagents to human therapeutics using antibody guided selection. Methods 36(1):61-68 (2005).
Osol et al., eds. Remington's Pharmaceutical Sciences. Easton, PA USA. Mack Publishing Company. 1980. 16th edition.

Owais et al. Chloroquine encapsulated in malaria-infected erythrocyte-specific antibody-bearing liposomes effectively controls chloroquine-resistant Plasmodium berghei infections in mice. Antimicrob. Agents Chemother. 39:180-184 (1995).
Padlan, et al.: A possible procedure for reducing the immunogenicity of antibody variable domains while preserving their ligand-binding properties. Mol Immunol 28(4-5):489-498 (1991).
"Page et al., "Deep Sequencing of T-cell Receptor DNA as a biomarker of Clonally Expanded TILs in Breast Cancer after Immunotherapy" (2016) Cancer Immunolo Res 4: pp. 835-844".
Pardoll, D.M., "The blockade of immune checkpoints in cancer immunotherapy", Nat Rev Cancer, 2012, vol. 12, pp. 252-264.
Park, Y.P. et al., "Complex Regulation of human NKG2D-DAP10 cell surface expression: opposing roles of the γc cytokines and TGF-β1", Blood, 2011, vol. 118, No. 11, pp. 3019-3027.
Pasche, N. et al., "Immunocytokines: a novel class of potent armed antibodies," Drug Discovery Today, 2012;17(11):583-590.
Paul, S. et al., "TCR beta chain-directed bispecific antibodies for the treatment of T-cell cancers," Science Translational Medicine, 2021, pp. 1-21.
Payne, J. et al., "Two Monoclonal Rat Antibodies with Specificity for the β-Chain Variable Region Vβ6 of the Murine T-Cell Receptor", Proc. Natl. Acad. Sci., 1988, vol. 85, pp. 7695-7698.
PCT/US2017/023483 International Search Report and Written Opinion dated Aug. 29, 2017.
PCT/US2019/022284 International Preliminary Report on Patentability dated Sep. 15, 2020.
PCT/US2019/022284 International Search Report and Written Opinion dated Sep. 10, 2019.
Pearson et al. Improved Tools for Biological Sequence Comparison. PNAS USA 85:2444-48 (1988).
Petkova, S.B. et al., Enhanced half-life of genetically engineered human IgG1 antibodies in a humanized FcRn mouse model: potential application in humorally mediated autoimmune disease, International Immunology, vol. 18, 12(2006): 1759-1769.
Pettit et al.: Structure-function studies of interleukin 15 using site-specific mutagenesis, polyethylene glycol conjugation, and homology modeling. J Biol Chem. 272(4):2312-2318 (1997).
"Pilch, et al., "Improved Assessment of T-Cell Receptor (TCR) VB Repertoire in clinical Specimens: Combination of TCR-CDR3 Spectratyping with Flow Cytometry-Based TCR VB Frequency Analysis" (2002) Clinical and Diagnostic Laboratory Immunology, p. 257-266".
Pluckthun, Antibodies from *Escherichia coli*. The Pharmacology of Monoclonal Antibodies 113(11):269-315 (1994).
Posnett, D.N. et al., "Inherited polymorphism of the human T-cell antigen receptor detected by a monoclonal antibody," PNAS, 1986;83:7888-7892.
Presta et al.: Humanization of an antibody directed against IgE. J Immunol 151:2623-2632 (1993).
Presta, et al. Humanization of an anti-vascular endothelial growth factor monoclonal antibody for the therapy of solid tumors and other disorders. Cancer Res. Oct. 15, 1997;57(20):4593-9.
"Presta, Leonard, "Antibody engineering", Curr. Op. Struct. Biol., 1992, vol. 2, No. 4, pp. 593-596".
Provenzano et al.: Enzymatic targeting of the stroma ablates physical barriers to treatment of pancreatic ductal adenocarcinoma. Cancer Cell. 21(3):418-429 doi:10.1016/j.ccr.2012.01.007 (2012).
Qi, et al., "Potent and selective antitumor activity of a T cell-engaging bispecific antibody targeting a membrane-proximal epitope of ROR1," PNAS, 2018;115(24):E5467-E5476.
Queen et al., A humanized antibody that binds to the interleukin 2 receptor. PNAS USA 86:10029-10033 (1989).
Rabia, L. et al., "Understanding and overcoming trade-offs between antibody affinity, specificity, stability and solubility," Biochemical Engineering Journal, 2018;137:365-374.
Rakoff-Nahoum, S. et al., "Toll-like receptors and cancer", Nat Revs Cancer, 2009, vol. 9, pp. 57-63.
Ranade. Drug delivery systems. 1. site-specific drug delivery using liposomes as carriers. J. Clin. Pharmacol. 29:685 (1989).
Rath, et al., "Engineering Strategies to Enhance TCR-Based Adoptive T Cell Therapy" (2020) Cells, 9, 1485, p. 1-34.

(56) References Cited

OTHER PUBLICATIONS

Reiter, Y et al., "Antibody Engineering of Recombinant Fv Immunotoxins for Improved Targeting of Cancer: Disulfide-stabilized Fv Immunotoxins", Clin Cancer Res, 1996, vol. 2, pp. 245-252.
Ridgway, J. et al., Knobs-into holes engineering of antibody CH3 domains for heavy chain heterodimerization, Protein Engineering, 1996, vol. 9, No. 7. pp. 617-621.
"Riechmann, L. et al., "Reshaping human antibodies for therapy", Nature, 1988, vol. 332, No. 24, pp. 323-327".
Riemer, A.B. et al., "Matching of trastuzumab (Herceptin) epitope mimics onto the surface of Her-2/neu—a new method of epitope definition," Molecular Immunology, 2005;42:1121-1124.
Ring et al.: Mechanistic and structural insight into the functional dichotomy between interleukin-2 and interleukin-15. Nat Immunol. 13(12):1187-1195 (2012).
Ripka et al.: Two Chinese hamster ovary glycosylation mutants affected in the conversion of GDP-mannose to GDP-fucose. Arch Biochem Biophys. 249(2):533-545 (Sep. 1986).
Roda-Navarro, P. et al., "Understanding the Spatial Topology of Artificial Immunology Synapses Assembled in T Cell-Redirecting Strategies: A Major Issue in Cancer Immunotherapy", Frontiers in Cell and Developmental Biology, 2020, vol. 7, No. 370.
Rohena-Rivera et al.: IL-15 regulates migration, invasion, angiogenesis and genes associated with lipid metabolism and inflammation in prostate cancer. PloS one 12(4):e0172786:1-27 (2017).
Rosenberg, S. et al., "Use of Tumor-Infiltrating Lymphocytes and Interleukin-2 in the Immunotherapy of Patients with Metastatic Melanoma", New Eng J of Med, 1988, vol. 319, pp. 1676-1680.
Rosok et al.: A Combinatorial Library Strategy for the Rapid Humanization of Anticarcinoma BR96 Fab. J Biol Chem 271:22611-22618 (1996).
Rossolini et al., Use Of Deoxyinosine-containing Primers Vs Degenerate Primers For Polymerase Chain Reaction Based On Ambiguous Sequence Information. Molecular and Cellular Probes 8(2):91-98 (1994).
Rudikoff et al., Single Amino Acid Substitution Altering Antigen-binding Specificity. PNAS USA 79(6):1979-1983 (1982).
"Ruggiero et al., "High-resolution analysis of the human T-cell receptor repertoire" Nature Communication (2014) p. 1-7".
Salameire, et al., "Accurate detection of the tumor clone in peripheral T-cell lymphoma biopsies by flow cytometric analysis of TCR-V B repertoire" Modern Pathology (2012) 25, p. 1246-1257.
Saleh, M.N. et al., "A phase II trial of murine monoclonal antibody 17-1A and interferon-γ: clinical and immunological data", Cancer Immunol Immunother, 1990, vol. 32, pp. 185-190.
Sanchez-Ruiz, J M, et al., Differential scanning calorimetry of the irreversible thermal denaturation of thermolysin. Biochemistry 27(5):1648-1652 (1988).
Sano, Y. et al., "Properties of Blocking and Non-blocking Monoclonal Antibodies Specific for Human Macrophage Galactose-type C-type Lectin (MGL/ClecSF10A/CD301)," J. Biochem., 2007;127-136.
Saudek, C. D. et al.,"A preliminary trial of the programmable implantable medication system for insulin delivery", The New England Journal of Medicine, 1989, vol. 321, No. 9, pp. 574-579.
Saunders. Conceptual Approaches to Modulating Antibody Effector Functions and Circulation Half-Life. Front Immunol 10:1296 (2019).
Schachter, H, et al., Biosynthetic controls that determine the branching and microheterogeneity of protein-bound oligosaccharides. Biochem Cell Biol 64(3):163-181 (1986).
Scheid et al., Sequence and Structural Convergence of Broad and Potent HIV Antibodies that Mimic CD4 Binding, Science 333(6049):1633-1637 (2011).
Schleinitz, N. et al., "Natural killer cells in human autoimmune diseases," Immunology, 2010;131(4):451-458.
Schliemann et al.: Targeting interleukin-2 to the bone marrow stroma for therapy of acute myeloid leukemia relapsing after allogeneic hematopoietic stem cell transplantation. Cancer immunology research 3(5):547-556 (2015).
Schreier, H. et al., "Targeting of Liposomes to Cells Expressing CD4 Using Glycosylphosphatidylinositol-anchored gp120 Influence of Liposome Composition on Intracellular Trafficking", J. Biol. Chem., 1994, vol. 269, No. 12, pp. 9090-9098.
Scodeller, Pablo, "Hyaluronidase and other Extracellular Matrix Degrading Enzymes for Cancer Therapy: New Uses and Nano-Formulations", Journal of Carcinogenesis & Mutagenesis, 2014, vol. 5, No. 4, pp. 1-5.
Seidel, U. et al., "Natural killer cell mediated antibody-dependent cellular cytotoxicity in tumor immunotherapy with therapeutic antibodies", frontiers in Immunology, 2013, vol. 4, No. 76, pp. 1-8.
Sekine, T. et al., "A feasible method for expansion of peripheral blood lymphocytes by culture with immobilized anti-CD3 monoclonal antibody and interleukin-2 for use in adoptive immunotherapy of cancer patients," Biomed & Pharmacother, 1993;47:73-78.
Sen, S. et al., "Expression of epithelial cell adhesion molecule (EpCAM) in oral squamous cell carcinoma," Histopathology, 2015:6:897-904. Abstract only.
Shaw, D. et al., "Mouse/human chimeric antibodies to a tumor-associated antigen: biologic activity of the four human IgG subclasses", Journal of the National Cancer Institute, 1988, vol. 80, No. 19. pp. 1553-1559.
Shi, M. et al., "A recombinant anti-erbB2, scFv-Fc-IL-2 fusion protein retains antigen specificity and cytokine function," Biotechnology letters, 2003;25:815-819.
Shields et al.: High Resolution Mapping of the Binding Site on Human IgG1 for FcγRI, FcγRII, FcγRIII, and FcRn and Design of IgG1 Variants with Improved Binding to the FcγR. J Biol Chem 276(9):6591-6604 (2001).
Sidhu, et al. Phage-displayed antibody libraries of synthetic heavy chain complementarity determining regions. J Mol Biol. Apr. 23, 2004;338(2):299-310.
Sims et al. A humanized CD18 antibody can block function without cell destruction. J Immunol. 151:2296-2308 (1993).
Skegro, D. et al., "Immunoglobulin domain interface exchange as a platform technology for the generation of Fc heterodimers and bispecific antibodies," J Biol Chem, 2017, vol. 292, No. 23, pp. 9745-9759.
Song et al. CD27 costimulation augments the survival and antitumor activity of redirected human T cells in vivo. Blood 119(3):696-706 (2012).
Spiess, C. et al., "Alternative molecular formats and therapeutic applications for bispecific antibodies", Molecular Immunology, 2015, vol. 67, pp. 95-106.
Stauber, D.J. et al., "Crystal structure of the IL-2 signaling complex: Paradigm for a heterotrimeric cytokine receptor," PNAS, 2006;103(8):2788-2793.
Stauber et al.: Nuclear and cytoplasmic survivin: molecular mechanism, prognostic, and therapeutic potential. Cancer Res. 67(13):5999-6002 (2007).
Streltsov, Victor A, et al., Structure of a shark IgNAR antibody variable domain and modeling of an early-developmental isotype. Protein Science 14(11):2901-2909 (2005).
Sun, L.K. et al., "Chimeric antibody with human constant regions and mouse variable regions directed against carcinoma-associated antigen 17-1A", PNAS, 1987, vol. 84, pp. 214-218.
Swencki-Underwood, B. et al., "Engineering human IL-18 with increased bioactivity and bioavailability," Cytokine, 2006, vol. 34, pp. 114-124.
Tang, et al., "Anti-TCR Antibody Treatment Activates a Novel Population of Nonintestinal CD8aa+TCRaB+ Regulatory T Cells and Prevents Experimental Autoimmune Encephalomyelitis" The Journal of Immunology (2007) p. 1-9.
Tang, Yong, et al., Regulation of antibody-dependent cellular cytotoxicity by IgG intrinsic and apparent affinity for target antigen. J Immunol 179(5):2815-2823 (2007).
"Tassev, D. V. et al., "Retargeting NK92 cells using an HLA-A2-restricted, EBNA3C-specific chimeric antigen receptor," Cancer Gene Ther, 2012, vol. 19, No. 2, pp. 84-100".
Thorpe, P. E., "Vascular Targeting Agents as Cancer Therapeutics", Clinc Cancer Res, 2004, vol. 10, pp. 415-427.

(56) References Cited

OTHER PUBLICATIONS

"Stivala, A. et al., "Automatic generation of protein structure cartoons with Pro-origami," Bioinformatics, 2011, vol. 27, No. 23, pp. 3315-3316".
Tomlinson, I. et al., "The repertoire of human germline vH sequences reveals about fifty groups of VH segments with different hypervariable loops", Journal of Molecular Biology, 1992, vol. 227, No. 3, pp. 776-798.
Tomonari, K. et al., "Epitope-specific binding of CD8 regulates activation of T cells and induction of cytotoxicity," International Immunology, 1990;2(12):1189-1194.
Torgov, Michael Y, et al., Generation of an intensely potent anthracycline by a monoclonal antibody-beta-galactosidase conjugate. Bioconjugate Chem 16(3):717-721 (2005).
Tramontano et al.: The making of the minibody: an engineered beta-protein for the display of conformationally constrained peptides. J. Mol. Recognition. 7:9-24 (1994).
Traunecker et al., Bispecific Single Chain Molecules (Janusins) Target Cytotoxic Lymphocytes On HIV Infected Cells. The EMBO Journal 10(12):3655-3659 (1991).
Trenevska et al.: Therapeutic Antibodies against Intracellular Tumor Antigens. Front Immunol. 8:1001 doi:10.3389/fimmu.2017.01001 [1-12] (2017).
Tsytsikov, V.N. et al., "Identification and Characterization of Two Alternative Splice Variants of Human Interleukin-2*" The Journal of Biological Chemistry, 1996;71(38):23055-23060.
Tuaillon, N. et al., "Human immunoglobulin heavy-chain minilocus recombination in transgenic mice: Gene-segment use in μ and γ transcripts," PNAS, 1993, vol. 90, pp. 3720-3724.
Tutt et al. Trispecific F(ab')3 derivatives that use cooperative signaling via the TCR/CD3 complex and CD2 to activate and redirect resting cytotoxic T cells. J Immunol. 147(1):60-69 (Jul. 1, 1991).
Umezawa et al. Liposome targeting to mouse brain: mannose as a recognition marker. Biochem. Biophys. Res. Commun. 153:1038 (1988).
U.S. Appl. No. 17/529,017 Non-Final Office Action dated Apr. 27, 2022.
U.S. Appl. No. 16/980,730 Office Action dated Feb. 12, 2024.
Suzuki, S. et al., "Formation of Three Types of Disulfated Disaccharides from Chondroitin Sulfates by Chondroitinase Digestion", The Journal of Biological Chemistry, 1968, vol. 243, No. 7, pp. 1543-1550.
Vallera et al.: Heterodimeric bispecific single-chain variable-fragment antibodies against EpCAM and CD16 induce effective antibody-dependent cellular cytotoxicity against human carcinoma cells. Cancer Biother Radiopharm. 28(4):274-282 doi:10.1089/cbr.2012.1329 (2013).
Van Dijk et al. Human antibodies as next generation therapeutics. Curr Opin Chem Biol. 5(4):368-74 (Aug. 2001).
Van Mierlo, C P, et al., Protein folding and stability investigated by fluorescence, circular dichroism (CD), and nuclear magnetic resonance (NMR) spectroscopy: the flavodoxin story. Journal of Biotechnology 79(3):281-298 (2000).
Verhoeyen, M. et al., "Reshaping Human Antibodies: Grafting an Antilysozyme Activity", Science, 1988, vol. 239, pp. 1534-1536.
Verma, B. et al., "TCR Mimic Monoclonal Antibody Targets a Specific Peptide/HLA Class I Complex and Significantly Impedes Tumor Growth In Vivo Using Breast Cancer Models," J Immunol, 2010, vol. 184, No. 4, pp. 2156-2165.
Verwilghen, J. et al., "Differences in the stimulating capacity of immobilized anti-CD3 monoclonal antibodies: variable dependence on interleukin-1 as a helper signal for T-cell activation," Immunology 72:269-276 (1991).
Vitetta et al. Redesigning nature's poisons to create anti-tumor reagents. Science 238(4830):1098-1104 (1987).
Vollmers, et al. Death by stress: natural IgM-induced apoptosis. Methods Find Exp Clin Pharmacol. Apr. 2005;27(3):185-91.
Vollmers et al.: The "early birds": natural IgM antibodies and immune surveillance. Histol Histopathol. 20(3):927-937 (2005).

"Vonderheid, et al., "Evidence for Restricted VB Usage in the Leukemic Phase of Cutaneous T Cell Lymphoma" (2015) The Society for Investigative Dermatology, Inc. p. 650-661".
Vyas, M. et al., "Natural ligands and antibody-based fusion proteins: harnessing the immune system against cancer", Trends in Molecular Medicine, 2014, vol. 20, No. 2, pp. 72-82.
Wadia, P. et al., "Impaired lymphocyte responses and their restoration in oral cancer patients expressing distinct TCR variable region," Cancer Investigation, 2008;26:471-480.
Wagner, E.K. et al., "Engineering therapeutics antibodies to combat infectious disease," Current Opinion in Chemical Engineering, 2018:19;131-141.
Wan, Y.Y. et al., "'Yin-Yang' functions of TGF-b and tregs in immune regulation," Immunol Rev., 2007;220:199-213.
Wang, C.Y. et al., "αβ T-cell receptor bias in disease and therapy (Review)", International Journal of Oncology, 2016, vol. 48, pp. 2247-2256.
Wang et al., Cloning genes encoding MHC class II-restricted antigens: mutated CDC27 as a tumor antigen. Science 284(5418):1351-1354 doi:10.1126/science.284.5418.1351 (1999).
Wang et al., RNA interference targeting CML66, a novel tumor antigen, inhibits proliferation, invasion and metastasis of Hela cells. Cancer Lett. 269(1):127-138 (2008).
Wang, H. et al., "Preparation and functional identification of a monoclonal antibody against the recombinant soluble human NKp30 receptor," Internal Immunopharmacology, 2011;11(11):1732-1739.
Warren, H.S. et al., "Evidence that the cellular ligand for the Human NK Cell Activation Receptor NKp30 is not a Heparan Sulfate Glycosaminoglycan," The Journal of Immunology, 2005;175(1):207-212.
Watanabe, M, et al., Interleukin-21 can efficiently restore impaired antibody-dependent cell-mediated cytotoxicity in patients with oesophageal squamous cell carcinoma. British Journal of Cancer 102(3):520-529 (2010).
Wei, S. et al., "Identification of a novel human T-cell receptor Vβ subfamily by genomic cloning", Human Immunology, 1994, vol. 41, No. 3, pp. 201-206.
Weidle, U. et al., "The Intriguing Options of Multispecific Antibody Formats for Treatment of Cancer", Cancer Genomics & Proteomics, 2013, vol. 1, pp. 1-18.
Weidle, U.H. et al., "Tumor-Antigen-Binding Bispecific Antibodies for Cancer Treatment", Seminars in Oncology, 2014, vol. 41, No. 5, pp. 653-660.
Willemsen, R A, et al., Grafting primary human T lymphocytes with cancer-specific chimeric single chain and two chain TCR. Gene Therapy 7(16):1369-1377 (2000).
"Williemsen, R. A. et al., "A phage display selected Fab fragment with MHC class I-restricted specificity for MAGE-A1 allows for retargeting of primary human T lymphocytes," Gene Therapy, 2001, vol. 8, No. 21, pp. 1601-1608".
Winkler, et al., Changing the Antigen Binding Specificity by Single Point Mutations of an Anti-p24 (HIV-1)Antibody. The Journal of Immunology. 165(8):4505-4514 (2000).
Winter et al.: Making antibodies by phage display technology. Annu Rev Immunol. 12:433-55 (1994).
Wood, C. R. et al., "The synthesis and in vivo assembly of functional antibodies in yeast", Nature Publishing Group, 1985, vol. 314, No. 4, pp. 446-449.
Wright et al. Effect of glycosylation on antibody function: implications for genetic engineering. TIBTECH 15:26-32 (1997).
Wu, M.R. et al., "B7H6-Specific Bispecific T Cell Engagers Lead to Tumor Elimination and Host Antitumor Immunity", The Journal of Immunology, 2015, vol. 194, No. 11, pp. 5305-5311.
Wurzer et al.: Nuclear Ras: unexpected subcellular distribution of oncogenic forms.J Cell Biochem Suppl. Suppl 36:1-11 doi:10.1002/jcb.1070 (2001).
Xiao, Y.F. et al., "Peptide-based treatment: A promising cancer therapy", Journal of Immunology Research, 2015, pp. 1-14.
Xiaoying, C. et al., "Fusion protein linkers: Property, design and functionality", Advanced Drug Delivery Reviews, 2012, vol. 65, No. 10, pp. 1357-1369.

(56) References Cited

OTHER PUBLICATIONS

Xu, X. et al., "Cytokine release syndrome in cancer immunotherapy with chimeric antigen receptor engineered T cells", Cancer Letters, 2014, vol. 343, No. 2, pp. 172-178.
Yamagata, T. et al., "Purification and Properties of Bacterial Chondroitinases and Chondrosulfatases", The Journal of Biological Chemistry, 1968, vol. 243, No. 7, pp. 1523-1535.
Yamane-Ohnuki, et al. "Establishment of FUT8 knockout Chinese hamster ovary cells: An ideal host cell line for producing completely defucosylated antibodies with enhanced antibody-dependent cellular cytotoxicity." Biotech. Bioeng. 87:614-622 (2004).
Yassai, M. et al., "A clonotype nomenclature for T cell receptors", Immunogenetics, 2009, vol. 61, pp. 493-502.
Yazaki and Wu, "Expression of Recombinant Antibodies in Mammalian Cell Lines", Methods in Molecular Biology, vol. 248, pp. 255-268, 2003.
Yoon et al.: Charged residues dominate a unique interlocking topography in the heterodimeric cytokine interleukin-12. The EMBO J. 19(14):3530-3541 (2000).
Yoon, S.T. et al., "Both high and low avidity antibodies to the T cell receptor can have agonist or antagonist activity," Immunity, 1994;1(7):563-569.
Zhang, T. et al., "Cancer Immunotherapy Using a Bispecific NK Receptor Fusion Protein that Engages both T Cells and Tumor Cells", Cancer Research, 2011, vol. 71, No. 6, pp. 2066-2076.
Zhang, Tong, et al., Transgenic TCR expression: comparison of single chain with full-length receptor constructs for T-cell function. Cancer Gene Therapy 11(7):487-496 (2004).
Aggen, D.H. et al., Single-chain V$\alpha$V$\beta$ T-cell receptors function without mispairing with endogenous TCR chains, Gene therapy, vol. 19, 4 (2012): 365-74.
Walker, L.M. et al., Broad neutralization coverage of HIV by multiple highly potent antibodies, Nature, vol. 477, 7365 (2011): 466-70.
McLellan, J.S et al., Structure of HIV-1 gp120 V1/V2 domain with broadly neutralizing antibody PG9, Nature, vol. 480, 7377 (2011): 336-43.
Walker, L.M. et al., Broad and potent neutralizing antibodies from an African donor reveal a new HIV-1 vaccine target, Science, vol. 326, 5950 (2009): 285-9.
Pejchal, R. et al., A potent and broad neutralizing antibody recognizes and penetrates the HIV glycan shield, Science, vol. 334, 6059 (2011): 1097-10.
Diskin, R. et al., Increasing the potency and breadth of an HIV antibody by using structure-based rational design, Science, vol. 334, 6060 (2011): 1289-9.
Akers, Michael J., et al. Peptides and proteins as parenteral solutions. Pharmaceutical formulation development of peptides and proteins. London: Taylor & Francis. pp. 145-177.(2000).
Allison, A C. The Mode of Action of Immunological Adjuvants. Developments in Biological Standardization 92:3-11 (1998).
Anderson, et al. Anti-CD3 + IL-2-stimulated murine killer cells. In vitro generation and in vivo antitumor activity. J Immunol 142 (4): 1383-1394 (1989).
Baxter, et al. Acquired mutation of the tyrosine kinase JAK2 in human myeloproliferative disorders. The Lancet. 2005. 365(9464):1054-1061.
Benati, Daniela et al. Public T Cell Receptors Confer High-avidity CD4 Responses to HIV Controllers. Journal of Clinical Investigation 126(6):2093-2108 (2016).
BENDIG. Humanization of rodent monoclonal antibodies by CDR grafting. Methods: A Companion to Methods in Enzymology 8:83-93 (1995).
Berge, Stephen M. et al. Pharmaceutical Salts. Journal of Pharmaceutical Sciences 66(1):1-19 (1977).
Biomunex Pharmaceuticals, "Disruptive biological approaches in immunotherapy, based on next generation BiXAb® bi-and multispecific antibody platform for cancer treatment," Mar. 2023 [PowerPoint Slides].

Bonsignori et al. Maturation Pathway from Germline to Broad HIV-1 Neutralizer of a CD4-Mimic Antibody. Cell 165(2):449-463 (2016).
Bovay, Amandine et al. T Cell Receptor Alpha Variable 12-2 Bias in the Immunodominant Response to Yellow Fever Virus. European Journal of Immunology 48(2):258-272 (2018).
Brennan, Rebekah M. et al. Predictable Alphabeta T-cell Receptor Selection Toward an HLA-B*3501-restricted Human Cytomegalovirus Epitope. Journal of Virology 81(13):7269-7273 (2007).
Brey, et al. A GB/CD3 bispecific BiTE antibody construct for targeting Human Cytomegalovirus-infected cells. Sci Rep 28;8(1):17453 (2018). 12 pages.
Buckland, et al. Fusion glycoprotein of measles virus: nucleotide sequence of the gene and comparison with other paramyxoviruses. Journal of General Virology 68(6):1695-1703 (1987).
Bulek, Anna M. et al. Structural Basis of Human $\beta$-cell Killing by CD8+ T cells in Type 1 Diabetes. Nature Immunology 13(3):283-289 (2012).
Caldas, Cristina et al. Humanization of the anti-CD18 antibody 6.7: an unexpected effect of a framework residue in binding to antigen. Molecular immunology 39(15):941-952 (2003).
Campbell, Peter J. The long-term outlook for essential thrombocythemia. Mayo Clin Proc 81(2):157-8 (2006).
Campbell, Peter J. The myeloproliferative disorders. N Engl J Med 355(23):2452-66 (2006).
Campisi, Laura et al. Clonally Expanded CD8 T Cells Characterize Amyotrophic Lateral Sclerosis-4. Nature 606(7916):945-952 (2022).
Carnero Contentti, Edgar, et al. Mucosal-Associated Invariant T Cell Features and TCR Repertoire Characteristics During the Course of Multiple Sclerosis. Frontiers in Immunology 10:1-17 (2019).
Chancellor, A. et al., "CD1b-restricted GEM T cell responses are modulated by *Mycobacterium tuberculosis* mycolic acid meromycolate chains," PNAS, 2017;114(51):E10956-E10964.
Chang, et al. Opportunities and challenges for TCR mimic antibodies in cancer therapy. Expert Opinion on Biological Therapy 16(8):979-987 (2016).
Chen, Lan et al. The T Cell Repertoires from Nickel Sensitized Joint Implant Failure Patients. International Journal of Molecular Sciences 22(5):2428, 1-13 (2021).
Cho, Bryan K. et al. Single-Chain Fv/Folate Conjugates Mediate Efficient Lysis of Folate-Receptor-Positive Tumor Cells. Bioconjugate Chemistry 8(3):338-346 (1997).
Choi, Yangwon et al. A method for production of antibodies to human T-cell receptor beta-chain variable regions. Proc Natl Acad Sci USA 88(19):8357-8361 (1991).
Clackson, Tim. et al. Making Antibody Fragments using Phage Display Libraries. Nature 352(6336):624-628 (1991).
ClinicalTrials.gov Identifier: NCT00001846. Collection and Distribution of Blood Components From Healthy Donors for In Vitro Research Use, Record created Nov. 3, 1999. pp. 1-10. [retrieved on Aug. 22, 2024] Available at URL: https://clinicaltrials.gov/study/NCT00001846.
ClinicalTrials.gov Identifier: NCT01004822. A Safety, Tolerability, And Pharmacokinetic Trial With CVX-241 In Patients With Advanced Solid Tumors, Record created Oct. 28, 2009. pp. 1-17. [retrieved on Jul. 12, 2024] Available at URL: https://clinicaltrials.gov/study/NCT01004822?cond=NCT01004822&rank=1.
ClinicalTrials.gov Identifier: NCT03427411. M7824 in Subjects With HPV Associated Malignancies, Record created Feb. 8, 2018. pp. 1-19. [retrieved on Aug. 22, 2024] Available at URL: https://clinicaltrials.gov/study/NCT03427411?term=NCT03427411&rank=1.
Cole, David K. et al. Germ Line-governed Recognition of a Cancer Epitope by an Immunodominant Human T-cell Receptor. Journal of Biological Chemistry 284(40):27281-27289 (2009).
Connolly, James L. et al. Tumor Structure and Tumor Stroma Generation. 6th Edition. Holland-Frei Cancer Medicine :1-5 (2003).
Consonni, M. et al., "Human T cells engineered with a leukemia lipid-specific TCR enables donor-unrestricted recognition of CD1c-expressing leukemia," Nat Commun., 2021;12(1):4844.
Co-pending U.S. Appl. No. 18/286,062, inventors Andreas; Loew et al., filed Oct. 6, 2023.

(56) References Cited

OTHER PUBLICATIONS

Co-pending U.S. Appl. No. 18/654,860, inventors Hayday; Adrian et al., filed May 3, 2024.
Co-pending U.S. Appl. No. 18/659,544, inventors Andreas; Loew et al., filed May 9, 2024.
Co-pending U.S. Appl. No. 18/749,969, inventors Hsu; Jonathan et al., filed Jun. 21, 2024.
Co-pending U.S. Appl. No. 18/779,692, inventor Andreas; Loew, filed Jul. 22, 2024.
Crowther, Michael D. et al. Genome-wide CRISPR-Cas9 Screening Reveals Ubiquitous T Cell Cancer Targeting via the Monomorphic MHC Class I-related Protein MR1. Nature Immunology 21(2):178-185 (2020).
Dahal-Koirala, S. et al. TCR Sequencing of Single Cells Reactive to DQ2.5-glia-α2 and DQ2.5-glia-ω2 Reveals Clonal Expansion and Epitope-specific V-gene Usage. 9(3):587-596 (2016).
Deak, Laura Codarri, et al., PD-1-cis IL-2R Agonism Yields Better Effectors from Stem-like CD8+ T Cells. Nature 610(7930):161-172 (2022).
Delhommeau, François et al. Mutation in TET2 in Myeloid Cancers. N Engl J Med 360(22):2289-2301 (2009).
Draghi, et al. P530 Novel bispecific antibody targeting NKp30 receptor enhances NK-mediated killing activity against multiple myeloma cells and overcomes CD16A deficiency. Abstract. In Meeting Abstracts: 33rd Annual Meeting & Pre-Conference Programs of the Society for Immunotherapy of Cancer (STIC 2018). 8 pages.
Du, Jiamu. et al. Molecular basis of recognition of human osteopontin by 23C3, a potential therapeutic antibody for treatment of rheumatoid arthritis. Journal of molecular biology 382(4):835-842 (2008).
Dupuis, Marc. et al. Dendritic Cells Internalize Vaccine Adjuvant After Intramuscular Injection. Cell Immunology 186(1):18-27 (1998).
Ernst, et al. Inactivating mutations of the histone methyltransferase gene EZH2 in myeloid disorders. Nat Genet 42(8):722-6 (2010).
Fernandez-Sesma, Ana. et al. A bispecific antibody recognizing influenza A virus M2 protein redirects effector cells to inhibit virus replication in vitro. Journal of virology 70(7):4800-4804 (1996).
Ferrari De Andrade, et al. Natural killer cells are essential for the ability of BRAF inhibitors to control BRAFV600E-mutant metastatic melanoma. Cancer research 74(24):7298-7308 (2014).
Fix, J A. et al. Oral Controlled Release Technology for Peptides: Status and Future Prospects. Pharmaceutical research 13(12):1760-1764 (1996).
Foley, Kendra C. et al. Combination immunotherapies implementing adoptive T-cell transfer for advanced-stage melanoma. Melanoma research 28(3):171-184 (2018).
Frick, Rahel. et al. A TRAV26-1-encoded Recognition Motif Focuses the Biased T Cell Response in Celiac Disease. European Journal of Immunology 50(1):142-145 (2020).
Gabrilovich, D I. et al. IL-12 And Mutant P53 Peptide-Pulsed Dendritic Cells For The Specific Immunotherapy Of Cancer. Journal of Immunotherapy with Emphasis on Tumor Immunology 19(6):414-418 (1996).
Gacerez, Albert T. et al. How Chimeric Antigen Receptor Design Affects Adoptive T Cell Therapy. Journal of cellular physiology 231(12):2590-2598 (2016).
Galvin, Teresa A. Effect of different promoters on immune responses elicited by HIV-1 gag/env multigenic DNA vaccine in Macaca mulatta and Macaca nemestrina. Vaccine 18(23):2566-2583 (2000).
Gamvrellis, Anita. et al. Vaccines That Facilitate Antigen Entry Into Dendritic Cells. Immunology & Cell Biology 82(5):506-516 (2004).
Gedda, Mallikarjuna R. et al. Longitudinal transcriptional analysis of peripheral blood leukocytes in COVID-19 convalescent donors. J Transl Med 20(1):587, 1-16 (2022).
Geissinger, E. et al., "Identification of the Tumor Cells in Peripheral T-Cell Lymphomas by Combined Polymerase Chain Reaction-Based T-Cell Receptor [3 Spectrotyping and Immunohistological Detection with T-Cell Receptor [3 Chain Variable Region Segment-Specific Antibodies," J. of Mol Diag., 2005;7(4):455-464.

GenBank Accession No. 2ERJ_D. Version 2ERJ_D. Chain D, Interleukin-2. Record created Mar. 21, 2006. 2 pages. Retrieved Jul. 15, 2024 at URL: https://www.ncbi.nlm.nih.gov/protein/90109213.
GenBank Accession No. AAA62478.2. Version No. AAA62478.2. induced by lymphocyte activation; similar to Human receptor protein encoded by GenBank Accession No. U03397 [*Homo sapiens*]. Record created Jun. 12, 1993. 2 Pages. Retrieved Aug. 1, 2024 at URL: https://www.ncbi.nlm.nih.gov/protein/AAA62478.
GenBank Accession No. AAH66254. Version No. AAH66254.1. Interleukin 2 [*Homo sapiens*]. Record created Feb. 12, 2004. 2 Pages. Retrieved Jul. 12, 2024 at URL: https://www.ncbi.nlm.nih.gov/protein/AAH66254.
GenBank Accession No. BAG36664. Version No. BAG36664.1. unnamed protein product [*Homo sapiens*]. Record created May 23, 2008. 2 Pages. Retrieved Aug. 1, 2024 at URL: https://www.ncbi.nlm.nih.gov/protein/BAG36664.
GenBank Accession No. NM_005191. Version No. NM_005191.4. *Homo sapiens* CD80 Molecule (CD80), mRNA. Record created May 24, 1999. Retrieved Aug. 2, 2024. Retrieved from: https://www.ncbi.nlm.nih.gov/nuccore/NM_005191.
GenBank Accession No. NP002174. Version No. NP_002174.1. interleukin-3 receptor subunit alpha isoform 1 precursor [*Homo sapiens*]. Record created Mar. 14, 2021. 3 Pages. Retrieved Aug. 1, 2024 at URL: https://www.ncbi.nlm.nih.gov/protein/NP_002174.
Giaccone, Giuseppe. et al. A phase I study of the natural killer T-cell ligand alpha-galactosylceramide (KRN7000) in patients with solid tumors. Clinical cancer research 8(12):3702-3709 (2002).
Godfrey, Dale I. et al. The Burgeoning Family of Unconventional T Cells. Nature Immunology 16(11):1114-1123 (2015).
Harutyunyan, et al. p53 lesions in leukemic transformation. N Engl J Med 364(5):488-90 (2011).
Harutyunyan, et al. Rare germline variants in regions of loss of heterozygosity may influence clinical course of hematological malignancies. Leukemia 25(11):1782-4 (2011).
Hashimoto, M, et al., PD-1 Combination Therapy with IL-2 Modifies CD8+ T Cell Exhaustion Program. Nature 610(7930):173-181 (2022).
He, X.Y. et al. TRAV gene expression in PBMCs and TILs in patients with breast cancer analyzed by a DNA melting curve (FQ-PCR) technique for TCR α chain CDR3 spectratyping. Neoplasma 59(6):693-699 (2012).
Helliwell, P S, and W J Taylor. Classification and Diagnostic Criteria for Psoriatic Arthritis. Annals of the Rheumatic Diseases 64(Suppl 2):ii3-ii8 (2005).
Hinks, Timothy S. C. and Xia-Wei Zhang. MAIT Cell Activation and Functions. Frontiers in Immunology 11:1014, 1-10 (2020).
Holmström, M O. et al. The calreticulin (CALR) exon 9 mutations are promising targets for cancer immune therapy. Leukemia 32(2):429-437 (2018).
Holmström, Morten Orebo, and Hans Carl Hasselbalch. Cancer immune therapy for myeloid malignancies: present and future. Seminars in Immunopathology 41(1):97-109 (2019).
Hong, Sung Noh et al. Reduced diversity of intestinal T-cell receptor repertoire in patients with Crohn's disease. Frontiers in Cellular and Infection Microbiology 12:1-12 (2022).
Horna, Pedro et al. Utility of TRBC1 expression in the diagnosis of peripheral blood involvement by cutaneous T-cell lymphoma. Journal of Investigative Dermatology 141(4):821-829.e2 (2021).
Howson, Lauren J. et al. MAIT cell clonal expansion and TCR repertoire shaping in human volunteers challenged with Salmonella Paratyphi A. Nat Commun 9(1):253, 1-11 (2018).
Hsu, Jonathan. et al. AT cell receptor β chain-directed antibody fusion molecule activates and expands subsets of T cells to promote antitumor activity. Science translational medicine 15(724):eadi0258, 1-18 (2023).
Hsu, Jonathan. et al. Supplementary Materials for: A T Cell Receptor β Chain-directed Antibody Fusion Molecule Activates and Expands Subsets of T Cells to Promote Antitumor Activity. Science Translational Medicine 15(724):eadi0258, 1-39 (2023).
Huang, Huang. et al. Select sequencing of clonally expanded CD8+ T cells reveals limits to clonal expansion. Proc Natl Acad Sci U S A 116(18):8995-9001 (2019).

(56) References Cited

OTHER PUBLICATIONS

Huda, Taha I. et al. Specific HLA Alleles, Paired With TCR V- and J-gene Segment Usage, Link to Distinct Multiple Myeloma Survival Rates. Leukemia & Lymphoma 62(7):1711-1720 (2021).
Hudson, K.R. et al., "Two Adjacent Residues in Staphylococcal EnterotoxIns A and E Determine T Cell Receptor Vbeta Specificity," J.Exp. Med., 1993;177:175-184.
Human NKp30/NCR3 Antibody. Catalog No. MAB1849. Clone 210845 was used by HLDA to establish CD designation. [Website] R&D Systems. Retrieved Jul. 27, 2024 at URL: https://www.rndsystems.com/products/human-nkp30-ncr3-antibody-210845_mab1849. 7 pages.
Human NKp30/NCR3 Antibody. Catalog No. MAB18491. Source: Monoclonal Mouse IgG2A Clone No. 210847. [Website] R&D Systems. Retrieved Nov. 23, 2023 at URL: https://www.rndsystems.com/products/human-nkp30-ncr3-antibody-210847_mab18491#productdetails. 6 pages.
Hussain, Khiyam. et al. 1392 An Atypical Central Memory like Phenotype Can be Induced in Human T Cells by Innate TCRa Engagement. J. Immuno Ther. Cancer 10(suppl 2):A1447 (2022).
Ipilimumab. CAS 477202-00-9. chemicalbook.com [Website] Retrieved Oct. 8, 2024 at: https://www.chemicalbook.com/CASEN_477202-00-9.htm. 3 pages.
James, et al. A JAK2 mutation in myeloproliferative disorders: pathogenesis and therapeutic and scientific prospects. Trends Mol Med 11(12):546-54 (2005).
James, et al. A unique clonal JAK2 mutation leading to constitutive signalling causes polycythaemia vera. Nature. 2005;434:1144-1148.
Jones, Peter T. et al. Replacing The Complementarity-determining Regions In A Human Antibody With Those From A Mouse. Nature 321(6069):522-525 (1986).
Kasmar, A.G. et al., "CD1b tetramers bind αβ T cell receptors to identify a mycobacterial glycolipid-reactive T cell repertoire in humans," J Exp Med., 2011;208(9):1741-1747.
Klampfl, Thorsten et al. Genome Integrity of Myeloproliferative Neoplasms in Chronic Phase and During Disease Progression. Blood 118(1):167-176 (2011).
Kralovics, et al. Altered gene expression in myeloproliferative disorders correlates with activation of signaling by the V617F mutation of Jak2. Blood 106(10):3374-6 (2005).
Kralovics, et al. Molecular pathogenesis of Philadelphia chromosome negative myeloproliferative disorders. Blood Rev 19(1):1-13 (2005).
Kralovics, Robert et al. A Gain-of-function Mutation of JAK2 in Myeloproliferative Disorders. The New England Journal of Medicine 352(17):1779-1790 (2005).
Kralovics, Robert. Genetic Complexity of Myeloproliferative Neoplasms. Leukemia 22(10):1841-1848 (2008).
Kronenberg, M. et al., "A 'GEM' of a cell," Nat Immunol., 2013;14(7):694-695.
Kunik, Vered et al. Structural consensus among antibodies defines the antigen binding site. PLoS computational biology 8(2):e1002388, 1-12 (2012).
Lepore, Marco. et al. Functionally Diverse Human T cells Recognize non-microbial Antigens Presented by MR1.Elife 6:e24476, 1-22 (2017).
Levine, et al. The JAK2V617F activating mutation occurs in chronic myelomonocytic leukemia and acute myeloid leukemia, but not in acute lymphoblastic leukemia or chronic lymphocytic leukemia. Blood 106(10):3377-9 (2005).
Levine, Ross L. et al. Activating Mutation in the Tyrosine Kinase JAK2 in Polycythemia Vera, Essential Thrombocythemia, and Myeloid Metaplasia With Myelofibrosis. Cancer Cell 7(4):387-397 (2005).
Li, Yangqiu. et al. Restricted TRBV repertoire in CD4+ and CD8+ T-cell subsets from CML patients. Hematology 16(1):43-49 (2011).
Lopez, K. et al., "CD1b Tetramers Broadly Detect T Cells That Correlate With Mycobacterial Exposure but Not Tuberculosis Disease State," Front Immunol., 2020;11:199.

Lossius, Andreas. et al. High-throughput Sequencing of TCR Repertoires in Multiple Sclerosis Reveals Intrathecal Enrichment of EBV-reactive CD8+ T Cells. European Of Journal Immunnology 44(11):3439-3452 (2014).
Lu, Chenyang. et al. Clinical Significance of T Cell Receptor Repertoire in Primary Sjogren's Syndrome. EBioMedicine 84:104252, 1-12 (2022).
Maciocia, Paul M. et al. Supplemental Figures: Targeting the T cell receptor β-chain constant region for immunotherapy of T cell malignancies. Nature Medicine 23(12):1416-1423 (2017). Retrieved Oct. 8, 2024 at URL: https://static-content.springer.com/esm/art%3A10.1038%2Fnm.4444/MediaObjects/41591_2017_BFnm4444_MOESM1_ESM.pdf. 6 pages.
Maeda, T. et al. Amelioration of acute graft-versus-host disease and re-establishment of tolerance by short-term treatment with an anti-TCR antibody. Journal of immunology 153(9):4311-4320 (1994).
Martin, Andrew CR. Protein Sequence and Structure Analysis of Antibody Variable Domains. Antibody Engineering:422-439 (2001).
Matsumoto, Y. et al. Successful prevention and treatment of autoimmune encephalomyelitis by short-term administration of anti-T-cell receptor alpha beta antibody. Immunology 81(1):1-7 (1994).
Mayer, Gene et al. Chapter 10: Major Histocompatibility Complex (MHC) And T-Cell Receptors—Role In Immune Responses. In: Microbiology and Immunology on-line, University of South Carolina School of Medicine: 1-6 (2010).
McGoff, Paul, and David S. Scher. Solution Formulation of Proteins/Peptides:In McNally EJ., ed, Protein Formulation and Delivery:139-158 (2000).
Meermeier, Erin W. et al. Human TRAV1-2-negative MR1-restricted T cells detect *S. pyogenes* and alternatives to MAIT riboflavin-based antigens. Nat Commun 7:12506, 1-12 (2016).
Meeting Abstracts. 33rd Annual Meeting & Pre-Conference Programs of the Society for Immunotherapy of Cancer (SITC 2018). Journal for Immunotherapy of Cancer 6(Suppl 1):207-398 (2018).
Meilleur, Courtney. et al. Bacterial Superantigens Expand and Activate, Rather than Delete or Incapacitate, Preexisting Antigen-Specific Memory CD8+ T Cells. J Infect Dis 219(8):1307-1317 (2019). Published online Nov. 12, 2018.
Milosevic, Jelena D, and Robert Kralovics. Genetic and Epigenetic Alterations of Myeloproliferative Disorders. International Journal of Hematology 97(2):183-197 (2013). Published Online Dec. 12, 2012.
Miyahara, Y. et al. Anti-TCRβ mAb induces long-term allograft survival by reducing antigen-reactive T cells and sparing regulatory T cells. American journal of transplantation12(6):1409-1418 (2012).
Moore, et al. Abstract C180: A novel bispecific platform for potent redirected killing of B-cell lymphoma. Mol Cancer Ther 8 (12_Supplement): C180 (2009).
Morrison, Sherie L. et al. Chimeric Human Antibody Molecules: Mouse Antigen-Binding Domains With Human Constant Region Domains. PNAS USA 81(21):6851-6855 (1984).
Mosca, Paul J. et al. Dendritic cell vaccines. Frontiers in Bioscience 12:4050-4060 (2007).
Motozono, Chihiro. et al. Molecular Basis of a Dominant T Cell Response to an HIV Reverse Transcriptase 8-mer Epitope Presented by the Protective Allele HLA-B*51:01. Journal of Immunology 192(7):3428-3434 (2014).
Muller, Klaus-Peter, and Bruno A. Kyewski. T Cell Receptor Targeting to Thymic Cortical Epithelial Cells in Vivo Induces Survival, Activation and Differentiation of Immature Thymocytes. European Journal of Immunology 23(7):1661-1670 (1993).
Myers, et al. Optimal alignments in linear space. CABIOS 4(1):11-17 (1988).
Ni, Jian. Research Progress and Prospects of Antibodymoics and Antibody-Based Drugs, Modern Immunology 26(4):265-268 (2006). Abstract Only. One page.
No Author, "33rd Annual Meeting & Pre-Conference Programs of the Society for Immunotherapy of Cancer (SITC 2018)", Journal for Immuno Therapy of Cancer, 2018, vol. 6(1), No. 115, pp. 1-192.
Nomoto, K. et al. Tolerance induction in a fully allogeneic combination using anti-T cell receptor-alpha beta monoclonal antibody, low dose irradiation, and donor bone marrow transfusion. Transplantation 59(3):395-401 (1995).

(56) References Cited

OTHER PUBLICATIONS

Panka, David J. et al. Variable region framework differences result in decreased or increased affinity of variant anti-digoxin antibodies. Proceedings of the National Academy of Sciences of the United States of America 85(9):3080-3084 (1988).
Pardanani, Animesh D. et al. MPL515 Mutations in Myeloproliferative and Other Myeloid Disorders: a Study of 1182 Patients. Blood 108(10):3472-3476 (2006).
Pardanani, et al. Discordant distribution of JAK2V617F mutation in siblings with familial myeloproliferative disorders. Blood 107(11):4572-3 (2006).
Paul: Fundamental Immunology. 3rd Edition. 292-295 (1993).
PCT/US2020/019329 International Search Report and Written Opinion dated Jun. 26, 2020.
PCT/US2020/060557 International Search Report and Written Opinion dated Mar. 30, 2021.
PCT/US2021/047574 International Search Report and Written Opinion dated Feb. 17, 2022.
PCT/US2021/047773 International Search Report and Written Opinion dated Dec. 23, 2021.
PCT/US2022/023922 International Search Report and Written Opinion dated Oct. 6, 2022.
PCT/US2022/049039 International Search Report and Written Opinion dated May 10, 2023.
PCT/US2022/053705 International Search Report and Written Opinion dated Jul. 7, 2023.
PCT/US2023/011280 International Search Report and Written Opinion dated Jun. 28, 2023.
PCT/US2023/034966 International Search Report and Written Opinion dated Mar. 29, 2024.
PCT/US2023/035056 International Search Report and Written Opinion dated Mar. 5, 2024.
PCT/US2024/026686 International Search Report and Written Opinion dated Sep. 23, 2024.
Petersen, Jan. et al. Diverse T Cell Receptor Gene Usage in HLA-DQ8-associated Celiac Disease Converges Into a Consensus Binding Solution. Structure 24(10):1643-1657 (2016).
Pikman, et al. MPLW515L Is a Novel Somatic Activating Mutation in Myelofibrosis with Myeloid Metaplasia. PLoS Med. 2006;3(7):e270.
Porritt, Rebecca A. et al. HLA Class I-associated Expansion of TRBV11-2 T Cells in Multisystem Inflammatory Syndrome in Children. The Journal of Clinical Investigation 131(10):e146614, 1-13 (2021).
Reinink, P. et al., "A TCR β-Chain Motif Biases toward Recognition of Human CD1 Proteins," J Immunol., 2019;203(12):3395-3406.
Riechmann, Lutz et al. Reshaping Human Antibodies for Therapy. Nature 332(6162):323-327 (1988).
Rowntree, Louise C. et al. A Shared TCR Bias Toward an Immunogenic EBV Epitope Dominates in HLA-B*07:02-Expressing Individuals. Journal of Immunology 205(6):1524-1534 (2020).
Samanen, James. et al. Chemical Approaches to Improve the Oral Bioavailability of Peptidergic Molecules. Journal of Pharmacy and Pharmacology 48(2):119-135 (1996).
Scheuermann, R.H. and Racila, E. CD19 Antigen in Leukemia and Lymphoma Diagnosis and Immunotherapy. Leukemia & Lymphoma 18(5-6):385-397 (1995).
Scott, et al. JAK2 exon 12 mutations in polycythemia vera and idiopathic erythrocytosis. N Engl J Med 356(5):459-68 (2007).
Sim, Gek Kee. et al. Primary Structure Of Human T-Cell Receptor Alpha-chain. Nature 312(5996):771-775 (1984).
Smith, et al. T cell inactivation and cytokine deviation promoted by anti-CD3 mAbs. Curr Opin Immunol 9(5):648-54 (1997).
Smith, Temple F, and Waterman Michael S. Comparison of Biosequences. Advances in applied mathematics 2(4):482-489 (1981).
Srivastava, Shivani, and Stanley R Riddell. Engineering CAR-T cells: Design concepts. Trends in immunology 36(8):494-502 (2015).
Staerz, Uwe D, and Michael J. Bevan. Activation of resting T lymphocytes by a monoclonal antibody directed against an allotypic determinant on the T cell receptor. Eur. J. Immunol 16:263-270 (1986).
Stegelmann, F. et al. DNMT3a Mutations in Myeloproliferative Neoplasms. Leukemia 25(7):1217-1219 (2011).
Stein, et al. Disruption of the ASXL1 gene is frequent in primary, post-essential thrombocytosis and post-polycythemia vera myelofibrosis, but not essential thrombocytosis or polycythemia vera: analysis of molecular genetics and clinical phenotypes. Haematologica 96(10):1462-9 (2011).
Stein, et al. Natural Killer (NK)- and T-Cell Engaging Antibody-Derived Therapeutics. Antibodies 1(1):88-123 (2012).
Stein, Sokrates. et al. Protective Roles of SIRT1 in Atherosclerosis. Cell Cycle 10(4):640-647 (2011).
Surman, Sherri L. et al. Clonally Related CD8+ T Cells Responsible for Rapid Population of Both Diffuse Nasal-associated Lymphoid Tissue and Lung After Respiratory Virus Infection. Journal of Immunology 187(2):835-841 (2011).
Suzuki-Inoue, et al. Involvement of the Snake Toxin Receptor CLEC-2, in Podoplanin-mediated Platelet Activation, by Cancer Cells. The Journal of Biological Chemistry, 282(36):25993-26001 (2007).
Szeto, Christopher et al. Molecular Basis of a Dominant SARS-CoV-2 Spike-Derived Epitope Presented by HLA-A*02:01 Recognised by a Public TCR. Cells 10(10):2646, 1-15 (2021).
Tan, Huo et al. Clonal expanded TRA and TRB subfamily T cells in peripheral blood from patients with diffuse large B-cell lymphoma. Hematology 15(2):81-87 (2010).
Tastan, Cihan. et al. Tuning of human MAIT cell activation by commensal bacteria species and MR1-dependent T-cell presentation. Mucosal Immunol 11(6):1591-1605 (2018).
Ten Berg et al. Selective expansion of a peripheral blood CD8+ memory T cell subset expressing both granzyme B and L-selectin during primary viral infection in renal allograft recipients. Transplant Proc 30(8):3975-3977 (1998).
UniProt reference No. P04626. Receptor Tyrosine-Protein Kinase erbB-2. Record created Nov. 1, 1988. pp. 1-19. Retrieved Sep. 27, 2024 at URL: https://www.uniprot.org/uniprotkb/P04626/entry.
UniProt reference No. Q9HBE4. Interleukin-21. Record created Mar. 1, 2001. pp. 1-9. Retrieved Sep. 27, 2024 at URL: https://www.uniprot.org/uniprotkb/Q9HBE4/entry.
UniProtKB Accession No. A0A075B6N4. T cell receptor beta variable 25-1. Record created Oct. 1, 2014. pp. 1-9. Retrieved Sep. 9, 2024 at URL: https://www.uniprot.org/uniprotkb/A0A075B6N4/entry.
UniProtKB Accession No. A0A0B4J240. T cell receptor alpha variable 10. Record created Mar. 11, 2015. pp. 1-9. Retrieved Sep. 9, 2024 at URL: https://www.uniprot.org/uniprotkb/A0A0B4J240/entry.
UniProtKB Accession No. A0A1G7UTW6_9SPHI. Uncharacterized protein Pedobacter terrae (Nov. 22, 2017). Retrieved Jul. 16, 2024 at URL: https://rest.uniprot.org/unisave/A0A1G7UTW6?format=txt&versions=1. One page.
UniProtKB Accession No. A0A2V7GPM2_9BACT. Uncharacterized protein Gemmatimonadetes bacterium (Sep. 12, 2018). Retrieved Jul. 16, 2024 at URL: https://rest.uniprot.org/unisave/A0A2V7GPM2?format=txt&versions=1. One page.
UniProtKB Accession No. O00220. Tumor necrosis factor receptor superfamily member 10A. Record created Jul. 1, 1997. Retrieved Aug. 16, 2024 at URL: https://www.uniprot.org/uniprotkb/O00220/entry pp. 1-9.
UniProtKB Accession No. O14763. Tumor necrosis factor receptor superfamily member 10B. Record created Jan. 1, 1998. Retrieved Aug. 16, 2024 at URL: https://www.uniprot.org/uniprotkb/O14763/entry pp. 1-10.
UniProtKB Accession No. O95760. Interleukin-33. Record created May 1, 1999. pp. 1-10. Retrieved Sep. 9, 2024 at URL: https://www.uniprot.org/uniprotkb/O95760/entry.
UniProtKB Accession No. O95866. Megakaryocyte and platelet inhibitory receptor G6b. Record created May 1, 1999. Retrieved Aug. 16, 2024 at URL: https://www.uniprot.org/uniprotkb/O95866/entry pp. 1-11.
UniProtKB Accession No. P01137. Transforming growth factor beta-1 proprotein. Record created Nov. 1, 1988. Retrieved Aug. 16, 2024 at URL: https://www.uniprot.org/uniprotkb/P01137/entry pp. 1-17.

(56) References Cited

OTHER PUBLICATIONS

UniProtKB Accession No. P01562. Interferon alpha-1/13. Record created Nov. 1, 1988. pp. 1-10. Retrieved Sep. 9, 2024 at URL: https://www.uniprot.org/uniprotkb/P01562/entry.
UniProtKB Accession No. P01563. Interferon alpha-2. Record created Nov. 1, 1988. pp. 1-12. Retrieved Oct. 9, 2024 at URL: https://www.uniprot.org/uniprotkb/P01563/entry.
UniProtKB Accession No. P01566. Interferon alpha-10. Record created Nov. 1, 1988. pp. 1-10. Retrieved Sep. 9, 2024 at URL: https://www.uniprot.org/uniprotkb/P01566/entry.
UniProtKB Accession No. P01567. Interferon alpha-7. Record created Nov. 1, 1988. pp. 1-7. Retrieved Sep. 9, 2024 at URL: https://www.uniprot.org/uniprotkb/P01567/entry.
UniProtKB Accession No. P01568. IFN21_HUMAN. Record created Nov. 1, 1988. pp. 1-7. Retrieved Sep. 9, 2024 at URL: https://www.uniprot.org/uniprotkb/P01568/entry.
UniProtKB Accession No. P01569. Interferon alpha-5. Record created Nov. 1, 1988. pp. 1-10. Retrieved Sep. 9, 2024 at URL: https://www.uniprot.org/uniprotkb/P01569/entry.
UniProtKB Accession No. P01570. IFN14_HUMAN. Record created Nov. 1, 1988. pp. 1-7. Retrieved Sep. 9, 2024 at URL: https://www.uniprot.org/uniprotkb/P01570/entry.
UniProtKB Accession No. P01574. Interferon beta. Record created Nov. 1, 1988. pp. 1-9. Retrieved Sep. 9, 2024 at URL: https://www.uniprot.org/uniprotkb/P01574/entry.
UniProtKB Accession No. P05013. Interferon alpha-6. Record created Nov. 1, 1988. pp. 1-11. Retrieved Sep. 9, 2024 at URL: https://www.uniprot.org/uniprotkb/P05013/entry.
UniProtKB Accession No. P05014. Interferon alpha-4. Record created Nov. 1, 1988. pp. 1-11. Retrieved Sep. 9, 2024 at URL: https://www.uniprot.org/uniprotkb/P05014/entry.
UniProtKB Accession No. P05106. Integrin beta-3. Record created Nov. 1, 1988. Retrieved Aug. 16, 2024 at URL: https://www.uniprot.org/uniprotkb/P05106/entry pp. 1-20.
UniProtKB Accession No. P05107. Integrin beta-2. Record created Nov. 1, 1988. Retrieved Aug. 16, 2024 at URL: https://www.uniprot.org/uniprotkb/P05107/entry pp. 1-15.
UniProtKB Accession No. P07359. Platelet glycoprotein Ib alpha chain. Record created Nov. 1, 1988. Retrieved Aug. 16, 2024 at URL: https://www.uniprot.org/uniprotkb/P07359/entry pp. 1-15.
UniProtKB Accession No. P08514. Integrin alpha-IIb. Record created Nov. 1, 1988. Retrieved Aug. 16, 2024 at URL: https://www.uniprot.org/uniprotkb/P08514/entry pp. 1-15.
UniProtKB Accession No. P10600. Transforming growth factor beta-3 proprotein. Record created Jul. 1, 1989. Retrieved Aug. 16, 2024 at URL: https://www.uniprot.org/uniprotkb/P10600/entry pp. 1-11.
UniProtKB Accession No. P10721. Mast/stem cell growth factor receptor Kit. Record created Jul. 1, 1989. Retrieved Aug. 16, 2024 at URL: https://www.uniprot.org/uniprotkb/P10721/entry pp. 1-20.
UniProtKB Accession No. P12318. Low affinity immunoglobulin gamma Fc region receptor II-a. Record created Oct. 1, 1989. Retrieved Aug. 16, 2024 at URL: https://www.uniprot.org/uniprotkb/P12318/entry pp. 1-9.
UniProtKB Accession No. P16109. P-selectin. Record created Apr. 1, 1990. Retrieved Aug. 16, 2024 at URL: https://www.uniprot.org/uniprotkb/P16109/entry pp. 1-12.
UniProtKB Accession No. P28906. Hematopoietic progenitor cell antigen CD34. Record created Dec. 1, 1992. Retrieved Aug. 16, 2024 at URL: https://www.uniprot.org/uniprotkb/P28906/entry pp. 1-10.
UniProtKB Accession No. P29459. Interleukin-12 subunit alpha. Record created Apr. 1, 1993. pp. 1-13. Retrieved Sep. 9, 2024 at URL: https://www.uniprot.org/uniprotkb/P29459/entry.
UniProtKB Accession No. P29460. Interleukin-12 subunit beta. Record created Apr. 1, 1993. pp. 1-10. Retrieved Sep. 9, 2024 at URL: https://www.uniprot.org/uniprotkb/P29460/entry.
UniProtKB Accession No. P30408. Transmembrane 4 L6 family member 1. Record created Apr. 1, 1993. Retrieved Aug. 16, 2024 at URL: https://www.uniprot.org/uniprotkb/P30408/entry pp. 1-7.
UniProtKB Accession No. P32881. Interferon alpha-8. Record created Oct. 1, 1993. pp. 1-7. Retrieved Sep. 9, 2024 at URL: https://www.uniprot.org/uniprotkb/P32881/entry.
UniProtKB Accession No. P36888. Receptor-type tyrosine-protein kinase FLT3. Record created Jun. 1, 1994. Retrieved Aug. 16, 2024 at URL: https://www.uniprot.org/uniprotkb/P36888/entry pp. 1-13.
UniProtKB Accession No. P36897. TGF-beta receptor type-1. Record created Jun. 1, 1994. Retrieved Aug. 16, 2024 at URL: https://www.uniprot.org/uniprotkb/P36897/entry pp. 1-16.
UniProtKB Accession No. P37173. TGF-beta receptor type-2. Record created Oct. 1, 1994. Retrieved Aug. 16, 2024 at URL: https://www.uniprot.org/uniprotkb/P37173/entry pp. 1-18.
UniProtKB Accession No. P40238. Thrombopoietin receptor. Record created Feb. 1, 1995. Retrieved Aug. 16, 2024 at URL: https://www.uniprot.org/uniprotkb/P40238/entry pp. 1-11.
UniProtKB Accession No. P40933. Interleukin-15. Record created Feb. 1, 1995. pp. 1-9. Retrieved Sep. 9, 2024 at URL: https://www.uniprot.org/uniprotkb/P40933/entry.
UniProtKB Accession No. P56856. CLD_HUMAN. 14 pages. Retrieved Oct. 7, 2024 at URL: https://www.uniprot.org/uniprotkb/P56856/entry.
UniProtKB Accession No. P60568. Interleukin-2. Record created Mar. 15, 2004. pp. 1-12. Retrieved Jul. 12, 2024 at URL: https://www.uniprot.org/uniprotkb/P60568/entry.
UniProtKB Accession No. P61812. Transforming growth factor beta-2 proprotein. Record created Jun. 7, 2004. Retrieved Aug. 16, 2024 at URL: https://www.uniprot.org/uniprotkb/P61812/entry pp. 1-12.
UniProtKB Accession No. Q02487. Desmocollin-2. Record created Feb. 1, 1994. Retrieved Aug. 16, 2024 at URL: https://www.uniprot.org/uniprotkb/Q02487/entry pp. 1-15.
UniProtKB Accession No. Q03167. Transforming growth factor beta receptor type 3. Record created Feb. 1, 1994. Retrieved Aug. 16, 2024 at URL: https://www.uniprot.org/uniprotkb/Q03167/entry pp. 1-10.
UniProtKB Accession No. Q14116. Interleukin-18. Record created Nov. 1, 1996. pp. 1-10. Retrieved Sep. 9, 2024 at URL: https://www.uniprot.org/uniprotkb/Q14116/entry.
UniProtKB Accession No. Q9H293. Interleukin-25. Record created Mar. 1, 2001. pp. 1-11. Retrieved Sep. 9, 2024 at URL: https://www.uniprot.org/uniprotkb/Q9H293/entry.
UniProtKB Accession No. Q9NPF7. Interleukin-23 subunit alpha. Record created Oct. 1, 2000. pp. 1-13. Retrieved Sep. 9, 2024 at URL: https://www.uniprot.org/uniprotkb/Q9NPF7/entry.
UniProtKB Accession No. Q9NYJ7. DLL3_HUMAN. Record created Oct. 1, 2000. pp. 1-13. Retrieved Jul. 12, 2024 at URL: https://www.uniprot.org/uniprotkb/Q9NYJ7.
Urakami, Akane. et al. An Envelope-Modified Tetravalent Dengue Virus-Like-Particle Vaccine Has Implications for Flavivirus Vaccine Design. Journal of virology 91(23):e00090-17, 1-16 (2017).
U.S. Appl. No. 15/465,564 Notice of Allowance dated Nov. 10, 2021.
U.S. Appl. No. 15/465,564 Notice of Allowance dated Oct. 29, 2021.
U.S. Appl. No. 15/465,564 Office Action dated Apr. 29, 2020.
U.S. Appl. No. 15/465,564 Office Action dated May 26, 2021.
U.S. Appl. No. 15/465,564 Office Action dated Oct. 13, 2020.
U.S. Appl. No. 15/465,564 Office Action dated Sep. 9, 2019.
U.S. Appl. No. 16/980,730 Notice of Allowance dated Jun. 13, 2024.
U.S. Appl. No. 16/980,771 Office Action dated Jan. 10, 2024.
U.S. Appl. No. 17/256,917 Notice of Allowance dated Sep. 7, 2023.
U.S. Appl. No. 17/366,638 Office Action dated Apr. 25, 2024.
U.S. Appl. No. 17/366,638 Office Action dated Aug. 27, 2024.
U.S. Appl. No. 17/402,325 Office Action dated Sep. 24, 2024.
U.S. Appl. No. 17/529,017 Office Action dated Nov. 18, 2022.
U.S. Appl. No. 17/820,634 Office Action dated Apr. 19, 2023.
U.S. Appl. No. 17/820,634 Office Action dated Aug. 11, 2023.
U.S. Appl. No. 17/820,634 Office Action dated Aug. 15, 2023.
U.S. Appl. No. 17/820,794 Notice of Allowance dated Feb. 1, 2024.
U.S. Appl. No. 17/820,794 Office Action dated Dec. 29, 2023.
U.S. Appl. No. 17/820,794 Office Action dated Mar. 31, 2023.
U.S. Appl. No. 17/820,794 Office Action dated Sep. 15, 2023.

(56) References Cited

OTHER PUBLICATIONS

U.S. Appl. No. 17/820,800 Office Action dated Feb. 21, 2023.
U.S. Appl. No. 17/820,800 Office Action dated Jun. 1, 2023.
U.S. Appl. No. 17/820,805 Office Action dated Apr. 26, 2024.
U.S. Appl. No. 17/820,805 Office Action dated Aug. 14, 2023.
U.S. Appl. No. 17/820,806 Office Action dated Apr. 12, 2023.
U.S. Appl. No. 17/820,806 Office Action dated Aug. 15, 2023.
U.S. Appl. No. 17/820,811 Office Action dated Feb. 14, 2024.
U.S. Appl. No. 17/820,811 Office Action dated May 25, 2023.
U.S. Appl. No. 17/820,818 Office Action dated Jun. 1, 2023.
U.S. Appl. No. 17/820,818 Office Action dated Mar. 12, 2024.
U.S. Appl. No. 18/341,688 Office Action dated Jan. 25, 2024.
U.S. Appl. No. 18/341,688 Office Action dated May 10, 2024.
Valkenburg, Sophie A. et al. Molecular Basis for Universal HLA-A*0201-restricted CD8+ T-cell Immunity Against Influenza Viruses. Proceedings of the National Academy of Sciences of the United States of America 113(16):4440-4445 (2016).
Van Rhijn, I. et al., "A conserved human T cell population targets mycobacterial antigens presented by CD1b," Nat Immunol., 2013;14(7):706-713.
Van Rhijn, I. et al., "TCR bias and affinity define two compartments of the CD1b-glycolipid-specific T Cell repertoire," J Immunol., 2014;192(9):4054-4060.
Vantourout, Pierre et al. Innate TCRβ-chain engagement drives human T cells toward distinct memory-like effector phenotypes with immunotherapeutic potentials. Science Advances 9(49):eadj6174, 1-19 (2023).
Viney, Joanne L. et al. Generation of Monoclonal Antibodies Against a Human T Cell Receptor Beta Chain Expressed in Transgenic Mice. Hybridoma 11(6):701-713 (1992).
Wang, Zhenguang. et al. Current status and perspectives of chimeric antigen receptor modified T cells for cancer treatment. Protein and Cell 8(12):896-925 (2017).
Xiang, Jianhua H. et al. Modification in Framework Region I Results in a Decreased Affinity of Chimeric Anti-TAG72 antibody. Molecular Immunology 28(1-2):141-148 (1991).
Xu, Jian. et al. MIR548P and TRAV39 Are Potential Indicators of Tumor Microenvironment and Novel Prognostic Biomarkers of Esophageal Squamous Cell Carcinoma. Journal of Clinical Oncology 2022:3152114, 1-20 (2022).
Yang, Xinbo. et al. Structural basis for clonal diversity of the human T-cell response to a dominant influenza virus epitope. J Biol Chem 292(45):18618-18627 (2017).
Yohannes, Dawit A. et al. Deep Sequencing of Blood and Gut T-cell Receptor B-chains Reveals Gluten-induced Immune Signatures in Celiac Disease. Scientific Reports 7(1):17977, 1-12 (2017).
Zhang, Tong. et al. An NKp30-Based Chimeric Antigen Receptor Promotes T cell Effector Functions and Antitumor Efficacy In Vivo. Journal of Immunology 189(5):2290-2299 (2012).
Zhou, Hongyu. et al. A Novel Risk Score System of Immune Genes Associated With Prognosis in Endometrial Cancer. Cancer Cell International 20:240, 1-12 (2020).
Zitti, et al. Natural killer cells in inflammation and autoimmunity. Cytokine & Growth Factor Reviews 42:37-46 (2018).

\* cited by examiner

CALRETICULIN BINDING CONSTRUCTS AND ENGINEERED T CELLS FOR THE TREATMENT OF DISEASES

CROSS-REFERENCE

This application claims priority to U.S. Provisional Application No. 62/615,270, filed Jan. 9, 2018, and International Application No. PCT/US2019/012900, filed Jan. 9, 2019, which are incorporated herein by reference in their entireties.

SEQUENCE LISTING

The instant application contains a Sequence Listing which has been submitted electronically in ASCII format and is hereby incorporated by reference in its entirety. Said ASCII copy, created on Feb. 26, 2019, is named 53676-701_601_SL.txt and is 61,764 bytes in size.

BACKGROUND

Primary myelofibrosis (PMF), essential thrombocythemia (ET) and polycythemia vera (PV) are monoclonal hematological disorders that belong to the classical BCR-ABL negative myeloproliferative neoplasms (MPN) (Campbell & Green, 2006). Since the 2005 discovery of a somatic mutation in the JAK2 kinase gene, a tremendous progress has been made in molecular diagnosis, clinical management, treatment and molecular understanding of MPN. The valine to phenylalanine (V617F) mutation constitutively activates the Jak2 kinase resulting in increased phosphorylation of its substrates (Stat5, Stat3, Erk, etc.) and leading to increased cytokine responsiveness of myeloid cells (Baxter et al, 2005; James et al, 2005; Kralovics et al, 2005; Levine et al, 2005). Identification of additional mutations soon followed such as in JAK2 exon 12 in PV (Scott et al, 2007) and in the thrombopoietin receptor gene MPL in PMF and ET (Pardanani et al, 2006; Pikman et al, 2006). Although the three MPN disease entities differ in their clinical presentation, they share many molecular as well as clinical features. The JAK2-V617F mutation is present in about 95% of PV cases, 60% PMF and 50% of ET cases, respectively. Mutations in JAK2 exon 12 are specific to about 3% of PV cases whereas MPL mutations are restricted to the PMF (5%) and ET (3%). All three MPN entities are predisposed at a variable degree to thrombosis, bleeding and leukemic transformation (Sverdlow et al, 2008). Although patients may remain in the chronic phase of MPN for several years, disease progression occurs in a form of secondary myelofibrosis in PV and ET, development of accelerated phase with variable degree of pancytopenia followed by leukemic transformation affecting all three MPN entities (Sverdlow et al, 2008).

Somatic mutations accumulate during the entire clonal evolution of MPN hematopoietic stem cells. These acquired genetic alterations may be point mutations, chromosomal lesions and epigenetic defects and they all may contribute to the fitness of the evolving clone (Klampfl et al, 2011; Kralovics, 2008). These mutations may accelerate proliferation by various means, decrease differentiation potential of progenitors or render them less susceptible to apoptosis. Mutations affecting these mechanisms have been described in genes such as TET2 (Delhommeau et al, 2009), EZH2 (Ernst et al, 2010), DNMT3A (Stegelmann et al, 2011), ASXL1 (Stein et al, 2011), and TP53 (Harutyunyan et al, 2011) in different types of myeloid malignancies including MPN (Milosevic & Kralovics, 2013). However, so far only JAK2 and MPL mutations are considered strongly MPN associated and they represent the most useful molecular markers of MPN.

Despite the progress made in the understanding of the molecular pathogenesis of MPN approximately half of the patients with PMF and ET lack a molecular marker for diagnosis as these patients are negative for both JAK2 and MPL mutations. The mutant calreticulin specific antibody domain constructs provided herein solve these problems.

SUMMARY

Mutant calreticulin proteins has been identified and found to be associated with PMF and ET (see, e.g., Klampfl et al. (N Engl J Med 2013; 369:2379-2390 Dec. 19, 2013), Nangalia et al. (N Engl J Med 2013; 369:2391-2405) and Cazzola and Kralovics (Blood 2014; 123(24):3714-9).

In one aspect, provided herein is a composition comprising a nucleic acid comprising a sequence encoding a chimeric antigen receptor (CAR), wherein the CAR comprises an antibody domain comprising a mutant calreticulin binding domain, a transmembrane domain, and an intracellular signaling domain.

In one aspect, provided herein is a composition comprising a nucleic acid comprising a sequence encoding a human or humanized antibody domain comprising a mutant calreticulin binding domain.

In one aspect, provided herein is a composition comprising a nucleic acid comprising a sequence encoding an antibody domain comprising a mutant calreticulin binding domain, wherein the mutant calreticulin binding domain binds to an epitope of a mutant calreticulin polypeptide with $K_D$ of 200 nM or less.

In one aspect, provided herein is a composition comprising a nucleic acid comprising a sequence encoding an antibody domain comprising a mutant calreticulin binding domain, wherein the mutant calreticulin binding domain comprises: a heavy chain variable domain ($V_H$) amino acid sequence with at least 77% sequence identity to SEQ ID NO: 1, at least 75% sequence identity to SEQ ID NO: 2, at least one, two or three modifications but not more than 30, 20 or 10 modifications of the amino acid sequence of SEQ ID NO: 1, or at least one, two or three modifications but not more than 30, 20 or 10 modifications of the amino acid sequence of SEQ ID NO: 2; and/or a light chain variable domain ($V_L$) amino acid sequence with at least 93% sequence identity to SEQ ID NO: 3, or least one, two or three modifications but not more than 30, 20 or 10 modifications of the amino acid sequence of SEQ ID NO: 3.

In some embodiments, the mutant calreticulin binding domain binds to an epitope of a mutant calreticulin polypeptide with $K_D$ of 200 nM or less.

In some embodiments, the antibody domain is a human or humanized antibody domain.

In some embodiments, the nucleic acid comprises a sequence encoding a chimeric antigen receptor (CAR), wherein the CAR comprises the antibody domain comprising the mutant calreticulin binding domain, a transmembrane domain, and an intracellular signaling domain.

In some embodiments, the mutant calreticulin binding domain comprises a heavy chain variable domain ($V_H$) amino acid sequence with at least 77% sequence identity to SEQ ID NO: 1, at least 75% sequence identity to SEQ ID NO: 2, at least one, two or three modifications but not more than 30, 20 or 10 modifications of the amino acid sequence of SEQ ID NO: 1, or at least one, two or three modifications but not more than 30, 20 or 10 modifications of the amino acid sequence of SEQ ID NO: 2; and/or a light chain variable domain (V$_L$) amino acid sequence with at least 93% sequence identity to SEQ ID NO: 3, or at least one, two or three modifications but not more than 30, 20 or 10 modifications of the amino acid sequence of SEQ ID NO: 3.

In some embodiments, the mutant calreticulin binding domain comprises a V$_H$ amino acid sequence with at least 77% sequence identity to SEQ ID NO: 1, or at least one, two or three modifications but not more than 30, 20 or 10 modifications of the amino acid sequence of SEQ ID NO: 1; and a V$_L$ amino acid sequence with at least 93% sequence identity to SEQ ID NO: 3, or at least one, two or three modifications but not more than 30, 20 or 10 modifications of the amino acid sequence of SEQ ID NO: 3.

In some embodiments, the mutant calreticulin binding domain comprises a V$_H$ amino acid sequence with at least 75% sequence identity to SEQ ID NO: 2, or at least one, two or three modifications but not more than 30, 20 or 10 modifications of the amino acid sequence of SEQ ID NO: 2; and a V$_L$ amino acid sequence with at least 93% sequence identity to SEQ ID NO: 3, or at least one, two or three modifications but not more than 30, 20 or 10 modifications of the amino acid sequence of SEQ ID NO: 3.

In some embodiments, the mutant calreticulin binding domain comprises: a heavy chain complementary determining region 1 (HC CDR1) with an amino acid sequence of any one of SEQ ID NOs: 7 or 10; a heavy chain complementary determining region 2 (HC CDR2) with an amino acid sequence of any one of SEQ ID NOs: 8 or 11; and a heavy chain complementary determining region 3 (HC CDR3) with an amino acid sequence of any one of SEQ ID NOs: 9 or 12 or 16; and a light chain complementary determining region 1 (LC CDR1) with an amino acid sequence of SEQ ID NO: 13; a light chain complementary determining region 2 (LC CDR2) with an amino acid sequence of SEQ ID NO: 14; and a light chain complementary determining region 3 (LC CDR3) with an amino acid sequence of SEQ ID NOs: 15. In some embodiments, the mutant calreticulin binding domain comprises: a HC CDR1 with an amino acid sequence of SEQ ID NO: 7, a HC CDR2 with an amino acid sequence of SEQ ID NO: 8, and a HC CDR3 with an amino acid sequence of SEQ ID NO: 9; and a LC CDR1 with an amino acid sequence of SEQ ID NO: 13, a LC CDR2 with an amino acid sequence of SEQ ID NO: 14, and a LC CDR3 with an amino acid sequence of SEQ ID NO: 15. In some embodiments, the mutant calreticulin binding domain comprises: a HC CDR1 with an amino acid sequence of SEQ ID NO: 10, a HC CDR2 with an amino acid sequence of SEQ ID NO: 11, and a HC CDR3 with an amino acid sequence of SEQ ID NO: 12; and a LC CDR1 with an amino acid sequence of SEQ ID NO: 13, a LC CDR2 with an amino acid sequence of SEQ ID NO: 14, and a LC CDR3 with an amino acid sequence of SEQ ID NO: 15. In some embodiments, the mutant calreticulin binding domain comprises: a HC CDR1 with an amino acid sequence of SEQ ID NO: 10, a HC CDR2 with an amino acid sequence of SEQ ID NO: 11, and a HC CDR3 with an amino acid sequence of SEQ ID NO: 16; and a LC CDR1 with an amino acid sequence of SEQ ID NO: 13, a LC CDR2 with an amino acid sequence of SEQ ID NO: 14, and a LC CDR3 with an amino acid sequence of SEQ ID NO: 15.

In some embodiments, the nucleic acid further encodes a leader sequence comprising an amino acid sequence with at least 95% sequence identity to SEQ ID NO: 17; or an amino acid sequence comprising at least one, two or three modifications but not more than 20, 10 or 5 modifications of the amino acid sequence of SEQ ID NO: 17.

In some embodiments, the CAR comprises an extracellular domain.

In some embodiments, the encoded antibody domain is connected to (i) the encoded transmembrane domain or (ii) the encoded extracellular domain, by a hinge domain.

In some embodiments, the encoded hinge domain comprises a CD8 amino acid sequence with at least 95% sequence identity to SEQ ID NO: 19; or a CD8 amino acid sequence comprising at least one, two or three modifications but not more than 20, 10 or 5 modifications of the amino acid sequence of SEQ ID NO: 19.

In some embodiments, the encoded hinge domain comprises an IgG4 amino acid sequence with at least 95% sequence identity to SEQ ID NO: 33; or an IgG4 amino acid sequence comprising at least one, two or three modifications but not more than 20, 10 or 5 modifications of the amino acid sequence of SEQ ID NO: 33.

In some embodiments, the encoded hinge domain comprises $(G_4S)n$, wherein G is glycine, S is serine, and n is an integer from 1 to 4 (SEQ ID NO: 46).

In some embodiments, the encoded transmembrane domain comprises a transmembrane domain of a protein selected from the group consisting of the alpha, beta or zeta chain of the T-cell receptor, CD28, CD3 epsilon, CD45, CD4, CDS, CD8, CD9, CD16, CD22, CD33, CD37, CD64, CD80, CD86, CD134, CD137 and CD154; or a CD8 amino acid sequence with at least 95% sequence identity to SEQ ID NO: 21; or a CD8 amino acid sequence comprising at least one, two or three modifications but not more than 20, 10 or 5 modifications of the amino acid sequence of SEQ ID NO: 21.

In some embodiments, the encoded intracellular domain comprises a costimulatory domain, wherein the costimulatory domain comprises a functional signaling domain derived from a protein selected from the group consisting of a MHC class I molecule, a TNF receptor protein, an Immunoglobulin-like protein, a cytokine receptor, an integrin, a signaling lymphocytic activation molecule (SLAM protein), an activating NK cell receptor, BTLA, a Toll ligand receptor, OX40, CD2, CD7, CD27, CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, $V_L$A1, CD49a, ITGA4, IA4, CD49D, ITGA6, $V_L$A-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83.

In some embodiments, the costimulatory domain comprises a 4-1BB amino acid sequence with at least 95% sequence identity to SEQ ID NO: 23; or a 4-1BB amino acid sequence comprising at least one, two or three modifications but not more than 20, 10 or 5 modifications of the amino acid sequence of SEQ ID NO: 23.

In some embodiments, the costimulatory domain comprises a CD28 amino acid sequence with at least 95% sequence identity to SEQ ID NO: 25; or a CD28 amino acid sequence comprising at least one, two or three modifications but not more than 20, 10 or 5 modifications of the amino acid sequence of SEQ ID NO: 25.

In some embodiments, the costimulatory domain comprises an ICOS amino acid sequence with at least 95% sequence identity to SEQ ID NO: 27; or an ICOS amino acid sequence comprising at least one, two or three modifications but not more than 20, 10 or 5 modifications of the amino acid sequence of SEQ ID NO: 27.

In some embodiments, the encoded intracellular domain comprises a CD3 zeta amino acid sequence with at least 95% sequence identity to SEQ ID NO: 29; or a CD3 zeta amino acid sequence comprising at least one, two or three modifications but not more than 20, 10 or 5 modifications of the amino acid sequence of SEQ ID NO: 29.

In some embodiments, the encoded intracellular domain comprises a CD3 zeta amino acid sequence with at least 95% sequence identity to SEQ ID NO: 31; or a CD3 zeta amino acid sequence comprising at least one, two or three modifications but not more than 20, 10 or 5 modifications of the amino acid sequence of SEQ ID NO: 31.

In some embodiments, the encoded intracellular domain comprises a functional signaling domain of 4-1BB and a functional signaling domain of CD3 zeta.

In some embodiments, the encoded intracellular domain comprises an amino acid sequence with at least 95% sequence identity to SEQ ID NO: 35; or an amino acid sequence comprising at least one, two or three modifications but not more than 20, 10 or 5 modifications of the amino acid sequence of SEQ ID NO: 35.

In some embodiments, the encoded intracellular signaling domain comprises a primary signaling domain comprising a functional signaling domain derived from CD3 zeta, TCR zeta, FcR gamma, FcR beta, CD3 gamma, CD3 delta, CD3 epsilon, CDS, CD22, CD79a, CD79b, CD278, FcεRI, DAP10, DAP12, or CD66d.

In some embodiments, the encoded antibody domain is a single chain antibody domain or an scFv antibody domain.

In some embodiments, the encoded antibody domain comprises a single polypeptide chain comprising the $V_H$ amino acid sequence and the $V_L$ amino acid sequence.

In some embodiments, the encoded $V_H$ amino acid sequence is connected to the encoded $V_L$ amino acid sequence by a linker.

In some embodiments, the encoded antibody domain comprises a single polypeptide chain comprising the encoded HC CDR1, HC CDR2, HC CDR3, LC CDR1, LC CDR2 and LC CDR3 amino acid sequences.

In some embodiments, the encoded HC CDR1, HC CDR2 and HC CDR3 amino acid sequence are connected to the encoded LC CDR1, LC CDR2 and LC CDR3 amino acid sequences by a linker.

In some embodiments, the encoded linker sequence comprises $(G_4S)n$, wherein G is glycine, S is serine, and n is an integer from 1 to 4 (SEQ ID NO: 46).

In some embodiments, n is 4.

In some embodiments, the encoded linker sequence comprises the amino acid sequence of SEQ ID NO: 36.

In some embodiments, the nucleic acid encodes an amino acid sequence with at least 80% sequence identity to SEQ ID NO: 37; or an amino acid sequence comprising at least one, two or three modifications but not more than 30, 20, 10 or 5 modifications of the amino acid sequence of SEQ ID NO: 37.

In some embodiments, the nucleic acid encodes an amino acid sequence with at least 80% sequence identity to SEQ ID NO: 38; or an amino acid sequence comprising at least one, two or three modifications but not more than 30, 20, 10 or 5 modifications of the amino acid sequence of SEQ ID NO: 38.

In some embodiments, the nucleic acid encodes an amino acid sequence with at least 80% sequence identity to SEQ ID NO: 39; or an amino acid sequence comprising at least one, two or three modifications but not more than 30, 20, 10 or 5 modifications of the amino acid sequence of SEQ ID NO: 39.

In some embodiments, the nucleic acid encodes an amino acid sequence with at least 80% sequence identity to SEQ ID NO: 40; or an amino acid sequence comprising at least one, two or three modifications but not more than 30, 20, 10 or 5 modifications of the amino acid sequence of SEQ ID NO: 40.

In some embodiments, the nucleic acid encodes an amino acid sequence with at least 80% sequence identity to SEQ ID NO: 41; or an amino acid sequence comprising at least one, two or three modifications but not more than 30, 20, 10 or 5 modifications of the amino acid sequence of SEQ ID NO: 41.

In some embodiments, the nucleic acid encodes an amino acid sequence with at least 80% sequence identity to SEQ ID NO: 42; or an amino acid sequence comprising at least one, two or three modifications but not more than 30, 20, 10 or 5 modifications of the amino acid sequence of SEQ ID NO: 42

In some embodiments, the antibody domain binds to an epitope of mutant calreticulin comprising a mutant calreticulin type 1 mutation. A CALR type 1 mutation can be encoded by a 52-bp deletion (p.L367fs*46). In some embodiments, the antibody domain binds to an epitope of mutant calreticulin comprising a mutant calreticulin type 2 mutation. A CALR type 2 mutation epitope can be encoded by a 5-bp TTGTC insertion (p.K385fs*47).

In some embodiments, the antibody domain is a monoclonal antibody domain.

In some embodiments, the antibody domain is a human antibody domain.

In some embodiments, the antibody domain is a humanized antibody domain.

In some embodiments, the antibody domain is a chimeric antibody domain.

In one aspect, provided herein is a composition comprising a vector comprising a nucleic acid described herein.

In some embodiments, the vector is a DNA vector, an RNA vector, a plasmid, a lentivirus vector, adenoviral vector, or a retrovirus vector.

In one aspect, provided herein is a composition comprising a polypeptide encoded by a nucleic acid described herein.

In some embodiments, the polypeptide is a CAR.

In some embodiments, the polypeptide is an antibody or fragment thereof.

In some embodiments, the antibody is an IgG class antibody.

In one aspect, provided herein is a composition comprising an immunoconjugate comprising a polypeptide composition described herein, wherein the polypeptide is conjugated to a therapeutic agent.

In one aspect, provided herein is a composition comprising a cell comprising a composition described herein.

In some embodiments, the cell is an immune cell.

In some embodiments, the cell is an immune effector cell.

In some embodiments, the cell is a $CD8^+$ or $CD4^+$ T cell.

In some embodiments, the cell is a human cell.

In some embodiments, the cell is an autologous cell.

In some embodiments, the cell is an allogenic cell.

In some embodiments, the cell further expresses a chimeric molecule that comprises a first polypeptide that comprises at least a portion of an inhibitory molecule, associated with a second polypeptide that comprises a positive signal from an intracellular signaling domain.

In one aspect, provided herein is a pharmaceutical composition comprising a cell described herein; and a pharmaceutically acceptable carrier, diluent or excipient.

In one aspect, provided herein is a method of making an immune effector cell, comprising transducing the immune effector cell with a vector composition described herein.

In one aspect, provided herein is a method of generating a population of RNA-engineered cells, comprising introducing an in vitro transcribed RNA or synthetic RNA into a cell, wherein the RNA comprises a nucleic acid composition described herein.

In one aspect, provided herein is a method of providing an anti-tumor immunity in a mammal, comprising administering to the mammal an effective amount of a cell composition described herein.

In one aspect, provided herein is a use of a composition described herein, in the manufacture of a medicament.

In some embodiments, the medicament is for treatment of a disease associated with expression of mutant calreticulin.

In one aspect, provided herein is a use of a composition described herein, for treating a disease associated with expression of mutant calreticulin.

In one aspect, provided herein is a method of treating a mammal having a disease associated with expression of mutant calreticulin, comprising administering to the mammal an effective amount of a cell composition described herein.

In some embodiments, the disease is a myeloid malignancy.

In some embodiments, the disease is selected from the group consisting of acute myeloid leukemia (AML), acute lymphoblastic leukemia (ALL), acute lymphoblastic B-cell leukemia (B-cell acute lymphoid leukemia, BALL), acute lymphoblastic T-cell leukemia (T-cell acute lymphoid leukemia (TALL), B-cell prolymphocytic leukemia, chronic lymphocytic leukemia, chronic myeloid leukemia (CML), hairy cell leukemia, Hodgkin lymphoma, a histiocytic disorder, a mast cell disorder, a myelodysplasia, a myelodysplastic syndrome, a myeloproliferative neoplasm, a plasma cell myeloma, a plasmacytoid dendritic cell neoplasm, and combinations thereof.

In some embodiments, the cell is administered in combination with one or more of: an agent that increases the efficacy of the cell; an agent that ameliorates one or more side effects associated with administration of the cell; or an agent that treats the disease associated with the expression of mutant calreticulin.

In some embodiments, the agent is a JAK2 inhibitor.

In some embodiments, the cell comprises an mRNA encoding a CAR.

In some embodiments, the cell is administered in combination with second therapeutic agent or procedure selected from the group consisting of a chemotherapy, a targeted anti-cancer therapy, an oncolytic drug, a cytotoxic agent, a cytokine, surgical procedure, a radiation procedure, an agonist of a costimulatory molecule, an inhibitor of an immune checkpoint molecule, a vaccine, or a second CAR-based immunotherapy.

In some embodiments, the cell is administered in combination with:
an agonist of a costimulatory molecule selected from the group consisting of OX40, CD2, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3 or CD83 ligand; or
an inhibitor of an immune checkpoint molecule selected from the group consisting of PD1, PD-L1, PD-L2, CTLA4, TIM3, CEACAM-1, CEACAM-3, CEACAM-5, LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GALS, adenosine, or TGFR.

In some embodiments, the cell is administered in combination with a PD-1 inhibitor, a TIM-3 inhibitor, a CEACAM-1 inhibitor, or a combination thereof.

In some embodiments, the method further comprises administering a T cell depleting agent after treatment with the cell, thereby depleting the cell.

In some embodiments, the T cell depleting agent is a CD52 inhibitor and is administered one, two, three, four, or five weeks after administration of the cell.

In some embodiments, the cell expresses a mutant calreticulin CAR polypeptide and a target protein recognized by the T cell depleting agent, wherein the target protein is CD20 and the T cell depleting agent is an anti-CD20 antibody.

DETAILED DESCRIPTION

Provided herein are nucleic acid constructs, polypeptides and T cells related to antigen binding domains that binds to mutant calreticulin; and methods of use thereof for the treatment of diseases, including cancer and myeloid malignancies.

Definitions

Unless defined otherwise, all technical and scientific terms used herein have the same meaning as commonly understood by one of ordinary skill in the art to which the invention pertains.

The term "a" and "an" refers to one or to more than one (i.e., to at least one) of the grammatical object of the article. By way of example, "an element" means one element or more than one element.

As used herein, "about" can mean plus or minus less than 1 or 1, 2, 3, 4, 5, 6, 7, 8, 9, 10, 11, 12, 13, 14, 15, 16, 17, 18, 19, 20, 25, 30, or greater than 30 percent, depending upon the situation and known or knowable by one skilled in the art.

The term "Chimeric Antigen Receptor" or alternatively a "CAR" refers to a recombinant polypeptide construct comprising at least an extracellular antigen binding domain, a transmembrane domain and a cytoplasmic signaling domain (also referred to herein as "an intracellular signaling domain") comprising a functional signaling domain derived from a stimulatory molecule as defined below. In some embodiments, the domains in the CAR polypeptide construct are in the same polypeptide chain, e.g., comprise a chimeric fusion protein. In some embodiments, the domains in the CAR polypeptide construct are not contiguous with each other, e.g., are in different polypeptide chains, e.g., as provided in an RCAR as described herein.

In one aspect, the stimulatory molecule of the CAR is the zeta chain associated with the T cell receptor complex. In one aspect, the cytoplasmic signaling domain comprises a primary signaling domain (e.g., a primary signaling domain of CD3-zeta). In one aspect, the cytoplasmic signaling domain further comprises one or more functional signaling domains derived from at least one costimulatory molecule as defined below. In one aspect, the costimulatory molecule is chosen from 4-1BB (i.e., CD137), CD27, ICOS, and/or CD28. In one aspect, the CAR comprises a chimeric fusion protein comprising an extracellular antigen recognition domain, a transmembrane domain and an intracellular signaling domain comprising a functional signaling domain derived from a stimulatory molecule. In one aspect, the CAR comprises a chimeric fusion protein comprising an extracellular antigen recognition domain, a transmembrane domain and an intracellular signaling domain comprising a functional signaling domain derived from a co-stimulatory molecule and a functional signaling domain derived from a stimulatory molecule. In one aspect, the CAR comprises a chimeric fusion protein comprising an extracellular antigen recognition domain, a transmembrane domain and an intracellular signaling domain comprising two functional signaling domains derived from one or more co-stimulatory molecule(s) and a functional signaling domain derived from a stimulatory molecule. In one aspect, the CAR comprises a chimeric fusion protein comprising an extracellular antigen recognition domain, a transmembrane domain and an intracellular signaling domain comprising at least two functional signaling domains derived from one or more co-stimulatory molecule(s) and a functional signaling domain derived from a stimulatory molecule. In one aspect the CAR comprises an optional leader sequence at the amino-terminus (N-ter) of the CAR fusion protein. In one aspect, the CAR further comprises a leader sequence at the N-terminus of the extracellular antigen recognition domain, wherein the leader sequence is optionally cleaved from the antigen recognition domain (e.g., aa scFv) during cellular processing and localization of the CAR to the cellular membrane.

A CAR that comprises an antigen binding domain (e.g., a scFv, a single domain antibody, or TCR (e.g., a TCR alpha binding domain or TCR beta binding domain)) that specifically binds a specific tumor marker X, wherein X can be a tumor marker as described herein, is also referred to as XCAR. For example, a CAR that comprises an antigen binding domain that specifically binds mutant calreticulin is referred to as mutant calreticulin CAR. The CAR can be expressed in any cell, e.g., an immune effector cell as described herein (e.g., a T cell or an NK cell).

The term "signaling domain" refers to the functional portion of a protein which acts by transmitting information within the cell to regulate cellular activity via defined signaling pathways by generating second messengers or functioning as effectors by responding to such messengers.

As used herein, the terms "alpha subunit of the IL-3 receptor," "IL3Rα," "mutant calreticulin," "IL3Rα chain" and "IL3Rα subunit" refer interchangeably to an antigenic determinant known to be detectable on leukemia precursor cells. The human and murine amino acid and nucleic acid sequences can be found in a public database, such as GenBank, UniProt and Swiss-Prot. For example, the amino acid sequence of human IL3Rα can be found at Accession No. NP 002174 and the nucleotide sequence encoding of the human IL3Rα can be found at Accession No. NM 005191. In one aspect the antigen-binding portion of the CAR recognizes and binds an epitope within the extracellular domain of the mutant calreticulin protein. In one aspect, the mutant calreticulin protein is expressed on a cancer cell. As used herein, "mutant calreticulin" includes proteins comprising mutations, e.g., point mutations, fragments, insertions, deletions and splice variants of full length wild-type mutant calreticulin.

The term "antibody," as used herein, refers to a protein, or polypeptide sequence derived from an immunoglobulin molecule which specifically binds with an antigen. Antibodies can be polyclonal or monoclonal, multiple or single chain, or intact immunoglobulins, and may be derived from natural sources or from recombinant sources. Antibodies can be tetramers of immunoglobulin molecules.

The term "antibody fragment" refers to at least one portion of an intact antibody, or recombinant variants thereof, and refers to the antigen binding domain, e.g., an antigenic determining variable region of an intact antibody, that is sufficient to confer recognition and specific binding of the antibody fragment to a target, such as an antigen. Examples of antibody fragments include, but are not limited to, Fab, Fab', F(ab')$_2$, and Fv fragments, scFv antibody fragments, linear antibodies, single domain antibodies such as sdAb (either $V_L$ or $V_H$), camelid VHH domains, and multi-specific antibodies formed from antibody fragments such as a bivalent fragment comprising two Fab fragments linked by a disulfide bridge at the hinge region, and an isolated CDR or other epitope binding fragments of an antibody. An antigen binding fragment can also be incorporated into single domain antibodies, maxibodies, minibodies, nanobodies, intrabodies, diabodies, triabodies, tetrabodies, v-NAR and bis-scFv (see, e.g., Hollinger and Hudson, Nature Biotechnology 23:1126-1136, 2005). Antigen binding fragments can also be grafted into scaffolds based on polypeptides such as a fibronectin type III (Fn3)(see U.S. Pat. No. 6,703,199, which describes fibronectin polypeptide minibodies).

The term "scFv" refers to a fusion protein comprising at least one antibody fragment comprising a variable region of a light chain and at least one antibody fragment comprising a variable region of a heavy chain, wherein the light and heavy chain variable regions are contiguously linked via a short flexible polypeptide linker, and capable of being expressed as a single chain polypeptide, and wherein the scFv retains the specificity of the intact antibody from which it is derived. Unless specified, as used herein an scFv may have the $V_L$ and $V_H$ variable regions in either order, e.g., with respect to the N-terminal and C-terminal ends of the polypeptide, the scFv may comprise $V_L$-linker-$V_H$ or may comprise $V_H$-linker-$V_L$.

The term "complementarity determining region" or "CDR," as used herein, refers to the sequences of amino acids within antibody variable regions which confer antigen specificity and binding affinity. For example, in general, there are three CDRs in each heavy chain variable region (e.g., HCDR1, HCDR2, and HCDR3) and three CDRs in each light chain variable region (LCDR1, LCDR2, and LCDR3). The precise amino acid sequence boundaries of a given CDR can be determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme), Al-Lazikani et al., (1997) JMB 273,927-948 ("Chothia" numbering scheme), or a combination thereof. Under the Kabat numbering scheme, in some embodiments, the CDR amino acid residues in the heavy chain variable domain ($V_H$) are numbered 31-35 (HCDR1), 50-65 (HCDR2), and 95-102 (HCDR3); and the CDR amino acid residues in the light chain variable domain ($V_L$) are numbered 24-34 (LCDR1), 50-56 (LCDR2), and 89-97 (LCDR3). Under the Chothia numbering scheme, in some embodiments, the CDR amino acids in the $V_H$ are numbered 26-32 (HCDR1), 52-56 (HCDR2), and 95-102 (HCDR3); and the CDR amino acid residues in the $V_L$ are numbered 26-32 (LCDR1), 50-52 (LCDR2), and 91-96 (LCDR3). In a combined Kabat and Chothia numbering scheme, in some embodiments, the CDRs correspond to the amino acid residues that are part of a Kabat CDR, a Chothia CDR, or both. For instance, in some embodiments, the CDRs correspond to amino acid residues 26-35 (HCDR1), 50-65 (HCDR2), and 95-102 (HCDR3) in a $V_H$, e.g., a mammalian $V_H$, e.g., a human $V_H$; and amino acid residues 24-34 (LCDR1), 50-56 (LCDR2), and 89-97 (LCDR3) in a $V_L$, e.g., a mammalian $V_L$, e.g., a human $V_L$.

The portion of the CAR composition comprising an antibody or antibody fragment thereof may exist in a variety of forms where the antigen binding domain is expressed as part of a contiguous polypeptide chain including, for example, a single domain antibody fragment (sdAb), a single chain antibody (scFv) and a humanized or human antibody (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426). In one aspect, the antigen binding domain of a CAR composition comprises an antibody fragment. In a further aspect, the CAR comprises an antibody fragment that comprises a scFv.

As used herein, the term "binding domain" or "antibody molecule" (also referred to herein as "anti-target (e.g., mutant calreticulin) binding domain") refers to a protein, e.g., an immunoglobulin chain or fragment thereof, comprising at least one immunoglobulin variable domain sequence. The term "binding domain" or "antibody molecule" encompasses antibodies and antibody fragments. In an embodiment, an antibody molecule is a multispecific antibody molecule, e.g., it comprises a plurality of immunoglobulin variable domain sequences, wherein a first immunoglobulin variable domain sequence of the plurality has binding specificity for a first epitope and a second immunoglobulin variable domain sequence of the plurality has binding specificity for a second epitope. In an embodiment, a multispecific antibody molecule is a bispecific antibody molecule. A bispecific antibody has specificity for no more than two antigens. A bispecific antibody molecule is characterized by a first immunoglobulin variable domain sequence which has binding specificity for a first epitope and a second immunoglobulin variable domain sequence that has binding specificity for a second epitope.

The term "antibody heavy chain," refers to the larger of the two types of polypeptide chains present in antibody molecules in their naturally occurring conformations, and which normally determines the class to which the antibody belongs.

The term "antibody light chain," refers to the smaller of the two types of polypeptide chains present in antibody molecules in their naturally occurring conformations. Kappa (κ) and lambda (λ) light chains refer to the two major antibody light chain isotypes.

The term "recombinant antibody" refers to an antibody which is generated using recombinant DNA technology, such as, for example, an antibody expressed by a bacteriophage or yeast expression system. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using recombinant DNA or amino acid sequence technology which is available and well known in the art.

The term "antigen" or "Ag" refers to a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to encode polypeptides that elicit the desired immune response. Moreover, a skilled artisan will understand that an antigen need not be encoded by a "gene" at all. It is readily apparent that an antigen can be generated synthesized or can be derived from a biological sample, or might be macromolecule besides a polypeptide. Such a biological sample can include, but is not limited to a tissue sample, a tumor sample, a cell or a fluid with other biological components.

The term "anti-tumor effect" refers to a biological effect which can be manifested by various means, including but not limited to, e.g., a decrease in tumor volume, a decrease in the number of tumor cells, a decrease in the number of metastases, an increase in life expectancy, decrease in tumor cell proliferation, decrease in tumor cell survival, or amelioration of various physiological symptoms associated with the cancerous condition. An "anti-tumor effect" can also be manifested by the ability of the peptides, polynucleotides, cells and antibodies in prevention of the occurrence of tumor in the first place.

The term "anti-cancer effect" refers to a biological effect which can be manifested by various means, including but not limited to, e.g., a decrease in tumor volume, a decrease in the number of cancer cells, a decrease in the number of metastases, an increase in life expectancy, decrease in cancer cell proliferation, decrease in cancer cell survival, or amelioration of various physiological symptoms associated with the cancerous condition. An "anti-cancer effect" can also be manifested by the ability of the peptides, polynucleotides, cells and antibodies in prevention of the occurrence of cancer in the first place.

The term "anti-tumor effect" refers to a biological effect which can be manifested by various means, including but not limited to, e.g., a decrease in tumor volume, a decrease in the number of tumor cells, a decrease in tumor cell proliferation, or a decrease in tumor cell survival.

The term "autologous" refers to any material derived from the same individual to whom it is later to be re-introduced into the individual.

The term "allogeneic" refers to any material derived from a different animal of the same species as the individual to whom the material is introduced. Two or more individuals are said to be allogeneic to one another when the genes at one or more loci are not identical. In some aspects, allogeneic material from individuals of the same species may be sufficiently unlike genetically to interact antigenically.

The term "xenogeneic" refers to a graft derived from an animal of a different species. The term "apheresis" as used herein refers to the art-recognized extracorporeal process by which the blood of a donor or patient is removed from the donor or patient and passed through an apparatus that separates out selected particular constituent(s) and returns the remainder to the circulation of the donor or patient, e.g., by retransfusion. Thus, in the context of "an apheresis sample" refers to a sample obtained using apheresis.

The term "combination" refers to either a fixed combination in one dosage unit form, or a combined administration where a compound of the present invention and a combination partner (e.g. another drug as explained below, also referred to as "therapeutic agent" or "co-agent") may be administered independently at the same time or separately within time intervals, especially where these time intervals allow that the combination partners show a cooperative, e.g. synergistic effect. The single components may be packaged in a kit or separately. One or both of the components (e.g., powders or liquids) may be reconstituted or diluted to a desired dose prior to administration. The terms "co-administration" or "combined administration" or the like as utilized herein are meant to encompass administration of the selected combination partner to a single subject in need thereof (e.g. a patient), and are intended to include treatment regimens in which the agents are not necessarily administered by the same route of administration or at the same time. The term "pharmaceutical combination" as used herein means a product that results from the mixing or combining of more than one active ingredient and includes both fixed and non-fixed combinations of the active ingredients. The term "fixed combination" means that the active ingredients, e.g. a compound of the present invention and a combination partner, are both administered to a patient simultaneously in the form of a single entity or dosage. The term "non-fixed combination" means that the active ingredients, e.g. a compound of the present invention and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more active ingredients.

The term "cancer" refers to a disease characterized by the rapid and uncontrolled growth of aberrant cells. Cancer cells can spread locally or through the bloodstream and lymphatic system to other parts of the body. Examples of various cancers are described herein and include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like. The terms "tumor" and "cancer" are used interchangeably herein, e.g., both terms encompass solid and liquid, e.g., diffuse or circulating, tumors. As used herein, the term "cancer" or "tumor" includes premalignant, as well as malignant cancers and tumors.

"Derived from" as that term is used herein, indicates a relationship between a first and a second molecule. It generally refers to structural similarity between the first molecule and a second molecule and does not connotate or include a process or source limitation on a first molecule that is derived from a second molecule. For example, in the case of an intracellular signaling domain that is derived from a CD3zeta molecule, the intracellular signaling domain retains sufficient CD3zeta structure such that is has the required function, namely, the ability to generate a signal under the appropriate conditions. It does not connotate or include a limitation to a particular process of producing the intracellular signaling domain, e.g., it does not mean that, to provide the intracellular signaling domain, one must start with a CD3zeta sequence and delete unwanted sequence, or impose mutations, to arrive at the intracellular signaling domain.

The phrase "disease associated with expression of mutant calreticulin" as used herein includes but is not limited to, a disease associated with expression of mutant calreticulin or condition associated with a cell which expresses mutant calreticulin (e.g., wild-type or mutant calreticulin) including, e.g., a proliferative disease such as a cancer or malignancy; a precancerous condition such as a myelodysplasia, a myelodysplastic syndrome or a preleukemia; or a non-cancer related indication associated with a cell which expresses mutant calreticulin (e.g., wild-type or mutant calreticulin). In one aspect, a cancer associated with expression of mutant calreticulin (e.g., wild-type or mutant calreticulin) is a hematological cancer. In one aspect, the disease includes AML, ALL, hairy cell leukemia, Prolymphocytic leukemia, Chronic myeloid leukemia (CML), Hodgkin lymphoma, Blastic plasmacytoid dendritic cell neoplasm, lymphoblastic B-cell leukemia (B-cell acute lymphoid leukemia, BALL), acute lymphoblastic T-cell leukemia (T-cell acute lymphoid leukemia (TALL); myelodysplastic syndrome; a myeloproliferative neoplasm; a histiocytic disorder (e.g., a mast cell disorder or a blastic plasmacytoid dendritic cell neoplasm); a mast cell disorder, e.g., systemic mastocytosis or mast cell leukemia, and the like. Further disease associated with expression of mutant calreticulin expression include, but are not limited to, e.g., atypical and/or non-classical cancers, malignancies, precancerous conditions or proliferative diseases associated with expression of mutant calreticulin. Non-cancer related indications associated with expression of mutant calreticulin may also be included.

In some embodiments, the tumor antigen (e.g., mutant calreticulin)-expressing cell expresses, or at any time expressed, mRNA encoding the tumor antigen. In an embodiment, the tumor antigen (e.g., mutant calreticulin)-expressing cell produces the tumor antigen protein (e.g., wild-type or mutant), and the tumor antigen protein may be present at normal levels or reduced levels. In an embodiment, the tumor antigen (e.g., mutant calreticulin)-expressing cell produced detectable levels of a tumor antigen protein at one point, and subsequently produced substantially no detectable tumor antigen protein.

The term "conservative sequence modifications" refers to amino acid modifications that do not significantly affect or alter the binding characteristics of the antibody or antibody fragment containing the amino acid sequence. Such conservative modifications include amino acid substitutions, additions and deletions. Modifications can be introduced into an antibody or antibody fragment by standard techniques known in the art, such as site-directed mutagenesis and PCR-mediated mutagenesis. Conservative substitutions are ones in which the amino acid residue is replaced with an amino acid residue having a similar side chain Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within a CAR can be replaced with other amino acid residues from the same side chain family and the altered CAR can be tested using the functional assays described herein.

The term "stimulation," refers to a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-β, and/or reorganization of cytoskeletal structures, and the like.

The term "stimulatory molecule," refers to a molecule expressed by a T cell that provides the primary cytoplasmic signaling sequence(s) that regulate primary activation of the TCR complex in a stimulatory way for at least some aspect of the T cell signaling pathway. In one aspect, the primary signal is initiated by, for instance, binding of a TCR/CD3 complex with an MHC molecule loaded with peptide, and which leads to mediation of a T cell response, including, but not limited to, proliferation, activation, differentiation, and the like. A primary cytoplasmic signaling sequence (also referred to as a "primary signaling domain") that acts in a stimulatory manner may contain a signaling motif which is known as immunoreceptor tyrosine-based activation motif or ITAM. Examples of an ITAM containing primary cytoplasmic signaling sequence that is of particular use in the invention includes, but is not limited to, those derived from TCR zeta, FcR gamma, FcR beta, CD3 gamma, CD3 delta, CD3 epsilon, CD5, CD22, CD79a, CD79b, CD278 (also known as "ICOS"), FcεRI, CD66d, DAP10 and DAP12. In a specific CAR, the intracellular signaling domain in any one or more CARS comprises an intracellular signaling sequence, e.g., a primary signaling sequence of CD3-zeta. In a specific CAR, the primary signaling sequence of CD3-zeta is the sequence provided as SEQ ID NO:9, or the equivalent residues from a non-human species, e.g., mouse, rodent, monkey, ape and the like. In a specific CAR, the primary signaling sequence of CD3-zeta is the sequence as provided in SEQ ID NO:10, or the equivalent residues from a non-human species, e.g., mouse, rodent, monkey, ape and the like.

The term "antigen presenting cell" or "APC" refers to an immune system cell such as an accessory cell (e.g., a B-cell, a dendritic cell, and the like) that displays a foreign antigen complexed with major histocompatibility complexes (MHC's) on its surface. T-cells may recognize these complexes using their T-cell receptors (TCRs). APCs process antigens and present them to T-cells.

An "intracellular signaling domain," as the term is used herein, refers to an intracellular portion of a molecule. The intracellular signaling domain can generate a signal that promotes an immune effector function of the CAR containing cell, e.g., a CART cell or CAR-expressing NK cell. Examples of immune effector function, e.g., in a CART cell or CAR-expressing NK cell, include cytolytic activity and helper activity, including the secretion of cytokines. In embodiments, the intracellular signal domain transduces the effector function signal and directs the cell to perform a specialized function. While the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

In an embodiment, the intracellular signaling domain can comprise a primary intracellular signaling domain. Exemplary primary intracellular signaling domains include those derived from the molecules responsible for primary stimulation, or antigen dependent simulation. In an embodiment, the intracellular signaling domain can comprise a costimulatory intracellular domain. Exemplary costimulatory intracellular signaling domains include those derived from molecules responsible for costimulatory signals, or antigen independent stimulation. For example, in the case of a CAR-expressing immune effector cell, e.g., CART cell or CAR-expressing NK cell, a primary intracellular signaling domain can comprise a cytoplasmic sequence of a T cell receptor, and a costimulatory intracellular signaling domain can comprise cytoplasmic sequence from co-receptor or costimulatory molecule.

A primary intracellular signaling domain can comprise a signaling motif which is known as an immunoreceptor tyrosine-based activation motif or ITAM. Examples of ITAM containing primary cytoplasmic signaling sequences include, but are not limited to, those derived from CD3 zeta, FcR gamma, FcR beta, CD3 gamma, CD3 delta, CD3 epsilon, CDS, CD22, CD79a, CD79b, CD278 ("ICOS"), FcεRI, CD66d, DAP10, and DAP12.

The term "zeta" or alternatively "zeta chain", "CD3-zeta" or "TCR-zeta" is defined as the protein provided as GenBan Acc. No. BAG36664.1, or the equivalent residues from a non-human species, e.g., mouse, rodent, monkey, ape and the like, and a "zeta stimulatory domain" or alternatively a "CD3-zeta stimulatory domain" or a "TCR-zeta stimulatory domain" is defined as the amino acid residues from the cytoplasmic domain of the zeta chain that are sufficient to functionally transmit an initial signal necessary for T cell activation. In one aspect the cytoplasmic domain of zeta comprises residues 52 through 164 of GenBank Acc. No. BAG36664.1 or the equivalent residues from a non-human species, e.g., mouse, rodent, monkey, ape and the like, that are functional orthologs thereof.

The term "costimulatory molecule" refers to the cognate binding partner on a T cell that specifically binds with a costimulatory ligand, thereby mediating a costimulatory response by the T cell, such as, but not limited to, proliferation. Costimulatory molecules are cell surface molecules other than antigen receptors or their ligands that are required for an efficient immune response. Costimulatory molecules include, but are not limited to an a MHC class I molecule, TNF receptor proteins, Immunoglobulin-like proteins, cytokine receptors, integrins, signaling lymphocytic activation molecules (SLAM proteins), activating NK cell receptors, BTLA, a Toll ligand receptor, OX40, CD2, CD7, CD27, CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, $V_L$A1, CD49a, ITGA4, IA4, CD49D, ITGA6, $V_L$A-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83.

A costimulatory intracellular signaling domain refers to the intracellular portion of a costimulatory molecule. The intracellular signaling domain can comprise the entire intracellular portion, or the entire native intracellular signaling domain, of the molecule from which it is derived, or a functional fragment thereof.

The term "4-1BB" refers to a member of the TNFR superfamily with an amino acid sequence provided as GenBank Acc. No. AAA62478.2, or the equivalent residues from a non-human species, e.g., mouse, rodent, monkey, ape and the like; and a "4-1BB costimulatory domain" is defined as amino acid residues 214-255 of GenBank Acc. No. AAA62478.2, or the equivalent residues from a non-human species, e.g., mouse, rodent, monkey, ape and the like. In one aspect, the "4-1BB costimulatory domain" is the sequence provided as SEQ ID NO:7 or the equivalent residues from a non-human species, e.g., mouse, rodent, monkey, ape and the like.

"Immune effector cell," as that term is used herein, refers to a cell that is involved in an immune response, e.g., in the promotion of an immune effector response. Examples of immune effector cells include T cells, e.g., alpha/beta T cells and gamma/delta T cells, B cells, natural killer (NK) cells, natural killer T (NKT) cells, mast cells, and myeloic-derived phagocytes.

"Immune effector function or immune effector response," as that term is used herein, refers to function or response, e.g., of an immune effector cell, that enhances or promotes an immune attack of a target cell. E.g., an immune effector function or response refers a property of a T or NK cell that promotes killing or the inhibition of growth or proliferation, of a target cell. In the case of a T cell, primary stimulation and co-stimulation are examples of immune effector function or response.

The term "effector function" refers to a specialized function of a cell. Effector function of a T cell, for example, may be cytolytic activity or helper activity including the secretion of cytokines.

The term "encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (e.g., rRNA, tRNA and mRNA) or a defined sequence of amino acids and the biological properties resulting therefrom. Thus, a gene, cDNA, or RNA, encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or a RNA may also include introns to the extent that the nucleotide sequence encoding the protein may in some version contain an intron(s).

The term "effective amount" or "therapeutically effective amount" are used interchangeably herein, and refer to an amount of a compound, formulation, material, or composition, as described herein effective to achieve a particular biological result.

The term "endogenous" refers to any material from or produced inside an organism, cell, tissue or system.

The term "exogenous" refers to any material introduced from or produced outside an organism, cell, tissue or system.

The term "expression" refers to the transcription and/or translation of a particular nucleotide sequence driven by a promoter.

The term "transfer vector" refers to a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "transfer vector" includes an autonomously replicating plasmid or a virus. The term should also be construed to further include non-plasmid and non-viral compounds which facilitate transfer of nucleic acid into cells, such as, for example, a polylysine compound, liposome, and the like. Examples of viral transfer vectors include, but are not limited to, adenoviral vectors, adeno-associated virus vectors, retroviral vectors, lentiviral vectors, and the like.

The term "expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, including cosmids, plasmids (e.g., naked or contained in liposomes) and viruses (e.g., lentiviruses, retroviruses, adenoviruses, and adeno-associated viruses) that incorporate the recombinant polynucleotide.

The term "vector" as used herein refers to any vehicle that can be used to deliver and/or express a nucleic acid molecule. It can be a transfer vector or an expression vector as described herein.

The term "lentivirus" refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector.

The term "lentiviral vector" refers to a vector derived from at least a portion of a lentivirus genome, including especially a self-inactivating lentiviral vector as provided in Milone et al., Mol. Ther. 17(8): 1453-1464 (2009). Other examples of lentivirus vectors that may be used in the clinic, include but are not limited to, e.g., the LENTIVECTOR® gene delivery technology from Oxford BioMedica, the LENTIMAX™ vector system from Lentigen and the like. Nonclinical types of lentiviral vectors are also available and would be known to one skilled in the art.

The term "homologous" or "identity" refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous or identical at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

"Humanized" forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. For the most part, humanized antibodies and antibody fragments thereof are human immunoglobulins (recipient antibody or antibody fragment) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, a humanized antibody/antibody fragment can comprise residues which are found neither in the recipient antibody nor in the imported CDR or framework sequences. These modifications can further refine and optimize antibody or antibody fragment performance. In general, the humanized antibody or antibody fragment thereof will comprise substantially all of at least one, and typically two, variable domains, in which all or substantially all of the CDR regions correspond to those of a non-human immunoglobulin and all or a significant portion of the FR regions are those of a human immunoglobulin sequence. The humanized antibody or antibody fragment can also comprise at least a portion of an immunoglobulin constant region (Fc), typically that of a human immunoglobulin. For further details, see Jones et al., Nature, 321: 522-525, 1986; Reichmann et al., Nature, 332: 323-329, 1988; Presta, Curr. Op. Struct. Biol., 2: 593-596, 1992.

"Fully human" refers to an immunoglobulin, such as an antibody or antibody fragment, where the whole molecule is of human origin or consists of an amino acid sequence identical to a human form of the antibody or immunoglobulin.

The term "isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

The term "operably linked" or "transcriptional control" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Operably linked DNA sequences can be contiguous with each other and, e.g., where necessary to join two protein coding regions, are in the same reading frame.

The term "parenteral" administration of an immunogenic composition includes, e.g., subcutaneous (s.c.), intravenous (i.v.), intramuscular (i.m.), or intrasternal injection, intratumoral, or infusion techniques.

The term "nucleic acid," "polynucleotide," or "nucleic acid molecule" refers to deoxyribonucleic acid (DNA) or ribonucleic acid (RNA), or a combination of a DNA or RNA thereof, and polymers thereof in either single- or double-stranded form. The term "nucleic acid" includes a gene, cDNA or an mRNA. In one embodiment, the nucleic acid molecule is synthetic (e.g., chemically synthesized) or recombinant. Unless specifically limited, the term encompasses nucleic acids containing analogues or derivatives of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

The terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. A polypeptide includes a natural peptide, a recombinant peptide, or a combination thereof.

The term "promoter" refers to a DNA sequence recognized by the synthetic machinery of the cell, or introduced synthetic machinery, required to initiate the specific transcription of a polynucleotide sequence.

The term "promoter/regulatory sequence" refers to a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

The term "constitutive" promoter refers to a nucleotide sequence which, when operably linked with a polynucleotide which encodes or specifies a gene product, causes the gene product to be produced in a cell under most or all physiological conditions of the cell.

The term "inducible" promoter refers to a nucleotide sequence which, when operably linked with a polynucleotide which encodes or specifies a gene product, causes the gene product to be produced in a cell substantially only when an inducer which corresponds to the promoter is present in the cell.

The term "tissue-specific" promoter refers to a nucleotide sequence which, when operably linked with a polynucleotide encodes or specified by a gene, causes the gene product to be produced in a cell substantially only if the cell is a cell of the tissue type corresponding to the promoter.

The term "cancer associated antigen" or "tumor antigen" interchangeably refers to a molecule (typically a protein, carbohydrate or lipid) that is expressed on the surface of a cancer cell, either entirely or as a fragment (e.g., MHC/peptide), and which is useful for the preferential targeting of a pharmacological agent to the cancer cell. In some embodiments, a tumor antigen is a marker expressed by both normal cells and cancer cells. In some embodiments, a tumor antigen is a cell surface molecule that is overexpressed in a cancer cell in comparison to a normal cell, for instance, 1-fold over expression, 2-fold overexpression, 3-fold overexpression or more in comparison to a normal cell. In some embodiments, a tumor antigen is a cell surface molecule that is inappropriately synthesized in the cancer cell, for instance, a molecule that contains deletions, additions or mutations in comparison to the molecule expressed on a normal cell. In some embodiments, a tumor antigen will be expressed exclusively on the cell surface of a cancer cell, entirely or as a fragment (e.g., MHC/peptide), and not synthesized or expressed on the surface of a normal cell. In some embodiments, the CARs of the present invention includes CARs comprising an antigen binding domain (e.g., antibody or antibody fragment) that binds to a MHC presented peptide. Normally, peptides derived from endogenous proteins fill the pockets of Major histocompatibility complex (MHC) class I molecules, and are recognized by T cell receptors (TCRs) on $CD8^+$ T lymphocytes. The MHC class I complexes are constitutively expressed by all nucleated cells. In cancer, virus-specific and/or tumor-specific peptide/MHC complexes represent a unique class of cell surface targets for immunotherapy. TCR-like antibodies targeting peptides derived from viral or tumor antigens in the context of human leukocyte antigen (HLA)-A1 or HLA-A2 have been described (see, e.g., Sastry et al., J Virol. 2011 85(5):1935-1942; Sergeeva et al., Blood, 2011 117(16): 4262-4272; Verma et al., J Immunol 2010 184(4):2156-2165; Willemsen et al., Gene Ther 2001 8(21):1601-1608; Dao et al., Sci Transl Med 2013 5(176):176ra33; Tassev et al., Cancer Gene Ther 2012 19(2):84-100). For example, TCR-like antibody can be identified from screening a library, such as a human scFv phage displayed library.

The term "flexible polypeptide linker" or "linker" as used in the context of a scFv refers to a peptide linker that consists of amino acids such as glycine and/or serine residues used alone or in combination, to link variable heavy and variable light chain regions together. In one embodiment, the flexible polypeptide linker is a Gly/Ser linker and comprises the amino acid sequence (Gly-Gly-Gly-Ser)n, where n is a positive integer equal to or greater than 1 (SEQ ID NO: 47). For example, n=1, n=2, n=3. n=4, n=5 and n=6, n=7, n=8, n=9 and n=10 In one embodiment, the flexible polypeptide linkers include, but are not limited to, $(Gly_4 Ser)_4$ (SEQ ID NO: 36) or $(Gly_4 Ser)_3$ (SEQ ID NO: 48). In another embodiment, the linkers include multiple repeats of $(Gly_2Ser)$, (GlySer) or $(Gly_3Ser)$ (SEQ ID NO: 49). Also included within the scope are linkers described in WO2012/138475, incorporated herein by reference).

As used herein, a 5' cap (also termed an RNA cap, an RNA 7-methylguanosine cap or an RNA m7G cap) is a modified guanine nucleotide that has been added to the "front" or 5' end of a eukaryotic messenger RNA shortly after the start of transcription. The 5' cap consists of a terminal group which is linked to the first transcribed nucleotide. Its presence is critical for recognition by the ribosome and protection from RNases. Cap addition is coupled to transcription, and occurs co-transcriptionally, such that each influences the other. Shortly after the start of transcription, the 5' end of the mRNA being synthesized is bound by a cap-synthesizing complex associated with RNA polymerase. This enzymatic complex catalyzes the chemical reactions that are required for mRNA capping. Synthesis proceeds as a multi-step biochemical reaction. The capping moiety can be modified to modulate functionality of mRNA such as its stability or efficiency of translation.

As used herein, "in vitro transcribed RNA" refers to RNA, preferably mRNA, that has been synthesized in vitro. Generally, the in vitro transcribed RNA is generated from an in vitro transcription vector. The in vitro transcription vector comprises a template that is used to generate the in vitro transcribed RNA.

As used herein, a "poly(A)" is a series of adenosines attached by polyadenylation to the mRNA. In the preferred embodiment of a construct for transient expression, the polyA is between 50 and 5000 (SEQ ID NO: 43), preferably greater than 64, more preferably greater than 100, most preferably greater than 300 or 400. poly(A) sequences can be modified chemically or enzymatically to modulate mRNA functionality such as localization, stability or efficiency of translation.

As used herein, "polyadenylation" refers to the covalent linkage of a polyadenylyl moiety, or its modified variant, to a messenger RNA molecule. In eukaryotic organisms, most messenger RNA (mRNA) molecules are polyadenylated at the 3' end. The 3' poly(A) tail is a long sequence of adenine nucleotides (often several hundred) added to the pre-mRNA through the action of an enzyme, polyadenylate polymerase. In higher eukaryotes, the poly(A) tail is added onto transcripts that contain a specific sequence, the polyadenylation signal. The poly(A) tail and the protein bound to it aid in protecting mRNA from degradation by exonucleases. Polyadenylation is also important for transcription termination, export of the mRNA from the nucleus, and translation. Polyadenylation occurs in the nucleus immediately after transcription of DNA into RNA, but additionally can also occur later in the cytoplasm. After transcription has been terminated, the mRNA chain is cleaved through the action of an endonuclease complex associated with RNA polymerase. The cleavage site is usually characterized by the presence of the base sequence AAUAAA near the cleavage site. After the mRNA has been cleaved, adenosine residues are added to the free 3' end at the cleavage site.

As used herein, "transient" refers to expression of a non-integrated transgene for a period of hours, days or weeks, wherein the period of time of expression is less than the period of time for expression of the gene if integrated into the genome or contained within a stable plasmid replicon in the host cell.

As used herein, the terms "treat", "treatment" and "treating" refer to the reduction or amelioration of the progression, severity and/or duration of a proliferative disorder, or the amelioration of one or more symptoms (preferably, one or more discernible symptoms) of a proliferative disorder resulting from the administration of one or more therapies (e.g., one or more therapeutic agents such as a CAR). In specific embodiments, the terms "treat", "treatment" and "treating" refer to the amelioration of at least one measurable physical parameter of a proliferative disorder, such as growth of a tumor, not necessarily discernible by the patient. In other embodiments the terms "treat", "treatment" and "treating"-refer to the inhibition of the progression of a proliferative disorder, either physically by, e.g., stabilization of a discernible symptom, physiologically by, e.g., stabilization of a physical parameter, or both. In other embodiments the terms "treat", "treatment" and "treating" refer to the reduction or stabilization of tumor size or cancerous cell count.

The term "signal transduction pathway" refers to the biochemical relationship between a variety of signal transduction molecules that play a role in the transmission of a signal from one portion of a cell to another portion of a cell. The phrase "cell surface receptor" includes molecules and complexes of molecules capable of receiving a signal and transmitting signal across the membrane of a cell.

The term "subject" is intended to include living organisms in which an immune response can be elicited (e.g., mammals, human).

The term, a "substantially purified" cell refers to a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some aspects, the cells are cultured in vitro. In other aspects, the cells are not cultured in vitro.

The term "therapeutic" as used herein means a treatment. A therapeutic effect is obtained by reduction, suppression, remission, or eradication of a disease state.

The term "prophylaxis" as used herein means the prevention of or protective treatment for a disease or disease state.

In the context of the present invention, "tumor antigen" or "hyperproliferative disorder antigen" or "antigen associated with a hyperproliferative disorder" refers to antigens that are common to specific hyperproliferative disorders. In certain aspects, the hyperproliferative disorder antigens of the present invention are derived from, cancers including but not limited to primary or metastatic melanoma, thymoma, lymphoma, sarcoma, lung cancer, liver cancer, non-Hodgkin lymphoma, non-Hodgkin lymphoma, leukemias, uterine cancer, cervical cancer, bladder cancer, kidney cancer and adenocarcinomas such as breast cancer, prostate cancer, ovarian cancer, pancreatic cancer, and the like.

The term "transfected" or "transformed" or "transduced" refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The term "specifically binds," refers to an antibody, or a ligand, which recognizes and binds with a cognate binding partner (e.g., a stimulatory and/or costimulatory molecule present on a T cell) protein present in a sample, but which antibody or ligand does not substantially recognize or bind other molecules in the sample.

"Regulatable chimeric antigen receptor (RCAR)," as used herein, refers to a set of polypeptides, typically two in the simplest embodiments, which when in an immune effector cell, provides the cell with specificity for a target cell, typically a cancer cell, and with regulatable intracellular signal generation. In some embodiments, an RCAR comprises at least an extracellular antigen binding domain, a transmembrane and a cytoplasmic signaling domain (also referred to herein as "an intracellular signaling domain") comprising a functional signaling domain derived from a stimulatory molecule and/or costimulatory molecule as defined herein in the context of a CAR molecule. In some embodiments, the set of polypeptides in the RCAR are not contiguous with each other, e.g., are in different polypeptide chains. In some embodiments, the RCAR includes a dimerization switch that, upon the presence of a dimerization molecule, can couple the polypeptides to one another, e.g., can couple an antigen binding domain to an intracellular signaling domain. In some embodiments, the RCAR is expressed in a cell (e.g., an immune effector cell) as described herein, e.g., an RCAR-expressing cell (also referred to herein as "RCARX cell"). In an embodiment the RCARX cell is a T cell, and is referred to as a RCART cell. In an embodiment the RCARX cell is an NK cell, and is referred to as a RCARN cell. The RCAR can provide the RCAR-expressing cell with specificity for a target cell, typically a cancer cell, and with regulatable intracellular signal generation or proliferation, which can optimize an immune effector property of the RCAR-expressing cell. In embodiments, an RCAR cell relies at least in part, on an antigen binding domain to provide specificity to a target cell that comprises the antigen bound by the antigen binding domain.

"Membrane anchor" or "membrane tethering domain", as that term is used herein, refers to a polypeptide or moiety, e.g., a myristoyl group, sufficient to anchor an extracellular or intracellular domain to the plasma membrane.

"Switch domain," as that term is used herein, e.g., when referring to an RCAR, refers to an entity, typically a polypeptide-based entity, that, in the presence of a dimerization molecule, associates with another switch domain. The association results in a functional coupling of a first entity linked to, e.g., fused to, a first switch domain, and a second entity linked to, e.g., fused to, a second switch domain. A first and second switch domain are collectively referred to as a dimerization switch. In embodiments, the first and second switch domains are the same as one another, e.g., they are polypeptides having the same primary amino acid sequence, and are referred to collectively as a homodimerization switch. In embodiments, the first and second switch domains are different from one another, e.g., they are polypeptides having different primary amino acid sequences, and are referred to collectively as a heterodimerization switch. In embodiments, the switch is intracellular. In embodiments, the switch is extracellular. In embodiments, the switch domain is a polypeptide-based entity, e.g., FKBP or FRB-based, and the dimerization molecule is small molecule, e.g., a rapalogue. In embodiments, the switch domain is a polypeptide-based entity, e.g., an scFv that binds a myc peptide, and the dimerization molecule is a polypeptide, a fragment thereof, or a multimer of a polypeptide, e.g., a myc ligand or multimers of a myc ligand that bind to one or more myc scFvs. In embodiments, the switch domain is a polypeptide-based entity, e.g., myc receptor, and the dimerization molecule is an antibody or fragments thereof, e.g., myc antibody.

"Dimerization molecule," as that term is used herein, e.g., when referring to an RCAR, refers to a molecule that promotes the association of a first switch domain with a second switch domain. In embodiments, the dimerization molecule does not naturally occur in the subject, or does not occur in concentrations that would result in significant dimerization. In embodiments, the dimerization molecule is a small molecule, e.g., rapamycin or a rapalogue, e.g, RAD001.

The term "bioequivalent" refers to an amount of an agent other than the reference compound (e.g., RAD001), required to produce an effect equivalent to the effect produced by the reference dose or reference amount of the reference compound (e.g., RAD001). In an embodiment the effect is the level of mTOR inhibition, e.g., as measured by P70 S6 kinase inhibition, e.g., as evaluated in an in vivo or in vitro assay, e.g., as measured by an assay described herein, e.g., the Boulay assay, or measurement of phosphorylated S6 levels by western blot. In an embodiment, the effect is alteration of the ratio of PD-1 positive/PD-1 negative immune effector cells, e.g., T cells or NK cells, as measured by cell sorting. In an embodiment a bioequivalent amount or dose of an mTOR inhibitor is the amount or dose that achieves the same level of P70 S6 kinase inhibition as does the reference dose or reference amount of a reference compound. In an embodiment, a bioequivalent amount or dose of an mTOR inhibitor is the amount or dose that achieves the same level of alteration in the ratio of PD-1 positive/PD-1 negative immune effector cells, e.g., T cells or NK cells as does the reference dose or reference amount of a reference compound.

Ranges: throughout this disclosure, various aspects can be presented in a range format. It should be understood that the description in range format is merely for convenience and brevity and should not be construed as an inflexible limitation on the scope. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. As another example, a range such as 95-99% identity, includes something with 95%, 96%, 97%, 98% or 99% identity, and includes subranges such as 96-99%, 96-98%, 96-97%, 97-99%, 97-98% and 98-99% identity. This applies regardless of the breadth of the range.

Ranges: throughout this disclosure, various aspects can be presented in a range format. It should be understood that the description in range format is merely for convenience and brevity and should not be construed as an inflexible limitation on the scope. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. As another example, a range such as 95-99% identity, includes something with 95%, 96%, 97%, 98% or 99% identity, and includes subranges such as 96-99%, 96-98%, 96-97%, 97-99%, 97-98% and 98-99% identity. This applies regardless of the breadth of the range.

Compositions and Methods

This invention is based, at least in part, on an unexpected discovery of antibody domains that specifically bind to mutant calreticulin. The invention provides anti-mutant calreticulin antibody binding domain construct domain constructs that find use in treating and/or diagnosing diseases associated with expression of mutant calreticulin. The anti-mutant calreticulin antibody binding domain construct domain constructs can specifically bind to mutant calreticulin. In some embodiments, anti-mutant calreticulin antibody binding domain construct domain constructs with enhanced effector function that bind to mutant calreticulin are provided.

Provided herein are anti-mutant calreticulin antibody binding domain constructs that specifically bind to an epitope of mutant calreticulin protein. In some embodiments, an anti-mutant calreticulin antibody binding domain construct binds to the mutant sequence RKMSPARPRTSCREACLQGWTEA (SEQ ID NO: 50) or a fragment thereof or an epitope thereof. In some embodiments, an anti-mutant calreticulin antibody binding domain construct binds to the same epitope of mutant calreticulin as the epitope to which an antibody produced by the hybridoma 8B2-H6-10.7 (deposited under accession number DSM ACC3249 with the depositary institute DSMZ on Sep. 12, 2014 binds).

Provided herein are anti-mutant calreticulin antibody binding domain constructs that can be used in the diagnosis of a myeloid malignancy or in the therapy of a myeloid malignancy. A myeloid malignancy is, for example, a myeloproliferative neoplasm or a myelodysplastic syndrome. The myeloproliferative neoplasm can be primary myelofibrosis (PMF) or essential thrombocythemia (ET). The myelodysplastic syndrome can be refractory anemia with ringed sideroblasts and thrombocythemia (RARS-T).

The anti-mutant calreticulin antibody binding domain constructs can be conjugated to cytotoxic agents and the can be internalized by the cells leading to cell death. The anti-mutant calreticulin antibody binding domain constructs can be used to generate an immune response against the mutant CALR protein, so that the endogenous immune system would recognize it as 'non-self'. The mutant CALR expressing cells can then be killed by the complement system and/or by antibody dependent cellular cytotoxicity (ADCC).

In a certain aspect, the present invention relates to the anti-mutant calreticulin antibody binding domain constructs as defined and provided herein, the anti-mutant calreticulin antibody binding domain constructs as produced by the herein described process, the nucleic acid molecule as described herein, the vector as described herein, the host, the hybridoma and/or the composition as described herein for use in the treatment a myeloid malignancy.

In a certain aspect, the present invention relates a method for the treatment of a myeloid malignancy, said method comprising the administration of the anti-mutant calreticulin antibody binding domain construct as defined and provided herein, the anti-mutant calreticulin antibody binding domain construct as produced by the herein described process, the nucleic acid molecule as described herein, the vector as described herein, the host, the hybridoma and/or the composition as described herein to a subject in need of such a treatment.

In one aspect, the treatment of the myeloid malignancy comprises administering to the subject or patient a therapeutically effective amount of an anti-mutant calreticulin antibody binding domain construct that specifically binds to a mutant calreticulin protein. In one aspect, the anti-mutant calreticulin antibody binding domain construct that specifically binds to a mutant calreticulin protein can reduce expression levels of mutant calreticulin. In one aspect, the anti-mutant calreticulin antibody binding domain construct that specifically binds to a mutant calreticulin protein can reduce levels of activity of mutant calreticulin protein. In one aspect, the anti-mutant calreticulin antibody binding domain construct that specifically binds to a mutant calreticulin protein inhibits or reduces proliferation; causes cytotoxicity; inhibits or reduces metastasis; modulates, inhibits or reduces cell adhesion; modulates, inhibits or reduces migration; or modulates, inhibits or reduces invasion of myeloid malignancy cells expressing mutant calreticulin protein. In one aspect, the anti-mutant calreticulin antibody binding domain construct that specifically binds to a mutant calreticulin protein inhibits or reduces proliferation of myeloid malignancy cells expressing mutant calreticulin protein. In one aspect, the anti-mutant calreticulin antibody binding domain construct that specifically binds to a mutant calreticulin protein causes cytotoxicity to myeloid malignancy cells expressing mutant calreticulin protein. In one aspect, the anti-mutant calreticulin antibody binding domain construct that specifically binds to a mutant calreticulin protein reduces or inhibits migration of myeloid malignancy cells expressing mutant calreticulin protein.

Confirming the anti-myeloid malignancy properties of the anti-mutant calreticulin antibody binding domain constructs can be done using standard assays. For example, a myeloid malignancy cell line is grown and propagated in culture according to methods well known to one of ordinary skill in the art. Various dosages of potentially therapeutic anti-mutant calreticulin antibody binding domain constructs are applied to various cultures of the cell line. The treated cultures and control cultures are then followed over time and scored for reduction in proliferation; reduction in cellular growth; reduction in colony formation; appearance of cytotoxicity; reduction in cell-adhesion; reduction of cell invasion; reduction of degradation of the extracellular matrix; or reduction in cell migration or reduction in cell action through different extracellular matrix proteins. In vivo, the anti-mutant calreticulin antibody binding domain constructs can be tested in animal models of myeloid malignancy. Routes of anti-mutant calreticulin construct administration into animal models like mice, rats etc. include intravenous or intraperitoneal administration. Various dosages of potentially therapeutic anti-mutant calreticulin antibody binding domain constructs can be tested in in vivo models. The treated animals and control are then followed over time and scored for reduction pathological symptoms, like appearance of cytotoxicity; reduction in tumor cell-adhesion; reduction in tumor cell migration or increase in survival.

In one aspect, the anti-mutant calreticulin antibody binding domain construct that specifically binds to mutant calreticulin protein induces, enhances, or mediates ADCC (antibody dependent cellular cytotoxicity) against cells to which it binds. ADCC is one of the mechanism by which an antibody can have a therapeutic effect. ADCC is a cell mechanism where an effector cell of the immune system, mainly Natural Killer cells (NK), lyses a target cell which has been previously bound by specific antibodies. NK cells have specific receptors such as FcγRIIIa which recognize the Fc fragment of immunoglobulins and are responsible for the ADCC response. To test if the anti-mutant calreticulin antibody binding domain constructs have a therapeutic effect through a ADCC mechanism, an in vitro assay can be performed in which target cells will be incubated with different anti-mutant calreticulin antibody binding domain constructs and natural killer cells from human or mouse origin. The effect of the anti-mutant calreticulin antibody binding domain constructs on the cells can be measured by the occurred lyses.

In one aspect, the anti-mutant calreticulin antibody binding domain construct that specifically binds to mutant calreticulin protein induces, enhances, or mediates CDC (complement dependent cytotoxicity) against cells to which it binds. CDC is another immune mechanism to exert cytotoxicity on tumor cells. CDC is a cytolytic cascade mediated by complement proteins in the serum. CDC is initiated by the binding of C1q to the constant region of cell bound anti-mutant calreticulin molecule.

The anti-mutant calreticulin antibody binding domain construct that specifically binds to mutant calreticulin protein can be conjugated to another molecule. In a more specific aspect, the anti-mutant calreticulin antibody binding domain construct is conjugated to a therapeutic agent, such as a toxin, a radioactive agent, inhibitory peptide, or an anti-tumor drug as described herein. The anti-mutant calreticulin antibody binding domain construct can be provided as a pharmaceutical composition comprising the anti-mutant calreticulin antibody binding domain construct conjugated to the therapeutic agent and a pharmaceutically acceptable excipient.

Pharmaceutical compositions of this invention also can be administered in combination therapy ("cotherapy"), i.e., combined with other agents. For example, the combination therapy can include an anti-mutant calreticulin antibody binding domain construct specifically binding to a mutant calreticulin protein of combined with at least one other therapeutic agent (e.g. anti-myeloid malignancy agent) or other therapeutic intervention. If the at least one other therapeutic agent is used in such a "cotherapy" the therapeutic agent is not conjugated (as defined above) to the anti-mutant calreticulin antibody binding domain construct. It is envisaged that the anti-mutant calreticulin antibody binding domain construct used in cotherapy with one or more other therapeutic agents may, in itself, be conjugated to one or more of the therapeutic agents as defined herein above.

The administration of the other therapeutic agent can be prior to, concurrent to or after the administration of the anti-mutant calreticulin antibody binding domain construct. The anti-mutant calreticulin antibody binding domain construct and the one or more other therapeutic agents may also be combined into a single dosage unit. Furthermore, the invention includes a pharmaceutical composition comprising two or more anti-mutant calreticulin antibody binding domain constructs to mutant calreticulin protein. Examples of therapeutic agents that can be used in combination therapy are described in greater detail below.

In one aspect, the therapy can comprise identifying a patient having a risk factor for myeloid malignancy or being suspected of suffering from a myeloid malignancy. In one aspect, the risk factor for a myeloid malignancy can be age, ethnicity, family history of myeloid malignancy, or a genetic predisposing gene or variant thereof. Risk factors for a myeloid malignancy are known to the skilled artisan. Mutant calreticulin protein itself can be a risk factor. For example, the presence of mutant calreticulin protein (or a fragment thereof) (or corresponding nucleic acid encoding same or a part thereof) in a sample of a patient being suspected of suffering from a myeloid malignancy or having a risk factor for myeloid malignancy (like age, ethnicity, family history of myeloid malignancy, or a genetic predisposing gene or variant thereof) can be determined. A patient with a detectable level of mutant calreticulin protein can be treated with the herein provided anti-mutant calreticulin antibody binding domain constructs.

In one embodiment the subject or patient to be treated was previously treated or is currently being treated with radiation therapy. In a more specific embodiment, the invention provides a method of treatment of a myeloid malignancy in a patient wherein said patient was previously treated or is currently being treated with radiation therapy. In one aspect of this embodiment, the treatment comprises identifying a patient previously treated or is currently being treated with radiation therapy and administering to said patient a therapeutic anti-mutant calreticulin antibody binding domain construct. Radiation therapy for a myeloid malignancy is generally classified as external or internal. External radiation therapy usually involves the focusing of high energy beams of energy (e.g., x-rays) on the affected area. Internal radiation therapy involves implanting a radioactive substance or composition comprising a radioactive substance near or inside the myeloid malgi (also referred to as brachytherapy, internal radiation therapy, and/or radiation brachytherapy).

In a certain aspect, the subject or patient will be treated or is currently being treated with a chemotherapy or a radiotherapy.

A patient suffering from a myeloid malignancy can be treated in accordance with the present invention, wherein said patient had discontinued a prior treatment due to disease progression. In one aspect, disease progression occurred due to the developed chemoresistance to the prior treatment. In one aspect, said chemoresistance was or is correlated to (increased) expression or activation of mutant calreticulin. In a specific aspect the anti-mutant calreticulin antibody binding domain constructs confer chemosensitivity to chemoresistant cells, or increase chemosensitivity of the cells.

The following relates to antibody dependent and complement dependent cytotoxicity. In one embodiment, the invention relates to an anti-mutant calreticulin construct specifically binding to mutant calreticulin protein that induces, enhances, or mediates antibody-dependent cellular cytotoxicity (ADCC). ADCC as described above is a type of immune reaction in which a target cell is coated with antibodies and killed by certain types of white blood cells, particularly NK cells. The white blood cells bind to the antibodies and release substances that kill the target cells or microbes. Not all antibodies produce ADCC. Thus, in one aspect, the invention relates to an anti-mutant calreticulin antibody binding domain construct specifically binding to mutant calreticulin protein that can induce, enhance or mediate ADCC. Furthermore, antibodies specifically binding to mutant calreticulin protein can be engineered to have improved, increased or enhanced ADCC. For example an anti-mutant calreticulin antibody binding domain construct that does not induce, enhance, or mediate ADCC can be engineered, e.g., by making certain amino acid modifications to the anti-mutant calreticulin antibody binding domain construct or by producing the anti-mutant calreticulin antibody binding domain construct in certain strains of cells, to induce, enhance or mediate ADCC or have improved/enhanced ADCC properties.

In one aspect, an anti-mutant calreticulin antibody binding domain construct specifically binding to mutant calreticulin protein has antibody-dependent cellular cytotoxicity when used in a human subject. One example of an anti-mutant calreticulin antibody binding domain construct with increased or improved ADCC activity is an anti-mutant calreticulin antibody binding domain construct specifically binding to mutant calreticulin protein that is defucosylated. The anti-mutant calreticulin antibody binding domain construct specifically binding to mutant calreticulin protein and having ADCC or increased ADCC can be generated by producing the anti-mutant calreticulin antibody binding domain construct in a cell-line that lacks or has decreased alpha-1,6-fucosyltransferase activity. The anti-mutant calreticulin antibody binding domain construct specifically binding to mutant calreticulin protein and having ADCC or increased ADCC can be generated by producing the anti-mutant calreticulin antibody binding domain construct in a cell-line that has reduced or lacks GDP-fucose transporter activity. The anti-mutant calreticulin antibody binding domain construct specifically binding to mutant calreticulin protein having ADCC or increased ADCC can be generated by producing the anti-mutant calreticulin antibody binding domain construct in a cell-line that has reduced or lacks GDP-mannose 4,6-dehydratase activity. The anti-mutant calreticulin antibody binding domain construct specifically binding to mutant calreticulin protein and having ADCC or increased ADCC is generated by producing the anti-mutant calreticulin antibody binding domain construct in a cell-line that has reduced or lacks both alpha-1,6-fucosyltransferase activity and GDP-mannose 4,6-dehydratase activity; see e.g., Yamane-Ohnuki et al. (2004) Biotechnol Bioeng. 87(5): 614-22; Imai-Nishiya et al. (2007) BMC Biotechnology 7:84. ADCC can be enhanced or improved by increasing the levels of interleukin-21 (IL-21) in a patient or by treating the patient with IL-21 in combination with the antibody. See e.g., Watanabe et al. Br J Cancer. 2010, 102(3), 520-9.

The anti-mutant calreticulin antibody binding domain construct specifically binding to mutant calreticulin protein can enhance, induce or mediate complement dependent cytotoxicty (CDC). Antibodies can be engineered to have improved, increased or enhanced CDC. For example, an anti-mutant calreticulin antibody binding domain construct that does not induce or mediate CDC can be engineered, e.g., by making certain modifications to the antibody like amino acid mutations in Fc or the hinge region thereby improving or enhancing CDC. Another method of producing CDC or enhancing an anti-mutant calreticulin antibody binding domain construct's CDC is by shuffling IgG1 and IgG3 sequences within the heavy chain constant region. See e.g., Natsume et al. (2008) Cancer Res. 68:3863-3872.

The predominant mutations of CALR are type 1 (CALR del52 mutation) and type 2 mutations. CALR type 1 mutation can be a 52-bp deletion (p.L367fs*46). CALR type 2 mutation can be a 5-bp TTGTC insertion (p.K385fs*47).

It is envisaged herein that the herein provided antibodies can specifically bind to a fragment or part of the C-terminus of mutant calreticulin protein. It is preferred that the herein provided antibodies specifically bind to RRKMSPARPRTSCREACLQGWTEA (SEQ ID NO: 51).

The last 4 amino acids of wild-type calreticulin (KDEL (SEQ ID NO: 52) containing the endoplasmic reticulum retention signal is absent in the mutant calreticulin. This suggests that the mutant protein is less represented in the ER compared to the wild type protein.

In view of the altered C-terminus of mutant calreticulin and the absent KDEL sequence (SEQ ID NO: 52) it was not clear whether mutant calreticulin would have similar biological activities as wild-type calreticulin. For example, it was not known whether mutant calreticulin would be present on the cell surface.

The antibodies provided herein are able to specifically bind to mutant calreticulin in a FACS assay using mutant calreticulin expressing cells. This indicates that mutant calreticulin protein is localized on the cell surface/present on the extracellular side of the plasma membrane/localized at the extracellular side of a plasma membrane. Thus, mutant calreticulin protein can be involved in the same regulatory mechanisms as wild-type calreticulin.

Due to its presence on the cellular surface, mutant calreticulin can be used as a cell surface marker using e.g. cells expressing mutant calreticulin and/or patient samples containing whole/living cells (like blood samples, serum samples or bone marrow samples). For example, patient samples containing whole/living cells can be used in the diagnosis of myeloid malignancies, like for example in the diagnosis of meyloproliferative neoplasms like primary myelofibrosis (PMF) or essential thrombocythemia (ET) or in the diagnosis of a myelodysplastic syndrome, like refractory anemia with ringed sideroblasts and thrombocythemia (RARS-T) using the herein provided antibodies. For example, flow cytometry techniques, like fluorescence-activated cell sorting (FACS) assays, can be used in this analysis. The use of the herein provided antibodies in such assays allows are more convenient and/or quicker analysis compared to Western Blot or ELISA techniques. As a further advantage, such assays require less patient material.

The antibody provided herein can have the capacity to specifically bind/recognize mutant calreticulin protein (or an epitope thereof) when the protein is present on the surface of a cell or when the protein is present on the extracellular side of a plasma membrane or when the protein is localized at the extracellular side of a plasma membrane. The cells can express mutant calreticulin protein. The cells can be part of a sample from a patient. The cells can be derived from (e.g. purified from) a sample from a patient). The cells can be intact, living or whole cells or fixed in formaldehyde/paraformaldehyde. The sample can, for example, be a blood samples, a serum sample or a bone marrow sample.

The anti-mutant calreticulin constructs provided herein can have the capacity to specifically bind/recognize mutant calreticulin protein (or an epitope thereof) when the protein is present on the surface of a cell expressing mutant calreticulin protein or when the protein is present on the extracellular side of a plasma membrane of a cell expressing mutant calreticulin protein or when the protein is localized at the extracellular side of a plasma membrane of a cell expressing mutant calreticulin protein.

Exemplary Anti-Mutant Calreticulin Antibody Binding Domain Construct Domains

In one aspect, the invention provides isolated anti-mutant calreticulin antibody binding domain construct domain constructs that bind to mutant calreticulin. An isolated anti-mutant calreticulin antibody binding domain construct domain construct is one which has been separated from a component of its natural environment. In some embodiments, an anti-mutant calreticulin antibody binding domain construct domain construct is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). (See, e.g., Flatman et al., J. Chromatogr. B 848:79-87 (2007)).

In particular, the anti-mutant calreticulin antibody binding domain construct domains provided bind to a human mutant calreticulin protein. In particular, the anti-mutant calreticulin antibody binding domain constructs provided bind to an epitope of a human mutant calreticulin protein comprising a type 1 or type 2 mutation. A CALR type 1 mutation can be a 52-bp deletion (p.L367fs*46). A CALR type 2 mutation can be a 5-bp TTGTC insertion (p.K385fs*47).

In some embodiments, the anti-mutant calreticulin antibody binding domain construct domains induce lysis of cells expressing mutant calreticulin. Lysis can be induced by any mechanism, such as by mediating an effector function, such as C1q binding and complement dependent cytotoxicity (CDC); Fc receptor binding; antibody-dependent cell-mediated cytotoxicity (ADCC); phagocytosis; downregulation of cell surface receptors (e.g., B cell receptor); B cell activation, or direct induction of cell apoptosis.

In some embodiments, the construct comprising the anti-mutant calreticulin antibody binding domain construct domain is engineered to have at least one increase in effector function as compared to the non-engineered construct comprising the anti-mutant calreticulin antibody binding domain construct domain. Effector functions are biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation. For example, the anti-mutant calreticulin antibody binding domain construct can be glycoengineered to have at least one increase in effector function as compared to the non-glycoengineered parent anti-mutant calreticulin antibody binding domain construct. Antibody-dependent cell-mediated cytotoxicity (ADCC) is the result of the formation of a complex between the IgG Fab portion of the antibody with the mutated calreticulin protein on the cell surface and binding of the Fc portion to the Fc receptors (FcγRs), on effector cells. The increase in effector function can be increased binding affinity to an Fc receptor, increased ADCC; increased phagocytosis; increased cell mediated immunity; increased binding to cytotoxic CD8 T cells; increased binding to NK cells; increased binding to macrophages; increased binding to polymorphonuclear cells; increased binding to monocytes; increased binding to macrophages; increased binding to large granular lymphocytes; increased binding to granulocytes; direct signaling inducing apoptosis; increased dendritic cell maturation; or increased T cell priming. The glycoengineered anti-mutant calreticulin antibody binding domain constructs provide a survival benefit in subjects suffering from cancers which express mutant calreticulin as compared to non-glycoengineered antibodies directed to the same epitope of mutant calreticulin.

In one aspect, an anti-mutant calreticulin antibody binding domain construct comprises a $V_H$ sequence having at least 75%, 80%, 85%, 90%, 91%, 92%, 93%, 94%, 95%, 96%, 97%, 98%, 99%, or 100% sequence identity to the amino acid sequence of SEQ ID NO: 1 or 2. In some embodiments, a $V_H$ sequence having at least 75%, 80%, 85%, 90%, 91%, 92%, 93%, 94%, 95%, 96%, 97%, 98%, or 99% identity contains substitutions (e.g., conservative substitutions), insertions, or deletions relative to the reference sequence, but an anti-mutant calreticulin antibody binding domain construct comprising that sequence retains the ability to bind to mutant calreticulin. The anti-mutant calreticulin antibody binding domain construct can retain the ability to bind to mutant calreticulin. In some embodiments, a total of 1 to 10 amino acids have been substituted, inserted and/or deleted in the amino acid sequence of SEQ ID NO: 1 or 2. In some embodiments, substitutions, insertions, or deletions occur in regions outside the CDRs (e.g., in the FRs). Optionally, the anti-mutant calreticulin antibody binding domain construct comprises the $V_H$ sequence of the amino acid sequence of SEQ ID NO: 1 or 2, including post-translational modifications of that sequence. In a particular embodiment, the $V_H$ comprises one, two or three CDRs selected from: (a) CDR-H1 comprising the amino acid sequence of SEQ ID NO: 7 or 10, (b) CDR-H2 comprising the amino acid sequence of SEQ ID NO: 8 or 11, and (c) CDR-H3 comprising the amino acid sequence of SEQ ID NO: 9 or 12 or 16.

In one aspect, an anti-mutant calreticulin antibody binding domain construct is provided, wherein the antibody comprises a light chain variable domain ($V_L$) having at least 75%, 80%, 85%, 90%, 91%, 92%, 93%, 94%, 95%, 96%, 97%, 98%, 99%, or 100% sequence identity to the amino acid sequence of SEQ ID NO: 3. In some embodiments, a $V_L$ sequence having at least 75%, 80%, 85%, 90%, 91%, 92%, 93%, 94%, 95%, 96%, 97%, 98%, or 99% identity contains substitutions (e.g., conservative substitutions), insertions, or deletions relative to the reference sequence, but an anti-mutant calreticulin antibody binding domain construct comprising that sequence retains the ability to bind to mutant calreticulin. In some embodiments, a total of 1 to 10 amino acids have been substituted, inserted and/or deleted in the amino acid sequence of SEQ ID NO: 3. In some embodiments, the substitutions, insertions, or deletions occur in regions outside the CDRs (e.g., in the FRs). Optionally, the anti-mutant calreticulin antibody binding domain construct comprises the $V_L$ sequence of SEQ ID NO: 3, including post-translational modifications of that sequence. In a particular embodiment, the $V_L$ comprises one, two or three CDRs selected from (a) CDR-L1 comprising the amino acid sequence of SEQ ID NO: 13; (b) CDR-L2 comprising the amino acid sequence of SEQ ID NO: 14; and (c) CDR-L3 comprising the amino acid sequence of SEQ ID NO: 15.

In one aspect, an anti-mutant calreticulin antibody binding domain construct is provided, wherein the antibody comprises a $V_H$ as in any of the embodiments provided above, and a $V_L$ as in any of the embodiments provided above. In some embodiments, the antibody comprises a $V_H$ comprising the amino acid sequence of SEQ ID NO: 1 or 2, and a $V_L$ sequence of SEQ ID NO: 3, including post-translational modifications of those sequences.

In one aspect, an anti-mutant calreticulin antibody binding domain construct is provided, wherein the antibody comprises a $V_H$ selected from any $V_H$ in Table 1. In one aspect, an anti-mutant calreticulin antibody binding domain construct is provided, wherein the antibody comprises a $V_L$ selected from any $V_L$ in Table 2. In one aspect, an anti-mutant calreticulin antibody binding domain construct is provided, wherein the antibody comprises a $V_H$ selected from any $V_H$ in Table 1 and a $V_L$ selected from any $V_L$ in Table 2. In one aspect, an anti-mutant calreticulin antibody binding domain construct is provided, wherein the antibody comprises a $V_H$ selected from any $V_H$ in Table 1 and a $V_L$ selected from any $V_L$ in Table 2, wherein the selected $V_H$ and $V_L$ are paired according to Table 3 or Table 4.

In one aspect, the invention provides an anti-mutant calreticulin antibody binding domain construct comprising at least one or both variable regions selected from (a) $V_H$ comprising the amino acid sequence of SEQ ID NO: 1 and (b) $V_L$ comprising the amino acid sequence of SEQ ID NO: 3.

In one aspect, the invention provides an anti-mutant calreticulin antibody binding domain construct comprising at least one, two, three, four, five, or six CDRs selected from (a) CDR-H1 comprising the amino acid sequence of SEQ ID NO: 7; (b) CDR-H2 comprising the amino acid sequence of SEQ ID NO: 8; (c) CDR-H3 comprising the amino acid sequence of SEQ ID NO: 9; (d) CDR-L1 comprising the amino acid sequence of SEQ ID NO: 13; (e) CDR-L2 comprising the amino acid sequence of SEQ ID NO: 14; and (f) CDR-L3 comprising the amino acid sequence of SEQ ID NO: 15.

In one aspect, the invention provides an anti-mutant calreticulin antibody binding domain construct comprising at least one, at least two, or all three $V_H$ CDR sequences selected from (a) CDR-H1 comprising the amino acid sequence of SEQ ID NO: 7; (b) CDR-H2 comprising the amino acid sequence of SEQ ID NO: 8; and (c) CDR-H3 comprising the amino acid sequence of SEQ ID NO: 9. In one aspect, the invention provides an anti-mutant calreticulin antibody binding domain construct comprising at least one, at least two, or all three $V_H$ CDR sequences selected from (a) CDR-H1 comprising the amino acid sequence of SEQ ID NO: 7; (b) CDR-H2 comprising the amino acid sequence of SEQ ID NO: 8; and (c) CDR-H3 comprising the amino acid sequence of SEQ ID NO: 9; and (d) a $V_L$ comprising the amino acid sequence of SEQ ID NO: 3.

In one aspect, the invention provides an anti-mutant calreticulin antibody binding domain construct comprising at least one, at least two, or all three $V_H$ CDR sequences selected from (a) CDR-H1 comprising the amino acid sequence of SEQ ID NO: 10; (b) CDR-H2 comprising the amino acid sequence of SEQ ID NO: 11; and (c) CDR-H3 comprising the amino acid sequence of SEQ ID NO: 12. In one aspect, the invention provides an anti-mutant calreticulin antibody binding domain construct comprising at least one, at least two, or all three $V_H$ CDR sequences selected from (a) CDR-H1 comprising the amino acid sequence of SEQ ID NO: 10; (b) CDR-H2 comprising the amino acid sequence of SEQ ID NO: 11; and (c) CDR-H3 comprising the amino acid sequence of SEQ ID NO: 2; and (d) a $V_L$ comprising the amino acid sequence of SEQ ID NO: 3.

In one aspect, the invention provides an anti-mutant calreticulin antibody binding domain construct comprising at least one, at least two, or all three $V_L$ CDR sequences selected from (a) CDR-L1 comprising the amino acid sequence of SEQ ID NO: 13; (b) CDR-L2 comprising the amino acid sequence of SEQ ID NO:14 and (c) CDR-L3 comprising the amino acid sequence of SEQ ID NO: 15. In one aspect, the invention provides an anti-mutant calreticulin antibody binding domain construct comprising at least one, at least two, or all three $V_L$ CDR sequences selected from (a) CDR-L1 comprising the amino acid sequence of SEQ ID NO: 13; (b) CDR-L2 comprising the amino acid sequence of SEQ ID NO: 14 and (c) CDR-L3 comprising the amino acid sequence of SEQ ID NO: 15; and (d) a $V_H$ comprising the amino acid sequence of SEQ ID NO: 1. In one aspect, the invention provides an anti-mutant calreticulin antibody binding domain construct comprising at least one, at least two, or all three $V_L$ CDR sequences selected from (a) CDR-L1 comprising the amino acid sequence of SEQ ID NO: 13; (b) CDR-L2 comprising the amino acid sequence of SEQ ID NO: 14 and (c) CDR-L3 comprising the amino acid sequence of SEQ ID NO: 15; and (d) a $V_H$ comprising the amino acid sequence of SEQ ID NO: 2.

Nucleic Acids, Vectors and Cells

The nucleic acid molecules described herein can be a DNA molecule, an RNA molecule, or a combination thereof. In one embodiment, the nucleic acid molecule is an mRNA encoding a CAR polypeptide as described herein. In other embodiments, the nucleic acid molecule is a vector that includes any of the aforesaid nucleic acid molecules.

In another aspect, the invention pertains to a vector comprising a nucleic acid molecule described herein, e.g., a nucleic acid molecule encoding a CAR described herein. In one embodiment, the vector is selected from the group consisting of a DNA molecule or an RNA molecule (e.g., a plasmid, a lentivirus vector, adenoviral vector, or a retrovirus vector).

In one embodiment, the vector is a lentivirus vector. In one embodiment, the vector further comprises a promoter. In one embodiment, the promoter is an EF-1 promoter. In one embodiment, the EF-1 promoter comprises a sequence of SEQ ID NO: 11. In another embodiment, the promoter is a PGK promoter, e.g., a truncated PGK promoter as described herein.

In one embodiment, the vector is an in vitro transcribed vector, e.g., a vector that transcribes RNA of a nucleic acid molecule described herein. In one embodiment, the nucleic acid sequence in the vector further comprises a poly(A) tail, e.g., a poly A tail described herein, (e.g., comprising about 150 adenosine bases (SEQ ID NO: 45)). In one embodiment, the nucleic acid sequence in the vector further comprises a 3'UTR, e.g., a 3' UTR described herein, e.g., comprising at least one repeat of a 3'UTR derived from human beta-globulin. In one embodiment, the nucleic acid sequence in the vector further comprises promoter, e.g., a T2A promoter.

In another aspect, the invention pertains to a cell comprising a nucleic acid molecule or a vector, or expressing a CAR polypeptide as described herein. In one embodiment, the cell is a cell described herein, e.g., an immune effector cell (e.g., a human T cell or NK cell, e.g., a human T cell or NK cell as described herein, or a cell population thereof). In one embodiment, the human T cell is a CD8$^+$ T cell. In some embodiments, the cell expresses the CAR nucleic acid or polypeptide, or at some point expressed the CAR nucleic acid or polypeptide (e.g., a transiently expressed CAR molecule).

In some embodiment, the cell (e.g., the CAR-expressing cell) described herein can further express another agent, e.g., an agent which enhances the activity of a CAR-expressing cell. For example, in one embodiment, the agent can be a chimeric molecule that comprises an inhibitory molecule or a domain thereof. Examples of inhibitory molecules include PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR (e.g., TGFRbeta), e.g., as described herein. In one embodiment, the chimeric molecule comprises a first polypeptide, e.g., an inhibitory molecule, associated with a second polypeptide that provides a positive signal to the cell, e.g., an intracellular signaling domain described herein. In one embodiment, the agent comprises a first polypeptide, e.g., of an inhibitory molecule such as PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR (e.g., TGFRbeta), or a fragment of any of these (e.g., at least a portion of the extracellular domain of any of these), and a second polypeptide which is an intracellular signaling domain described herein (e.g., comprising a costimulatory domain (e.g., 41BB, CD27 or CD28, e.g., as described herein) and/or a primary signaling domain (e.g., a CD3 zeta signaling domain described herein). In one embodiment, the agent comprises a first polypeptide of PD1 or a fragment thereof (e.g., at least a portion of the extracellular domain of PD1), and a second polypeptide of an intracellular signaling domain described herein (e.g., a CD28 signaling domain described herein and/or a CD3 zeta signaling domain described herein).

In another aspect, the invention pertains to a method of making a cell, e.g., an immune effector cell. The method includes introducing into, e.g., transducing, the immune effector cell with a nucleic acid molecule described herein (e.g., an RNA molecule, e.g., an mRNA), or a vector comprising a nucleic acid molecule encoding a CAR, e.g., a CAR described herein.

The present invention also provides a method of generating a population of cells (e.g., RNA-engineered cells transiently expressing an exogenous RNA). The method includes introducing into the cell an RNA as described herein (e.g., an in vitro transcribed RNA or synthetic RNA; an mRNA sequence encoding a CAR polypeptide as described herein). In embodiments, the RNA expresses the CAR polypeptide transiently. In one embodiment, the cell is a cell as described herein, e.g., an immune effector cell (e.g., T cells or NK cells, or cell population).

Therapeutic Uses

In another aspect, the invention pertains to a method of providing an anti-tumor immunity in a mammal comprising administering to the mammal an effective amount of a cell expressing a CAR molecule, e.g., a cell expressing a CAR molecule described herein. In one embodiment, the cell is an autologous immune effector cell, e.g., T cell or NK cell. In one embodiment, the cell is an allogeneic immune effector cell, e.g., T cell or NK cell. In one embodiment, the mammal is a human, e.g., a patient with a hematologic cancer.

In another aspect, the invention pertains to a method of treating a mammal having a disease associated with expression of mutant calreticulin (e.g., a proliferative disease, a precancerous condition, or a non-cancer related indication associated with the expression of mutant calreticulin). The method includes administering to the mammal an effective amount of the cells expressing a CAR molecule, e.g., a CAR molecule described herein. In one embodiment, the mammal is a human, e.g., a patient with a hematologic cancer.

In one embodiment, the disease is a disease described herein. In one embodiment, the disease associated with mutant calreticulin expression is chosen from: a proliferative disease such as a cancer or a malignancy; a precancerous condition such as a myelodysplasia, a myelodysplastic syndrome or a preleukemia; or a non-cancer related indication associated with expression of mutant calreticulin. In one embodiment, the disease is a hematologic cancer. In other embodiments, the disease is chosen from one or more acute leukemias, including but not limited to, acute myeloid leukemia (AML), acute lymphoblastic leukemia (ALL), acute lymphoblastic B-cell leukemia (B-cell acute lymphoid leukemia, BALL), and acute lymphoblastic T-cell leukemia (T-cell acute lymphoid leukemia (TALL); myelodysplastic syndrome; a myeloproliferative neoplasm; a histiocytic disorder (e.g., a mast cell disorder or a blastic plasmacytoid dendritic cell neoplasm); a mast cell disorder, e.g., systemic mastocytosis or mast cell leukemia; a chronic myeloid leukemia (CML); and a blastic plasmacytoid dendritic cell neoplasm. In other embodiments, the disease associated with mutant calreticulin expression, includes, but is not limited to, atypical and/or non-classical cancer, a malignancy, a precancerous condition or a proliferative disease expressing mutant calreticulin; and a combination thereof.

In one embodiment, the disease is chosen from one or more of acute myeloid leukemia (AML), acute lymphoblastic leukemia (ALL), acute lymphoblastic B-cell leukemia (B-cell acute lymphoid leukemia, BALL), acute lymphoblastic T-cell leukemia (T-cell acute lymphoid leukemia (TALL), B-cell prolymphocytic leukemia, chronic lymphocytic leukemia, chronic myeloid leukemia (CML), hairy cell leukemia, Hodgkin lymphoma, a mast cell disorder, a histiocytic disorder, a myelodysplastic syndrome, a myeloproliferative neoplasm, a plasma cell myeloma, a blastic plasmacytoid dendritic cell neoplasm, or a combination thereof. In one embodiment, the disease is a leukemia, e.g., ALL (e.g., relapsing and refractory ALL) or AML. In other embodiments, the disease is a CD19-negative cancer, e.g., a CD19-negative relapsed cancer.

In some embodiments of any of the aforesaid methods, the cell, e.g., the population of immune effector cells, comprises a vector, e.g., a lentiviral vector, comprising a nucleic acid molecule encoding the CAR polypeptide as described herein.

In other embodiments of any of the aforesaid methods, the cell, e.g., the population of immune effector cells, comprises an mRNA encoding the CAR polypeptide as described herein. In one embodiment, the cell is a CAR-expressing population of RNA-engineered cells, e.g., a population of transiently expressing cells.

In some embodiments of any of the aforesaid methods, the method further includes administering one or more doses of a cell (e.g., an immune cell containing a CAR nucleic acid or CAR polypeptide as described herein), to a mammal (e.g., a mammal having a cancer, e.g., a hematologic cancer as described herein (e.g., AML or ALL)). In some embodiments, the one or more doses of CAR cells (e.g., mutant calreticulin CAR cells) comprises at least about $1\times10^6$, $5\times10^6$, $1\times10^7$, $2\times10^7$, $5\times10^7$, $1\times10^8$, $2\times10^8$, $5\times10^8$, $1\times10^9$, $2\times10^9$, or $5\times10^9$ cells.

In one embodiment, up to 10, 9, 8, 7, 6, 5, 4, 3, or 2 doses of cells are administered. In other embodiments, one, two, three, four, five or 6 doses of the cells are administered to the mammal, e.g., in a treatment interval of one, two, three, four or more weeks. In one embodiment, up to 6 doses are administered in two weeks. The doses may the same or different. In one embodiment, a lower dose is administered initially, followed by one or more higher doses. In one exemplary embodiment, the lower dose is about $1\times10^5$ to $1\times10^9$ cells/kg, or $1\times10^6$ to $1\times10^8$ cells/kg; and the higher dose is about $2\times10^5$ to $2\times10^9$ cells/kg or $2\times10^6$ to $2\times10^8$ cells/kg, followed by 3-6 doses of about $4\times10^5$ to $4\times10^9$ cells/kg, or $4\times10^6$ to $4\times10^8$ cells/kg.

In one embodiment, the one or more doses of the cells are administered after one or more lymphodepleting therapies, e.g., a lymphodepleting chemotherapy. In one embodiment, the lymphodepleting therapy includes a chemotherapy (e.g., cyclophosphamide).

In one embodiment, the one or more doses is followed by a cell transplant, e.g., an allogeneic hematopoietic stem cell transplant. For example, the allogeneic hematopoietic stem cell transplant occurs between about 20 to about 35 days, e.g., between about 23 and 33 days.

In some embodiments, the cell, e.g., the population of immune effector cells (e.g., cells expressing a CAR molecule described herein) is administered in combination with one or more therapeutic agents or procedures as described herein.

In one embodiment, the cell, e.g., the population of immune effector cells (e.g., cells expressing a CAR molecule described herein) is administered in combination with an agent that increases the efficacy of a cell expressing a CAR molecule, e.g., an agent described herein.

In an embodiment this approach can be used to optimize the performance of CAR cells described herein in the subject. While not wishing to be bound by theory, it is believed that, in an embodiment, the performance of endogenous, non-modified immune effector cells, e.g., T cells, is improved. While not wishing to be bound by theory, it is believed that, in an embodiment, the performance of a mutant calreticulin CAR expressing cell is improved. In other embodiments, cells, e.g., T cells, which have, or will be engineered to express a CAR, can be treated ex vivo by contact with an amount of an mTOR inhibitor that increases the number of PD1 negative immune effector cells (e.g., T cells or NK cells), or increases the ratio of PD1 negative immune effector cells, e.g., T cells or NK cells/PD1 positive immune effector cells, e.g., T cells or NK cells.

In an embodiment, administration of a dose of a JAK2 inhibitor is initiated prior to administration of an CAR expressing cell described herein, e.g., T cells or NK cells. In another embodiment, the cell, e.g., the population of immune effector cells (e.g., cells expressing a CAR molecule described herein) is administered in combination with an agent that ameliorates one or more side effect associated with administration of a cell expressing a CAR molecule, e.g., an agent described herein.

In one embodiment, the cell, e.g., the population of immune effector cells (e.g., cells expressing a CAR molecule described herein), is administered in combination with an agent that treats the disease associated with mutant calreticulin, e.g., an agent described herein.

In one embodiment, the cell, e.g., the population of immune effector cells (e.g., cells expressing a CAR molecule described herein) is administered in combination with a second therapeutic agent or procedure chosen from one or more of chemotherapy, a targeted anti-cancer therapy, an oncolytic drug, a cytotoxic agent, a cytokine, surgical procedure, a radiation procedure, an agonist of a costimulatory molecule, an inhibitor of an immune checkpoint molecule, a vaccine, or a second CAR-based immunotherapy.

In one embodiment, the cell, e.g., the population of immune effector cells (e.g., cells expressing a CAR molecule described herein) is administered in combination with an agonist of a costimulatory molecule, e.g., an agonist of a costimulatory molecule chosen from one or more of a MHC class I molecule, TNF receptor proteins, Immunoglobulin-like proteins, cytokine receptors, integrins, signaling lymphocytic activation molecules (SLAM proteins), activating NK cell receptors, BTLA, a Toll ligand receptor, OX40, CD2, CD7, CD27, CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, $V_L$A1, CD49a, ITGA4, IA4, CD49D, ITGA6, $V_L$A-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83.

In other embodiments, the cell, e.g., the population of immune effector cells (e.g., cells expressing a CAR molecule described herein) is administered in combination with an inhibitor of an immune checkpoint molecule chosen from one or more of PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GALS, adenosine, TGFR (e.g., TGFR beta), or a combination thereof.

In one embodiment, the inhibitor of the immune checkpoint molecule or the agonist of the costimulatory molecule is an antibody molecule, e.g., a monospecific antibody molecule or a bispecific antibody molecule. For example, the cell, e.g., the population of immune effector cells, can be administered in combination with a PD-1 inhibitor, a TIM-3 inhibitor, a CEACAM-1 inhibitor, or a combination thereof. In one embodiment, the PD-1 inhibitor and the TIM-3 inhibitor are administered in combination. In other embodiments, the TIM-3 inhibitor and the CEACAM-1 inhibitor are administered in combination.

In some embodiments, the inhibitor of the immune checkpoint molecule is administered subsequent to the administration of the cell, e.g., the population of immune effector cells, e.g., about 3-7 days after the administration of the cell, e.g., the population of immune effector cells.

In yet other embodiments, the methods disclosed herein further include administering a T cell depleting agent after treatment with the cell (e.g., an immune effector cell as described herein), thereby reducing (e.g., depleting) the CAR-expressing cells (e.g., the mutant calreticulin CAR-expressing cells). Such T cell depleting agents can be used to effectively deplete CAR-expressing cells (e.g., mutant calreticulin CAR-expressing cells) to mitigate toxicity.

For example, alternatively or in combination with the methods disclosed herein, a method of reducing (e.g., depleting) a CAR-expressing cell after a CAR therapy (e.g., a CAR therapy disclosed herein) is disclosed. The method includes administering to a mammal a T cell depleting agent, in an amount to reduce (e.g., deplete) the CAR-expressing cells. In some embodiments, the T cell depleting agent is administered after treatment of the mammal with a cell, e.g., a population of immune effector cells (e.g., a CAR-expressing population of cells), thereby reducing (e.g., depleting) the cell (e.g., the CAR-expressing cell).

In some embodiments, the method further includes transplanting a cell, e.g., a hematopoietic stem cell, or a bone marrow, into the mammal.

In some embodiments, the mammal has a leukemia, e.g., acute lymphoblastic leukemia.

In some embodiments, the T cell depleting agent is administered one, two, three, four, or five weeks after administration of the cell, e.g., the population of immune effector cells, described herein.

In one embodiment, the T cell depleting agent is an agent that depletes CAR-expressing cells, e.g., by inducing antibody dependent cell-mediated cytotoxicity (ADCC) and/or complement-induced cell death. For example, CAR-expressing cells described herein may also express an antigen (e.g., a target antigen) that is recognized by molecules capable of inducing cell death, e.g., ADCC or complement-induced cell death. For example, CAR expressing cells described herein may also express a target protein (e.g., a receptor) capable of being targeted by an antibody or antibody fragment. Examples of such target proteins include, but are not limited to, EpCAM, VEGFR, integrins (e.g., integrins αvβ3, α4, α4β7, α5β1, αvβ3, αv), members of the TNF receptor superfamily (e.g., TRAIL-R1, TRAIL-R2), PDGF Receptor, interferon receptor, folate receptor, GPNMB, ICAM-1, HLA-DR, CEA, CA-125, MUC1, TAG-72, IL-6 receptor, 5T4, GD2, GD3, CD2, CD3, CD4, CD5, CD11, CD11a/LFA-1, CD15, CD18/ITGB2, CD19, CD20, CD22, CD23/IgE Receptor, CD25, CD28, CD30, CD33, CD38, CD40, CD41, CD44, CD51, CD52, CD62L, CD74, CD80, CD125, CD147/basigin, CD152/CTLA-4, CD154/ CD40L, CD195/CCR5, CD319/SLAMF7, and EGFR, and truncated versions thereof (e.g., versions preserving one or more extracellular epitopes but lacking one or more regions within the cytoplasmic domain).

In some embodiments, the CAR expressing cell co-expresses the CAR and the target protein, e.g., naturally expresses the target protein or is engineered to express the target protein. For example, the cell, e.g., the population of immune effector cells, can include a nucleic acid (e.g., vector) comprising the CAR nucleic acid (e.g., a CAR nucleic acid as described herein) and a nucleic acid encoding the target protein.

In one embodiment, the T cell depleting agent is a CD52 inhibitor, e.g., an anti-CD52 antibody molecule, e.g., alemtuzumab.

In other embodiments, the cell, e.g., the population of immune effector cells, expresses a CAR molecule as described herein (e.g., mutant calreticulin CAR) and the target protein recognized by the T cell depleting agent. In one embodiment, the target protein is CD20. In embodiments where the target protein is CD20, the T cell depleting agent is an anti-CD20 antibody, e.g., rituximab.

In further embodiments of any of the aforesaid methods, the methods further include transplanting a cell, e.g., a hematopoietic stem cell, or a bone marrow, into the mammal.

In another aspect, the invention features a method of conditioning a mammal prior to cell transplantation. The method includes administering to the mammal an effective amount of the cell comprising the CAR nucleic acid as described herein, or the polypeptide as described herein. In some embodiments, the cell transplantation is a stem cell transplantation, e.g., a hematopoietic stem cell transplantation, or a bone marrow transplantation. In other embodiments, conditioning a subject prior to cell transplantation includes reducing the number of mutant calreticulin-expressing cells in a subject, e.g., mutant calreticulin-expressing normal cells or mutant calreticulin-expressing cancer cells.

In another aspect, the invention pertains to the isolated nucleic acid molecule encoding a CAR, the isolated polypeptide molecule of a CAR, the vector comprising a CAR, and the cell comprising a CAR for use as a medicament, e.g., as described herein (e.g., for use in the treatment of a disease associated with expression of mutant calreticulin).

In another aspect, the invention pertains to the isolated nucleic acid molecule encoding a CAR, the isolated polypeptide molecule of a CAR, the vector comprising a CAR, and the cell comprising a CAR for use in the treatment of a disease expressing mutant calreticulin, e.g., a disease expressing mutant calreticulin as described herein. In certain embodiments, the disease is a hematologic cancer, e.g., as described herein. In some embodiments, the disease is chosen from: an acute leukemia, including but not limited to, acute myeloid leukemia (AML), acute lymphoblastic leukemia (ALL), acute lymphoblastic B-cell leukemia (B-cell acute lymphoid leukemia, BALL), and acute lymphoblastic T-cell leukemia (T-cell acute lymphoid leukemia (TALL); myelodysplastic syndrome; a myeloproliferative neoplasm; a histiocytic disorder (e.g., a mast cell disorder or a blastic plasmacytoid dendritic cell neoplasm); a mast cell disorder, e.g., systemic mastocytosis or mast cell leukemia; a chronic myeloid leukemia (CML); or a blastic plasmacytoid dendritic cell neoplasm.

Affinity

Affinity is the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($k_d$). Affinity can be measured by common methods known in the art, including those described herein. Specific illustrative and exemplary embodiments for measuring binding affinity are described in the following.

In some embodiments, an antibody provided herein has a dissociation constant ($K_D$) of about 1 µM, 100 nM, 10 nM, 5 nM, 2 nM, 1 nM, 0.5 nM, 0.1 nM, 0.05 nM, 0.01 nM, or 0.001 nM or less (e.g., $10^{-8}$M or less, e.g., from $10^{-8}$M to $10^{-13}$M, e.g., from $10^{-9}$M to $10^{-13}$M) for the antibody target. The antibody target can be an mutant calreticulin target.

Another aspect provides for an anti-mutant calreticulin antibody binding domain construct with an increased affinity for its mutant calreticulin target, for example, an affinity matured anti-mutant calreticulin antibody binding domain construct. An affinity matured antibody is an antibody with one or more alterations in one or more hypervariable regions (HVRs), compared to a parent antibody which does not possess such alterations, such alterations resulting in an improvement in the affinity of the antibody for antigen. These antibodies can bind to mutant calreticulin with a $K_D$ of about $5\times10^{-9}$M, $2\times10^{-9}$M, $1\times10^{-9}$M, $5\times10^{-10}$M, $2\times10^{-9}$M, $1\times10^{-10}$M, $5\times10^{-11}$M, $1\times10^{-11}$M, $5\times10^{-12}$M, $1\times10^{-12}$M, or less. In some embodiments, the invention provides an anti-mutant calreticulin antibody binding domain construct which has an increased affinity of at least 1.5 fold, 2 fold, 2.5 fold, 3 fold, 4 fold, 5 fold, 10 fold, 20 fold or greater as compared to a germline anti-mutant calreticulin antibody binding domain construct containing the heavy chain sequence of SEQ ID NO: 69, the light chain sequence of SEQ ID NO: 70, or both. In other embodiments, an antibody is provided that competes for binding to the same epitope as an anti-mutant calreticulin antibody binding domain construct as described herein. In some embodiments, the antibody that binds to the same epitope, and/or competes for binding to the same epitope as an anti-mutant calreticulin antibody binding domain construct exhibits effector function activities, such as, for example, Fc-mediated cellular cytotoxicity, including ADCC activity.

$K_D$ can be measured by any suitable assay. For example, $K_D$ can be measured by a radiolabeled antigen binding assay (RIA) (See, e.g., Chen et al., J. Mol. Biol. 293:865-881 (1999); Presta et al., Cancer Res. 57:4593-4599 (1997)). For example, $K_D$ can be measured using surface plasmon resonance assays (e.g., using a BIACORE®-2000 or a BIACORE®-3000).

Antibody Fragments

An antibody fragment comprises a portion of an intact antibody, such as the antigen binding or variable region of the intact antibody. In a further aspect, an anti-mutant calreticulin antibody binding domain construct according to any of the above embodiments is a monoclonal antibody, including a chimeric, humanized or human antibody. Antibody fragments include, but are not limited to, Fab, Fab', Fab'-SH, F(ab')$_2$, Fv, diabody, linear antibodies, multispecific formed from antibody fragments antibodies and scFv fragments, and other fragments described below. In another embodiment, the antibody is a full length antibody, e.g., an intact IgG1 antibody or other antibody class or isotype as described herein. (See, e.g., Hudson et al. Nat. Med. 9:129-134 (2003); Pluckthiin, The Pharmacology of Monoclonal Antibodies, vol. 113, pp. 269-315 (1994); Hollinger et al., Proc. Natl. Acad. Sci. USA 90: 6444-6448 (1993); WO93/01161; and U.S. Pat. Nos. 5,571,894, 5,869,046, 6,248,516, and 5,587,458). A full length antibody, intact antibody, or whole antibody is an antibody having a structure substantially similar to a native antibody structure or having heavy chains that contain an Fc region as defined herein. Antibody fragments can be made by various techniques, including but not limited to proteolytic digestion of an intact antibody as well as production by recombinant host cells (e.g., E. coli or phage), as described herein.

An Fv is the minimum antibody fragment that contains a complete antigen-recognition and antigen-binding site. This fragment contains a dimer of one heavy- and one light-chain variable region domain in tight, non-covalent association. From the folding of these two domains emanate six hypervariable loops (three loops each from the H and L chain) that contribute the amino acid residues for antigen binding and confer antigen binding specificity to the antibody. However, even a single variable region (or half of an Fv comprising only three CDRs specific for an antigen) has the ability to recognize and bind antigen, although at a lower affinity than the entire binding site.

A single-chain Fv (sFv or scFv) is an antibody fragment that comprises the $V_H$ and $V_L$ antibody domains connected into a single polypeptide chain. The sFv polypeptide can further comprise a polypeptide linker between the $V_H$ and $V_L$ domains that enables the sFv to form the desired structure for antigen binding. (See, e.g., Pluckthun in The Pharmacology of Monoclonal Antibodies, vol. 113, Rosenburg and Moore eds., Springer-Verlag, New York, pp. 269-315 (1994); Borrebaeck 1995, infra. The sFv can be used in a chimeric antigen receptor (CAR).

A diabody is a small antibody fragment prepared by constructing an sFv fragment with a short linker (about 5-10 residues) between the $V_H$ and VI, domains such that interchain but not intra-chain pairing of the V domains is achieved, resulting in a bivalent fragment. Bispecific diabodies are heterodimers of two crossover sFv fragments in which the $V_H$ and $V_L$ domains of the two antibodies are present on different polypeptide chains (See, e.g., EP 404,097; WO 93/11161; and Hollinger et al, Proc. Natl. Acad. Sci. USA, 90:6444-6448 (1993)).

Domain antibodies (dAbs), which can be produced in fully human form, are the smallest known antigen-binding fragments of antibodies, ranging from about 11 kDa to about 15 kDa. DAbs are the robust variable regions of the heavy and light chains of immunoglobulins ($V_H$ and $V_L$, respectively). They are highly expressed in microbial cell culture, show favorable biophysical properties including, for example, but not limited to, solubility and temperature stability, and are well suited to selection and affinity maturation by in vitro selection systems such as, for example, phage display. DAbs are bioactive as monomers and, owing to their small size and inherent stability can be formatted into larger molecules to create drugs with prolonged serum half-lives or other pharmacological activities. (See, e.g., WO9425591 and US20030130496).

Fv and sFv are the only species with intact combining sites that are devoid of constant regions. Thus, they are suitable for reduced nonspecific binding during in vivo use. sFv fusion proteins can be constructed to yield fusion of an effector protein at either the amino or the carboxy terminus of an sFv. The antibody fragment also can be a "linear antibody. (See, e.g., U.S. Pat. No. 5,641,870). Such linear antibody fragments can be monospecific or bispecific.

Chimeric Antigen Receptors (CARs)

A CAR can comprise an intracellular domain comprising an intracellular domain of a T cell receptor, and an extracellular portion comprising an antigen binding portion of an antibody, e.g., an sFv of an antibody. A chimeric antigen receptor (CAR) can be a genetically engineered T cell receptor, which is designed to redirect a T cell to target cells that express certain antigens. A CAR can comprise an intracellular domain comprising a co-stimulatory domain and an intracellular domain of a T cell receptor, and an extracellular portion comprising a transmembrane hinge and an sFv of an antibody. An sFv can comprise a $V_H$ domain and a $V_L$ domain of an antibody. For example, an sFv can comprise a $V_H$ domain described herein in combination with a $V_L$ domain described herein. For example, an sFv can be created by the synthesis of codon-optimized sequences for the heavy and light chains separated by a (GGGGS)$_4$ linker (SEQ ID NO: 36), and then can be substituted for the single-chain antibody in a second-generation CAR vector containing a 4-1BB signaling domain fused to a CD3ζ signaling domain. This CAR vector can be transfected into T cells. The T cells can be CD8$^+$ T cells. In some embodiments, CD8$^+$ T cells that were transfected and express the CAR can recognize mutant calreticulin expressing cells. In other embodiments, the T cell transfected with a CAR can be a CD4$^+$ T cell. A T cell transfected with a CAR can also be modified to lack other coreceptors involved in mutant calreticulin pathogenesis. For example, T cells can be transfected with reagents, such as siRNA, to decrease or knockdown expression of one or more coreceptors involved in mutant calreticulin pathogenesis.

Chimeric and Humanized Antibodies

In some embodiments, an antibody provided herein is a chimeric antibody (See, e.g., U.S. Pat. No. 4,816,567; and Morrison et al., Proc. Natl. Acad. Sci. USA, 81:6851-6855 (1984)). A chimeric antibody is an antibody in which a portion of the heavy and/or light chain is derived from a particular source or species, while the remainder of the heavy and/or light chain is derived from a different source or species. In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In some embodiments, a chimeric antibody is a humanized antibody (See, e.g., Almagro and Fransson, Front. Biosci. 13:1619-1633 (2008); Riechmann et al., Nature 332:323-329 (1988); Queen et al., Proc. Nat'l Acad. Sci. USA 86:10029-10033 (1989); U.S. Pat. Nos. 5,821,337, 7,527,791, 6,982,321, and 7,087,409; Kashmiri et al., Methods 36:25-34 (2005); Padlan, Mol. Immunol. 28:489-498 (1991); Dall'Acqua et al., Methods 36:43-60 (2005); Osbourn et al., Methods 36:61-68 (2005); and Klimka et al., Br. J. Cancer, 83:252-260 (2000)). A humanized antibody is a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody.

A non-human antibody can be humanized to reduce immunogenicity to humans, while retaining the specificity and affinity of the parental non-human antibody. A humanized antibody can comprise one or more variable domains comprising one or more CDRs, or portions thereof, derived from a non-human antibody. A humanized antibody can comprise one or more variable domains comprising one or more FRs, or portions thereof, derived from human antibody sequences. A humanized antibody can optionally comprise at least a portion of a human constant region. In some embodiments, one or more FR residues in a humanized antibody are substituted with corresponding residues from a non-human antibody (e.g., the antibody from which the CDR residues are derived), e.g., to restore or improve antibody specificity or affinity.

Human framework regions that may be used for humanization include but are not limited to: framework regions selected using a "best-fit" method; framework regions derived from the consensus sequence of human antibodies of a particular subgroup of light or heavy chain variable regions; human mature (somatically mutated) framework regions or human germline framework regions; and framework regions derived from screening FR libraries (See, e.g., Sims et al. J. Immunol. 151:2296 (1993); Carter et al. Proc. Natl. Acad. Sci. USA, 89:4285 (1992); Presta et al. J. Immunol., 151:2623 (1993); Baca et al., J. Biol. Chem. 272:10678-10684 (1997); and Rosok et al., J. Biol. Chem. 271:22611-22618 (1996)).

Human Antibodies

In some embodiments, an antibody provided herein is a human antibody Human antibodies can be produced using various techniques known in the art (See, e.g., van Dijk and van de Winkel, Curr. Opin. Pharmacol. 5: 368-74 (2001); and Lonberg, Curr. Opin. Immunol. 20:450-459 (2008)). A human antibody is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues. Human antibodies may be prepared by administering an immunogen (e.g., an mutant calreticulin immunogen) to a transgenic animal that has been modified to produce intact human antibodies or intact antibodies with human variable regions in response to antigenic challenge. (See, e.g., Lonberg, Nat. Biotech. 23:1117-1125 (2005); U.S. Pat. Nos. 6,075,181, 6,150,584, 5,770,429, and 7,041,870; and U.S. Pat. App. Pub. No. US 2007/0061900). Human variable regions from intact antibodies generated by such animals may be further modified, e.g., by combining with a different human constant region.

Human antibodies can also be made by hybridoma-based methods. For example, human antibodies can be produced from human myeloma and mouse-human heteromyeloma cell lines, using human B-cell hybridoma technology, and other methods (See, e.g., Kozbor J. Immunol., 133: 3001 (1984); Brodeur et al., Monoclonal Antibody Production Techniques and Applications, pp. 51-63 (1987); Boerner et al., J. Immunol., 147: 86 (1991); Li et al., Proc. Natl. Acad., 103:3557-3562 (2006); U.S. Pat. No. 7,189,826; Ni, Xiandai Mianyixue, 26(4):265-268 (2006); Vollmers and Brandlein, Histology and Histopathology, 20(3):927-937 (2005); and Vollmers and Brandlein, Methods and Findings in Experimental and Clinical *Pharmacology*, 27(3):185-91 (2005)) Human antibodies may also be generated by isolating Fv clone variable domain sequences selected from human-derived phage display libraries. Such variable domain sequences may then be combined with a desired human constant domain.

Library-Derivation

Antibodies may be isolated by screening combinatorial libraries for antibodies with the desired activity or activities. (See, e.g., in Hoogenboom et al., *Methods in Molecular Biology* 178:1-37 (2001); McCafferty et al., Nature 348:552-554; Clackson et al., Nature 352: 624-628 (1991); Marks et al., J. Mol. Biol. 222: 581-597 (1992); Marks and Bradbury, Methods in Molecular Biology 248:161-175 (2003); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132 (2004)). Repertoires of $V_H$ and $V_L$ genes can be cloned separately (e.g., by PCR) and recombined randomly in libraries (e.g., phage libraries), and screened (See, e.g., Winter et al., Ann. Rev. Immunol., 12: 433-455 (1994)). Alternatively, the naive repertoire can be cloned (e.g., from human) to provide a single source of antibodies to a wide range of non-self and also self-antigens without any immunization (See, e.g., Griffiths et al., EMBO J, 12: 725-734 (1993). Alternatively, naive libraries can be synthetically made by cloning unrearranged V-gene segments from stem cells, and encoding the CDR3 regions using random primers or to rearrange the V-gene segments in vitro (See, e.g., Hoogenboom and Winter, J. Mol. Biol., 227: 381-388 (1992); U.S. Pat. No. 5,750,373, and U.S. Pat. Pub. Nos. US 2005/0079574, US 2005/0119455, US 2005/0266000, US 2007/0117126, US 2007/0160598, US 2007/0237764, US 2007/0292936, and US 2009/0002360. Antibodies or antibody fragments isolated from human antibody libraries are considered human antibodies or human antibody fragments herein.

Multispecificity

In some embodiments, an antibody provided herein is a multispecific antibody, e.g., a bispecific antibody. Multispecific antibodies are monoclonal antibodies that have binding specificities for at least two different sites (See, e.g., U.S. Pat. Pub. No. US 2008/0069820). In some embodiments, one of the binding specificities is for mutant calreticulin and the other is for any other antigen. In some embodiments, bispecific antibodies may bind to two different epitopes of mutant calreticulin. Bispecific antibodies may also be used to localize cytotoxic agents to cells expressing mutant calreticulin. Bispecific antibodies can be prepared as full length antibodies or antibody fragments.

Exemplary techniques for making multispecific antibodies include recombinant co-expression of two immunoglobulin heavy chain-light chain pairs having different specificities, engineering electrostatic steering effects for making antibody Fc-heterodimeric molecules, cross-linking two or more antibodies or fragments, using leucine zippers to produce bi-specific antibodies, using "diabody" technology for making bispecific antibody fragments, using single-chain Fv (sFv) dimers, preparing trispecific antibodies, and "knob-in-hole" engineering (See, e.g., Milstein and Cuello, Nature 305: 537 (1983); WO09/089004A1; WO93/08829; Traunecker et al., EMBO J. 10: 3655 (1991); U.S. Pat. Nos. 4,676,980 and 5,731,168; Brennan et al., Science, 229: 81 (1985); Kostelny et al., J. Immunol., 148(5):1547-1553 (1992); Hollinger et al., Proc. Natl. Acad. Sci. USA, 90:6444-6448 (1993); Gruber et al., J. Immunol., 152:5368 (1994)); and Tutt et al. J. Immunol. 147: 60 (1991)). Engineered antibodies with three or more functional antigen binding sites are also included (See, e.g., US 2006/0025576).

In some embodiments, amino acid sequence variants of the antibodies provided herein are contemplated. A variant typically differs from a polypeptide specifically disclosed herein in one or more substitutions, deletions, additions and/or insertions. Such variants can be naturally occurring or can be synthetically generated, for example, by modifying one or more of the above polypeptide sequences and evaluating one or more biological activities of the polypeptide as described herein and/or using any of a number of techniques well known in the art. For example, it may be desirable to improve the binding affinity and/or other biological properties of the antibody Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

Substitution, Insertion, and Deletion Variants

In some embodiments, antibody variants having one or more amino acid substitutions are provided. Sites of interest for mutagenesis by substitution include the CDRs and FRs Amino acid substitutions may be introduced into an antibody of interest and the products screened for a desired activity, e.g., retained/improved antigen binding, decreased immunogenicity, or improved ADCC or CDC.

| Original Residue | Exemplary Conserved Substitutions |
|---|---|
| Ala (A) | Val; Leu; Ile |
| Arg (R) | Lys; Gln; Asn |
| Asn (N) | Gln; His; Asp, Lys; Arg |
| Asp (D) | Glu; Asn |
| Cys (C) | Ser; Ala |
| Gln (Q) | Asn; Glu |
| Glu (E) | Asp; Gln |
| Gly (G) | Ala |
| His (H) | Asn; Gln; Lys; Arg |
| Ile (I) | Leu; Val; Met; Ala; Phe; Norleucine |
| Leu (L) | Norleucine; Ile; Val; Met; Ala; Phe |
| Lys (K) | Arg; Gln; Asn |
| Met (M) | Leu; Phe; Ile |
| Phe (F) | Trp; Leu; Val; Ile; Ala; Tyr |
| Pro (P) | Ala |
| Ser (S) | Thr |
| Thr (T) | Val; Ser |
| Trp (W) | Tyr; Phe |
| Tyr (Y) | Trp; Phe; Thr; Ser |
| Val (V) | Ile; Leu; Met; Phe; Ala; Norleucine |

Hydrophobic amino acids include: Norleucine, Met, Ala, Val, Leu, and Ile. Neutral hydrophilic amino acids include: Cys, Ser, Thr, Asn, and Gln. Acidic amino acids include: Asp and Glu. Basic amino acids include: His, Lys, and Arg. Amino acids with residues that influence chain orientation include: Gly and Pro. Aromatic amino acids include: Trp, Tyr, and Phe.

In some embodiments, substitutions, insertions, or deletions may occur within one or more CDRs, wherein the substitutions, insertions, or deletions do not substantially reduce antibody binding to antigen. For example, conservative substitutions that do not substantially reduce binding affinity may be made in CDRs. Such alterations may be outside of CDR "hotspots" or SDRs. In some embodiments of the variant $V_H$ and $V_L$ sequences, each CDR either is unaltered, or contains no more than one, two or three amino acid substitutions.

Alterations (e.g., substitutions) may be made in CDRs, e.g., to improve antibody affinity. Such alterations may be made in CDR encoding codons with a high mutation rate during somatic maturation (See, e.g., Chowdhury, Methods Mol. Biol. 207:179-196 (2008)), and the resulting variant can be tested for binding affinity. Affinity maturation (e.g., using error-prone PCR, chain shuffling, randomization of CDRs, or oligonucleotide-directed mutagenesis) can be used to improve antibody affinity (See, e.g., Hoogenboom et al. in Methods in Molecular Biology 178:1-37 (2001)). CDR residues involved in antigen binding may be specifically identified, e.g., using alanine scanning mutagenesis or modeling (See, e.g., Cunningham and Wells Science, 244:1081-1085 (1989)). CDR-H3 and CDR-L3 in particular are often targeted. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions and deletions include amino- and/or carboxyl-terminal fusions ranging in length from one residue to polypeptides containing a hundred or more residues, as well as intrasequence insertions and deletions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody. Examples of intrasequence insertion variants of the antibody molecules include an insertion of 3 amino acids in the light chain. Examples of terminal deletions include an antibody with a deletion of 7 or less amino acids at an end of the light chain Glycosylation Variants In some embodiments, the antibodies are altered to increase or decrease their glycosylation (e.g., by altering the amino acid sequence such that one or more glycosylation sites are created or removed). A carbohydrate attached to an Fc region of an antibody may be altered. Native antibodies from mammalian cells typically comprise a branched, biantennary oligosaccharide attached by an N-linkage to Asn297 of the CH2 domain of the Fc region (See, e.g., Wright et al. TIBTECH 15:26-32 (1997)). The oligosaccharide can be various carbohydrates, e.g., mannose, N-acetyl glucosamine (GlcNAc), galactose, sialic acid, fucose attached to a GlcNAc in the stem of the biantennary oligosaccharide structure. Modifications of the oligosaccharide in an antibody can be made, for example, to create antibody variants with certain improved properties. Antibody glycosylation variants can have improved ADCC and/or CDC function.

In some embodiments, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn297 (See, e.g., WO 08/077546). Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants can have improved ADCC function (See, e.g., Pat. Pub. Nos. US 2003/0157108; US 2004/0093621; US 2003/0157108; WO00/61739; WO01/29246; US 2003/0115614; US 2002/0164328; 2004/0093621; US 2004/0132140; US 2004/0110704; US 2004/0110282; US 2004/0109865; WO03/085119; WO03/084570; WO05/035586; WO05/035778; WO05/053742; WO02/031140; Okazaki et al. J. Mol. Biol. 336:1239-1249 (2004); and Yamane-Ohnuki et al. Biotech. Bioeng. 87: 614 (2004)). Cell lines, e.g., knockout cell lines and methods of their use can be used to produce defucosylated antibodies, e.g., Lec13 CHO cells deficient in protein fucosylation and alpha-1,6-fucosyltransferase gene (FUT8) knockout CHO cells (See, e.g., Ripka et al. Arch. Biochem. Biophys. 249:533-545 (1986); Yamane-Ohnuki et al. Biotech. Bioeng. 87: 614 (2004); Kanda, Y. et al., Biotechnol. Bioeng., 94(4):680-688 (2006); WO03/085107; EP 1176195A1, WO04/056312; WO04/057002; WO03/084570; WO03/085119; WO03/05691; 4 WO04/024927; and U.S. Pat. Pub. Nos. US 2003/0157108; US 2003/0115614, US 2004/093621, US 2004/110282, US 2004/110704, and US 2004/132140). Other antibody glycosylation variants are also included (See, e.g., U.S. Pat. No. 6,602,684; Pat. Pub. No. US 2005/0123546; WO03/011878; WO97/30087; WO98/58964; and WO99/22764.

Accordingly, the anti-mutant calreticulin antibody binding domain constructs of the present invention can be produced by a host cell with one or more of exogenous and/or high endogenous glycosyltransferase activities. Genes with glycosyltransferase activity include $\beta(1,4)$-N-acetylglucosaminyltransferase III (GnTIII), $\alpha$-mannosidase II (ManII), $\beta(1,4)$-galactosyltransferase (GalT), $\beta(1,2)$-N-acetylglucosaminyltransferase I (GnTI), and $\beta(1,2)$-N-acetylglucosaminyltransferase II (GnTII). The glycotranferases can comprise a fusion comprising a Golgi localization domain (See, e.g., Lifely et al., Glycobiology 318:813-22 (1995); Schachter, Biochem. Cell Biol. 64:163-81 (1986); U.S. Prov. Pat. App. Nos. 60/495,142 and 60/441,307; Pat. Pub. Nos. US 2003/0175884 and US 2004/0241817; and WO04/065540). In some embodiments, an anti-mutant calreticulin antibody binding domain construct can be expressed in a host cell comprising a disrupted or deactivated glycosyltransferase gene. Accordingly, in some embodiments, the present invention is directed to a host cell comprising (a) an isolated nucleic acid comprising a sequence encoding a polypeptide having a glycosyltransferase activity; and (b) an isolated polynucleotide encoding an anti-mutant calreticulin antibody binding domain construct of the present invention that binds human mutant calreticulin. In a particular embodiment, the modified anti-mutant calreticulin antibody binding domain construct produced by the host cell has an IgG constant region or a fragment thereof comprising the Fc region. In another particular embodiment the anti-mutant calreticulin antibody binding domain construct is a humanized antibody or a fragment thereof comprising an Fc region. An isolated nucleic acid is a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

Anti-mutant calreticulin antibody binding domain constructs with altered glycosylation produced by the host cells can exhibit increased Fc receptor binding affinity (e.g., increased binding to a Fc$\gamma$ activating receptor, such as the Fc$\gamma$RIIIa receptor) and/or increased effector function. The increased effector function can be an increase in one or more of the following: increased antibody-dependent cellular cytotoxicity, increased antibody-dependent cellular phagocytosis (ADCP), increased cytokine secretion, increased immune-complex-mediated antigen uptake by antigen-presenting cells, increased Fc-mediated cellular cytotoxicity, increased binding to NK cells, increased binding to macrophages, increased binding to polymorphonuclear cells (PMNs), increased binding to monocytes, increased cross-linking of target-bound antibodies, increased direct signaling inducing apoptosis, increased dendritic cell maturation, and increased T cell priming. Accordingly, in one aspect, the present invention provides glycoforms of an anti-mutant calreticulin antibody binding domain construct having increased effector function as compared to the anti-mutant calreticulin antibody binding domain construct that has not been glycoengineered. (See, e.g., Tang et al., J. Immunol. 179:2815-2823 (2007)).

The present invention is also directed to a method for producing an anti-mutant calreticulin antibody binding domain construct of the present invention having modified oligosaccharides, comprising (a) culturing a host cell engineered to express at least one nucleic acid encoding a polypeptide having glycosyltransferase activity under conditions which permit the production of an anti-mutant calreticulin antibody binding domain construct according to the present invention, wherein said polypeptide having glycosyltransferase activity is expressed in an amount sufficient to modify the oligosaccharides in the Fc region of said anti-mutant calreticulin antibody binding domain construct produced by said host cell; and (b) isolating said anti-mutant calreticulin antibody binding domain construct. In another embodiment, there are two polypeptides having glycosyltransferase activity. The anti-mutant calreticulin antibody binding domain constructs produced by the methods of the present invention can have increased Fc receptor binding affinity and/or increased effector function.

In some embodiments, the percentage of bisected N-linked oligosaccharides in the Fc region of the anti-mutant calreticulin antibody binding domain construct is at least about 10% to about 100%, specifically at least about 50%, more specifically, at least about 60%, at least about 70%, at least about 80%, or at least about 90-95% of the total oligosaccharides. In yet another embodiment, the antibody produced by the methods has an increased proportion of nonfucosylated oligosaccharides in the Fc region as a result of the modification of its oligosaccharides by the methods of the present invention. In some embodiments, the percentage of nonfucosylated oligosaccharides is at least about 20% to about 100%, specifically at least about 50%, at least about 60% to about 70%, and more specifically, at least about 75%. The nonfucosylated oligosaccharides may be of the hybrid or complex type. In yet another embodiment, the antibody produced by the methods has an increased proportion of bisected oligosaccharides in the Fc region as a result of the modification of its oligosaccharides by the methods of the present invention. In some embodiments, the percentage of bisected oligosaccharides is at least about 20% to about 100%, specifically at least about 50%, at least about 60% to about 70%, and more specifically, at least about 75%.

In another embodiment, the present invention is directed to an anti-mutant calreticulin antibody binding domain construct engineered to have increased effector function and/or increased Fc receptor binding affinity, produced by the methods. In some embodiments, the antibody is an intact antibody. In some embodiments, the antibody is an antibody fragment containing the Fc region, or a fusion protein that includes a region equivalent to the Fc region of an immunoglobulin.

In one aspect, the present invention provides host cell expression systems for the generation of the antibodies of the present invention having modified glycosylation patterns. In particular, the present invention provides host cell systems for the generation of glycoforms of the antibodies of the present invention having an improved therapeutic value. Therefore, the invention provides host cell expression systems selected or engineered to express a polypeptide having a glycosyltransferase activity.

Generally, any type of cultured cell line, including the cell lines discussed above, can be used as a background to engineer the host cell lines of the present invention. In some embodiments, CHO cells, BHK cells, NS0 cells, SP2/0 cells, YO myeloma cells, P3X63 mouse myeloma cells, PER cells, PER.C6 cells or hybridoma cells, other mammalian cells, yeast cells, insect cells, or plant cells are used as the background cell line to generate the engineered host cells.

The host cells which contain the coding sequence of an antibody and which express the biologically active gene products may be identified by at least four general approaches; (a) DNA-DNA or DNA-RNA hybridization; (b) the presence or absence of "marker" gene functions; (c) assessing the level of transcription as measured by the expression of the respective mRNA transcripts in the host cell; and (d) detection of the gene product as measured by immunoassay or by its biological activity.

Fc Region Variants

In some embodiments, one or more amino acid modifications may be introduced into the Fc region of an antibody provided herein, thereby generating an Fc region variant. An Fc region herein is a C-terminal region of an immunoglobulin heavy chain that contains at least a portion of the constant region. An Fc region includes native sequence Fc regions and variant Fc regions. The Fc region variant may comprise a human Fc region sequence (e.g., a human IgG1, IgG2, IgG3 or IgG4 Fc region) comprising an amino acid modification (e.g., a substitution) at one or more amino acid positions.

In some embodiments, the invention contemplates an antibody variant that possesses some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. Non-limiting examples of in vitro assays to assess ADCC activity of a molecule of interest is described in U.S. Pat. Nos. 5,500,362 and 5,821,337. Alternatively, non-radioactive assays methods may be employed (e.g., ACTI™ and CytoTox 96® non-radioactive cytotoxicity assays). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model (See, e.g., Clynes et al. Proc. Nat'l Acad. Sci. USA 95:652-656 (1998). C1q binding assays may also be carried out to confirm that the antibody is able or unable bind C1q and hence contains or lacks CDC activity (See, e.g., WO06/029879, WO99/51642, and WO05/100402; U.S. Pat. No. 6,194,551; and Idusogie et al. J. Immunol. 164: 4178-4184

(2000)). To assess complement activation, a CDC assay may be performed (See, e.g., Gazzano-Santoro et al., J. Immunol. Methods 202:163 (1996); Cragg, M. S. et al., Blood 101: 1045-1052 (2003); and Cragg et al., Blood 103:2738-2743 (2004)). FcRn binding and in vivo clearance/half-life determinations can also be performed using methods known in the art (See, e.g., Petkova, S. B. et al., Int'l. Immunol. 18(12):1759-1769 (2006)). Antibodies with reduced effector function include those with substitution of one or more of Fc region residues 238, 265, 269, 270, 297, 327 and 329; or two or more of amino acid positions 265, 269, 270, 297 and 327, such as an Fc mutant with substitution of residues 265 and 297 to alanine (See, e.g., U.S. Pat. Nos. 6,737,056 and 7,332,581). Antibody variants with improved or diminished binding to FcRs are also included (See, e.g., U.S. Pat. No. 6,737,056; WO04/056312, and Shields et al., J. Biol. Chem. 9(2): 6591-6604 (2001)). In some embodiments, an antibody variant comprises an Fc region with one or more amino acid substitutions which improve ADCC, e.g., substitutions at positions 298, 333, and/or 334 of the Fc region.

Antibodies can have increased half-lives and improved binding to the neonatal Fc receptor (FcRn) (See, e.g., US 2005/0014934). Such antibodies can comprise an Fc region with one or more substitutions therein which improve binding of the Fc region to FcRn, and include those with substitutions at one or more of Fc region residues: 238, 256, 265, 272, 286, 303, 305, 307, 311, 312, 317, 340, 356, 360, 362, 376, 378, 380, 382, 413, 424 or 434 (See, e.g., U.S. Pat. No. 7,371,826). Other examples of Fc region variants are also contemplated (See, e.g., Duncan & Winter, Nature 322:738-40 (1988); U.S. Pat. Nos. 5,648,260 and 5,624,821; and WO94/29351).

Cysteine Engineered Antibody Variants

In some embodiments, it may be desirable to create cysteine engineered antibodies, e.g., "thioMAbs," in which one or more residues of an antibody are substituted with cysteine residues. In some embodiments, the substituted residues occur at accessible sites of the antibody. Reactive thiol groups can be positioned at sites for conjugation to other moieties, such as drug moieties or linker-drug moieties, to create an immunoconjugate. In some embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described (See, e.g., U.S. Pat. No. 7,521,541.

Antibody Derivatives

In some embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, polypropylene glycol homopolymers, polypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water.

The polymer may be of any molecular weight, and may be branched or unbranched. The number of polymers attached to the antibody may vary, and if two or more polymers are attached, they can be the same or different molecules.

In another embodiment, conjugates of an antibody and nonproteinaceous moiety that may be selectively heated by exposure to radiation are provided. In some embodiments, the nonproteinaceous moiety is a carbon nanotube (See, e.g., Kam et al., Proc. Natl. Acad. Sci. USA 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

Recombinant Methods and Compositions

Antibodies may be produced using recombinant methods and compositions (See, e.g., U.S. Pat. No. 4,816,567). In some embodiments, an isolated nucleic acid encoding an anti-mutant calreticulin antibody binding domain construct described herein is provided. Such nucleic acid may encode an amino acid sequence comprising the $V_L$ and/or an amino acid sequence comprising the $V_H$ of the antibody. In a further embodiment, one or more vectors comprising such nucleic acid are provided. A vector is a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked.

In a further embodiment, a host cell comprising such nucleic acid is provided. Host cells are cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein. In one such embodiment, a host cell comprises (e.g., has been transformed with) a vector comprising a nucleic acid that encodes an amino acid sequence comprising the $V_L$ of the antibody and an amino acid sequence comprising the $V_H$ of the antibody or a first vector comprising a nucleic acid that encodes an amino acid sequence comprising the $V_L$ of the antibody and a second vector comprising a nucleic acid that encodes an amino acid sequence comprising the $V_H$ of the antibody. In some embodiments, the host cell is eukaryotic, e.g., a Chinese Hamster Ovary (CHO) cell or lymphoid cell (e.g., Y0, NS0, Sp20 cell). In some embodiments, a method of making an anti-mutant calreticulin antibody binding domain construct is provided, wherein the method comprises culturing a host cell comprising a nucleic acid encoding the antibody, as provided above, under conditions suitable for expression of the antibody, and optionally recovering the antibody from the host cell or host cell culture medium.

For recombinant production of an anti-mutant calreticulin antibody binding domain construct, an isolated nucleic acid encoding an antibody, e.g., as described above, is inserted into one or more vectors for further cloning and/or expression in a host cell. Such nucleic acid may be readily isolated and sequenced using conventional procedures.

Suitable host cells for cloning or expression of antibody-encoding vectors include prokaryotic or eukaryotic cells described herein. For example, antibodies may be produced in bacteria, e.g., when glycosylation and Fc effector function are not needed (See, e.g., U.S. Pat. Nos. 5,648,237, 5,789,199, and 5,840,523; Charlton, Methods in Molecular Biology, Vol. 248, pp. 245-254 (2003)). After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors (See, e.g., Gerngross, Nat. Biotech. 22:1409-1414 (2004), and Li et al., Nat. Biotech. 24:210-215 (2006)). Suitable host cells for the expression of glycosylated antibody are also derived from multicellular organisms, including invertebrates and vertebrates. Examples of invertebrates include plant and insect cells (See, e.g., U.S. Pat. Nos. 5,959,177, 6,040,498, 6,420,548, 7,125,978, and 6,417,429). Examples of vertebrate cells include mammalian cell lines, monkey kidney CV1 line transformed by SV40 (COS-7); human embryonic kidney line (293 or 293 cells as described, e.g., in Graham et al., J. Gen Virol. 36:59 (1977)); baby hamster kidney cells (BHK); mouse sertoli cells (TM4 cells); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TR1 cells; MRC 5 cells; FS4 cells; Chinese hamster ovary (CHO) cells, including DHFR− CHO cells; and myeloma cell lines such as Y0, NS0 and Sp2/0. (See, e.g., Yazaki and Wu, Methods in Molecular Biology, Vol. 248, pp. 255-268 (2003).

Assays

Anti-mutant calreticulin antibody binding domain constructs provided herein may be identified, screened for, or characterized for their physical/chemical properties and/or biological activities by various assays known in the art.

In one aspect, an antibody is tested for its antigen binding activity, e.g., by ELISA, Western blot, etc. In one aspect, competition assays may be used to identify an antibody that competes with the anti-mutant calreticulin antibody binding domain constructs described herein for binding to mutant calreticulin. In some embodiments, such a competing antibody binds to the same epitope (e.g., a linear or a conformational epitope) that is bound by the anti-mutant calreticulin antibody binding domain constructs described herein. Exemplary epitope mapping methods are known (See, e.g., Morris "Epitope Mapping Protocols," in Methods in Molecular Biology vol. 66 (1996)).

In an exemplary competition assay, immobilized mutant calreticulin is incubated in a solution comprising a first labeled antibody that binds to mutant calreticulin and a second unlabeled antibody that is being tested for its ability to compete with the first antibody for binding to mutant calreticulin. The second antibody may be present in a hybridoma supernatant. As a control, immobilized mutant calreticulin is incubated in a solution comprising the first labeled antibody but not the second unlabeled antibody. After incubation under conditions permissive for binding of the first antibody to mutant calreticulin, excess unbound antibody is removed, and the amount of label associated with immobilized mutant calreticulin is measured. If the amount of label associated with immobilized mutant calreticulin is substantially reduced in the test sample relative to the control sample, then that indicates that the second antibody is competing with the first antibody for binding to mutant calreticulin (See, e.g., Harlow and Lane Antibodies: A Laboratory Manual ch. 14 (1996)).

In one aspect, assays are provided for identifying anti-mutant calreticulin antibody binding domain constructs thereof having biological activity. In some embodiments, assays are provided for identifying anti-mutant calreticulin antibody binding domain constructs thereof having neutralization activity for mutant calreticulin. Antibodies having such biological activity in vivo and/or in vitro are also provided. In some embodiments, an antibody is tested for such biological activity.

Immunoconjugates

The invention also provides immunoconjugates comprising an anti-mutant calreticulin antibody binding domain construct. An immunoconjugate is an antibody conjugated to one or more heterologous molecule(s). For example, an immunoconjugate can comprise an anti-mutant calreticulin antibody binding domain construct conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In some embodiments, an immunoconjugate is an antibody-drug conjugate (ADC) in which an antibody is conjugated to one or more drugs, including but not limited to a maytansinoid; an auristatin such as monomethylauristatin drug moieties DE and DF (MMAE and MMAF); a dolastatin; a calicheamicin or derivative thereof; an anthracycline such as daunomycin or doxorubicin; methotrexate; vindesine; a taxane such as docetaxel, paclitaxel, larotaxel, tesetaxel, and ortataxel; a trichothecene; and CC1065 (See, e.g., U.S. Pat. Nos. 5,208,020, 5,416,064, 5,635,483, 5,780,588, 7,498,298, 5,712,374, 5,714,586, 5,739,116, 5,767,285, 5,770,701, 5,770,710, 5,773,001, 6,630,579, and 5,877,296; EP0425235B1; Hinman et al., Cancer Res. 53:3336-3342 (1993); Lode et al., Cancer Res. 58:2925-2928 (1998); Kratz et al., Current Med. Chem. 13:477-523 (2006); Jeffrey et al., Bioorganic & Med. Chem. Letters 16:358-362 (2006); Torgov et al., Bioconj. Chem. 16:717-721 (2005); Nagy et al., Proc. Natl. Acad. Sci. USA 97:829-834 (2000); Dubowchik et al., Bioorg. & Med. Chem. Letters 12:1529-1532 (2002); and King et al., J. Med. Chem. 45:4336-4343 (2002)).

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. Exemplary radioactive isotopes available for the production of radioconjugates include $At^{211}$, $I^{113}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. A radioconjugate can comprise a radioactive atom for scintigraphic detection (e.g., tc99m or 1123, or a spin label for nuclear magnetic resonance (NMR) imaging, such as iodine-123 again, iodine-131, indium-111, fluorine-19, carbon-13, nitrogen-15, oxygen-17, gadolinium, manganese or iron).

Conjugates of an antibody and cytotoxic agent can be made using bifunctional protein coupling agents, such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (e.g., disuccinimidyl suberate), aldehydes (e.g., glutaraldehyde), bis-azido compounds (e.g., bis(p-azidobenzoyl) hexanediamine), bis-diazonium derivatives (e.g., bis-(p-diazoniumbenzoyl)-ethylenediamine), diisocyanates (such as toluene 2,6-diisocyanate), and bis-active fluorine compounds (e.g., 1,5-difluoro-2,4-dinitrobenzene). For example, a ricin immunotoxin can be prepared (See, e.g., Vitetta et al., Science 238:1098 (1987)). Carbon-14-labeled 1-isothiocyanatobenzyl-3-methyldiethylene triaminepentaacetic acid (MX-DTPA) is an exemplary chelating agent for conjugation of radionucleotide to the antibody (See, e.g., WO94/11026). The linker may be cleavable, facilitating release of a cytotoxic drug in the cell. Exemplary cleavable linkers include an acid-labile linker, peptidase-sensitive linker, photolabile linker, dimethyl linker and disulfide-containing linker (See, e.g., Chari et al., Cancer Res. 52:127-131 (1992); U.S. Pat. No. 5,208,020).

Immunoconjugates or ADCs herein expressly contemplate conjugates prepared with cross-linker reagents. Exemplary cross-linker reagents include BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate).

Bispecific CARs

In an embodiment a multispecific antibody molecule is a bispecific antibody molecule. A bispecific antibody has specificity for no more than two antigens. A bispecific antibody molecule is characterized by a first immunoglobulin variable domain sequence which has binding specificity for a first epitope and a second immunoglobulin variable domain sequence that has binding specificity for a second epitope. In an embodiment the first and second epitopes are on the same antigen, e.g., the same protein (or subunit of a multimeric protein). In an embodiment the first and second epitopes overlap. In an embodiment the first and second epitopes do not overlap. In an embodiment the first and second epitopes are on different antigens, e.g., different proteins (or different subunits of a multimeric protein). In an embodiment a bispecific antibody molecule comprises a heavy chain variable domain sequence and a light chain variable domain sequence which have binding specificity for a first epitope and a heavy chain variable domain sequence and a light chain variable domain sequence which have binding specificity for a second epitope. In an embodiment a bispecific antibody molecule comprises a half antibody having binding specificity for a first epitope and a half antibody having binding specificity for a second epitope. In an embodiment a bispecific antibody molecule comprises a half antibody, or fragment thereof, having binding specificity for a first epitope and a half antibody, or fragment thereof, having binding specificity for a second epitope. In an embodiment a bispecific antibody molecule comprises a scFv, or fragment thereof, have binding specificity for a first epitope and a scFv, or fragment thereof, have binding specificity for a second epitope.

In certain embodiments, the antibody molecule is a multi-specific (e.g., a bispecific or a trispecific) antibody molecule. Protocols for generating bispecific or heterodimeric antibody molecules are known in the art; including but not limited to, for example, the "knob in a hole" approach described in, e.g., U.S. Pat. No. 5,731,168; the electrostatic steering Fc pairing as described in, e.g., WO 09/089004, WO 06/106905 and WO 2010/129304; Strand Exchange Engineered Domains (SEED) heterodimer formation as described in, e.g., WO 07/110205; Fab arm exchange as described in, e.g., WO 08/119353, WO 2011/131746, and WO 2013/060867; double antibody conjugate, e.g., by antibody cross-linking to generate a bi-specific structure using a heterobifunctional reagent having an amine-reactive group and a sulfhydryl reactive group as described in, e.g., U.S. Pat. No. 4,433,059; bispecific antibody determinants generated by recombining half antibodies (heavy-light chain pairs or Fabs) from different antibodies through cycle of reduction and oxidation of disulfide bonds between the two heavy chains, as described in, e.g., U.S. Pat. No. 4,444,878; trifunctional antibodies, e.g., three Fab' fragments cross-linked through sulfhdryl reactive groups, as described in, e.g., U.S. Pat. No. 5,273,743; biosynthetic binding proteins, e.g., pair of scFvs cross-linked through C-terminal tails preferably through disulfide or amine-reactive chemical cross-linking, as described in, e.g., U.S. Pat. No. 5,534,254; bifunctional antibodies, e.g., Fab fragments with different binding specificities dimerized through leucine zippers (e.g., c-fos and c-jun) that have replaced the constant domain, as described in, e.g., U.S. Pat. No. 5,582,996; bispecific and oligospecific mono- and oligovalent receptors, e.g., $V_H$-CH1 regions of two antibodies (two Fab fragments) linked through a polypeptide spacer between the CH1 region of one antibody and the $V_H$ region of the other antibody typically with associated light chains, as described in, e.g., U.S. Pat. No. 5,591,828; bispecific DNA-antibody conjugates, e.g., crosslinking of antibodies or Fab fragments through a double stranded piece of DNA, as described in, e.g., U.S. Pat. No. 5,635,602; bispecific fusion proteins, e.g., an expression construct containing two scFvs with a hydrophilic helical peptide linker between them and a full constant region, as described in, e.g., U.S. Pat. No. 5,637,481; multivalent and multispecific binding proteins, e.g., dimer of polypeptides having first domain with binding region of Ig heavy chain variable region, and second domain with binding region of Ig light chain variable region, generally termed diabodies (higher order structures are also encompassed creating for bispecifc, trispecific, or tetraspecific molecules, as described in, e.g., U.S. Pat. No. 5,837,242; minibody constructs with linked $V_L$ and $V_H$ chains further connected with peptide spacers to an antibody hinge region and CH3 region, which can be dimerized to form bispecific/multivalent molecules, as described in, e.g., U.S. Pat. No. 5,837,821; $V_H$ and $V_L$ domains linked with a short peptide linker (e.g., 5 or 10 amino acids) or no linker at all in either orientation, which can form dimers to form bispecific diabodies; trimers and tetramers, as described in, e.g., U.S. Pat. No. 5,844,094; String of $V_H$ domains (or $V_L$ domains in family members) connected by peptide linkages with cross-linkable groups at the C-terminus further associated with $V_L$ domains to form a series of FVs (or scFvs), as described in, e.g., U.S. Pat. No. 5,864,019; and single chain binding polypeptides with both a $V_H$ and a $V_L$ domain linked through a peptide linker are combined into multivalent structures through non-covalent or chemical crosslinking to form, e.g., homobivalent, heterobivalent, trivalent, and tetravalent structures using both scFV or diabody type format, as described in, e.g., U.S. Pat. No. 5,869,620. Additional exemplary multispecific and bispecific molecules and methods of making the same are found, for example, in U.S. Pat. Nos. 5,910,573, 5,932,448, 5,959,083, 5,989,830, 6,005,079, 6,239,259, 6,294,353, 6,333,396, 6,476,198, 6,511,663, 6,670,453, 6,743,896, 6,809,185, 6,833,441, 7,129,330, 7,183,076, 7,521,056, 7,527,787, 7,534,866, 7,612,181, US2002004587A1, US2002076406A1, US2002103345A1, US2003207346A1, US2003211078A1, US2004219643A1, US2004220388A1, US2004242847A1, US2005003403A1, US2005004352A1, US2005069552A1, US2005079170A1, US2005100543A1, US2005136049A1, US2005136051A1, US2005163782A1, US2005266425A1, US2006083747A1, US2006120960A1, US2006204493A1, US2006263367A1, US2007004909A1, US2007087381A1, US2007128150A1, US2007141049A1, US2007154901A1, US2007274985A1, US2008050370A1, US2008069820A1, US2008152645A1, US2008171855A1, US2008241884A1, US2008254512A1, US2008260738A1, US2009130106A1, US2009148905A1, US2009155275A1, US2009162359A1, US2009162360A1, US2009175851A1, US2009175867A1, US2009232811A1, US2009234105A1, US2009263392A1, US2009274649A1, EP346087A2, WO0006605A2, WO02072635A2, WO04081051A1, WO06020258A2, WO2007044887A2, WO2007095338A2, WO2007137760A2, WO2008119353A1, WO2009021754A2, WO2009068630A1, WO9103493A1, WO9323537A1, WO9409131A1, WO9412625A2, WO9509917A1, WO9637621A2, WO9964460A1. The contents of the above-referenced applications are incorporated herein by reference in their entireties.

Within each antibody or antibody fragment (e.g., scFv) of a bispecific antibody molecule, the $V_H$ can be upstream or downstream of the $V_L$. In some embodiments, the upstream antibody or antibody fragment (e.g., scFv) is arranged with its $V_H$ ($V_H1$) upstream of its $V_L$ ($V_L1$) and the downstream antibody or antibody fragment (e.g., scFv) is arranged with its $V_L$ ($V_L2$) upstream of its $V_H$ ($V_H2$), such that the overall bispecific antibody molecule has the arrangement $V_H1$-$V_L1$-$V_L2$-$V_H2$. In other embodiments, the upstream antibody or antibody fragment (e.g., scFv) is arranged with its $V_L$ ($V_L1$) upstream of its $V_H$ ($V_H1$) and the downstream antibody or antibody fragment (e.g., scFv) is arranged with its $V_H$ ($V_H2$) upstream of its $V_L$ ($V_L2$), such that the overall bispecific antibody molecule has the arrangement $V_L1$-$V_H1$-$V_H2$-$V_L2$. Optionally, a linker is disposed between the two antibodies or antibody fragments (e.g., scFvs), e.g., between $V_L1$ and $V_L2$ if the construct is arranged as $V_H1$-$V_L1$-$V_L2$-$V_H2$, or between $V_H1$ and $V_H2$ if the construct is arranged as $V_L1$-$V_H1$-$V_H2$-$V_L2$. The linker may be a linker as described herein, e.g., a $(Gly_4$-$Ser)n$ linker, wherein n is 1, 2, 3, 4, 5, or 6, preferably 4 (SEQ ID NO: 64 44). In general, the linker between the two scFvs should be long enough to avoid mispairing between the domains of the two scFvs. Optionally, a linker is disposed between the $V_L$ and $V_H$ of the first scFv. Optionally, a linker is disposed between the $V_L$ and $V_H$ of the second scFv. In constructs that have multiple linkers, any two or more of the linkers can be the same or different. Accordingly, in some embodiments, a bispecific CAR comprises $V_L$s, $V_H$s, and optionally one or more linkers in an arrangement as described herein.

In one aspect, the bispecific antibody molecule is characterized by a first immunoglobulin variable domain sequence, e.g., a scFv, which has binding specificity for mutant calreticulin, e.g., comprises a scFv as described herein, e.g., as described in Table 2, Table 6, or Table 9, or comprises the light chain CDRs and/or heavy chain CDRs from a mutant calreticulin scFv described herein, and a second immunoglobulin variable domain sequence that has binding specificity for a second epitope on a different antigen. In some aspects the second immunoglobulin variable domain sequence has binding specificity for an antigen expressed on AML cells, e.g., an antigen other than mutant calreticulin. For example, the second immunoglobulin variable domain sequence has binding specificity for CLL-1. As another example, the second immunoglobulin variable domain sequence has binding specificity for CD33. As another example, the second immunoglobulin variable domain sequence has binding specificity for CD34. As another example, the second immunoglobulin variable domain sequence has binding specificity for FLT3. For example, the second immunoglobulin variable domain sequence has binding specificity for folate receptor beta. In some aspects, the second immunoglobulin variable domain sequence has binding specificity for an antigen expressed on B-cells, for example, CD19, CD20, CD22 or ROR1.

Chimeric TCR

In one aspect, the mutant calreticulin antibodies and antibody fragments of the present invention (can be grafted to one or more constant domain of a T cell receptor ("TCR") chain, for example, a TCR alpha or TCR beta chain, to create an chimeric TCR that binds specificity to mutant calreticulin. Without being bound by theory, it is believed that chimeric TCRs will signal through the TCR complex upon antigen binding. For example, a mutant calreticulin scFv as disclosed herein, can be grafted to the constant domain, e.g., at least a portion of the extracellular constant domain, the transmembrane domain and the cytoplasmic domain, of a TCR chain, for example, the TCR alpha chain and/or the TCR beta chain. As another example, a mutant calreticulin antibody fragment, for example a $V_L$ domain as described herein, can be grafted to the constant domain of a TCR alpha chain, and a mutant calreticulin antibody fragment, for example a $V_H$ domain as described herein, can be grafted to the constant domain of a TCR beta chain (or alternatively, a $V_L$ domain may be grafted to the constant domain of the TCR beta chain and a $V_H$ domain may be grafted to a TCR alpha chain). As another example, the CDRs of a mutant calreticulin antibody or antibody fragment, e.g., the CDRs of a mutant calreticulin antibody or antibody fragment as described in Tables 3, 4, 5, 6, 7, 8, 10, 11, 12 or 13 may be grafted into a TCR alpha and/or beta chain to create a chimeric TCR that binds specifically to mutant calreticulin. For example, the LCDRs disclosed herein may be grafted into the variable domain of a TCR alpha chain and the HCDRs disclosed herein may be grafted to the variable domain of a TCR beta chain, or vice versa. Such chimeric TCRs may be produced by methods known in the art (For example, Willemsen R A et al, Gene Therapy 2000; 7: 1369-1377; Zhang T et al, Cancer Gene Ther 2004; 11: 487-496; Aggen et al, Gene Ther. 2012 April; 19(4):365-74).

Stability and Mutations

The stability of a mutant calreticulin binding domain, e.g., scFv molecules (e.g., soluble scFv) can be evaluated in reference to the biophysical properties (e.g., thermal stability) of a conventional control scFv molecule or a full length antibody. In one embodiment, the human scFv has a thermal stability that is greater than about 0.1, about 0.25, about 0.5, about 0.75, about 1, about 1.25, about 1.5, about 1.75, about 2, about 2.5, about 3, about 3.5, about 4, about 4.5, about 5, about 5.5, about 6, about 6.5, about 7, about 7.5, about 8, about 8.5, about 9, about 9.5, about 10 degrees, about 11 degrees, about 12 degrees, about 13 degrees, about 14 degrees, or about 15 degrees Celsius than a control binding molecule (e.g. a conventional scFv molecule) in the described assays.

The improved thermal stability of the mutant calreticulin binding domain, e.g., scFv is subsequently conferred to the entire CAR-T mutant calreticulin construct, leading to improved therapeutic properties of the CAR-T mutant calreticulin construct. The thermal stability of the mutant calreticulin binding domain, e.g., scFv can be improved by at least about 2° C. or 3° C. as compared to a conventional antibody. In one embodiment, the mutant calreticulin binding domain, e.g., scFv has a 1° C. improved thermal stability as compared to a conventional antibody. In another embodiment, the mutant calreticulin binding domain, e.g., scFv has a 2° C. improved thermal stability as compared to a conventional antibody. In another embodiment, the scFv has a 4, 5, 6, 7, 8, 9, 10, 11, 12, 13, 14, 15° C. improved thermal stability as compared to a conventional antibody. Comparisons can be made, for example, between the scFv molecules disclosed herein and full length antibodies. Thermal stability can be measured using methods known in the art. For example, in one embodiment, Tm can be measured. Methods for measuring Tm and other methods of determining protein stability are described in more detail below.

Mutations in scFv alter the stability of the scFv and improve the overall stability of the scFv and the CAR-T mutant calreticulin construct. Stability of the humanized or human scFv is determined using measurements such as Tm, temperature denaturation and temperature aggregation.

In one embodiment, the mutant calreticulin binding domain, e.g., scFv comprises at least one mutation such that the mutated scFv confers improved stability to the CAR-T mutant calreticulin construct. In another embodiment, the mutant calreticulin binding domain, e.g., scFv comprises at least 1, 2, 3, 4, 5, 6, 7, 8, 9, 10 mutations arising from the humanization process such that the mutated scFv confers improved stability to the CAR-T mutant calreticulin construct.

Methods of Evaluating Protein Stability

The stability of an antigen binding domain may be assessed using, e.g., the methods described below. Such methods allow for the determination of multiple thermal unfolding transitions where the least stable domain either unfolds first or limits the overall stability threshold of a multidomain unit that unfolds cooperatively (e.g., a multidomain protein which exhibits a single unfolding transition). The least stable domain can be identified in a number of additional ways. Mutagenesis can be performed to probe which domain limits the overall stability. Additionally, protease resistance of a multidomain protein can be performed under conditions where the least stable domain is known to be intrinsically unfolded via DSC or other spectroscopic methods (Fontana, et al., (1997) Fold. Des., 2: R17-26; Dimasi et al. (2009) J. Mol. Biol. 393: 672-692). Once the least stable domain is identified, the sequence encoding this domain (or a portion thereof) may be employed as a test sequence in the methods.

The thermal stability of the compositions may be analyzed using a number of non-limiting biophysical or biochemical techniques known in the art. In certain embodiments, thermal stability is evaluated by analytical spectroscopy.

An exemplary analytical spectroscopy method is Differential Scanning calorimetry (DSC). DSC employs a calorimeter which is sensitive to the heat absorbances that accompany the unfolding of most proteins or protein domains (see, e.g. Sanchez-Ruiz, et al., Biochemistry, 27: 1648-52, 1988). To determine the thermal stability of a protein, a sample of the protein is inserted into the calorimeter and the temperature is raised until the Fab or scFv unfolds. The temperature at which the protein unfolds is indicative of overall protein stability.

Another exemplary analytical spectroscopy method is Circular Dichroism (CD) spectroscopy. CD spectrometry measures the optical activity of a composition as a function of increasing temperature. Circular dichroism (CD) spectroscopy measures differences in the absorption of left-handed polarized light versus right-handed polarized light which arise due to structural asymmetry. A disordered or unfolded structure results in a CD spectrum very different from that of an ordered or folded structure. The CD spectrum reflects the sensitivity of the proteins to the denaturing effects of increasing temperature and is therefore indicative of a protein's thermal stability (see van Mierlo and Steemsma, J. Biotechnol., 79(3):281-98, 2000).

Another exemplary analytical spectroscopy method for measuring thermal stability is Fluorescence Emission Spectroscopy (see van Mierlo and Steemsma, supra). Yet another exemplary analytical spectroscopy method for measuring thermal stability is Nuclear Magnetic Resonance (NMR) spectroscopy (see, e.g. van Mierlo and Steemsma, supra).

The thermal stability of a composition can be measured biochemically. An exemplary biochemical method for assessing thermal stability is a thermal challenge assay. In a "thermal challenge assay", a composition is subjected to a range of elevated temperatures for a set period of time. For example, in one embodiment, test scFv molecules or molecules comprising scFv molecules are subject to a range of increasing temperatures, e.g., for 1-1.5 hours. The activity of the protein is then assayed by a relevant biochemical assay. For example, if the protein is a binding protein (e.g. an scFv or scFv-containing polypeptide) the binding activity of the binding protein may be determined by a functional or quantitative ELISA.

Such an assay may be done in a high-throughput format and those disclosed in the Examples using *E. coli* and high throughput screening. A library of mutant calreticulin binding domains, e.g., scFv variants may be created using methods known in the art. mutant calreticulin binding domains, e.g., scFv expression may be induced and the mutant calreticulin binding domains, e.g., scFv may be subjected to thermal challenge. The challenged test samples may be assayed for binding and those mutant calreticulin binding domains, e.g., scFvs which are stable may be scaled up and further characterized.

Thermal stability is evaluated by measuring the melting temperature (Tm) of a composition using any of the above techniques (e.g. analytical spectroscopy techniques). The melting temperature is the temperature at the midpoint of a thermal transition curve wherein 50% of molecules of a composition are in a folded state (See e.g., Dimasi et al. (2009) J. Mol Biol. 393: 672-692). In one embodiment, Tm values for a mutant calreticulin binding domain, e.g., scFv are about 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., 100° C. In one embodiment, Tm values for an IgG is about 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., 100° C. In one embodiment, Tm values for an multivalent antibody is about 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74°

C., 75° C., 76° C., 77° C., 78° C., 79° C., 80° C., 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., 100° C.

Thermal stability is also evaluated by measuring the specific heat or heat capacity (Cp) of a composition using an analytical calorimetric technique (e.g. DSC). The specific heat of a composition is the energy (e.g. in kcal/mol) is required to rise by 1° C., the temperature of 1 mol of water. As large Cp is a hallmark of a denatured or inactive protein composition. The change in heat capacity (ΔCp) of a composition is measured by determining the specific heat of a composition before and after its thermal transition. Thermal stability may also be evaluated by measuring or determining other parameters of thermodynamic stability including Gibbs free energy of unfolding (ΔG), enthalpy of unfolding (ΔH), or entropy of unfolding (ΔS). One or more of the above biochemical assays (e.g. a thermal challenge assay) are used to determine the temperature (i.e. the TC value) at which 50% of the composition retains its activity (e.g. binding activity).

In addition, mutations to the mutant calreticulin binding domain, e.g., scFv alter the thermal stability of the mutant calreticulin binding domain, e.g., scFv compared with the unmutated mutant calreticulin binding domain, e.g., scFv. When the humanized or human mutant calreticulin binding domain, e.g., scFv is incorporated into a CAR-T mutant calreticulin construct, the mutant calreticulin binding domain, e.g., humanized or human scFv confers thermal stability to the overall mutant calreticulin CART construct. In one embodiment, the mutant calreticulin binding domain, e.g., scFv comprises a single mutation that confers thermal stability to the mutant calreticulin binding domain, e.g., scFv. In another embodiment, the mutant calreticulin binding domain, e.g., scFv comprises multiple mutations that confer thermal stability to the mutant calreticulin binding domain, e.g., scFv. In one embodiment, the multiple mutations in the mutant calreticulin binding domain, e.g., scFv have an additive effect on thermal stability of the mutant calreticulin binding domain, e.g., scFv.

The stability of a composition can be determined by measuring its propensity to aggregate. Aggregation can be measured by a number of non-limiting biochemical or biophysical techniques. For example, the aggregation of a composition may be evaluated using chromatography, e.g. Size-Exclusion Chromatography (SEC). SEC separates molecules on the basis of size. A column is filled with semi-solid beads of a polymeric gel that will admit ions and small molecules into their interior but not large ones. When a protein composition is applied to the top of the column, the compact folded proteins (i.e. non-aggregated proteins) are distributed through a larger volume of solvent than is available to the large protein aggregates. Consequently, the large aggregates move more rapidly through the column, and in this way the mixture can be separated or fractionated into its components. Each fraction can be separately quantified (e.g. by light scattering) as it elutes from the gel. Accordingly, the % aggregation of a composition can be determined by comparing the concentration of a fraction with the total concentration of protein applied to the gel. Stable compositions elute from the column as essentially a single fraction and appear as essentially a single peak in the elution profile or chromatogram.

The stability of a composition can be assessed by determining its target binding affinity. A wide variety of methods for determining binding affinity are known in the art. An exemplary method for determining binding affinity employs surface plasmon resonance. Surface plasmon resonance is an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Jonsson, U., et al. (1993) Ann. Biol. Clin. 51:19-26; Jonsson, U., i (1991) Biotechniques 11:620-627; Johnsson, B., et al. (1995) J. Mol. Recognit. 8:125-131; and Johnnson, B., et al. (1991) Anal. Biochem. 198:268-277.

In one aspect, the antigen binding domain of the CAR comprises an amino acid sequence that is homologous to an antigen binding domain amino acid sequence described herein, and the antigen binding domain retains the desired functional properties of the mutant calreticulin antibody fragments described herein. In one specific aspect, the CAR composition of the invention comprises an antibody fragment. In a further aspect, that antibody fragment comprises an scFv.

In various aspects, the antigen binding domain of the CAR is engineered by modifying one or more amino acids within one or both variable regions (e.g., $V_H$ and/or $V_L$), for example within one or more CDR regions and/or within one or more framework regions. In one specific aspect, the CAR composition of the invention comprises an antibody fragment. In a further aspect, that antibody fragment comprises an scFv.

It will be understood by one of ordinary skill in the art that the antibody or antibody fragment of the invention may further be modified such that they vary in amino acid sequence (e.g., from wild-type), but not in desired activity. For example, additional nucleotide substitutions leading to amino acid substitutions at "non-essential" amino acid residues may be made to the protein For example, a nonessential amino acid residue in a molecule may be replaced with another amino acid residue from the same side chain family. In another embodiment, a string of amino acids can be replaced with a structurally similar string that differs in order and/or composition of side chain family members, e.g., a conservative substitution, in which an amino acid residue is replaced with an amino acid residue having a similar side chain, may be made.

Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Percent identity in the context of two or more nucleic acids or polypeptide sequences, refers to two or more sequences that are the same. Two sequences are "substantially identical" if two sequences have a specified percentage of amino acid residues or nucleotides that are the same (e.g., 60% identity, optionally 70%, 71%. 72%. 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. Methods of alignment of sequences for comparison are well known in the art. Optimal alignment of sequences for comparison can be conducted, e.g., by the local homology algorithm of Smith and Waterman, (1970) Adv. Appl. Math. 2:482c, by the homology alignment algorithm of Needleman and Wunsch, (1970) J. Mol. Biol. 48:443, by the search for similarity method of Pearson and Lipman, (1988) Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Brent et al., (2003) Current Protocols in Molecular Biology).

Two examples of algorithms that are suitable for determining percent sequence identity and sequence similarity are the BLAST and BLAST 2.0 algorithms, which are described in Altschul et al., (1977) Nuc. Acids Res. 25:3389-3402; and Altschul et al., (1990) J. Mol. Biol. 215:403-410, respectively. Software for performing BLAST analyses is publicly available through the National Center for Biotechnology Information.

The percent identity between two amino acid sequences can also be determined using the algorithm of E. Meyers and W. Miller, (1988) Comput. Appl. Biosci. 4:11-17) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (1970) J. Mol. Biol. 48:444-453) algorithm which has been incorporated into the GAP program in the GCG software package (available at www.gcg.com), using either a Blossom 62 matrix or a PAM250 matrix, and a gap weight of 16, 14, 12, 10, 8, 6, or 4 and a length weight of 1, 2, 3, 4, 5, or 6.

In one aspect, the present invention contemplates modifications of the starting antibody or fragment (e.g., scFv) amino acid sequence that generate functionally equivalent molecules. For example, the $V_H$ or $V_L$ of a mutant calreticulin binding domain, e.g., scFv, comprised in the CAR can be modified to retain at least about 70%, 71%. 72%. 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identity of the starting $V_H$ or $V_L$ framework region of the mutant calreticulin binding domain, e.g., scFv. The present invention contemplates modifications of the entire CAR construct, e.g., modifications in one or more amino acid sequences of the various domains of the CAR construct in order to generate functionally equivalent molecules. The CAR construct can be modified to retain at least about 70%, 71%. 72%. 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identity of the starting CAR construct.

Transmembrane Domain

With respect to the transmembrane domain, in various embodiments, a CAR can be designed to comprise a transmembrane domain that is attached to the extracellular domain of the CAR. A transmembrane domain can include one or more additional amino acids adjacent to the transmembrane region, e.g., one or more amino acid associated with the extracellular region of the protein from which the transmembrane was derived (e.g., 1, 2, 3, 4, 5, 6, 7, 8, 9, 10 up to 15 amino acids of the extracellular region) and/or one or more additional amino acids associated with the intracellular region of the protein from which the transmembrane protein is derived (e.g., 1, 2, 3, 4, 5, 6, 7, 8, 9, 10 up to 15 amino acids of the intracellular region). In one aspect, the transmembrane domain is one that is associated with one of the other domains of the CAR is used. In some instances, the transmembrane domain can be selected or modified by amino acid substitution to avoid binding of such domains to the transmembrane domains of the same or different surface membrane proteins, e.g., to minimize interactions with other members of the receptor complex. In one aspect, the transmembrane domain is capable of homodimerization with another CAR on the CAR-expressing cell, e.g., CART cell, cell surface. In a different aspect the amino acid sequence of the transmembrane domain may be modified or substituted so as to minimize interactions with the binding domains of the native binding partner present in the same CAR-expressing cell, e.g., CART cell.

The transmembrane domain may be derived either from a natural or from a recombinant source. Where the source is natural, the domain may be derived from any membrane-bound or transmembrane protein. In one aspect the transmembrane domain is capable of signaling to the intracellular domain(s) whenever the CAR has bound to a target. A transmembrane domain of particular use in this invention may include at least the transmembrane region(s) of e.g., the alpha, beta or zeta chain of the T-cell receptor, CD28, CD3 epsilon, CD45, CD4, CD5, CD8 (e.g., CD8 alpha, CD8 beta), CD9, CD16, CD22, CD33, CD37, CD64, CD80, CD86, CD134, CD137, CD154. In some embodiments, a transmembrane domain may include at least the transmembrane region(s) of, e.g., KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), NKp44, NKp30, NKp46, CD160, CD19, IL2R beta, IL2R gamma, IL7Rα, ITGA1, $V_L$A1, CD49a, ITGA4, IA4, CD49D, ITGA6, $V_L$A-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKG2D, NKG2C, and CD19.

In some instances, the transmembrane domain can be attached to the extracellular region of the CAR, e.g., the antigen binding domain of the CAR, via a hinge, e.g., a hinge from a human protein. For example, in one embodiment, the hinge can be a human Ig (immunoglobulin) hinge, e.g., an IgG4 hinge, or a CD8a hinge.

In one aspect, the hinge or spacer comprises an IgG4 hinge. In one aspect, the hinge or spacer comprises an IgD hinge.

In one aspect, the transmembrane domain may be recombinant, in which case it will comprise predominantly hydrophobic residues such as leucine and valine. In one aspect a triplet of phenylalanine, tryptophan and valine can be found at each end of a recombinant transmembrane domain.

Optionally, a short oligo- or polypeptide linker, between 2 and 10 amino acids in length may form the linkage between the transmembrane domain and the cytoplasmic region of the CAR. A glycine-serine doublet provides a particularly suitable linker. For example, in one aspect, the linker comprises the amino acid sequence of GGGGSGGGGS (SEQ ID NO: 53). In one aspect, the hinge or spacer comprises a KIR2DS2 hinge.

Cytoplasmic Domain

The cytoplasmic domain or region of the present CAR includes an intracellular signaling domain. An intracellular signaling domain is capable of activation of at least one of the normal effector functions of the immune cell in which the CAR has been introduced.

Examples of intracellular signaling domains for use in the CAR of the invention include the cytoplasmic sequences of the T cell receptor (TCR) and co-receptors that act in concert to initiate signal transduction following antigen receptor engagement, as well as any derivative or variant of these sequences and any recombinant sequence that has the same functional capability.

It is known that signals generated through the TCR alone are insufficient for full activation of the T cell and that a secondary and/or costimulatory signal is also required. Thus, T cell activation can be said to be mediated by two distinct classes of cytoplasmic signaling sequences: those that initiate antigen-dependent primary activation through the TCR (primary intracellular signaling domains) and those that act in an antigen-independent manner to provide a secondary or costimulatory signal (secondary cytoplasmic domain, e.g., a costimulatory domain).

A primary signaling domain regulates primary activation of the TCR complex either in a stimulatory way, or in an inhibitory way. Primary intracellular signaling domains that act in a stimulatory manner may contain signaling motifs which are known as immunoreceptor tyrosine-based activation motifs or ITAMs.

Examples of ITAM containing primary intracellular signaling domains that are of particular use in the invention include those of TCR zeta, FcR gamma, FcR beta, CD3 gamma, CD3 delta, CD3 epsilon, CD5, CD22, CD79a, CD79b, CD278 (also known as "ICOS"), FcεRI, DAP10, DAP12, and CD66d. In one embodiment, a CAR of the invention comprises an intracellular signaling domain, e.g., a primary signaling domain of CD3-zeta.

In one embodiment, a primary signaling domain comprises a modified ITAM domain, e.g., a mutated ITAM domain which has altered (e.g., increased or decreased) activity as compared to the native ITAM domain. In one embodiment, a primary signaling domain comprises a modified ITAM-containing primary intracellular signaling domain, e.g., an optimized and/or truncated ITAM-containing primary intracellular signaling domain. In an embodiment, a primary signaling domain comprises one, two, three, four or more ITAM motifs.

Further examples of molecules containing a primary intracellular signaling domain that are of particular use in the invention include those of DAP10, DAP12, and CD32.

The intracellular signaling domain of the CAR can comprise the primary signaling domain, e.g., CD3-zeta signaling domain, by itself or it can be combined with any other desired intracellular signaling domain(s) useful in the context of a CAR of the invention. For example, the intracellular signaling domain of the CAR can comprise a primary signaling domain, e.g., CD3 zeta chain portion, and a costimulatory signaling domain. The costimulatory signaling domain refers to a portion of the CAR comprising the intracellular domain of a costimulatory molecule. A costimulatory molecule is a cell surface molecule other than an antigen receptor or its ligands that is required for an efficient response of lymphocytes to an antigen. Examples of such molecules include a MHC class I molecule, TNF receptor proteins, Immunoglobulin-like proteins, cytokine receptors, integrins, signaling lymphocytic activation molecules (SLAM proteins), activating NK cell receptors, BTLA, a Toll ligand receptor, OX40, CD2, CD7, CD27, CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, $V_L$A1, CD49a, ITGA4, IA4, CD49D, ITGA6, $V_L$A-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83. For example, CD27 costimulation has been demonstrated to enhance expansion, effector function, and survival of human CART cells in vitro and augments human T cell persistence and antitumor activity in vivo (Song et al. Blood. 2012; 119(3):696-706).

The intracellular signaling sequences within the cytoplasmic portion of the CAR of the invention may be linked to each other in a random or specified order. Optionally, a short oligo- or polypeptide linker, for example, between 2 and 10 amino acids (e.g., 2, 3, 4, 5, 6, 7, 8, 9, or 10 amino acids) in length may form the linkage between intracellular signaling sequence. In one embodiment, a glycine-serine doublet can be used as a suitable linker. In one embodiment, a single amino acid, e.g., an alanine, a glycine, can be used as a suitable linker.

In one aspect, the intracellular signaling domain is designed to comprise two or more, e.g., 2, 3, 4, 5, or more, costimulatory signaling domains. In an embodiment, the two or more, e.g., 2, 3, 4, 5, or more, costimulatory signaling domains, are separated by a linker molecule, e.g., a linker molecule described herein. In one embodiment, the intracellular signaling domain comprises two costimulatory signaling domains. In some embodiments, the linker molecule is a glycine residue. In some embodiments, the linker is an alanine residue.

In one aspect, the intracellular signaling domain is designed to comprise the signaling domain of CD3-zeta and the signaling domain of CD28. In one aspect, the intracellular signaling domain is designed to comprise the signaling domain of CD3-zeta and the signaling domain of 4-1BB.

In one aspect, the intracellular signaling domain is designed to comprise the signaling domain of CD3-zeta and the signaling domain of CD27.

In one aspect, the intracellular is designed to comprise the signaling domain of CD3-zeta and the signaling domain of CD28.

In one aspect, the intracellular is designed to comprise the signaling domain of CD3-zeta and the signaling domain of ICOS.

In one aspect, the CAR-expressing cell described herein can further comprise a second CAR, e.g., a second CAR that includes a different antigen binding domain, e.g., to the same target (mutant calreticulin) or a different target (e.g., CD19, CD33, CLL-1, CD34, FLT3, or folate receptor beta). In one embodiment, the second CAR includes an antigen binding domain to a target expressed on acute myeloid leukemia cells, such as, e.g., CD19, CD33, CLL-1, CD34, FLT3, or folate receptor beta. In one embodiment, the CAR-expressing cell comprises a first CAR that targets a first antigen and includes an intracellular signaling domain having a costimulatory signaling domain but not a primary signaling domain, and a second CAR that targets a second, different, antigen and includes an intracellular signaling domain having a primary signaling domain but not a costimulatory signaling domain. While not wishing to be bound by theory, placement of a costimulatory signaling domain, e.g., 4-1BB, CD28, CD27, ICOS or OX-40, onto the first CAR, and the primary signaling domain, e.g., CD3 zeta, on the second CAR can limit the CAR activity to cells where both targets are expressed. In one embodiment, the CAR expressing cell comprises a first mutant calreticulin CAR that includes a mutant calreticulin binding domain, a transmembrane domain and a costimulatory domain and a second CAR that targets an antigen other than mutant calreticulin (e.g., an antigen expressed on AML cells, e.g., CD19, CD33, CLL-1, CD34, FLT3, or folate receptor beta) and includes an antigen binding domain, a transmembrane domain and a primary signaling domain. In another embodiment, the CAR expressing cell comprises a first mutant calreticulin CAR that includes a mutant calreticulin binding domain, a transmembrane domain and a primary signaling domain and a second CAR that targets an antigen other than mutant calreticulin (e.g., an antigen expressed on AML cells, e.g., CD19, CD33, CLL-1, CD34, FLT3, or folate receptor beta) and includes an antigen binding domain to the antigen, a transmembrane domain and a costimulatory signaling domain.

In one embodiment, the CAR-expressing cell comprises a mutant calreticulin CAR described herein and an inhibitory CAR. In one embodiment, the inhibitory CAR comprises an antigen binding domain that binds an antigen found on normal cells but not cancer cells, e.g., normal cells that also express mutant calreticulin. In one embodiment, the inhibitory CAR comprises the antigen binding domain, a transmembrane domain and an intracellular domain of an inhibitory molecule. For example, the intracellular domain of the inhibitory CAR can be an intracellular domain of PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GALS, adenosine, and TGFR (e.g., TGFR beta).

In one embodiment, when the CAR-expressing cell comprises two or more different CARs, the antigen binding domains of the different CARs can be such that the antigen binding domains do not interact with one another. For example, a cell expressing a first and second CAR can have an antigen binding domain of the first CAR, e.g., as a fragment, e.g., an scFv, that does not form an association with the antigen binding domain of the second CAR, e.g., the antigen binding domain of the second CAR is a $V_HH$.

In some embodiments, the antigen binding domain comprises a single domain antigen binding (SDAB) molecules include molecules whose complementary determining regions are part of a single domain polypeptide. Examples include, but are not limited to, heavy chain variable domains, binding molecules naturally devoid of light chains, single domains derived from conventional 4-chain antibodies, engineered domains and single domain scaffolds other than those derived from antibodies. SDAB molecules may be any of the art, or any future single domain molecules. SDAB molecules may be derived from any species including, but not limited to mouse, human, camel, llama, lamprey, fish, shark, goat, rabbit, and bovine. This term also includes naturally occurring single domain antibody molecules from species other than Camelidae and sharks.

In one aspect, an SDAB molecule can be derived from a variable region of the immunoglobulin found in fish, such as, for example, that which is derived from the immunoglobulin isotype known as Novel Antigen Receptor (NAR) found in the serum of shark. Methods of producing single domain molecules derived from a variable region of NAR ("IgNARs") are described in WO 03/014161 and Streltsov (2005) Protein Sci. 14:2901-2909.

According to another aspect, an SDAB molecule is a naturally occurring single domain antigen binding molecule known as heavy chain devoid of light chains. Such single domain molecules are disclosed in WO 9404678 and Hamers-Casterman, C. et al. (1993) Nature 363:446-448, for example. For clarity reasons, this variable domain derived from a heavy chain molecule naturally devoid of light chain is known herein as a VIM or nanobody to distinguish it from the conventional $V_H$ of four chain immunoglobulins. Such a $V_HH$ molecule can be derived from Camelidae species, for example in camel, llama, dromedary, alpaca and guanaco. Other species besides Camelidae may produce heavy chain molecules naturally devoid of light chain; such $V_H$Hs are within the scope of the invention.

The SDAB molecules can be recombinant, CDR-grafted, humanized, camelized, de-immunized and/or in vitro generated (e.g., selected by phage display).

It has also been discovered, that cells having a plurality of chimeric membrane embedded receptors comprising an antigen binding domain that interactions between the antigen binding domain of the receptors can be undesirable, e.g., because it inhibits the ability of one or more of the antigen binding domains to bind its cognate antigen. Accordingly, disclosed herein are cells having a first and a second non-naturally occurring chimeric membrane embedded receptor comprising antigen binding domains that minimize such interactions. Also disclosed herein are nucleic acids encoding a first and a second non-naturally occurring chimeric membrane embedded receptor comprising a antigen binding domains that minimize such interactions, as well as methods of making and using such cells and nucleic acids. In an embodiment the antigen binding domain of one of said first said second non-naturally occurring chimeric membrane embedded receptor, comprises an scFv, and the other comprises a single $V_H$ domain, e.g., a camelid, shark, or lamprey single $V_H$ domain, or a single $V_H$ domain derived from a human or mouse sequence.

In some embodiments, the claimed invention comprises a first and second CAR, wherein the antigen binding domain of one of said first CAR said second CAR does not comprise a variable light domain and a variable heavy domain. In some embodiments, the antigen binding domain of one of said first CAR said second CAR is an scFv, and the other is not an scFv. In some embodiments, the antigen binding domain of one of said first CAR said second CAR comprises a single $V_H$ domain, e.g., a camelid, shark, or lamprey single V$_H$ domain, or a single V$_H$ domain derived from a human or mouse sequence. In some embodiments, the antigen binding domain of one of said first CAR said second CAR comprises a nanobody. In some embodiments, the antigen binding domain of one of said first CAR said second CAR comprises a camelid V$_H$H domain.

In some embodiments, the antigen binding domain of one of said first CAR said second CAR comprises an scFv, and the other comprises a single V$_H$ domain, e.g., a camelid, shark, or lamprey single V$_H$ domain, or a single V$_H$ domain derived from a human or mouse sequence. In some embodiments, the antigen binding domain of one of said first CAR said second CAR comprises an scFv, and the other comprises a nanobody. In some embodiments, the antigen binding domain of one of said first CAR said second CAR comprises an scFv, and the other comprises a camelid V$_H$H domain.

In some embodiments, when present on the surface of a cell, binding of the antigen binding domain of said first CAR to its cognate antigen is not substantially reduced by the presence of said second CAR. In some embodiments, binding of the antigen binding domain of said first CAR to its cognate antigen in the presence of said second CAR is 85%, 90%, 95%, 96%, 97%, 98% or 99% of binding of the antigen binding domain of said first CAR to its cognate antigen in the absence of said second CAR.

In some embodiments, when present on the surface of a cell, the antigen binding domains of said first CAR said second CAR, associate with one another less than if both were scFv antigen binding domains. In some embodiments, the antigen binding domains of said first CAR said second CAR, associate with one another 85%, 90%, 95%, 96%, 97%, 98% or 99% less than if both were scFv antigen binding domains.

In another aspect, the CAR-expressing cell described herein can further express another agent, e.g., an agent which enhances the activity of a CAR-expressing cell. For example, in one embodiment, the agent can be an agent which inhibits an inhibitory molecule. Inhibitory molecules, e.g., PD1, can, in some embodiments, decrease the ability of a CAR-expressing cell to mount an immune effector response. Examples of inhibitory molecules include PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR (e.g., TGFR beta). In one embodiment, the agent which inhibits an inhibitory molecule, e.g., is a molecule described herein, e.g., an agent that comprises a first polypeptide, e.g., an inhibitory molecule, associated with a second polypeptide that provides a positive signal to the cell, e.g., an intracellular signaling domain described herein. In one embodiment, the agent comprises a first polypeptide, e.g., of an inhibitory molecule such as PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR (e.g., TGFR beta), or a fragment of any of these (e.g., at least a portion of an extracellular domain of any of these), and a second polypeptide which is an intracellular signaling domain described herein (e.g., comprising a costimulatory domain (e.g., 4-1BB, CD27 or CD28, e.g., as described herein) and/or a primary signaling domain (e.g., a CD3 zeta signaling domain described herein). In one embodiment, the agent comprises a first polypeptide of PD1 or a fragment thereof (e.g., at least a portion of an extracellular domain of PD1), and a second polypeptide of an intracellular signaling domain described herein (e.g., a CD28 signaling domain described herein and/or a CD3 zeta signaling domain described herein). In embodiments, the CAR-expressing cell described herein comprises a switch costimulatory receptor, e.g., as described in WO 2013/019615, which is incorporated herein by reference in its entirety. PD1 is an inhibitory member of the CD28 family of receptors that also includes CD28, CTLA-4, ICOS, and BTLA. PD-1 is expressed on activated B cells, T cells and myeloid cells (Agata et al. 1996 Int. Immunol 8:765-75). Two ligands for PD1, PD-L1 and PD-L2 have been shown to downregulate T cell activation upon binding to PD1 (Freeman et a. 2000 J Exp Med 192:1027-34; Latchman et al. 2001 Nat Immunol 2:261-8; Carter et al. 2002 Eur J Immunol 32:634-43). PD-L1 is abundant in human cancers (Dong et al. 2003 J Mol Med 81:281-7; Blank et al. 2005 Cancer Immunol. Immunother 54:307-314; Konishi et al. 2004 Clin Cancer Res 10:5094) Immune suppression can be reversed by inhibiting the local interaction of PD1 with PD-L1.

In one embodiment, the agent comprises the extracellular domain (ECD) of an inhibitory molecule, e.g., Programmed Death 1 (PD1), can be fused to a transmembrane domain and intracellular signaling domains such as 41BB and CD3 zeta (also referred to herein as a PD1 CAR). In one embodiment, the PD1 CAR, when used in combinations with a mutant calreticulin CAR described herein, improves the persistence of the CAR-expressing cell, e.g., T cell or NK cell.

Methods and Compositions for Diagnostics and Detection

In some embodiments, any of the anti-mutant calreticulin antibody binding domain constructs provided herein is useful for detecting the presence of mutant calreticulin in a biological sample. Detecting encompasses quantitative or qualitative detection.

The antibodies and compositions disclosed herein can be used for a variety of purposes, such as for detecting a disease associated with expression of mutant calreticulin or diagnosing a disease associated with expression of mutant calreticulin in a subject. These methods can include contacting a sample from the subject diagnosed with a disease associated with expression of mutant calreticulin with an antibody described herein, and detecting binding of the antibody to the sample. An increase in binding of the antibody to the sample relative to binding of the antibody to a control sample confirms that the subject has a disease associated with expression of mutant calreticulin. In some embodiments, the methods further comprise contacting a second antibody that binds mutant calreticulin with the sample, and detecting binding of the second antibody. In some non-limiting examples an increase in binding of the antibody to the sample relative to a control sample detects mutant calreticulin in the subject. In some embodiments, the methods further comprise contacting a second antibody that specifically recognizes the mutant calreticulin antibody binding domain construct with the sample and detecting binding of the second antibody.

According to another embodiment, the present invention provides diagnostic methods. Diagnostic methods generally involve contacting a biological sample obtained from a patient, such as, for example, blood, serum, saliva, urine, sputum, a cell swab sample, or a tissue biopsy, with an mutant calreticulin antibody binding domain construct and determining whether the antibody preferentially binds to the sample as compared to a control sample or predetermined cut-off value, thereby indicating the presence of a disease associated with expression of mutant calreticulin.

According to another embodiment, the present invention provides methods to detect the presence of the mutant calreticulin antibody binding domain constructs of the present invention in a biological sample from a patient. Detection methods generally involve obtaining a biological sample from a patient, such as, for example, blood, serum, saliva, urine, sputum, a cell swab sample, or a tissue biopsy and isolating mutant calreticulin antibody binding domain constructs or fragments thereof, or the nucleic acids that encode an mutant calreticulin antibody binding domain construct, and assaying for the presence of an mutant calreticulin antibody binding domain construct in the biological sample. Also, the present invention provides methods to detect the nucleotide sequence of an mutant calreticulin antibody binding domain construct in a cell. The nucleotide sequence of an mutant calreticulin antibody binding domain construct may also be detected using the primers disclosed herein. The presence of the mutant calreticulin antibody binding domain construct in a biological sample from a patient may be determined utilizing known recombinant techniques and/or the use of a mass spectrometer.

In some embodiments, an anti-mutant calreticulin antibody binding domain construct for use in a method of diagnosis or detection is provided. In a further aspect, a method of detecting the presence of mutant calreticulin in a biological sample is provided. In some embodiments, the method comprises contacting the biological sample with an anti-mutant calreticulin antibody binding domain construct as described herein under conditions permissive for binding of the anti-mutant calreticulin antibody binding domain construct to mutant calreticulin, and detecting whether a complex is formed between the anti-mutant calreticulin antibody binding domain construct and mutant calreticulin. Such method may be an in vitro or in vivo method. In some embodiments, an anti-mutant calreticulin antibody binding domain construct is used to select subjects eligible for therapy with an anti-mutant calreticulin antibody binding domain construct, e.g., where mutant calreticulin is a biomarker for selection of patients.

Exemplary disorders that may be diagnosed using an antibody include diseases associated with expression of mutant calreticulin.

In some embodiments, labeled anti-mutant calreticulin antibody binding domain constructs are provided. Labels include, but are not limited to, labels or moieties that are detected directly (e.g., fluorescent, chromophoric, electron-dense, chemiluminescent, and radioactive labels), as well as moieties detected indirectly, e.g., through an enzymatic reaction or molecular interaction (e.g., enzymes or ligands). Exemplary labels include radioisotopes (e.g., $^{32}$P, $^{14}$C, $^{125}$I, $^{3}$H, and $^{131}$I), fluorophores (e.g., rare earth chelates or fluorescein and its derivatives, rhodamine and its derivatives, dansyl, umbelliferone, luceriferases (See, e.g., U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, heterocyclic oxidases, coupled with an enzyme that employs hydrogen peroxide to oxidize a dye precursor, biotin/avidin, spin labels, bacteriophage labels, stable free radicals, and the like.

Pharmaceutical Formulations

Pharmaceutical formulations of an anti-mutant calreticulin antibody binding domain construct as described herein are prepared by mixing such antibody having the desired degree of purity with one or more optional pharmaceutically acceptable carriers (See, e.g., Remington's Pharmaceutical Sciences 16th edition, Osol, A. Ed. (1980)), in the form of lyophilized formulations or aqueous solutions. Pharmaceutically acceptable carriers are generally nontoxic to recipients at the dosages and concentrations employed. Exemplary pharmaceutical acceptable carriers include buffers (e.g., phosphate, citrate, and other organic acids); antioxidants (e.g., ascorbic acid and methionine); preservatives (e.g., octadecyldimethylbenzyl ammonium chloride); hexamethonium chloride; benzalkonium chloride; benzethonium chloride; phenol, butyl or benzyl alcohol; alkyl parabens (e.g., methyl or propyl paraben); catechol; resorcinol; cyclohexanol; 3-pentanol; and m-cresol; low molecular weight (less than about 10 residues) polypeptides; proteins, (e.g., serum albumin, gelatin, or immunoglobulins); hydrophilic polymers (e.g., polyvinylpyrrolidone); amino acids (e.g., glycine, glutamine, asparagine, histidine, arginine, or lysine); monosaccharides, disaccharides, and other carbohydrates (e.g., glucose, mannose, or dextrins); chelating agents (e.g., EDTA); sugars (e.g., sucrose, mannitol, trehalose or sorbitol); salt-forming counter-ions (e.g., sodium); metal complexes (e.g., Zn-protein complexes); and/or non-ionic surfactants (e.g., polyethylene glycol (PEG)). Exemplary pharmaceutically acceptable carriers herein further include insterstitial drug dispersion agents (e.g., soluble neutral-active hyaluronidase glycoproteins (sHASEGP)) (See, e.g., U.S. Pat. Pub. Nos. US 2005/0260186 and US 2006/0104968). In one aspect, a sHASEGP is combined with one or more additional glycosaminoglycanases (e.g., chondroitinases).

Antibody formulations can be lyophilized (See, e.g., U.S. Pat. No. 6,267,958). Antibody formulations can be aqueous antibody (See, e.g., U U.S. Pat. No. 6,171,586 and WO06/044908).

The formulation herein may also contain more than one active ingredient as necessary for the particular indication being treated (e.g., a disease associated with expression of mutant calreticulin).

Active ingredients may be entrapped in microcapsules (e.g., hydroxymethylcellulose or gelatin-microcapsules and poly-(methylmethacylate) Active ingredients may be entrapped in microcapsules in colloidal drug delivery systems (e.g., liposomes, albumin microspheres, microemulsions, nano-particles and nanocapsules) or in macroemulsions. Sustained-release preparations may be prepared. Suitable examples of sustained-release preparations include semipermeable matrices of solid hydrophobic polymers containing the antibody, which matrices are in the form of shaped articles (e.g., films or microcapsules).

The formulations to be used for in vivo administration are generally sterile (e.g., by filtration through sterile filtration membranes).

A pharmaceutical composition of this disclosure also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole $(BHA)_5$ butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of this disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of this disclosure is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient (i.e. the herein provided antibody, nucleic acid molecules etc.) which can be combined with a excipient to produce a single dosage form will vary depending upon the subject being treated, and the particular mode of administration. The amount of active ingredient which can be combined with a excipient to produce a single dosage form will generally be that amount of the composition which produces a therapeutic effect. Generally, this amount will range from about 0.01 percent to about ninety-nine percent of active ingredient, preferably from about 0.1 percent to about 70 percent, most preferably from about 1 percent to about 30 percent of active ingredient in combination with (a) pharmaceutically acceptable excipient(s).

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical excipient. The specification for the dosage unit forms of this disclosure are dictated by and directly dependent on (a) the unique characteristics of the active compound and the particular therapeutic effect to be achieved, and (b) the limitations inherent in the art of compounding such an active compound for the treatment of sensitivity in individuals. For administration of the antibody, the dosage typically ranges from about 0.0001 to 100 mg/kg, and more usually 0.01 to 10 mg/kg, of the host body weight. Typically, when the antibody is administered as an ADC, the ADC will be administered at a dose of less than 1 mg/kg.

Antibody/binding molecules etc. can also be administered as a sustained release formulation, in which case less frequent administration is required. Dosage and frequency vary depending on the half-life of the antibody in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of disease is reduced or terminated, and preferably until the patient shows partial or complete amelioration of symptoms of disease. Thereafter, the patient can be administered a prophylactic regime.

Actual dosage levels of the active ingredients in the pharmaceutical compositions of the present disclosure may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present disclosure employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A composition of the present disclosure can be administered via one or more routes of administration using one or more of a variety of methods known in the art. As will be appreciated by the skilled artisan, the route and/or mode of administration will vary depending upon the desired results. Preferred routes of administration for antibodies of this disclosure include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, an antibody of this disclosure can be administered via a non-parenteral route, such as a topical, epidermal or mucosal route of administration, for example, intranasally, orally, vaginally, rectally, sublingually or topically.

The active compounds can be prepared with excipients that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, eds, Marcel Dekker, Inc., New York, 1978. Therapeutic compositions can be administered with medical devices known in the art. For example, in a preferred embodiment, a therapeutic composition of this disclosure can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present disclosure include: U.S. Pat. No. 4,487,603, which discloses an implantable microinfusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art. In certain embodiments, therapeutic antibodies of this disclosure can be formulated to ensure proper distribution in vivo. For example, the blood-brain barrier (BBB) excludes many highly hydrophilic compounds. To ensure that the therapeutic compounds of this disclosure cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) *J. Clin. Pharmacol.* 29:685). Exemplary targeting moieties include folate or biotin (see, e.g., U.S. Pat. No. 5,416,016 to Low et al.); marmosides (Umezawa et al. (1988) *Biochem. Biophys. Res. Commun.* 153:1038); antibodies (P. G. Bloeman et al. (1995) *FEBS Lett.* 357: 140; M. Owais et al. (1995) *Antimicrob. Agents Chemother.* 39: 180); surfactant protein A receptor (Briscoe et al. (1995) *Am. J. Physiol.* 1233:134); pi 20 (Schreier et al. (1994) *J. Biol. Chem.* 269:9090); see also K. Keinanen; M. L. Laukkanen (1994) *FEBS Lett.* 346: 123; J J. Killion; I J. Fidler (1994) *Immunomethods* 4:273.

When used in the therapy of myeloid malignancies, examples of chemotherapeutic agents that may be used in combination with the antibodies include, but are not limited to, antimetabolites (e.g., methotrexate, azathioprine, 6-mercaptopurine, 6-thioguanine, cytarabine, 5-fluorouracil, decarbazine, capecitabine), alkylating agents (e.g., mechlorethamine, thiotepa, chlorambucil, melphalan, carmustine (BCNU), lomustine (CCNU), cyclophosphamide, ifosfamide, busulfan, dibromomannitol, streptozotocin, mitomycin C, cis-dichlorodiamine platinum (II) (DDP), cisplatin, carboplatin, oxaliplatin, nedaplatin, satraplatin, triplatin tetranitrate, procarbazine, altretamine and tetrazines), anthracyclines (e.g., daunorubicin, doxorubicin, valrubicin, idarubicin, epirubicin, and mitoxantrone), antibiotics (e.g., dactinomycin, bleomycin, mithramycin, and anthramycin (AMC)), topoisomerase inhibitors (e.g. irinotecan, topotecan and camptothecin), anti-mitotic agents (e.g., vinca alkaloids such as vincristine and vinblastine, taxanes such as paclitaxel (also known as taxol), cabazitaxel and docetaxel, and other tubulin polimeryzation inhibitors such as monomethyl auristatin E (MMAE), maytansine derivatives like mertansine (also known as DM1) and DM4), and protein kinase inhibitors such as imatinib (gleevec), nilotinib and dasatinib.

For other co-therapeutic approaches for example for the use of the inventive antibodies/binding molecules in anti-inflammatory therapy, the following drugs/agents may be employed: steroids such as Glucocorticoids, Non-Steroidal anti-inflammatory drugs such as aspirin. ibuprofen, naproxen or Immune Selective Anti-Inflammatory Derivatives (ImSAIDs) such as the peptide phenylalanine-glutamine-glycine (FEG). For the treatment of atherosclerosis the antibodies can be combined with e.g. statins or niacin.

Therapeutic Methods

Any of the anti-mutant calreticulin antibody binding domain constructs provided herein may be used in therapeutic methods. The present invention provides a method for treating a mammal with a disease associated with expression of mutant calreticulin, comprising administering to said mammal a pharmaceutical composition comprising the mutant calreticulin antibody binding domain constructs disclosed herein. Methods for reducing an increase in mutant calreticulin activity or an amount of an mutant calreticulin protein in a subject are further provided.

In one aspect, an anti-mutant calreticulin antibody binding domain construct for use as a medicament is provided. In further aspects, an anti-mutant calreticulin antibody binding domain construct for use in treating a disease associated with expression of mutant calreticulin is provided. In some embodiments, the invention provides an anti-mutant calreticulin antibody binding domain construct for use in a method of treating an individual with a disease associated with expression of mutant calreticulin comprising administering to the individual an effective amount of the anti-mutant calreticulin antibody binding domain construct. An effective amount of an agent, is an amount effective, at dosages and for periods of time necessary, to achieve the desired therapeutic or prophylactic result. In one such embodiment, the method can further comprise administering to the individual an effective amount of at least one additional therapeutic agent. The individual can be a human.

In a further aspect, the invention provides for the use of an anti-mutant calreticulin antibody binding domain construct in the manufacture or preparation of a medicament. In some embodiments, the medicament is for treatment of a disease associated with expression of mutant calreticulin. In a further embodiment, the medicament is for use in a method of treating a disease associated with expression of mutant calreticulin comprising administering to an individual having a disease associated with expression of mutant calreticulin an effective amount of the medicament. In a further aspect, the invention provides a method for treating a disease associated with expression of mutant calreticulin. In some embodiments, the method comprises administering to an individual having such a disease associated with expression of mutant calreticulin an effective amount of an anti-mutant calreticulin antibody binding domain construct. In some embodiments, the mutant calreticulin of the disease is expressed on the surface of diseased cells.

According to another embodiment, the present invention provides methods for the preparation and administration of an mutant calreticulin antibody binding domain construct composition that is suitable for administration to a human or non-human primate patient having a disease associated with expression of mutant calreticulin, or at risk of a disease associated with expression of mutant calreticulin, in an amount and according to a schedule sufficient to induce a protective immune response against mutant calreticulin, or reduction of the mutant calreticulin, in a human.

According to another embodiment, the present invention provides a vaccine comprising at least one antibody binding domain construct and a pharmaceutically acceptable carrier. According to one embodiment, the vaccine is a vaccine comprising at least one antibody binding domain construct described herein and a pharmaceutically acceptable carrier. The vaccine can include a plurality of the antibody binding domain constructs having the characteristics described herein in any combination and can further include antibody binding domain constructs to mutant calreticulin as are known in the art.

It is to be understood that compositions can be a single or a combination of antibodies disclosed herein, which can be the same or different, in order to prophylactically or therapeutically treat the progression of various subtypes of diseases associated with expression of mutant calreticulin. Such combinations can be selected according to the desired immunity. When an antibody binding domain construct is administered to an animal or a human, it can be combined with one or more pharmaceutically acceptable carriers, excipients or adjuvants as are known to one of ordinary skilled in the art.

Further, with respect to determining the effective level in a patient for treatment of mutant calreticulin, in particular, suitable animal models that ae available may be implemented for evaluating the in vivo efficacy against mutant calreticulin of various gene therapy protocols. These models may include mice, monkeys and cats.

The pharmaceutical composition can contain other pharmaceuticals, in conjunction with a vector according to the invention, when used to therapeutically treat diseases associated with expression of mutant calreticulin. These other pharmaceuticals can be used in their traditional fashion. The antibody-based pharmaceutical composition of the present invention may be formulated by any number of strategies known in the art (See, e.g., McGoff and Scher, 2000, Solution Formulation of Proteins/Peptides: In McNally, E. J., ed. Protein Formulation and Delivery. New York, N.Y.: Marcel Dekker; pp. 139-158; Akers and Defilippis, 2000, Peptides and Proteins as Parenteral Solutions. In: Pharmaceutical Formulation Development of Peptides and Proteins. Philadelphia, PA: Talyor and Francis; pp. 145-177; Akers, et al., 2002, Pharm. Biotechnol. 14:47-127).

In another embodiment, the present invention provides a method for detecting an mutant calreticulin antibody binding domain construct comprising a heavy chain comprising a highly conserved consensus sequence and a light chain comprising a highly conserved consensus sequence in a biological sample, comprising obtaining an immunoglobulin-containing biological sample from a mammalian subject, isolating an mutant calreticulin antibody binding domain construct from said sample, and identifying the highly conserved consensus sequences of the heavy chain and the light chain. The biological sample may be blood, serum, saliva, urine, sputum, a cell swab sample, or a tissue biopsy. The amino acid sequences may be determined by methods known in the art including, for example, PCR and mass spectrometry.

In a further aspect, the invention provides pharmaceutical formulations comprising any of the anti-mutant calreticulin antibody binding domain constructs provided herein (e.g., for use in any of the above therapeutic methods). In some embodiments, a pharmaceutical formulation comprises any of the anti-mutant calreticulin antibody binding domain constructs provided herein and a pharmaceutically acceptable carrier. In another embodiment, a pharmaceutical formulation comprises any of the anti-mutant calreticulin antibody binding domain constructs provided herein and at least one additional therapeutic agent.

Antibodies can be used either alone or in combination with other agents in a therapy. For instance, an antibody may be co-administered with at least one additional therapeutic agent. For example, the antibodies can be used either alone or in combination with one or more than one antibody (for example, a plurality or pool of antibodies). For example, the antibodies can be used either alone or in combination with one or more other antibodies (e.g., mutant calreticulin neutralizing antibodies) known in the art, for example, but not limited to VRCO1, VRC02, VRC03, VRC-PG-04, VRC-PG-05, b12, (CD4bs), (PGTs, PG9, and PG16. (See, Science 333(6049): 1633-1637; Nature 477(7365):466-470; Science 334(6060): 1289-1293; Science 326(5950):285-289; Science 334(6059): 1097-1103; and Nature 480(7377):336-343.)

According to another embodiment, the present invention provides a method for treating a mammal with a disease associated with mutant calreticulin expression, comprising administering to said mammal a pharmaceutical composition comprising the mutant calreticulin antibody binding domain constructs disclosed herein. According to one embodiment, the method for treating a mammal expressing mutant calreticulin comprises administering to said mammal a pharmaceutical composition that comprises an antibody of the present invention, or a fragment thereof.

Such combination therapies noted above encompass combined administration (where two or more therapeutic agents are included in the same or separate formulations), and separate administration, in which case, administration of the antibody can occur prior to, simultaneously, and/or following, administration of the additional therapeutic agent and/or adjuvant.

An antibody (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route. For example, dosing can be by injections (e.g., intravenous or subcutaneous injections). Various dosing schedules including but not limited to single or multiple administrations over various time-points, bolus administration, and pulse infusion are contemplated herein.

Antibodies would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. About 1 µg/kg to 15 mg/kg (e.g., 0.1 mg/kg-10 mg/kg) of antibody can be an initial candidate dosage for administration to the patient (e.g., by one or more separate administrations, or by continuous infusion). A daily dosage might range from about 1 µg/kg to 100 mg/kg or more. For repeated administrations over several days or longer the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently (e.g., every week or every three weeks). An initial higher loading dose, followed by one or more lower doses may be administered.

It is understood that any of the above formulations or therapeutic methods may be carried out using an immunoconjugate in place of or in addition to an anti-mutant calreticulin antibody binding domain construct.

Administration of a prophylactic agent can occur prior to the manifestation of symptoms characteristic of mutant calreticulin-related disease or disorder, such that a disease or disorder is prevented or, alternatively, delayed in its progression.

Articles of Manufacture

In one aspect, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody. The label or package insert indicates that the composition is used for treating the condition of choice. Moreover, the article of manufacture may comprise (a) a first container with a composition contained therein, wherein the composition comprises an antibody; and (b) a second container with a composition contained therein, wherein the composition comprises a further cytotoxic or otherwise therapeutic agent. The article of manufacture in this embodiment may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

TABLE 1

Heavy Chain Variable Domain Amino Acid Sequences

| Ab ID | FWR1 | CDR1 | FWR2 | CDR2 | FWR3 | CDR3 | FWR4 |
|---|---|---|---|---|---|---|---|
| AbH-1H (Full length sequence disclosed as SEQ ID NO: 1) | QVQLVQSGAEVKK PGASVKVSCKASG (SEQ ID NO: 54) | YSFTGYY IH (SEQ ID NO: 7) | WVRQAPG QELGWMG (SEQ ID NO: 58) | YISCYNG ASSYNQK FKG (SEQ ID NO: 8) | RVTMTVDTSISTAYT ELSSLRSEDTATYYC A (SEQ ID NO: 62) | SSMDY (SEQ ID NO: 9) | WGQGTLV TVSS (SEQ ID NO: 66) |
| AbH-2H (Full length sequence disclosed as SEQ ID NO: 2) | QVTLKESGPVLVK PTETLTLTCTVSG (SEQ ID NO: 55) | YSITSDY AWN (SEQ ID NO: 10) | WIRQPPG KALEWLA (SEQ ID NO: 59) | YISYSGS TSYNPSL KS (SEQ ID NO: 11) | RLSITKDTSKSQVVL TMTNMDPVDTATYYC AR (SEQ ID NO: 63) | DPPYYYG S (SEQ ID NO: 12) | WGQGTTV TVSS (SEQ ID NO: 67) |
| AbH-1H (Full length sequence disclosed as SEQ ID NO: 3) | EVQLEQSGPELVK TGASVKISCKASG (SEQ ID NO: 56) | YSFTGYY IH (SEQ ID NO: 7) | WVKQSHG KSLEWIG (SEQ ID NO: 60) | YISCYNG ASYNQKF KG (SEQ ID NO: 8) | KATFTVDTSSSTAYM QFNSLTSGDSAVYYC A (SEQ ID NO: 64) | SSMDY (SEQ ID NO: 9) | WGQGTSV TVSS (SEQ ID NO: 68) |

TABLE 1-continued

Heavy Chain Variable Domain Amino Acid Sequences

| Ab ID | FWR1 | CDR1 | FWR2 | CDR2 | FWR3 | CDR3 | FWR4 |
|---|---|---|---|---|---|---|---|
| AbM-2H (Full length sequence disclosed as SEQ ID NO: 4) | DVQLQESGPGLVK NSQSLSLTCTVTG (SEQ ID NO: 57) | YSITSDY AWN (SEQ ID NO: 10) | WIRQFPG NKLEWMG (SEQ ID NO: 61) | YISYSGS TSYNPSL KS (SEQ ID NO: 11) | RISITRDTSKNQFFL QLNSVTPEDTATYYC AR (SEQ ID NO: 65) | DPPYYYG SNGT (SEQ ID NO: 16) | WGQGTSV TVSS (SEQ ID NO: 68) |

TABLE 2

Light Chain Variable Domain Amino Acid Sequences

| Ab ID | FWR1 | CDR1 | FWR2 | CDR2 | FWR3 | CDR3 | FWR4 |
|---|---|---|---|---|---|---|---|
| AbH-1L/AbH-2L (Full length sequence disclosed as SEQ ID NO: 5) | DVVMTQSPLSLPV TLGQPASISC (SEQ ID NO: 69) | KSSQSLL DSDGKTY LN (SEQ ID NO: 13) | WLQQRPG QSPRRLI Y (SEQ ID NO: 71) | LVSKLDS (SEQ ID NO: 14) | GVPDRFSGSGSGTDF TLKISRVEAEDVGVY HC (SEQ ID NO: 73) | WGQTHFP YT (SEQ ID NO: 15) | FGGGTKV EIK (SEQ ID NO: 75) |
| AbM-1L/AbM-2L (Full length sequence disclosed as SEQ ID NO: 6) | DVVMTQTPLTLSV TIGQPASISC (SEQ ID NO: 70) | KSSQSLL DSDGKTY LN (SEQ ID NO: 13) | WLLQRPG QSPKRLI Y (SEQ ID NO: 72) | LVSKLDS (SEQ ID NO: 14) | GVPDRFTGSGSGTDF TLKISRVEAEDLGVY HC (SEQ ID NO: 74) | WGQTHFP YT (SEQ ID NO: 15) | FGGGTKL EIK (SEQ ID NO: 76) |

TABLE 3

Heavy and Light Chain Variable Domain Pairings
SEQ ID NOs

| | Variable Region | | CDRs 1-3 | |
|---|---|---|---|---|
| Ab ID | Heavy Chain (H) | Light Chain (L) | Heavy Chain (H) | Light Chain (L) |
| AbH-1 | SEQ ID NO: 1 | SEQ ID NO: 3 | SEQ ID NOs: 7-9 | SEQ ID NOs: 13-15 |
| AbH-2 | SEQ ID NO: 2 | SEQ ID NO: 3 | SEQ ID NOs: 10-12, 16 | SEQ ID NOs: 13-15 |

TABLE 4

Heavy and Light Chain Variable Domain Pairings

| | SEQ ID NOs | | | |
|---|---|---|---|---|
| Ab ID | Variable Region | | Variable Region | |
| AbM-3 | SEQ ID NO: 4 | SEQ ID NO: 6 | SEQ ID NOs: 7-9 | SEQ ID NOs: 13-15 |
| AbM-4 | SEQ ID NO: 5 | SEQ ID NO: 6 | SEQ ID NOs: 10-12, 16 | SEQ ID NOs: 13-15 |

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein. Without further description, it is believed that one of ordinary skill in the art can, using the preceding description and the following illustrative examples, make and utilize the compounds of the present invention and practice the claimed methods. The following working examples specifically point out various aspects of the present invention, and are not to be construed as limiting in any way the remainder of the disclosure.

Example 1—Determination of $K_D$ Values $K_D$ is measured by a radiolabeled antigen binding assay (RIA) performed with the Fab version of an antibody of interest and its antigen as described by the following assay. Solution binding affinity of scFvs Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (See, e.g., Chen et al., J. Mol. Biol. 293:865-881 (1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 25 pM [$^{125}$I]-antigen are mixed with serial dilutions of a Fab of interest (e.g., consistent with assessment of the anti-VEGF antibody, Fab-12, in Presta et al., Cancer Res. 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 μl/well of scintillant (MICROSCINT-20™; Packard) is added, and the plates are counted on a TOP-COUNT™ gamma counter (Packard) for ten minutes. Concentrations of each Fab that give less than or equal to 20% of maximal binding are chosen for use in competitive binding assays.

Alternatively. $K_D$ is measured using surface plasmon resonance assays using a BIACORE®-2000 or a BIACORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 μg/ml (0.2 μM) before injection at a flow rate of 5 μl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 μl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant ($K_d$) is calculated as the ratio $k_{off}/k_{on}$. See, e.g., Chen et al., J. Mol. Biol. 293:865-881 (1999). If the on-rate exceeds $10^6$ M−1 s−1 by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

ELISAs

High-binding 96-well ELISA plates (Costar) are coated overnight with 100 ng/well of purified mutant calreticulin in PBS. After washing, the plates are blocked for 2 h with 2% BSA, 1 μM EDTA, 0.05% Tween-PBS (blocking buffer) and then incubated for 2 h with IgGs at concentrations of 26.7 nM and 7 consecutive 1:4 dilutions in PBS. After washing, the plates are developed by incubation with goat HRP-conjugated anti-human IgG antibodies (Jackson ImmunoReseach) (at 0.8 μg/ml in blocking buffer) for 1 h, and by addition of HRP chromogenic substrate (ABTS solution, Invitrogen). Antibody binding to the selected mutant calreticulin overlapping peptides is tested using a previously described peptide-ELISA method.

For competition ELISAs, mutant calreticulin-coated plates are blocked for 2 h with blocking buffer and then incubated for 2 h with biotinylated antibodies in 1:2 serially diluted solutions of antibody competitors in PBS (IgG concentration range from 5.2 to 667 nM). Plates are developed as described above using HRP-conjugated streptavidin (Jackson ImmunoReseach) (at 0.8 μg/ml in blocking buffer). All experiments are performed at least in duplicate.

Surface Plasmon Resonance

Experiments are performed using a Biacore T100 (Biacore, Inc.). Briefly, mutant calreticulin proteins are primary amine-coupled on CM5 chips (Biacore, Inc.) at a coupling density of 300 RUs. Anti-mutant calreticulin IgGs are injected over flow cells at 1 μM and 10 μM, respectively, at flow rates of 35 μl/min with 3 min association and 5 min dissociation phases. The sensor surface is regenerated by a 30 sec injection of 10 mM glycine-HCl pH 2.5 at a flow rate of 50 μl/min. Dissociation ($k_d$ (s$^{-1}$)), association ($k_a$ (M$^{-1}$ s$^{-1}$) and binding constants ($K_D$, (M) or $K_A$ (M$^{-1}$) are calculated from kinetic analyses after subtraction of backgrounds using a 1:1 binding model without a bulk reflective index (RI) correction (Biacore T100 Evaluation software).

Crystallization and Structure Determinations

6x-His (SEQ ID NO: 77) tagged scFvs or Fabs for crystallization are expressed. scFvs or Fabs are purified from the supernatants of transiently-transfected HEK 293-6E cells by sequential Ni-NTA affinity (Qiagen) and Superdex200 10/300 (GE Healthcare) size exclusion chromatography. For crystals of the non-ligand bound scFvs or Fab, IgG is isolated from the supernatants of transiently-transfected HEK 293-6E cells by Protein A affinity chromatography (Pierce). Fab fragments are obtained by papain cleavage of the IgG and further purification using Superdex200 10/300 (GE Healthcare) size exclusion chromatography.

Purified scFvs or Fabs are concentrated to 8-20 mg/mL in PBS buffer. The "ligand bound" scFvs or Fab crystals are prepared from a protein sample (final concentration:15 mg/mL) that is mixed with a 3-fold molar excess of mutant calreticulin and incubated at 20° C. for 2 hours. Crystallization conditions are screened at 20° C. using a Mosquito® crystallization robot (TTP labs) in 400 nL drops using a 1:1 protein to reservoir ratio. Crystals of non-ligand bound scFvs or Fabs are obtained in 24% PEG 4,000, 0.1 M Tris-HCl pH 8.5, 10 mM CuCl$_2$ and crystals of ligand bound scFvs or Fabs grow in 17% PEG 10,000, 0.1M Bis-Tris pH 5.5, 0.1M CH$_3$COOHNH$_4$. Crystals of scFvs or Fabs are obtained in 25% PEG 3,350, 0.1 M Bis-Tris pH 5.5, 0.2 M NaCl, and crystals of scFvs or Fabs grow in 20% PEG 3,350, 0.24 M sodium malonate pH 7.0, 10 mM MnCl$_2$. Crystals are cryoprotected by soaking in mother liquor containing 20% glycerol or 20% ethylene glycol and subsequently flash-cooled in liquid nitrogen.

Diffraction data are collected at beamline 12-2 on a Pilatus 6M pixel detector (Dectris). Data are indexed, integrated and scaled using XDS. Using the data obtained from the non-ligand bound scFv or Fab crystals, Phenix is used to find a molecular replacement solution for one scFv or Fab per asymmetric unit using two search models, the $C_H$-$C_L$ domains of the scFv or Fab and the $V_H$-$V_L$ domains of the scFv or Fab after omitting residues in the CDRH3 and CDRL3 loops. Subsequently, the non-ligand bound the scFv or Fab structures are used as a search model to find molecular replacement solutions for ligand bound the scFvs or Fabs.

Iterative refinement is performed using Phenix and manually fitting models into electron density maps using Coot. PyMOL is used for molecular visualization and to generate figures of the scFv or Fab structures. Buried surface area calculations are performed with Areaimol (CCP4 Suite) using a 1.4 A probe. the scFv or Fab structures are aligned using the Super script in PyMOL. Pairwise Ca alignments are performed using PDBeFold.

Example 2—Cloning and Production of Antibodies and Proteins

Mutant calreticulin antibody binding domain constructs are cloned and produced following mutant calreticulin-specific single B-cell capture. Glycoengineered antibodies are generated by substituting residues at various heavy chain positions. Binding properties of anti-mutant calreticulin antibody binding domain constructs to mutant calreticulin proteins are assayed by ELISA, SPR and microarray assays. Structures of antibodies bound and unbound to ligand, and Fab fragments, are solved by molecular replacement to high resolution.

Purified digested PCR products were cloned into human Igγ1-, or Igλ-expressing vectors. Vectors containing IgH and Igλ genes are then sequenced and compared to the original PCR product sequences. To generate His-tagged Fabs, the $V_H$ genes are subcloned into an expression vector to encode the IgG1 CH1 domain followed by a 6×-His tag (SEQ ID NO: 77). IgH DNA fragments encoding antibodies are obtained as a synthetic minigene (IDT) and subcloned into Igγ1-expressing vectors.

Antibodies and Fab fragments are produced by transient transfection of IgH and IgL expression plasmids into exponentially growing HEK 293T cells (ATCC, CRL-11268) using the polyethyleneimine (PEI)-precipitation method. IgG antibodies are affinity purified using Protein G sepharose beads (GE Healthcare) according to the manufacturer's instructions. Fab fragments are affinity purified using His-Pur™ Cobalt Resin (Thermo scientific) according to the manufacturer's instructions.

Mutant Calreticulin-1 Proteins

Calreticulin type 1 or type 2 mutations are introduced into calreticulin vector using the QuikChange Site-Directed Mutagenesis kit (Stratagene) according to the manufacturer's instructions. Mutations are verified by DNA sequencing.

Expression vectors encoding mutant calreticulin proteins are used to transfect HEK 293T cells. Culture supernatants are harvested and concentrated using centrifugation-based filtration devices that allowed buffer exchange of the samples into 10 mM imidazole, 50 mM sodium phosphate, 300 mM sodium chloride; pH 7.4. Proteins are purified by affinity chromatography using HisPur™ Cobalt Resin (Thermo scientific) according to the manufacturer's instructions.

Example 3—Anti-Mutant Calreticulin Chimeric Antigen Receptor (CAR) T Cells

Genes for anti-mutant calreticulin single-chain (sFv) versions of are created by the synthesis of codon-optimized sequences for the heavy and light chains, which are separated by a $(GGGGS)_4$ linker (SEQ ID NO: 36). For each anti-mutant calreticulin antibody binding domain construct, a sFv gene is substituted for the sFv in a second generation CAR vector containing the 4-1BB signaling domain fused to the CD3 ζ signaling domain to create a lentiviral anti-mutant calreticulin CAR vector. Primary CD8$^+$ T cells are transduced with a lentiviral anti-mutant calreticulin CAR vector.

Characterization of CD8$^+$ T Cells Expressing Anti-Mutant Calreticulin CARs

Enriched anti-mutant calreticulin CAR-transduced CD8$^+$ T cells are tested for their capacity to proliferate in response to cells expressing mutant calreticulin. The anti-mutant calreticulin CAR-transduced CD8$^+$ T cells are labeled with CellTrace Violet and then are co-cultured with cells expressing mutant calreticulin. The proliferation of anti-mutant calreticulin CAR-transduced CD8$^+$ T cells is measured by flow cytometry, and is shown to be increased over non-transduced CD8$^+$ T cells.

Enriched anti-mutant calreticulin CAR-transduced CD8$^+$ T cells are tested for their ability to mediate specific killing of cells expressing mutant calreticulin. Anti-mutant calreticulin CAR-transduced CD8$^+$ T cells are assayed in a chromium release assay when co-cultured with cells expressing mutant calreticulin. Specific lysis of cells expressing mutant calreticulin is measured, and specific lysis is shown to occur due to the anti-mutant calreticulin CAR-transduced CD8$^+$ T cells.

Treatment with CD8$^+$ T Cells Expressing CARs

CD8$^+$ T cells from a subject with cells expressing mutant calreticulin are transduced with anti-mutant calreticulin CAR vectors to express anti-mutant calreticulin CARs. The anti-mutant calreticulin CAR-transduced CD8$^+$ T cells are injected into the subject. Cells expressing mutant calreticulin are killed by the anti-mutant calreticulin CAR-transduced CD8$^+$ T cells.

Example 4—Human Specimens

Peripheral blood mononuclear cells (PBMC5) are obtained from a donor in a cohort of donors expressing mutant calreticulin. All human samples are collected with informed consent under clinical protocols approved by the appropriate institutional review board.

Example 5—Antibody and Protein Expression and Purification

Antibody sequences are synthesized and cloned into previously described heavy and light chain vectors. The plasmids are co-transfected (1:1 ratio) in either HEK 293T or 293 FreeStyle cells using Fugene 6 (Promega) or 293fectin (Invitrogen), respectively. Transfections are performed according to the manufacturer's protocol and antibody supernatants are harvested four days following transfection. Antibodies produced in 293T cells are quantified by ELISA and used directly in assays. Antibodies produced in 293 freestyle cells are further purified over a protein A column. Recombinant mutant calreticulin proteins are transfected in 293 FreeStyle cells using 293 fection (Invitrogen) and purified with *Galanthus nivalis* lectin column followed by size exclusion using Superdex 300 26/60 (GE Healthcare).

Example 6—Cell Surface Binding Assays

Titrating amounts of CAR-T cells or mAbs are added to mutant calreticulin transfected 293T cells and incubated for 1 h at 4° C. in 1×PBS. Following washing, cells are fixed with 2% PFA (PolySciences) for 20 min at RT. The cells are then washed and stained with a 1:200 dilution of phyco-erythrin-conjugated goat antibody that recognizes the CAR-T cells or monoclonal antibodies for 1 h at RT. Binding is analyzed using flow cytometry. Binding competitions are performed by titrating amounts of competitor CAR-T cells or monoclonal antibodies before adding biotinylated antibody at a concentration required to give $IC_{70}$ and then measuring binding with phycoerythrin-labeled streptavidin (Invitrogen). FlowJo software is used for data interpretation.

Example 7—ELISA Assays

Binding by ELISA is performed. Briefly, plates are coated with goat anti-human IgG Fc (Pierce) or with mutant calreticulin and binding is detected using goat anti-human IgG F(ab')2 conjugated to alkaline phosphatase (Pierce). For binding to mutant calreticulin extracted from lysed cells, plates are coated with 5 ng/μL of sheep anti-mutant calreticulin antibody. Supernatants are lysed using a final concentration of 1% NP-40 and incubated on coated plates for 2 h at 37° C. Detection is measured using goat anti-human IgG F(ab')2 conjugated to alkaline phosphatase (Pierce). Antibody concentration is calculated by linear regression using a standard concentration curve of purified IgG protein.

Example 8—Chemosensitivity Assay

The ability of an anti-mutant calreticulin antibody binding domain construct to confer or increase chemosensitivity to chemoresistant cells can be tested as follows. Chemoresistant target cells (e.g, expressing mutant calreticulin or overexpressing mutant calreticulin) are plated on 96 well plates and incubated with the anti-mutant calreticulin antibody binding domain constructs to be tested with and without a chemotherapeutic agent under conditions sufficient for cell growth and proliferation. The effect of the treatments on cell proliferation will be measured by an Alamar Blue assay or similar assays as described herein e.g., cytotoxicity.

Example 9—Sequences

```
AbH-1 heavy chain variable domain
                                                            SEQ ID NO: 1
QVQLVQSGAEVKKPGASVKVSCKASGYSFTGYYIHWVRQAPGQELGWMGYISCYNGASSYNQKFKGRVTMTVDTSISTAYTE

LSSLRSEDTATYYCASSMDYWGQGTLVTVSS

AbH-2 heavy chain variable domain
                                                            SEQ ID NO: 2
QVTLKESGPVLVKPTETLTLTCTVSGYSITSDYAWNWIRQPPGKALEWLAYISYSGSTSYNPSLKSRLSITKDTSKSQVVLT

MTNMDPVDTATYYCARDPPYYYGSWGQGTTVTVSS

AbH-1/AbH-2 light chain variable domain
                                                            SEQ ID NO: 3
DVVMTQSPLSLPVTLGQPASISCKSSQSLLDSDGKTYLNWLQQRPGQSPRRLIYLVSKLDSGVPDRFSGSGSGTDFTLKISR

VEAEDVGVYHCWQGTHFPYTFGGGTKVEIK

AbM-1 heavy chain variable domain
                                                            SEQ ID NO: 4
EVQLEQSGPELVKTGASVKISCKASGYSFTGYYIHWVKQSHGKSLEWIGYISCYNGASSYNQKFKGKATFTVDTSSSTAYMQ

FNSLTSGDSAVYYCASSMDYWGQGTSVTVSS

AbM-2 heavy chain variable domain
                                                            SEQ ID NO: 5
DVQLQESGPGLVKNSQSLSLTCTVTGYSITSDYAWNWIRQFPGNKLEWMGYISYSGSTSYNPSLKSRISITRDTSKNQFFLQ

LNSVTPEDTATYYCARDPPYYYGSNGTWGQGTSVTVSS

AbM-1/AbM-2 light chain variable domain
                                                            SEQ ID NO: 6
DVVMTQTPLTLSVTIGQPASISCKSSQSLLDSDGKTYLNWLLQRPGQSPKRLIYLVSKLDSGVPDRFTGSGSGTDFTLKISR

VEAEDLGVYHCWQGTHFPYTFGGGTKLEIK

Heavy and light chain CDR1, CDR2, and CDR3 sequences:
                                                            SEQ ID NO: 7
YSFTGYYIH

SEQ ID NO: 8
YISCYNGASSYNQKFKG

SEQ ID NO: 9
SSMDY

SEQ ID NO: 10
YSITSDYAWN

SEQ ID NO: 11
YISYSGSTSYNPSLKS

SEQ ID NO: 12
DPPYYYGS

SEQ ID NO: 13
KSSQSLLDSDGKTYLN
```

```
                                                          SEQ ID NO: 14
LVSKLDS

SEQ ID NO: 15
WQGTHFPYT

SEQ ID NO: 16
DPPYYYGSNGT

Leader (amino acid sequence)
                                                          SEQ ID NO: 17
MALPVTALLLPLALLLHAARP Leader (nucleic acid sequence)
                                                          SEQ ID NO: 18
ATGGCCCTGCCTGTGACAGCCCTGCTGCTGCCTCTGGCTCTGCTGCTGCATGCCGCTAGACCC CD8 hinge (amino acid sequence)
                                                          SEQ ID NO: 19
TTTPAPRPPTPAPTIASQPLSLRPEACRPAAGGAVHTRGLDFACD CD8 hinge (nucleic acid sequence)
                                                          SEQ ID NO: 20
ACCACGACGCCAGCGCCGCGACCACCAACACCGGCGCCCACCATCGCGTCGCAGCCCCTGTCCCTGCGCCCAGAGGCGTGCC

GGCCAGCGGCGGGGGGCGCAGTGCACACGAGGGGGCTGGACTTCGCCTGTGAT

CD8 transmembrane (amino acid sequence)
                                                          SEQ ID NO: 21
IYIWAPLAGTCGVLLLSLVITLYC CD8 transmembrane (nucleic acid sequence)
                                                          SEQ ID NO: 22
ATCTACATCTGGGCGCCCTTGGCCGGGACTTGTGGGGTCCTTCTCCTGTCACTGGTTATCACCCTTTACTGC 4-1BB Intracellular domain (amino acid sequence)
                                                          SEQ ID NO: 23
KRGRKKLLYIFKQPFMRPVQTTQEEDGCSCRFPEEEEGGCEL 4-1BB Intracellular domain (nucleic acid sequence)
                                                          SEQ ID NO: 24
AAACGGGGCAGAAAGAAACTCCTGTATATATTCAAACAACCATTTATGAGACCAGTACAAACTACTCAAGAGGAAGATGGCT

GTAGCTGCCGATTTCCAGAAGAAGAAGAAGGAGGATGTGAACTG

CD28 Intracellular domain (amino acid sequence)
                                                          SEQ ID NO: 25
RSKRSRLLHSDYMNMTPRRPGPTRKHYQPYAPPRDFAAYRS CD28 Intracellular domain (nucleotide sequence)
                                                          SEQ ID NO: 26
AGGAGTAAGAGGAGCAGGCTCCTGCACAGTGACTACATGAACATGACTCCCCGCCGCCCCGGGCCCACCCGCAAGCATTACC

AGCCCTATGCCCCACCACGCGACTTCGCAGCCTATCGCTCC

ICOS Intracellular domain (amino acid sequence)
                                                          SEQ ID NO: 27
TKKKYSSSVHDPNGEYMFMRAVNTAKKSRLTDVTL ICOS Intracellular domain (nucleotide sequence)
                                                          SEQ ID NO: 28
ACAAAAAAGAAGTATTCATCCAGTGTGCACGACCCTAACGGTGAATACATGTTCATGAGAGCAGTGAACACAGCCAAAAAT

CCAGACTCACAGATGTGACCCTA

CD3 zeta domain (amino acid sequence)
                                                          SEQ ID NO: 29
RVKFSRSADAPAYKQGQNQLYNELNLGRREEYDVLDKRRGRDPEMGGKPRRKNPQEGLYNELQKDKMAEAYSEIGMKGERRR

GKGHDGLYQGLSTATKDTYDALHMQALPPR

CD3 zeta (nucleic acid sequence)
                                                          SEQ ID NO: 30
AGAGTGAAGTTCAGCAGGAGCGCAGACGCCCCCGCGTACAAGCAGGGCCAGAACCAGCTCTATAACGAGCTCAATCTAGGAC GAAGAGAGGAGTACGATGTTTTGGACAAGAGACGTGGCCGGGACCCTGAGATGGGGGGAAAGCCGAGAAGGAAGAACCCTCA GGAAGGCCTGTACAATGAACTGCAGAAAGATAAGATGGCGGAGGCCTACAGTGAGATTGGGATGAAAGGCGAGCGCCGGAGG
```

```
GGCAAGGGGCACGATGGCCTTTACCAGGGTCTCAGTACAGCCACCAAGGACACCTACGACGCCCTTCACATGCAGGCCCTGC

CCCCTCGC
```

CD3 zeta domain (amino acid sequence; NCBI Reference Sequence NM_000734.3)
SEQ ID NO: 31
```
RVKFSRSADAPAYQQGQNQLYNELNLGRREEYDVLDKRRGRDPEMGGKPRRKNPQEGLYNELQKDKMAEAYSEIGMKGERRR

GKGHDGLYQGLSTATKDTYDALHMQALPPR
```

CD3 zeta (nucleic acid sequence; NCBI Reference Sequence NM_000734.3);
SEQ ID NO: 32
```
AGAGTGAAGTTCAGCAGGAGCGCAGACGCCCCCGCGTACCAGCAGGGCCAGAACCAGCTCTATAACGAGCTCAATCTAGGAC GAAGAGAGGAGTACGATGTTTTGGACAAGAGACGTGGCCGGGACCCTGAGATGGGGGGAAAGCCGAGAAGGAAGAACCCTCA GGAAGGCCTGTACAATGAACTGCAGAAAGATAAGATGGCGGAGGCCTACAGTGAGATTGGGATGAAAGGCGAGCGCCGGAGG GGCAAGGGGCACGATGGCCTTTACCAGGGTCTCAGTACAGCCACCAAGGACACCTACGACGCCCTTCACATGCAGGCCCTGC

CCCCTCGC
```

IgG4 Hinge (amino acid sequence)
SEQ ID NO: 33
```
ESKYGPPCPPCPAPEFLGGPSVFLFPPKPKDTLMISRTPEVTCVVVDVSQEDPEVQFNWYVDGVEVHNAKTKPREEQFNSTY RVVSVLTVLHQDWLNGKEYKCKVSNKGLPSSIEKTISKAKGQPREPQVYTLPPSQEEMTKNQVSLTCLVKGFYPSDIAVEWE

SNGQPENNYKTTPPVLDSDGSFFLYSRLTVDKSRWQEGNVFSCSVMHEALHNHYTQKSLSLSLGKM
```

IgG4 Hinge (nucleotide sequence)
SEQ ID NO: 34
```
GAGAGCAAGTACGGCCCTCCCTGCCCCCCTTGCCCTGCCCCCGAGTTCCTGGGCGGACCCAGCGTGTTCCTGTTCCCCCCA AGCCCAAGGACACCCTGATGATCAGCCGGACCCCCGAGGTGACCTGTGTGGTGGTGGACGTGTCCCAGGAGGACCCCGAGGT CCAGTTCAACTGGTACGTGGACGGCGTGGAGGTGCACAACGCCAAGACCAAGCCCCGGGAGGAGCAGTTCAATAGCACCTAC CGGGTGGTGTCCGTGCTGACCGTGCTGCACCAGGACTGGCTGAACGGCAAGGAATACAAGTGTAAGGTGTCCAACAAGGGCC TGCCCAGCAGCATCGAGAAAACCATCAGCAAGGCCAAGGGCCAGCCTCGGGAGCCCCAGGTGTACACCCTGCCCCCTAGCCA AGAGGAGATGACCAAGAACCAGGTGTCCCTGACCTGCCTGGTGAAGGGCTTCTACCCCAGCGACATCGCCGTGGAGTGGGAG AGCAACGGCCAGCCCGAGAACAACTACAAGACCACCCCCCCTGTGCTGGACAGCGACGGCAGCTTCTTCCTGTACAGCCGGC TGACCGTGGACAAGAGCCGGTGGCAGGAGGGCAACGTCTTTAGCTGCTCCGTGATGCACGAGGCCCTGCACAACCACTACAC

CCAGAAGAGCCTGAGCCTGTCCCTGGGCAAGATG
```

Intracellular Domain Sequence
SEQ ID NO: 35
```
KRGRKKLLYIFKQPFMRPVQTTQEEDGCSCRFPEEEEGGCELRVKFSRSADAPAYKQGQNQLYNELNLGRREEYDVLDKRRG

RDPEMGGKPRRKNPQEGLYNELQKDKMAEAYSEIGMKGERRRGKGHDGLYQGLSTATKDTYDALHMQALPPR
```

Linker Sequence [(GGGGS)4]
SEQ ID NO: 36
```
GGGGSGGGGSGGGGSGGGGS
``` scFv (AbH-1)
SEQ ID NO: 37
```
QVQLVQSGAEVKKPGASVKVSCKASGYSFTGYYIHWVRQAPGQELGWMGYISCYNGASSYNQKFKGRVTMTVDTSISTAYTE

LSSLRSEDTATYYCASSMDYWGQGTLVTVSSGGGGSGGGGSGGGGSGGGGSDVVMTQSPLSLPVTLGQPASISCKSSQSLLD

SDGKTYLNWLQQRPGQSPRRLIYLVSKLDSGVPDRFSGSGSGTDFTLKISRVEAEDVGVYHCWQGTHFPYTFGGGTKVEIK
``` scFv (AbH-2)
SEQ ID NO: 38
```
QVTLKESGPVLVKPTETLTLTCTVSGYSITSDYAWNWIRQPPGKALEWLAYISYSGSTSYNPSLKSRLSITKDTSKSQVVLT

MTNMDPVDTATYYCARDPPYYYGSWGQGTTVTVSSGGGGSGGGGSGGGGSGGGGSDVVMTQSPLSLPVTLGQPASISCKSSQ

SLLDSDGKTYLNWLQQRPGQSPRRLIYLVSKLDSGVPDRFSGSGSGTDFTLKISRVEAEDVGVYHCWQGTHFPYTFGGGTKV

EIK
```

CAR-T construct (AbM-1)
SEQ ID NO: 39
EVQLEQSGPELVKTGASVKISCKASGYSFTGYYIHWVKQSHGKSLEWIGYISCYNGASSYNQKFKGKATFTVDTSSSTAYMQ FNSLTSGDSAVYYCASSMDYWGQGTSVTVSSGGGGSGGGGSGGGGSGGGGSDVVMTQTPLTLSVTIGQPASISCKSSQSLLD SDGKTYLNWLLQRPGQSPKRLIYLVSKLDSGVPDRFTGSGSGTDFTLKISRVEAEDLGVYHCWQGTHFPYTFGGGTKLEIKT TTPAPRPPTPAPTIASQPLSLRPEACRPAAGGAVHTRGLDFACDIYIWAPLAGTCGVLLLSLVITLYCKRGRKKLLYIFKQP FMRPVQTTQEEDGCSCRFPEEEEGGCELRVKFSRSADAPAYKQGQNQLYNELNLGRREEYDVLDKRRGRDPEMGGKPRRKNP

QEGLYNELQKDKMAEAYSEIGMKGERRRGKGHDGLYQGLSTATKDTYDALHMQALPPR

CAR-T construct (AbM-2)
SEQ ID NO: 40
DVQLQESGPGLVKNSQSLSLTCTVTGYSITSDYAWNWIRQFPGNKLEWMGYISYSGSTSYNPSLKSRISITRDTSKNQFFLQ LNSVTPEDTATYYCARDPPYYYGSNGTWGQGTSVTVSSGGGGSGGGGSGGGGSGGGGSDVVMTQTPLTLSVTIGQPASISCK SSQSLLDSDGKTYLNWLLQRPGQSPKRLIYLVSKLDSGVPDRFTGSGSGTDFTLKISRVEAEDLGVYHCWQGTHFPYTFGGG TKLEIKTTTPAPRPPTPAPTIASQPLSLRPEACRPAAGGAVHTRGLDFACDIYIWAPLAGTCGVLLLSLVITLYCKRGRKKL LYIFKQPFMRPVQTTQEEDGCSCRFPEEEEGGCELRVKFSRSADAPAYKQGQNQLYNELNLGRREEYDVLDKRRGRDPEMGG

KPRRKNPQEGLYNELQKDKMAEAYSEIGMKGERRRGKGHDGLYQGLSTATKDTYDALHMQALPPR

CAR-T construct (AbH-1)
SEQ ID NO: 41
QVQLVQSGAEVKKPGASVKVSCKASGYSFTGYYIHWVRQAPGQELGWMGYISCYNGASSYNQKFKGRVTMTVDTSISTAYTE LSSLRSEDTATYYCASSMDYWGQGTLVTVSSGGGGSGGGGSGGGGSGGGGSDVVMTQSPLSLPVTLGQPASISCKSSQSLLD SDGKTYLNWLQQRPGQSPRRLIYLVSKLDSGVPDRFSGSGSGTDFTLKISRVEAEDVGVYHCWQGTHFPYTFGGGTKVEIKT TTPAPRPPTPAPTIASQPLSLRPEACRPAAGGAVHTRGLDFACDIYIWAPLAGTCGVLLLSLVITLYCKRGRKKLLYIFKQP FMRPVQTTQEEDGCSCRFPEEEEGGCELRVKFSRSADAPAYKQGQNQLYNELNLGRREEYDVLDKRRGRDPEMGGKPRRKNP

QEGLYNELQKDKMAEAYSEIGMKGERRRGKGHDGLYQGLSTATKDTYDALHMQALPPR

CAR-T construct (AbH-2)
SEQ ID NO: 42
QVTLKESGPVLVKPTETLTLTCTVSGYSITSDYAWNWIRQPPGKALEWLAYISYSGSTSYNPSLKSRLSITKDTSKSQVVLT MTNMDPVDTATYYCARDPPYYYGSWGQGTTVTVSSGGGGSGGGGSGGGGSGGGGSDVVMTQSPLSLPVTLGQPASISCKSSQ SLLDSDGKTYLNWLQQRPGQSPRRLIYLVSKLDSGVPDRFSGSGSGTDFTLKISRVEAEDVGVYHCWQGTHFPYTFGGGTKV EIKTTTPAPRPPTPAPTIASQPLSLRPEACRPAAGGAVHTRGLDFACDIYIWAPLAGTCGVLLLSLVITLYCKRGRKKLLYI FKQPFMRPVQTTQEEDGCSCRFPEEEEGGCELRVKFSRSADAPAYKQGQNQLYNELNLGRREEYDVLDKRRGRDPEMGGKPR

RKNPQEGLYNELQKDKMAEAYSEIGMKGERRRGKGHDGLYQGLSTATKDTYDALHMQALPPR

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments described herein may be employed in practicing the invention. It is intended that the following claims define the scope and that methods and structures within the scope of these claims and their equivalents be covered thereby.

What is claimed is:

1. A composition comprising a nucleic acid comprising a sequence encoding a chimeric antigen receptor (CAR), wherein the CAR comprises an antibody domain comprising a mutant calreticulin binding domain, a transmembrane domain, and an intracellular domain comprising an intracellular signaling domain;

wherein the mutant calreticulin binding domain comprises a heavy chain variable domain (VH) comprising an amino acid sequence with at least 77% sequence identity to SEQ ID NO: 1 or an amino acid sequence with at least 75% sequence identity to SEQ ID NO: 2 and a light chain variable domain (VL), wherein:

(I) the VH comprises a heavy chain complement determining region 1 (HC CDR1) with the amino acid sequence of SEQ ID NO: 7, a HC CDR2 with the amino acid sequence of SEQ ID NO: 8, and a HC CDR3 with the amino acid sequence of SEQ ID NO: 9; and the VL comprises a light chain CDR1 (LC CDR1) with the amino acid sequence of SEQ ID NO: 13, a LC CDR2 with the amino acid sequence of SEQ ID NO: 14, and a LC CDR3 with the amino acid sequence of SEQ ID NO: 15;

(II) the VH comprises a HC CDR1 with the amino acid sequence of SEQ ID NO: 10, a HC CDR2 with the amino acid sequence of SEQ ID NO: 11, and a HC CDR3 with the amino acid sequence of SEQ ID NO: 12; and the VL comprises a LC CDR1 with the amino acid sequence of SEQ ID NO: 13, a LC CDR2 with the amino acid sequence of SEQ ID NO: 14, and a LC CDR3 with the amino acid sequence of SEQ ID NO: 15; or (III) the VH comprises a HC CDR1 with the amino acid sequence of SEQ ID NO: 10, a HC CDR2 with the amino acid sequence of SEQ ID NO: 11, and a HC CDR3 with the amino acid sequence of SEQ ID NO: 16; and the VL comprises a LC CDR1 with the amino acid sequence of SEQ ID NO: 13, a LC CDR2 with the amino acid sequence of SEQ ID NO: 14, and a LC CDR3 with the amino acid sequence of SEQ ID NO: 15.

2. The composition of claim 1, wherein the mutant calreticulin binding domain comprises:

(a) a HC CDR1 with the amino acid sequence of SEQ ID NO: 7, a HC CDR2 with the amino acid sequence of SEQ ID NO: 8, and a HC CDR3 with the amino acid sequence of SEQ ID NO: 9; and (b) a LC CDR1 with the amino acid sequence of SEQ ID NO: 13, a LC CDR2 with the amino acid sequence of SEQ ID NO: 14, and a LC CDR3 with the amino acid sequence of SEQ ID NO: 15.

3. The composition of claim 1, wherein the mutant calreticulin binding domain comprises:

(a) a HC CDR1 with an amino acid sequence of SEQ ID NO: 10, a HC CDR2 with an amino acid sequence of SEQ ID NO: 11, and a HC CDR3 with an amino acid sequence of SEQ ID NO: 12; and (b) a LC CDR1 with an amino acid sequence of SEQ ID NO: 13, a LC CDR2 with an amino acid sequence of SEQ ID NO: 14, and a LC CDR3 with an amino acid sequence of SEQ ID NO: 15.

4. The composition of claim 1, wherein the mutant calreticulin binding domain comprises:

(a) a HC CDR1 with an amino acid sequence of SEQ ID NO: 10, a HC CDR2 with an amino acid sequence of SEQ ID NO: 11, and a HC CDR3 with an amino acid sequence of SEQ ID NO: 16; and (b) a LC CDR1 with an amino acid sequence of SEQ ID NO: 13, a LC CDR2 with an amino acid sequence of SEQ ID NO: 14, and a LC CDR3 with an amino acid sequence of SEQ ID NO: 15.

5. The composition of claim 1, wherein the VL comprises an amino acid sequence with at least 93% sequence identity to SEQ ID NO: 3.

6. The composition of claim 1, wherein the VH comprises an amino acid sequence with at least 75% sequence identity to SEQ ID NO: 2.

7. The composition of claim 6, wherein the VL comprises an amino acid sequence with at least 93% sequence identity to SEQ ID NO: 3.

8. The composition of claim 1, wherein the VH comprises an amino acid sequence with at least 90% sequence identity to SEQ ID NO: 1 and the VL comprises an amino acid sequence with at least 90% sequence identity to SEQ ID NO: 3.

9. The composition of claim 1, wherein the VH comprises an amino acid sequence with at least 90% sequence identity to SEQ ID NO: 2 and the VL comprises an amino acid sequence with at least 90% sequence identity to SEQ ID NO: 3.

10. The composition of claim 1, wherein the VH comprises an amino acid sequence with at least 95% sequence identity to SEQ ID NO: 1 and the VL comprises an amino acid sequence with at least 95% sequence identity to SEQ ID NO: 3.

11. The composition of claim 1, wherein the VH comprises an amino acid sequence with at least 95% sequence identity to SEQ ID NO: 2 and the VL comprises an amino acid sequence with at least 95% sequence identity to SEQ ID NO: 3.

12. The composition of claim 1, wherein the antibody domain is a human or humanized antibody domain.

13. The composition of claim 1, wherein the mutant calreticulin binding domain binds to an epitope of a mutant calreticulin polypeptide with $K_D$ of 200 nM or less.

14. The composition of claim 1, wherein the nucleic acid further includes a sequence that encodes a leader sequence.

15. The composition of claim 1, wherein the antibody domain is connected to the transmembrane domain by a hinge domain.

16. The composition of claim 15, wherein the hinge domain comprises a CD8 amino acid sequence or an IgG4 amino acid sequence.

17. The composition of claim 1, wherein the transmembrane domain comprises a transmembrane domain of a protein selected from the group consisting of a T-cell receptor alpha chain, a T-cell receptor beta chain, a T-cell receptor zeta chain, CD28, CD3 epsilon, CD45, CD4, CDS, CD8, CD9, CD16, CD22, CD33, CD37, CD64, CD80, CD86, CD134, 4-1BB (CD137), and CD154.

18. The composition of claim 1, wherein the intracellular signaling domain comprises a costimulatory domain, wherein the costimulatory domain comprises a functional signaling domain derived from a protein selected from the group consisting of a MHC class I molecule, a TNF receptor protein, an Immunoglobulin-like protein, a cytokine receptor, an integrin, a signaling lymphocytic activation molecule (SLAM protein), an activating NK cell receptor, BTLA, a Toll ligand receptor, OX40, CD2, CD7, CD27, CD28, CD30, CD40, CDS, ICAM-1, LFA-1 (CD1la/CD18), 4-1BB (CD137), B7-H3, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, IA4, CD49D, ITGA6, VLA-6, CD49f, ITGAD, CD11d, ITGAE, CD 103, ITGAL, ITGAM, CD11b, ITGAX, CD11c, ITGB1, CD29, ITGB2, ITGB7, NKG2D, NKG2C, TNFR2, TRANCE/RANKL, DNAM1 (CD226), SLAMF4 (CD244, 2B4), CD84, CD96 (Tactile), CEACAMI, CRTAM, Ly9 (CD229), CD160 (BY55), PSGL1, CD100 (SEMA4D), CD69, SLAMF6 (NTB-A, Ly108), SLAM (SLAMFI, CD150, IPO-3), BLAME (SLAMF8), SELPLG (CD162), LTBR, LAT, GADS, SLP-76, PAG/Cbp, CD19a, and a ligand that specifically binds with CD83.

19. The composition of claim 18, wherein the costimulatory domain comprises a 4-1BB (CD137) amino acid sequence, or a CD28 amino acid sequence, or an ICOS (CD278) amino acid sequence.

20. The composition of claim 1, wherein the intracellular signaling domain comprises a CD3 zeta amino acid sequence.

21. The composition of claim 1, wherein the intracellular signaling domain comprises a functional signaling domain of 4-1BB (CD137) or a functional signaling domain of CD3 zeta.

22. The composition of claim 1, wherein the intracellular signaling domain comprises a primary signaling domain comprising a functional signaling domain derived from CD3 zeta, TCR zeta, FcR gamma, FcR beta, CD3 gamma, CD3 delta, CD3 epsilon, CDS, CD22, CD79a, CD79b, CD278, FcεRI, DAP10, DAP12, or CD66d.

23. A composition comprising a cell comprising the composition of claim 1.

24. A pharmaceutical composition comprising
   (i) the cell of claim 23; and
   (ii) a pharmaceutically acceptable carrier, diluent or excipient.

* * * * *

SEQUENCE LISTING

<160> NUMBER OF SEQ ID NOS: 77

<210> SEQ ID NO 1
<211> LENGTH: 113
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Ile His Trp Val Arg Gln Ala Pro Gly Gln Glu Leu Gly Trp Met
        35                  40                  45

Gly Tyr Ile Ser Cys Tyr Asn Gly Ala Ser Ser Tyr Asn Gln Lys Phe
    50                  55                  60

Lys Gly Arg Val Thr Met Thr Val Asp Thr Ser Ile Ser Thr Ala Tyr
65                  70                  75                  80

Thr Glu Leu Ser Ser Leu Arg Ser Glu Asp Thr Ala Thr Tyr Tyr Cys
                85                  90                  95

Ala Ser Ser Met Asp Tyr Trp Gly Gln Gly Thr Leu Val Thr Val Ser
            100                 105                 110

Ser

<210> SEQ ID NO 2
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gln Val Thr Leu Lys Glu Ser Gly Pro Val Leu Val Lys Pro Thr Glu
1               5                   10                  15

Thr Leu Thr Leu Thr Cys Thr Val Ser Gly Tyr Ser Ile Thr Ser Asp
            20                  25                  30

Tyr Ala Trp Asn Trp Ile Arg Gln Pro Pro Gly Lys Ala Leu Glu Trp
        35                  40                  45

Leu Ala Tyr Ile Ser Tyr Ser Gly Ser Thr Ser Tyr Asn Pro Ser Leu
    50                  55                  60

Lys Ser Arg Leu Ser Ile Thr Lys Asp Thr Ser Lys Ser Gln Val Val
65                  70                  75                  80

Leu Thr Met Thr Asn Met Asp Pro Val Asp Thr Ala Thr Tyr Tyr Cys
                85                  90                  95

Ala Arg Asp Pro Pro Tyr Tyr Tyr Gly Ser Trp Gly Gln Gly Thr Thr
            100                 105                 110

Val Thr Val Ser Ser
        115

<210> SEQ ID NO 3
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
                20                  25                  30

Asp Gly Lys Thr Tyr Leu Asn Trp Leu Gln Gln Arg Pro Gly Gln Ser
            35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr His Cys Trp Gln Gly
                85                  90                  95

Thr His Phe Pro Tyr Thr Phe Gly Gly Gly Thr Lys Val Glu Ile Lys
            100                 105                 110

<210> SEQ ID NO 4
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Glu Val Gln Leu Glu Gln Ser Gly Pro Glu Leu Val Lys Thr Gly Ala
1               5                   10                  15

Ser Val Lys Ile Ser Cys Lys Ala Ser Gly Tyr Ser Phe Thr Gly Tyr
                20                  25                  30

Tyr Ile His Trp Val Lys Gln Ser His Gly Lys Ser Leu Glu Trp Ile
            35                  40                  45

Gly Tyr Ile Ser Cys Tyr Asn Gly Ala Ser Ser Tyr Asn Gln Lys Phe
    50                  55                  60

Lys Gly Lys Ala Thr Phe Thr Val Asp Thr Ser Ser Ser Thr Ala Tyr
65                  70                  75                  80

Met Gln Phe Asn Ser Leu Thr Ser Gly Asp Ser Ala Val Tyr Tyr Cys
                85                  90                  95

Ala Ser Ser Met Asp Tyr Trp Gly Gln Gly Thr Ser Val Thr Val Ser
            100                 105                 110

Ser

<210> SEQ ID NO 5
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Asp Val Gln Leu Gln Glu Ser Gly Pro Gly Leu Val Lys Asn Ser Gln
1               5                   10                  15

Ser Leu Ser Leu Thr Cys Thr Val Thr Gly Tyr Ser Ile Thr Ser Asp
                20                  25                  30

Tyr Ala Trp Asn Trp Ile Arg Gln Phe Pro Gly Asn Lys Leu Glu Trp
            35                  40                  45

Met Gly Tyr Ile Ser Tyr Ser Gly Ser Thr Ser Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Pro Glu Asp Thr Ala Thr Tyr Tyr Cys

```
                85                  90                  95
Ala Arg Asp Pro Pro Tyr Tyr Tyr Gly Ser Asn Gly Thr Trp Gly Gln
            100                 105                 110

Gly Thr Ser Val Thr Val Ser Ser
        115                 120

<210> SEQ ID NO 6
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr His Cys Trp Gln Gly
                85                  90                  95

Thr His Phe Pro Tyr Thr Phe Gly Gly Gly Thr Lys Leu Glu Ile Lys
            100                 105                 110

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Tyr Ser Phe Thr Gly Tyr Tyr Ile His
1               5

<210> SEQ ID NO 8
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Tyr Ile Ser Cys Tyr Asn Gly Ala Ser Ser Tyr Asn Gln Lys Phe Lys
1               5                   10                  15

Gly

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 9

Ser Ser Met Asp Tyr
1               5

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Tyr Ser Ile Thr Ser Asp Tyr Ala Trp Asn
1               5                   10

<210> SEQ ID NO 11
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Tyr Ile Ser Tyr Ser Gly Ser Thr Ser Tyr Asn Pro Ser Leu Lys Ser
1               5                   10                  15

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Asp Pro Pro Tyr Tyr Tyr Gly Ser
1               5

<210> SEQ ID NO 13
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Lys Ser Ser Gln Ser Leu Leu Asp Ser Asp Gly Lys Thr Tyr Leu Asn
1               5                   10                  15

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Leu Val Ser Lys Leu Asp Ser
1               5

<210> SEQ ID NO 15
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 15

Trp Gln Gly Thr His Phe Pro Tyr Thr
1               5

<210> SEQ ID NO 16
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Asp Pro Pro Tyr Tyr Tyr Gly Ser Asn Gly Thr
1               5                   10

<210> SEQ ID NO 17
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Met Ala Leu Pro Val Thr Ala Leu Leu Leu Pro Leu Ala Leu Leu Leu
1               5                   10                  15

His Ala Ala Arg Pro
            20

<210> SEQ ID NO 18
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
atggccctgc ctgtgacagc cctgctgctg cctctggctc tgctgctgca tgccgctaga    60
ccc                                                                 63

<210> SEQ ID NO 19
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 20
<211> LENGTH: 135
```

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
accacgacgc cagcgccgcg accaccaaca ccggcgccca ccatcgcgtc gcagcccctg      60
tccctgcgcc cagaggcgtg ccggccagcg gcggggggcg cagtgcacac gaggggctg     120 gacttcgcct gtgat                                                     135

<210> SEQ ID NO 21
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 22
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
atctacatct gggcgcoctt ggccgggact tgtggggtcc ttctcctgtc actggttatc      60
accctttact gc                                                         72

<210> SEQ ID NO 23
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 24
<211> LENGTH: 126
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24 aaacgggggca gaaagaaact cctgtatata ttcaaacaac catttatgag accagtacaa     60
```

```
actactcaag aggaagatgg ctgtagctgc cgatttccag aagaagaaga aggaggatgt    120
gaactg                                                              126
```

<210> SEQ ID NO 25
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

```
Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40
```

<210> SEQ ID NO 26
<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26

```
aggagtaaga ggagcaggct cctgcacagt gactacatga acatgactcc ccgccgcccc    60
gggcccaccc gcaagcatta ccagccctat gccccaccac gcgacttcgc agcctatcgc   120
tcc                                                                 123
```

<210> SEQ ID NO 27
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

```
Thr Lys Lys Lys Tyr Ser Ser Ser Val His Asp Pro Asn Gly Glu Tyr
1               5                   10                  15

Met Phe Met Arg Ala Val Asn Thr Ala Lys Lys Ser Arg Leu Thr Asp
            20                  25                  30

Val Thr Leu
        35
```

<210> SEQ ID NO 28
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28

```
acaaaaaaga agtattcatc cagtgtgcac gaccctaacg gtgaatacat gttcatgaga    60
gcagtgaaca cagccaaaaa atccagactc acagatgtga cccta                   105
```

<210> SEQ ID NO 29
<211> LENGTH: 112

<210> SEQ ID NO 29
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 29

```
Arg Val Lys Phe Ser Arg Ser Ala Asp Ala Pro Ala Tyr Lys Gln Gly
1               5                   10                  15
Gln Asn Gln Leu Tyr Asn Glu Leu Asn Leu Gly Arg Arg Glu Glu Tyr
            20                  25                  30
Asp Val Leu Asp Lys Arg Arg Gly Arg Asp Pro Glu Met Gly Gly Lys
        35                  40                  45
Pro Arg Arg Lys Asn Pro Gln Glu Gly Leu Tyr Asn Glu Leu Gln Lys
    50                  55                  60
Asp Lys Met Ala Glu Ala Tyr Ser Glu Ile Gly Met Lys Gly Glu Arg
65                  70                  75                  80
Arg Arg Gly Lys Gly His Asp Gly Leu Tyr Gln Gly Leu Ser Thr Ala
                85                  90                  95
Thr Lys Asp Thr Tyr Asp Ala Leu His Met Gln Ala Leu Pro Pro Arg
            100                 105                 110
```

<210> SEQ ID NO 30
<211> LENGTH: 336
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 30

```
agagtgaagt tcagcaggag cgcagacgcc cccgcgtaca agcagggcca gaaccagctc      60
tataacgagc tcaatctagg acgaagagag gagtacgatg ttttggacaa gagacgtggc     120
cgggaccctg agatgggggg aaagccgaga aggaagaacc ctcaggaagg cctgtacaat     180
gaactgcaga aagataagat ggcggaggcc tacagtgaga ttgggatgaa aggcgagcgc     240
cggagggggca aggggcacga tggcctttac cagggtctca gtacagccac caaggacacc     300
tacgacgccc ttcacatgca ggccctgccc cctcgc                               336
```

<210> SEQ ID NO 31
<211> LENGTH: 112
<212> TYPE: PRT
<213> ORGANISM: Homo sapiens

<400> SEQUENCE: 31

```
Arg Val Lys Phe Ser Arg Ser Ala Asp Ala Pro Ala Tyr Gln Gln Gly
1               5                   10                  15
Gln Asn Gln Leu Tyr Asn Glu Leu Asn Leu Gly Arg Arg Glu Glu Tyr
            20                  25                  30
Asp Val Leu Asp Lys Arg Arg Gly Arg Asp Pro Glu Met Gly Gly Lys
        35                  40                  45
Pro Arg Arg Lys Asn Pro Gln Glu Gly Leu Tyr Asn Glu Leu Gln Lys
    50                  55                  60
Asp Lys Met Ala Glu Ala Tyr Ser Glu Ile Gly Met Lys Gly Glu Arg
65                  70                  75                  80
Arg Arg Gly Lys Gly His Asp Gly Leu Tyr Gln Gly Leu Ser Thr Ala
                85                  90                  95
Thr Lys Asp Thr Tyr Asp Ala Leu His Met Gln Ala Leu Pro Pro Arg
```

<210> SEQ ID NO 32
<211> LENGTH: 336
<212> TYPE: DNA
<213> ORGANISM: Homo sapiens

<400> SEQUENCE: 32

```
agagtgaagt tcagcaggag cgcagacgcc cccgcgtacc agcagggcca gaaccagctc    60
tataacgagc tcaatctagg acgaagagag gagtacgatg ttttggacaa gagacgtggc   120
cgggaccctg agatgggggg aaagccgaga aggaagaacc ctcaggaagg cctgtacaat   180
gaactgcaga aagataagat ggcggaggcc tacagtgaga ttgggatgaa aggcgagcgc   240
cggaggggca aggggcacga tggcctttac cagggtctca gtacagccac caaggacacc   300
tacgacgccc ttcacatgca ggccctgccc cctcgc                             336
```

<210> SEQ ID NO 33
<211> LENGTH: 230
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 33

```
Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys Met
225                 230
```

<210> SEQ ID NO 34
<211> LENGTH: 690
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34

```
gagagcaagt acggccctcc ctgcccccct tgccctgccc ccgagttcct gggcggaccc      60
agcgtgttcc tgttcccccc caagcccaag gacaccctga tgatcagccg gacccccgag     120
gtgacctgtg tggtggtgga cgtgtcccag gaggacccg aggtccagtt caactggtac      180
gtggacggcg tggaggtgca acgccaag accaagcccc gggaggagca gttcaatagc       240
acctaccggg tggtgtccgt gctgaccgtg ctgcaccagg actggctgaa cggcaaggaa     300
tacaagtgta aggtgtccaa caagggcctg cccagcagca tcgagaaaac catcagcaag     360
gccaagggcc agcctcggga gccccaggtg tacaccctgc cccctagcca agaggagatg     420
accaagaacc aggtgtccct gacctgcctg gtgaagggct tctacccag cgacatcgcc      480
gtggagtggg agagcaacg ccagcccgag aacaactaca agaccacccc ccctgtgctg      540
gacagcgacg gcagcttctt cctgtacagc cggctgaccg tggacaagag ccggtggcag     600
gagggcaacg tctttagctg ctccgtgatg cacgaggccc tgcacaacca ctacacccag     660
aagagcctga gcctgtccct gggcaagatg                                      690
```

<210> SEQ ID NO 35
<211> LENGTH: 154
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

```
Lys Arg Gly Arg Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu Arg Val Lys Phe Ser Arg
        35                  40                  45

Ser Ala Asp Ala Pro Ala Tyr Lys Gln Gly Gln Asn Gln Leu Tyr Asn
    50                  55                  60

Glu Leu Asn Leu Gly Arg Arg Glu Glu Tyr Asp Val Leu Asp Lys Arg
65                  70                  75                  80

Arg Gly Arg Asp Pro Glu Met Gly Gly Lys Pro Arg Arg Lys Asn Pro
                85                  90                  95

Gln Glu Gly Leu Tyr Asn Glu Leu Gln Lys Asp Lys Met Ala Glu Ala
            100                 105                 110

Tyr Ser Glu Ile Gly Met Lys Gly Glu Arg Arg Arg Gly Lys Gly His
        115                 120                 125

Asp Gly Leu Tyr Gln Gly Leu Ser Thr Ala Thr Lys Asp Thr Tyr Asp
    130                 135                 140

Ala Leu His Met Gln Ala Leu Pro Pro Arg
145                 150
```

<210> SEQ ID NO 36
<211> LENGTH: 20
<212> TYPE: PRT

<213> ORGANISM: Artificial Sequence
<220> FEATURE:
<223> OTHER INFORMATION: Description of Artificial Sequence: Synthetic peptide

<400> SEQUENCE: 36

```
Gly Gly Gly Gly Ser Gly Gly Gly Ser Gly Gly Gly Ser Gly
1               5                   10                  15

Gly Gly Gly Ser
            20
```

<210> SEQ ID NO 37
<211> LENGTH: 245
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 37

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Ile His Trp Val Arg Gln Ala Pro Gly Gln Glu Leu Gly Trp Met
        35                  40                  45

Gly Tyr Ile Ser Cys Tyr Asn Gly Ala Ser Ser Tyr Asn Gln Lys Phe
    50                  55                  60

Lys Gly Arg Val Thr Met Thr Val Asp Thr Ser Ile Ser Thr Ala Tyr
65                  70                  75                  80

Thr Glu Leu Ser Ser Leu Arg Ser Glu Asp Thr Ala Thr Tyr Tyr Cys
                85                  90                  95

Ala Ser Ser Met Asp Tyr Trp Gly Gln Gly Thr Leu Val Thr Val Ser
            100                 105                 110

Ser Gly Gly Gly Gly Ser Gly Gly Gly Gly Ser Gly Gly Gly Gly Ser
        115                 120                 125

Gly Gly Gly Gly Ser Asp Val Val Met Thr Gln Ser Pro Leu Ser Leu
    130                 135                 140

Pro Val Thr Leu Gly Gln Pro Ala Ser Ile Ser Cys Lys Ser Ser Gln
145                 150                 155                 160

Ser Leu Leu Asp Ser Asp Gly Lys Thr Tyr Leu Asn Trp Leu Gln Gln
                165                 170                 175

Arg Pro Gly Gln Ser Pro Arg Arg Leu Ile Tyr Leu Val Ser Lys Leu
            180                 185                 190

Asp Ser Gly Val Pro Asp Arg Phe Ser Gly Ser Gly Ser Gly Thr Asp
        195                 200                 205

Phe Thr Leu Lys Ile Ser Arg Val Glu Ala Glu Asp Val Gly Val Tyr
    210                 215                 220

His Cys Trp Gln Gly Thr His Phe Pro Tyr Thr Phe Gly Gly Gly Thr
225                 230                 235                 240

Lys Val Glu Ile Lys
            245
```

<210> SEQ ID NO 38
<211> LENGTH: 249
<212> TYPE: PRT
<213> ORGANISM: Artificial Sequence
<220> FEATURE:
<223> OTHER INFORMATION: Description of Artificial Sequence: Synthetic -continued polypeptide

<400> SEQUENCE: 38

```
Gln Val Thr Leu Lys Glu Ser Gly Pro Val Leu Val Lys Pro Thr Glu
1               5                   10                  15

Thr Leu Thr Leu Thr Cys Thr Val Ser Gly Tyr Ser Ile Thr Ser Asp
            20                  25                  30

Tyr Ala Trp Asn Trp Ile Arg Gln Pro Pro Gly Lys Ala Leu Glu Trp
        35                  40                  45

Leu Ala Tyr Ile Ser Tyr Ser Gly Ser Thr Tyr Asn Pro Ser Leu
    50                  55                  60

Lys Ser Arg Leu Ser Ile Thr Lys Asp Thr Ser Lys Ser Gln Val Val
65                  70                  75                  80

Leu Thr Met Thr Asn Met Asp Pro Val Asp Thr Ala Thr Tyr Tyr Cys
                85                  90                  95

Ala Arg Asp Pro Pro Tyr Tyr Tyr Gly Ser Trp Gly Gln Gly Thr Thr
            100                 105                 110

Val Thr Val Ser Ser Gly Gly Gly Gly Ser Gly Gly Gly Gly Ser Gly
        115                 120                 125

Gly Gly Ser Gly Gly Gly Gly Ser Asp Val Val Met Thr Gln Ser
    130                 135                 140

Pro Leu Ser Leu Pro Val Thr Leu Gly Gln Pro Ala Ser Ile Ser Cys
145                 150                 155                 160

Lys Ser Ser Gln Ser Leu Leu Asp Ser Asp Gly Lys Thr Tyr Leu Asn
                165                 170                 175

Trp Leu Gln Gln Arg Pro Gly Gln Ser Pro Arg Arg Leu Ile Tyr Leu
            180                 185                 190

Val Ser Lys Leu Asp Ser Gly Val Pro Asp Arg Phe Ser Gly Ser Gly
        195                 200                 205

Ser Gly Thr Asp Phe Thr Leu Lys Ile Ser Arg Val Glu Ala Glu Asp
    210                 215                 220

Val Gly Val Tyr His Cys Trp Gln Gly Thr His Phe Pro Tyr Thr Phe
225                 230                 235                 240

Gly Gly Gly Thr Lys Val Glu Ile Lys
                245
```

<210> SEQ ID NO 39
<211> LENGTH: 468
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

```
Glu Val Gln Leu Glu Gln Ser Gly Pro Glu Leu Val Lys Thr Gly Ala
1               5                   10                  15

Ser Val Lys Ile Ser Cys Lys Ala Ser Gly Tyr Ser Phe Thr Gly Tyr
            20                  25                  30

Tyr Ile His Trp Val Lys Gln Ser His Gly Lys Ser Leu Glu Trp Ile
        35                  40                  45

Gly Tyr Ile Ser Cys Tyr Asn Gly Ala Ser Ser Tyr Asn Gln Lys Phe
    50                  55                  60

Lys Gly Lys Ala Thr Phe Thr Val Asp Thr Ser Ser Ser Thr Ala Tyr
65                  70                  75                  80

Met Gln Phe Asn Ser Leu Thr Ser Gly Asp Ser Ala Val Tyr Tyr Cys
```

```
            85                  90                  95
Ala Ser Ser Met Asp Tyr Trp Gly Gln Gly Thr Ser Val Thr Val Ser
            100                 105                 110

Ser Gly Gly Gly Gly Ser Gly Gly Gly Ser Gly Gly Gly Gly Ser
        115                 120                 125

Gly Gly Gly Gly Ser Asp Val Val Met Thr Gln Thr Pro Leu Thr Leu
        130                 135                 140

Ser Val Thr Ile Gly Gln Pro Ala Ser Ile Ser Cys Lys Ser Ser Gln
145                 150                 155                 160

Ser Leu Leu Asp Ser Asp Gly Lys Thr Tyr Leu Asn Trp Leu Leu Gln
            165                 170                 175

Arg Pro Gly Gln Ser Pro Lys Arg Leu Ile Tyr Leu Val Ser Lys Leu
            180                 185                 190

Asp Ser Gly Val Pro Asp Arg Phe Thr Gly Ser Gly Ser Gly Thr Asp
            195                 200                 205

Phe Thr Leu Lys Ile Ser Arg Val Glu Ala Glu Asp Leu Gly Val Tyr
            210                 215                 220

His Cys Trp Gln Gly Thr His Phe Pro Tyr Thr Phe Gly Gly Gly Thr
225                 230                 235                 240

Lys Leu Glu Ile Lys Thr Thr Thr Pro Ala Pro Arg Pro Pro Thr Pro
            245                 250                 255

Ala Pro Thr Ile Ala Ser Gln Pro Leu Ser Leu Arg Pro Glu Ala Cys
            260                 265                 270

Arg Pro Ala Ala Gly Gly Ala Val His Thr Arg Gly Leu Asp Phe Ala
            275                 280                 285

Cys Asp Ile Tyr Ile Trp Ala Pro Leu Ala Gly Thr Cys Gly Val Leu
            290                 295                 300

Leu Leu Ser Leu Val Ile Thr Leu Tyr Cys Lys Arg Gly Arg Lys Lys
305                 310                 315                 320

Leu Leu Tyr Ile Phe Lys Gln Pro Phe Met Arg Pro Val Gln Thr Thr
            325                 330                 335

Gln Glu Glu Asp Gly Cys Ser Cys Arg Phe Pro Glu Glu Glu Glu Gly
            340                 345                 350

Gly Cys Glu Leu Arg Val Lys Phe Ser Arg Ser Ala Asp Ala Pro Ala
            355                 360                 365

Tyr Lys Gln Gly Gln Asn Gln Leu Tyr Asn Glu Leu Asn Leu Gly Arg
            370                 375                 380

Arg Glu Glu Tyr Asp Val Leu Asp Lys Arg Arg Gly Arg Asp Pro Glu
385                 390                 395                 400

Met Gly Gly Lys Pro Arg Arg Lys Asn Pro Gln Glu Gly Leu Tyr Asn
            405                 410                 415

Glu Leu Gln Lys Asp Lys Met Ala Glu Ala Tyr Ser Glu Ile Gly Met
            420                 425                 430

Lys Gly Glu Arg Arg Arg Gly Lys Gly His Asp Gly Leu Tyr Gln Gly
            435                 440                 445

Leu Ser Thr Ala Thr Lys Asp Thr Tyr Asp Ala Leu His Met Gln Ala
            450                 455                 460

Leu Pro Pro Arg
465

<210> SEQ ID NO 40
<211> LENGTH: 475
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 40

Asp Val Gln Leu Gln Glu Ser Gly Pro Gly Leu Val Lys Asn Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Ser Tyr Ser Gly Ser Thr Ser Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Pro Glu Asp Thr Ala Thr Tyr Tyr Cys
                85                  90                  95

Ala Arg Asp Pro Pro Tyr Tyr Gly Ser Asn Gly Thr Trp Gly Gln
            100                 105                 110

Gly Thr Ser Val Thr Val Ser Ser Gly Gly Gly Ser Gly Gly Gly
            115                 120                 125

Gly Ser Gly Gly Gly Ser Gly Gly Gly Ser Asp Val Val Met
            130                 135                 140

Thr Gln Thr Pro Leu Thr Leu Ser Val Thr Ile Gly Gln Pro Ala Ser
145                 150                 155                 160

Ile Ser Cys Lys Ser Ser Gln Ser Leu Leu Asp Ser Asp Gly Lys Thr
            165                 170                 175

Tyr Leu Asn Trp Leu Leu Gln Arg Pro Gly Gln Ser Pro Lys Arg Leu
            180                 185                 190

Ile Tyr Leu Val Ser Lys Leu Asp Ser Gly Val Pro Asp Arg Phe Thr
            195                 200                 205

Gly Ser Gly Ser Gly Thr Asp Phe Thr Leu Lys Ile Ser Arg Val Glu
            210                 215                 220

Ala Glu Asp Leu Gly Val Tyr His Cys Trp Gln Gly Thr His Phe Pro
225                 230                 235                 240

Tyr Thr Phe Gly Gly Gly Thr Lys Leu Glu Ile Lys Thr Thr Thr Pro
            245                 250                 255

Ala Pro Arg Pro Pro Thr Pro Ala Pro Thr Ile Ala Ser Gln Pro Leu
            260                 265                 270

Ser Leu Arg Pro Glu Ala Cys Arg Pro Ala Ala Gly Gly Ala Val His
            275                 280                 285

Thr Arg Gly Leu Asp Phe Ala Cys Asp Ile Tyr Ile Trp Ala Pro Leu
            290                 295                 300

Ala Gly Thr Cys Gly Val Leu Leu Leu Ser Leu Val Ile Thr Leu Tyr
305                 310                 315                 320

Cys Lys Arg Gly Arg Lys Lys Leu Leu Tyr Ile Phe Lys Gln Pro Phe
            325                 330                 335

Met Arg Pro Val Gln Thr Thr Gln Glu Glu Asp Gly Cys Ser Cys Arg
            340                 345                 350

Phe Pro Glu Glu Glu Glu Gly Gly Cys Glu Leu Arg Val Lys Phe Ser
            355                 360                 365

Arg Ser Ala Asp Ala Pro Ala Tyr Lys Gln Gly Gln Asn Gln Leu Tyr
            370                 375                 380

Asn Glu Leu Asn Leu Gly Arg Arg Glu Glu Tyr Asp Val Leu Asp Lys
```

```
385                 390                 395                 400
Arg Arg Gly Arg Asp Pro Glu Met Gly Gly Lys Pro Arg Arg Lys Asn
                405                 410                 415

Pro Gln Glu Gly Leu Tyr Asn Glu Leu Gln Lys Asp Lys Met Ala Glu
            420                 425                 430

Ala Tyr Ser Glu Ile Gly Met Lys Gly Glu Arg Arg Arg Gly Lys Gly
        435                 440                 445

His Asp Gly Leu Tyr Gln Gly Leu Ser Thr Ala Thr Lys Asp Thr Tyr
    450                 455                 460

Asp Ala Leu His Met Gln Ala Leu Pro Pro Arg
465                 470                 475

<210> SEQ ID NO 41
<211> LENGTH: 468
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Ile His Trp Val Arg Gln Ala Pro Gly Gln Glu Leu Gly Trp Met
        35                  40                  45

Gly Tyr Ile Ser Cys Tyr Asn Gly Ala Ser Ser Tyr Asn Gln Lys Phe
    50                  55                  60

Lys Gly Arg Val Thr Met Thr Val Asp Thr Ser Ile Ser Thr Ala Tyr
65                  70                  75                  80

Thr Glu Leu Ser Ser Leu Arg Ser Glu Asp Thr Ala Thr Tyr Tyr Cys
                85                  90                  95

Ala Ser Ser Met Asp Tyr Trp Gly Gln Gly Thr Leu Val Thr Val Ser
            100                 105                 110

Ser Gly Gly Gly Gly Ser Gly Gly Gly Gly Ser Gly Gly Gly Gly Ser
        115                 120                 125

Gly Gly Gly Gly Ser Asp Val Val Met Thr Gln Ser Pro Leu Ser Leu
    130                 135                 140

Pro Val Thr Leu Gly Gln Pro Ala Ser Ile Ser Cys Lys Ser Ser Gln
145                 150                 155                 160

Ser Leu Leu Asp Ser Asp Gly Lys Thr Tyr Leu Asn Trp Leu Gln Gln
                165                 170                 175

Arg Pro Gly Gln Ser Pro Arg Arg Leu Ile Tyr Leu Val Ser Lys Leu
            180                 185                 190

Asp Ser Gly Val Pro Asp Arg Phe Ser Gly Ser Gly Ser Gly Thr Asp
        195                 200                 205

Phe Thr Leu Lys Ile Ser Arg Val Glu Ala Glu Asp Val Gly Val Tyr
    210                 215                 220

His Cys Trp Gln Gly Thr His Phe Pro Tyr Thr Phe Gly Gly Gly Thr
225                 230                 235                 240

Lys Val Glu Ile Lys Thr Thr Thr Pro Ala Pro Arg Pro Pro Thr Pro
                245                 250                 255

Ala Pro Thr Ile Ala Ser Gln Pro Leu Ser Leu Arg Pro Glu Ala Cys
            260                 265                 270
```

```
Arg Pro Ala Ala Gly Gly Ala Val His Thr Arg Gly Leu Asp Phe Ala
            275                 280                 285

Cys Asp Ile Tyr Ile Trp Ala Pro Leu Ala Gly Thr Cys Gly Val Leu
290                 295                 300

Leu Leu Ser Leu Val Ile Thr Leu Tyr Cys Lys Arg Gly Arg Lys Lys
305                 310                 315                 320

Leu Leu Tyr Ile Phe Lys Gln Pro Phe Met Arg Pro Val Gln Thr Thr
            325                 330                 335

Gln Glu Glu Asp Gly Cys Ser Cys Arg Phe Pro Glu Glu Glu Glu Gly
            340                 345                 350

Gly Cys Glu Leu Arg Val Lys Phe Ser Arg Ser Ala Asp Ala Pro Ala
            355                 360                 365

Tyr Lys Gln Gly Gln Asn Gln Leu Tyr Asn Glu Leu Asn Leu Gly Arg
            370                 375                 380

Arg Glu Glu Tyr Asp Val Leu Asp Lys Arg Arg Gly Arg Asp Pro Glu
385                 390                 395                 400

Met Gly Gly Lys Pro Arg Arg Lys Asn Pro Gln Glu Gly Leu Tyr Asn
                405                 410                 415

Glu Leu Gln Lys Asp Lys Met Ala Glu Ala Tyr Ser Glu Ile Gly Met
            420                 425                 430

Lys Gly Glu Arg Arg Arg Gly Lys Gly His Asp Gly Leu Tyr Gln Gly
            435                 440                 445

Leu Ser Thr Ala Thr Lys Asp Thr Tyr Asp Ala Leu His Met Gln Ala
            450                 455                 460

Leu Pro Pro Arg
465

<210> SEQ ID NO 42
<211> LENGTH: 472
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Gln Val Thr Leu Lys Glu Ser Gly Pro Val Leu Val Lys Pro Thr Glu
1               5                   10                  15

Thr Leu Thr Leu Thr Cys Thr Val Ser Gly Tyr Ser Ile Thr Ser Asp
            20                  25                  30

Tyr Ala Trp Asn Trp Ile Arg Gln Pro Pro Gly Lys Ala Leu Glu Trp
        35                  40                  45

Leu Ala Tyr Ile Ser Tyr Ser Gly Ser Thr Tyr Asn Pro Ser Leu
50                  55                  60

Lys Ser Arg Leu Ser Ile Thr Lys Asp Thr Ser Lys Ser Gln Val Val
65                  70                  75                  80

Leu Thr Met Thr Asn Met Asp Pro Val Asp Thr Ala Thr Tyr Tyr Cys
                85                  90                  95

Ala Arg Asp Pro Pro Tyr Tyr Tyr Gly Ser Trp Gly Gln Gly Thr Thr
            100                 105                 110

Val Thr Val Ser Ser Gly Gly Gly Gly Ser Gly Gly Gly Gly Ser Gly
        115                 120                 125

Gly Gly Gly Ser Gly Gly Gly Gly Ser Asp Val Val Met Thr Gln Ser
        130                 135                 140

Pro Leu Ser Leu Pro Val Thr Leu Gly Gln Pro Ala Ser Ile Ser Cys
145                 150                 155                 160
```

```
Lys Ser Ser Gln Ser Leu Leu Asp Ser Asp Gly Lys Thr Tyr Leu Asn
                165                 170                 175

Trp Leu Gln Gln Arg Pro Gly Gln Ser Pro Arg Leu Ile Tyr Leu
            180                 185                 190

Val Ser Lys Leu Asp Ser Gly Val Pro Asp Arg Phe Ser Gly Ser Gly
            195                 200                 205

Ser Gly Thr Asp Phe Thr Leu Lys Ile Ser Arg Val Glu Ala Glu Asp
        210                 215                 220

Val Gly Val Tyr His Cys Trp Gln Gly Thr His Phe Pro Tyr Thr Phe
225                 230                 235                 240

Gly Gly Gly Thr Lys Val Glu Ile Lys Thr Thr Thr Pro Ala Pro Arg
                245                 250                 255

Pro Pro Thr Pro Ala Pro Thr Ile Ala Ser Gln Pro Leu Ser Leu Arg
            260                 265                 270

Pro Glu Ala Cys Arg Pro Ala Ala Gly Gly Ala Val His Thr Arg Gly
        275                 280                 285

Leu Asp Phe Ala Cys Asp Ile Tyr Ile Trp Ala Pro Leu Ala Gly Thr
        290                 295                 300

Cys Gly Val Leu Leu Leu Ser Leu Val Ile Thr Leu Tyr Cys Lys Arg
305                 310                 315                 320

Gly Arg Lys Lys Leu Leu Tyr Ile Phe Lys Gln Pro Phe Met Arg Pro
                325                 330                 335

Val Gln Thr Thr Gln Glu Glu Asp Gly Cys Ser Cys Arg Phe Pro Glu
            340                 345                 350

Glu Glu Glu Gly Gly Cys Glu Leu Arg Val Lys Phe Ser Arg Ser Ala
        355                 360                 365

Asp Ala Pro Ala Tyr Lys Gln Gly Gln Asn Gln Leu Tyr Asn Glu Leu
        370                 375                 380

Asn Leu Gly Arg Arg Glu Glu Tyr Asp Val Leu Asp Lys Arg Arg Gly
385                 390                 395                 400

Arg Asp Pro Glu Met Gly Gly Lys Pro Arg Arg Lys Asn Pro Gln Glu
                405                 410                 415

Gly Leu Tyr Asn Glu Leu Gln Lys Asp Lys Met Ala Glu Ala Tyr Ser
            420                 425                 430

Glu Ile Gly Met Lys Gly Glu Arg Arg Arg Gly Lys Gly His Asp Gly
        435                 440                 445

Leu Tyr Gln Gly Leu Ser Thr Ala Thr Lys Asp Thr Tyr Asp Ala Leu
        450                 455                 460

His Met Gln Ala Leu Pro Pro Arg
465                 470

<210> SEQ ID NO 43
<211> LENGTH: 5000
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(5000)
<223> OTHER INFORMATION: This sequence may encompass 50-5000 nucleotides
<220> FEATURE:
<223> OTHER INFORMATION: See specification as filed for detailed
      description of substitutions and preferred embodiments

<400> SEQUENCE: 43
```

-continued

```
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaaaaaa     120
aaaaaaaaaa aaaaaaaaaa aaaaaaaaaa aaaaaaaaaa aaaaaaaaaa aaaaaaaaaa     180
aaaaaaaaaa aaaaaaaaaa aaaaaaaaaa aaaaaaaaaa aaaaaaaaaa aaaaaaaaaa     240
aaaaaaaaaa aaaaaaaaaa aaaaaaaaaa aaaaaaaaaa aaaaaaaaaa aaaaaaaaaa     300
aaaaaaaaaa aaaaaaaaaa aaaaaaaaaa aaaaaaaaaa aaaaaaaaaa aaaaaaaaaa     360
aaaaaaaaaa aaaaaaaaaa aaaaaaaaaa aaaaaaaaaa aaaaaaaaaa aaaaaaaaaa     420
aaaaaaaaaa aaaaaaaaaa aaaaaaaaaa aaaaaaaaaa aaaaaaaaaa aaaaaaaaaa     480
aaaaaaaaaa aaaaaaaaaa aaaaaaaaaa aaaaaaaaaa aaaaaaaaaa aaaaaaaaaa     540
aaaaaaaaaa aaaaaaaaaa aaaaaaaaaa aaaaaaaaaa aaaaaaaaaa aaaaaaaaaa     600
aaaaaaaaaa aaaaaaaaaa aaaaaaaaaa aaaaaaaaaa aaaaaaaaaa aaaaaaaaaa     660
aaaaaaaaaa aaaaaaaaaa aaaaaaaaaa aaaaaaaaaa aaaaaaaaaa aaaaaaaaaa     720
aaaaaaaaaa aaaaaaaaaa aaaaaaaaaa aaaaaaaaaa aaaaaaaaaa aaaaaaaaaa     780
aaaaaaaaaa aaaaaaaaaa aaaaaaaaaa aaaaaaaaaa aaaaaaaaaa aaaaaaaaaa     840
aaaaaaaaaa aaaaaaaaaa aaaaaaaaaa aaaaaaaaaa aaaaaaaaaa aaaaaaaaaa     900
aaaaaaaaaa aaaaaaaaaa aaaaaaaaaa aaaaaaaaaa aaaaaaaaaa aaaaaaaaaa     960
aaaaaaaaaa aaaaaaaaaa aaaaaaaaaa aaaaaaaaaa aaaaaaaaaa aaaaaaaaaa    1020
aaaaaaaaaa aaaaaaaaaa aaaaaaaaaa aaaaaaaaaa aaaaaaaaaa aaaaaaaaaa    1080
aaaaaaaaaa aaaaaaaaaa aaaaaaaaaa aaaaaaaaaa aaaaaaaaaa aaaaaaaaaa    1140
aaaaaaaaaa aaaaaaaaaa aaaaaaaaaa aaaaaaaaaa aaaaaaaaaa aaaaaaaaaa    1200
aaaaaaaaaa aaaaaaaaaa aaaaaaaaaa aaaaaaaaaa aaaaaaaaaa aaaaaaaaaa    1260
aaaaaaaaaa aaaaaaaaaa aaaaaaaaaa aaaaaaaaaa aaaaaaaaaa aaaaaaaaaa    1320
aaaaaaaaaa aaaaaaaaaa aaaaaaaaaa aaaaaaaaaa aaaaaaaaaa aaaaaaaaaa    1380
aaaaaaaaaa aaaaaaaaaa aaaaaaaaaa aaaaaaaaaa aaaaaaaaaa aaaaaaaaaa    1440
aaaaaaaaaa aaaaaaaaaa aaaaaaaaaa aaaaaaaaaa aaaaaaaaaa aaaaaaaaaa    1500
aaaaaaaaaa aaaaaaaaaa aaaaaaaaaa aaaaaaaaaa aaaaaaaaaa aaaaaaaaaa    1560
aaaaaaaaaa aaaaaaaaaa aaaaaaaaaa aaaaaaaaaa aaaaaaaaaa aaaaaaaaaa    1620
aaaaaaaaaa aaaaaaaaaa aaaaaaaaaa aaaaaaaaaa aaaaaaaaaa aaaaaaaaaa    1680
aaaaaaaaaa aaaaaaaaaa aaaaaaaaaa aaaaaaaaaa aaaaaaaaaa aaaaaaaaaa    1740
aaaaaaaaaa aaaaaaaaaa aaaaaaaaaa aaaaaaaaaa aaaaaaaaaa aaaaaaaaaa    1800
aaaaaaaaaa aaaaaaaaaa aaaaaaaaaa aaaaaaaaaa aaaaaaaaaa aaaaaaaaaa    1860
aaaaaaaaaa aaaaaaaaaa aaaaaaaaaa aaaaaaaaaa aaaaaaaaaa aaaaaaaaaa    1920
aaaaaaaaaa aaaaaaaaaa aaaaaaaaaa aaaaaaaaaa aaaaaaaaaa aaaaaaaaaa    1980
aaaaaaaaaa aaaaaaaaaa aaaaaaaaaa aaaaaaaaaa aaaaaaaaaa aaaaaaaaaa    2040
aaaaaaaaaa aaaaaaaaaa aaaaaaaaaa aaaaaaaaaa aaaaaaaaaa aaaaaaaaaa    2100
aaaaaaaaaa aaaaaaaaaa aaaaaaaaaa aaaaaaaaaa aaaaaaaaaa aaaaaaaaaa    2160
aaaaaaaaaa aaaaaaaaaa aaaaaaaaaa aaaaaaaaaa aaaaaaaaaa aaaaaaaaaa    2220
aaaaaaaaaa aaaaaaaaaa aaaaaaaaaa aaaaaaaaaa aaaaaaaaaa aaaaaaaaaa    2280
aaaaaaaaaa aaaaaaaaaa aaaaaaaaaa aaaaaaaaaa aaaaaaaaaa aaaaaaaaaa    2340
aaaaaaaaaa aaaaaaaaaa aaaaaaaaaa aaaaaaaaaa aaaaaaaaaa aaaaaaaaaa    2400
```

```
aaaaaaaaaa aaaaaaaaaa aaaaaaaaaa aaaaaaaaaa aaaaaaaaaa aaaaaaaaaa      2460
aaaaaaaaaa aaaaaaaaaa aaaaaaaaaa aaaaaaaaaa aaaaaaaaaa aaaaaaaaaa      2520
aaaaaaaaaa aaaaaaaaaa aaaaaaaaaa aaaaaaaaaa aaaaaaaaaa aaaaaaaaaa      2580
aaaaaaaaaa aaaaaaaaaa aaaaaaaaaa aaaaaaaaaa aaaaaaaaaa aaaaaaaaaa      2640
aaaaaaaaaa aaaaaaaaaa aaaaaaaaaa aaaaaaaaaa aaaaaaaaaa aaaaaaaaaa      2700
aaaaaaaaaa aaaaaaaaaa aaaaaaaaaa aaaaaaaaaa aaaaaaaaaa aaaaaaaaaa      2760
aaaaaaaaaa aaaaaaaaaa aaaaaaaaaa aaaaaaaaaa aaaaaaaaaa aaaaaaaaaa      2820
aaaaaaaaaa aaaaaaaaaa aaaaaaaaaa aaaaaaaaaa aaaaaaaaaa aaaaaaaaaa      2880
aaaaaaaaaa aaaaaaaaaa aaaaaaaaaa aaaaaaaaaa aaaaaaaaaa aaaaaaaaaa      2940
aaaaaaaaaa aaaaaaaaaa aaaaaaaaaa aaaaaaaaaa aaaaaaaaaa aaaaaaaaaa      3000
aaaaaaaaaa aaaaaaaaaa aaaaaaaaaa aaaaaaaaaa aaaaaaaaaa aaaaaaaaaa      3060
aaaaaaaaaa aaaaaaaaaa aaaaaaaaaa aaaaaaaaaa aaaaaaaaaa aaaaaaaaaa      3120
aaaaaaaaaa aaaaaaaaaa aaaaaaaaaa aaaaaaaaaa aaaaaaaaaa aaaaaaaaaa      3180
aaaaaaaaaa aaaaaaaaaa aaaaaaaaaa aaaaaaaaaa aaaaaaaaaa aaaaaaaaaa      3240
aaaaaaaaaa aaaaaaaaaa aaaaaaaaaa aaaaaaaaaa aaaaaaaaaa aaaaaaaaaa      3300
aaaaaaaaaa aaaaaaaaaa aaaaaaaaaa aaaaaaaaaa aaaaaaaaaa aaaaaaaaaa      3360
aaaaaaaaaa aaaaaaaaaa aaaaaaaaaa aaaaaaaaaa aaaaaaaaaa aaaaaaaaaa      3420
aaaaaaaaaa aaaaaaaaaa aaaaaaaaaa aaaaaaaaaa aaaaaaaaaa aaaaaaaaaa      3480
aaaaaaaaaa aaaaaaaaaa aaaaaaaaaa aaaaaaaaaa aaaaaaaaaa aaaaaaaaaa      3540
aaaaaaaaaa aaaaaaaaaa aaaaaaaaaa aaaaaaaaaa aaaaaaaaaa aaaaaaaaaa      3600
aaaaaaaaaa aaaaaaaaaa aaaaaaaaaa aaaaaaaaaa aaaaaaaaaa aaaaaaaaaa      3660
aaaaaaaaaa aaaaaaaaaa aaaaaaaaaa aaaaaaaaaa aaaaaaaaaa aaaaaaaaaa      3720
aaaaaaaaaa aaaaaaaaaa aaaaaaaaaa aaaaaaaaaa aaaaaaaaaa aaaaaaaaaa      3780
aaaaaaaaaa aaaaaaaaaa aaaaaaaaaa aaaaaaaaaa aaaaaaaaaa aaaaaaaaaa      3840
aaaaaaaaaa aaaaaaaaaa aaaaaaaaaa aaaaaaaaaa aaaaaaaaaa aaaaaaaaaa      3900
aaaaaaaaaa aaaaaaaaaa aaaaaaaaaa aaaaaaaaaa aaaaaaaaaa aaaaaaaaaa      3960
aaaaaaaaaa aaaaaaaaaa aaaaaaaaaa aaaaaaaaaa aaaaaaaaaa aaaaaaaaaa      4020
aaaaaaaaaa aaaaaaaaaa aaaaaaaaaa aaaaaaaaaa aaaaaaaaaa aaaaaaaaaa      4080
aaaaaaaaaa aaaaaaaaaa aaaaaaaaaa aaaaaaaaaa aaaaaaaaaa aaaaaaaaaa      4140
aaaaaaaaaa aaaaaaaaaa aaaaaaaaaa aaaaaaaaaa aaaaaaaaaa aaaaaaaaaa      4200
aaaaaaaaaa aaaaaaaaaa aaaaaaaaaa aaaaaaaaaa aaaaaaaaaa aaaaaaaaaa      4260
aaaaaaaaaa aaaaaaaaaa aaaaaaaaaa aaaaaaaaaa aaaaaaaaaa aaaaaaaaaa      4320
aaaaaaaaaa aaaaaaaaaa aaaaaaaaaa aaaaaaaaaa aaaaaaaaaa aaaaaaaaaa      4380
aaaaaaaaaa aaaaaaaaaa aaaaaaaaaa aaaaaaaaaa aaaaaaaaaa aaaaaaaaaa      4440
aaaaaaaaaa aaaaaaaaaa aaaaaaaaaa aaaaaaaaaa aaaaaaaaaa aaaaaaaaaa      4500
aaaaaaaaaa aaaaaaaaaa aaaaaaaaaa aaaaaaaaaa aaaaaaaaaa aaaaaaaaaa      4560
aaaaaaaaaa aaaaaaaaaa aaaaaaaaaa aaaaaaaaaa aaaaaaaaaa aaaaaaaaaa      4620
aaaaaaaaaa aaaaaaaaaa aaaaaaaaaa aaaaaaaaaa aaaaaaaaaa aaaaaaaaaa      4680
aaaaaaaaaa aaaaaaaaaa aaaaaaaaaa aaaaaaaaaa aaaaaaaaaa aaaaaaaaaa      4740
```

```
aaaaaaaaaa aaaaaaaaaa aaaaaaaaaa aaaaaaaaaa aaaaaaaaaa aaaaaaaaaa    4800
aaaaaaaaaa aaaaaaaaaa aaaaaaaaaa aaaaaaaaaa aaaaaaaaaa aaaaaaaaaa    4860
aaaaaaaaaa aaaaaaaaaa aaaaaaaaaa aaaaaaaaaa aaaaaaaaaa aaaaaaaaaa    4920
aaaaaaaaaa aaaaaaaaaa aaaaaaaaaa aaaaaaaaaa aaaaaaaaaa aaaaaaaaaa    4980
aaaaaaaaaa aaaaaaaaaa                                                5000

<210> SEQ ID NO 44
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(30)
<223> OTHER INFORMATION: This sequence may encompass 1-6 "Gly Gly Gly
      Gly Ser" repeating units
<220> FEATURE:
<223> OTHER INFORMATION: See specification as filed for detailed
      description of substitutions and preferred embodiments

<400> SEQUENCE: 44

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 45
<211> LENGTH: 150
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaaaaaa     120
aaaaaaaaaa aaaaaaaaaa aaaaaaaaaa                                     150

<210> SEQ ID NO 46
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(20)
<223> OTHER INFORMATION: This sequence may encompass 1-4 "Gly Gly Gly
      Gly Ser" repeating units

<400> SEQUENCE: 46

Gly Gly Gly Gly Ser Gly Gly Gly Gly Ser Gly Gly Gly Gly Ser Gly
1               5                   10                  15

Gly Gly Gly Ser
            20

<210> SEQ ID NO 47
<211> LENGTH: 4
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 47

Gly Gly Gly Ser
1

<210> SEQ ID NO 48
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gly Gly Gly Gly Ser Gly Gly Gly Gly Ser Gly Gly Gly Gly Ser
1               5                   10                  15

<210> SEQ ID NO 49
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gly Gly Gly Ser
1

<210> SEQ ID NO 50
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Arg Lys Met Ser Pro Ala Arg Pro Arg Thr Ser Cys Arg Glu Ala Cys
1               5                   10                  15

Leu Gln Gly Trp Thr Glu Ala
            20

<210> SEQ ID NO 51
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Arg Arg Lys Met Ser Pro Ala Arg Pro Arg Thr Ser Cys Arg Glu Ala
1               5                   10                  15

Cys Leu Gln Gly Trp Thr Glu Ala
            20

<210> SEQ ID NO 52
<211> LENGTH: 4
<212> TYPE: PRT
<213> ORGANISM: Unknown
```

```
<220> FEATURE:
<223> OTHER INFORMATION: Description of Unknown:
      Calreticulin peptide

<400> SEQUENCE: 52

Lys Asp Glu Leu
1

<210> SEQ ID NO 53
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gly Gly Gly Gly Ser Gly Gly Gly Gly Ser
1               5                   10

<210> SEQ ID NO 54
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gln Val Gln Leu Val Gln Ser Gly Ala Glu Val Lys Lys Pro Gly Ala
1               5                   10                  15

Ser Val Lys Val Ser Cys Lys Ala Ser Gly
            20                  25

<210> SEQ ID NO 55
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gln Val Thr Leu Lys Glu Ser Gly Pro Val Leu Val Lys Pro Thr Glu
1               5                   10                  15

Thr Leu Thr Leu Thr Cys Thr Val Ser Gly
            20                  25

<210> SEQ ID NO 56
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Glu Val Gln Leu Glu Gln Ser Gly Pro Glu Leu Val Lys Thr Gly Ala
1               5                   10                  15

Ser Val Lys Ile Ser Cys Lys Ala Ser Gly
            20                  25

<210> SEQ ID NO 57
<211> LENGTH: 26
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 57

Asp Val Gln Leu Gln Glu Ser Gly Pro Gly Leu Val Lys Asn Ser Gln
1               5                   10                  15

Ser Leu Ser Leu Thr Cys Thr Val Thr Gly
            20                  25

<210> SEQ ID NO 58
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Trp Val Arg Gln Ala Pro Gly Gln Glu Leu Gly Trp Met Gly
1               5                   10

<210> SEQ ID NO 59
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Trp Ile Arg Gln Pro Pro Gly Lys Ala Leu Glu Trp Leu Ala
1               5                   10

<210> SEQ ID NO 60
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Trp Val Lys Gln Ser His Gly Lys Ser Leu Glu Trp Ile Gly
1               5                   10

<210> SEQ ID NO 61
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Trp Ile Arg Gln Phe Pro Gly Asn Lys Leu Glu Trp Met Gly
1               5                   10

<210> SEQ ID NO 62
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62
```

```
Arg Val Thr Met Thr Val Asp Thr Ser Ile Ser Thr Ala Tyr Thr Glu
1               5                   10                  15

Leu Ser Ser Leu Arg Ser Glu Asp Thr Ala Thr Tyr Tyr Cys Ala
            20                  25                  30

<210> SEQ ID NO 63
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Arg Leu Ser Ile Thr Lys Asp Thr Ser Lys Ser Gln Val Val Leu Thr
1               5                   10                  15

Met Thr Asn Met Asp Pro Val Asp Thr Ala Thr Tyr Tyr Cys Ala Arg
            20                  25                  30

<210> SEQ ID NO 64
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Lys Ala Thr Phe Thr Val Asp Thr Ser Ser Ser Thr Ala Tyr Met Gln
1               5                   10                  15

Phe Asn Ser Leu Thr Ser Gly Asp Ser Ala Val Tyr Tyr Cys Ala
            20                  25                  30

<210> SEQ ID NO 65
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Arg Ile Ser Ile Thr Arg Asp Thr Ser Lys Asn Gln Phe Phe Leu Gln
1               5                   10                  15

Leu Asn Ser Val Thr Pro Glu Asp Thr Ala Thr Tyr Tyr Cys Ala Arg
            20                  25                  30

<210> SEQ ID NO 66
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Trp Gly Gln Gly Thr Leu Val Thr Val Ser Ser
1               5                   10

<210> SEQ ID NO 67
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 67

Trp Gly Gln Gly Thr Thr Val Thr Val Ser Ser
1               5                   10

<210> SEQ ID NO 68
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Trp Gly Gln Gly Thr Ser Val Thr Val Ser Ser
1               5                   10

<210> SEQ ID NO 69
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Asp Val Val Met Thr Gln Ser Pro Leu Ser Leu Pro Val Thr Leu Gly
1               5                   10                  15

Gln Pro Ala Ser Ile Ser Cys
            20

<210> SEQ ID NO 70
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Asp Val Val Met Thr Gln Thr Pro Leu Thr Leu Ser Val Thr Ile Gly
1               5                   10                  15

Gln Pro Ala Ser Ile Ser Cys
            20

<210> SEQ ID NO 71
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Trp Leu Gln Gln Arg Pro Gly Gln Ser Pro Arg Arg Leu Ile Tyr
1               5                   10                  15

<210> SEQ ID NO 72
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72
```

```
Trp Leu Leu Gln Arg Pro Gly Gln Ser Pro Lys Arg Leu Ile Tyr
1               5                   10                  15

<210> SEQ ID NO 73
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr His Cys
            20                  25                  30

<210> SEQ ID NO 74
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Gly Val Pro Asp Arg Phe Thr Gly Ser Gly Ser Gly Thr Asp Phe Thr
1               5                   10                  15

Leu Lys Ile Ser Arg Val Glu Ala Glu Asp Leu Gly Val Tyr His Cys
            20                  25                  30

<210> SEQ ID NO 75
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Phe Gly Gly Gly Thr Lys Val Glu Ile Lys
1               5                   10

<210> SEQ ID NO 76
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Phe Gly Gly Gly Thr Lys Leu Glu Ile Lys
1               5                   10

<210> SEQ ID NO 77
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 77

His His His His His His
1               5
```